United States Patent
Hoffman et al.

(10) Patent No.: US 10,967,223 B2
(45) Date of Patent: Apr. 6, 2021

(54) MONITORING AND TRACKING ATHLETIC ACTIVITY

(71) Applicant: NIKE, Inc., Beaverton, OR (US)

(72) Inventors: Michael T. Hoffman, Portland, OR (US); Kwamina Crankson, Portland, OR (US); Jason Nims, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 16/820,107

(22) Filed: Mar. 16, 2020

(65) Prior Publication Data
US 2020/0215392 A1   Jul. 9, 2020

Related U.S. Application Data

(63) Continuation of application No. 15/610,106, filed on May 31, 2017, now Pat. No. 10,625,117, which is a
(Continued)

(51) Int. Cl.
*G06F 3/048* (2013.01)
*A63B 24/00* (2006.01)
(Continued)

(52) U.S. Cl.
CPC ...... *A63B 24/0062* (2013.01); *A63B 24/0075* (2013.01); *A63B 69/0028* (2013.01);
(Continued)

(58) Field of Classification Search
CPC ............ A63B 24/0062; A63B 24/0075; A63B 69/0028; A63B 71/0622; A63B 71/0697;
(Continued)

(56) References Cited

U.S. PATENT DOCUMENTS

| 6,746,370 B1 | 6/2004 | Fleming et al. |
| 7,217,224 B2 | 5/2007 | Thomas |

(Continued)

FOREIGN PATENT DOCUMENTS

| CN | 1846213 A | 10/2006 |
| CN | 1988937 A | 6/2007 |

(Continued)

OTHER PUBLICATIONS

PCT/US2010/045250 International Search Report dated Nov. 12, 2010.
Mar. 15, 2012—(WO) IPRP—App No. PCT/US10/045250.

*Primary Examiner* — David Phantana-angkool
(74) *Attorney, Agent, or Firm* — Banner & Witcoff, Ltd.

(57) ABSTRACT

Tracking and monitoring athletic activity offers individuals with additional motivation to continue such behavior. An individual may track his or her athletic activity by completing goals. These goals may be represented by real-world objects such as food items, landmarks, buildings, statues, other physical structures, toys and the like. Each object may correspond to an athletic activity goal and require an amount of athletic activity to complete the goal. For example, a donut goal object may correspond to an athletic activity goal of burning 350 calories. The user may progress from goal object to goal object. Goal objects may increase in difficulty (e.g., amount of athletic activity required) and might only be available for selection upon completing an immediately previous goal object, a number of goal objects, an amount of athletic activity and the like.

20 Claims, 136 Drawing Sheets

Related U.S. Application Data continuation of application No. 15/138,920, filed on Apr. 26, 2016, now Pat. No. 10,420,983, which is a continuation of application No. 13/871,588, filed on Apr. 26, 2013, now Pat. No. 9,345,930, which is a continuation of application No. 12/855,301, filed on Aug. 12, 2010, now Pat. No. 8,533,620.

(60) Provisional application No. 61/359,278, filed on Jun. 28, 2010, provisional application No. 61/240,632, filed on Sep. 8, 2009, provisional application No. 61/240,185, filed on Sep. 4, 2009.

(51) Int. Cl.
| | |
|---|---|
| *A63B 71/06* | (2006.01) |
| *A63B 69/00* | (2006.01) |
| *G06F 1/16* | (2006.01) |
| *G16H 20/30* | (2018.01) |
| *G06Q 50/00* | (2012.01) |
| *A63B 22/00* | (2006.01) |
| *A63B 22/02* | (2006.01) |
| *A63B 22/06* | (2006.01) |

(52) U.S. Cl.
CPC ...... *A63B 71/0622* (2013.01); *A63B 71/0697* (2013.01); *G06F 1/163* (2013.01); *G06F 1/1626* (2013.01); *G06F 1/1632* (2013.01); *G06F 1/1698* (2013.01); *G06Q 50/01* (2013.01); *G16H 20/30* (2018.01); *A63B 22/0056* (2013.01); *A63B 22/0076* (2013.01); *A63B 22/02* (2013.01); *A63B 22/0605* (2013.01); *A63B 22/0664* (2013.01); *A63B 24/0084* (2013.01); *A63B 2024/0025* (2013.01); *A63B 2024/0068* (2013.01); *A63B 2071/065* (2013.01); *A63B 2071/0625* (2013.01); *A63B 2071/0647* (2013.01); *A63B 2071/0661* (2013.01); *A63B 2071/0663* (2013.01); *A63B 2220/12* (2013.01); *A63B 2220/13* (2013.01); *A63B 2220/17* (2013.01); *A63B 2220/20* (2013.01); *A63B 2220/30* (2013.01); *A63B 2220/34* (2013.01); *A63B 2220/40* (2013.01); *A63B 2220/51* (2013.01); *A63B 2220/56* (2013.01); *A63B 2220/803* (2013.01); *A63B 2220/836* (2013.01); *A63B 2225/15* (2013.01); *A63B 2225/20* (2013.01); *A63B 2225/50* (2013.01); *A63B 2225/54* (2013.01); *A63B 2230/00* (2013.01); *A63B 2230/04* (2013.01); *A63B 2230/207* (2013.01); *A63B 2230/75* (2013.01)

(58) Field of Classification Search
CPC ....... G16H 20/30; G06F 1/1626; G06F 1/163; G06F 1/1632; G06F 1/1698; G06Q 50/01
USPC .......................................................... 715/772
See application file for complete search history.

(56) References Cited

U.S. PATENT DOCUMENTS

| | | | |
|---|---|---|---|
| 7,662,065 B1 | 2/2010 | Kahn et al. | |
| 7,761,300 B2* | 7/2010 | Klingler | G10L 13/00 704/260 |
| 7,927,253 B2 | 4/2011 | Vincent et al. | |
| 8,257,228 B2 | 9/2012 | Quatrochi et al. | |
| 8,597,093 B2 | 12/2013 | Engelberg et al. | |
| 9,426,769 B2 | 8/2016 | Haro | |
| 9,728,059 B2 | 8/2017 | Arnold et al. | |
| 9,767,257 B2 | 9/2017 | McBrearty et al. | |
| 9,778,280 B2 | 10/2017 | Yuen et al. | |
| 9,891,999 B2 | 2/2018 | Gu et al. | |
| 9,953,060 B2 | 4/2018 | Cherukuri | |
| 10,222,909 B2* | 3/2019 | Shedletsky | G06F 3/0362 |
| 10,599,101 B2* | 3/2020 | Rothkopf | G06F 3/015 |
| 10,636,001 B2* | 4/2020 | Kongot | G06Q 10/063114 |
| 10,664,074 B2* | 5/2020 | Moussette | G06F 3/04845 |
| 10,699,247 B2* | 6/2020 | Johnson | G06Q 10/1093 |
| 10,712,824 B2* | 7/2020 | Moussette | G06F 3/0487 |
| 10,739,974 B2* | 8/2020 | Wilson | G06F 3/04883 |
| 2002/0016235 A1 | 2/2002 | Ashby et al. | |
| 2005/0192156 A1 | 9/2005 | Daikeler et al. | |
| 2005/0209050 A1 | 9/2005 | Bartels | |
| 2006/0063644 A1 | 3/2006 | Yang | |
| 2007/0197345 A1 | 8/2007 | Wallace et al. | |
| 2008/0051919 A1 | 2/2008 | Sakai et al. | |
| 2008/0076637 A1 | 3/2008 | Gilley et al. | |
| 2008/0096726 A1 | 4/2008 | Riley et al. | |
| 2008/0200312 A1 | 8/2008 | Tagliabue | |
| 2008/0307220 A1 | 12/2008 | Campbell | |
| 2009/0047644 A1 | 2/2009 | Mensah et al. | |
| 2009/0209393 A1 | 8/2009 | Crater et al. | |
| 2010/0331145 A1 | 12/2010 | Lakovic et al. | |
| 2012/0290109 A1 | 11/2012 | Engelberg et al. | |
| 2013/0123068 A1 | 5/2013 | Sultan et al. | |
| 2015/0145854 A1* | 5/2015 | Deshpande | G06Q 10/06 345/418 |
| 2016/0327911 A1* | 11/2016 | Eim | G06F 3/0362 |
| 2017/0031449 A1* | 2/2017 | Karsten | G06Q 10/109 |
| 2017/0216668 A1 | 8/2017 | Burton et al. | |
| 2018/0350173 A1 | 12/2018 | Smith et al. | |
| 2019/0281030 A1 | 9/2019 | Isaacson et al. | |
| 2019/0290219 A1 | 9/2019 | Pina et al. | |
| 2019/0290963 A1 | 9/2019 | Amis et al. | |
| 2019/0366157 A1 | 12/2019 | Weast et al. | |
| 2019/0370909 A1 | 12/2019 | Dyer et al. | |

FOREIGN PATENT DOCUMENTS

| | | |
|---|---|---|
| CN | 101111743 A | 1/2008 |
| CN | 101233503 A | 7/2008 |
| CN | 101242880 A | 8/2008 |
| CN | 101246518 A | 8/2008 |
| JP | H11164929 A | 6/1999 |
| JP | 2000288144 A | 10/2000 |
| JP | 2001009162 A | 1/2001 |
| JP | 2003108123 A | 4/2003 |
| JP | 2003111867 A | 4/2003 |
| JP | 2003154168 A | 5/2003 |
| JP | 2004024903 A | 1/2004 |
| JP | 2004118339 A | 4/2004 |
| JP | 2004141395 A | 5/2004 |
| JP | 2004174275 A | 6/2004 |
| JP | 2006239008 A | 9/2006 |
| JP | 2007226935 A | 9/2007 |
| JP | 2008048757 A | 3/2008 |
| JP | 2010517725 A | 5/2010 |
| JP | 2012527891 A | 11/2012 |
| JP | 5695052 B2 | 12/2012 |
| WO | 0156661 A1 | 8/2001 |
| WO | 2008101085 A2 | 8/2008 |
| WO | 2008120477 A1 | 10/2008 |
| WO | 2009031294 A1 | 3/2009 |
| WO | 2009073607 A2 | 6/2009 |
| WO | 2009076307 A2 | 6/2009 |
| WO | 2009108887 A2 | 9/2009 |
| WO | 2009111472 A2 | 9/2009 |
| WO | 2009129402 A1 | 10/2009 |

* cited by examiner

MONITORING AND TRACKING ATHLETIC ACTIVITY

CROSS REFERENCE TO RELATED APPLICATIONS

This application is a continuation of U.S. patent application Ser. No. 15/610,106, filed 31 May 2017, which is a continuation of U.S. patent application Ser. No. 15/138,920, filed Apr. 26, 2016, now U.S. Pat. No. 10,420,983, which is a continuation of U.S. patent application Ser. No. 13/871,588 filed Apr. 26, 2013, now U.S. Pat. No. 9,345,930, which is a continuation of U.S. patent application Ser. No. 12/855,301 filed Aug. 12, 2010, now U.S. Pat. No. 8,533,620, which claims the benefit of priority from U.S. Provisional Application No. 61/240,185, filed Sep. 4, 2009, U.S. Provisional Application No. 61/240,632, filed Sep. 8, 2009 and U.S. Provisional Application No. 61/359,278, filed Jun. 28, 2010. The contents of the above referenced applications are incorporated herein by reference in their entirety for any and all non-limiting purposes.

FIELD OF ART

The present invention relates to the collection and display of athletic information. Some aspects of the invention relate to the collection of step activity information and data over a network, and displaying the collected information.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Experienced athletes and trainers have found that feedback provides many people with motivation to maintain a regular exercise program. When a person can directly experience the results provided by an exercise program, that person typically will be encouraged to continue exercising. Unfortunately, the physical improvements obtained from exercise often come too slowly to provide sufficient motivation for many people to maintain a regular exercise program. It would therefore be useful for many athletes to have a more immediate, visual type of feedback to provide motivation for regular exercise.

Many experienced athletes and trainers also have found that competition may provide an even stronger motivation to maintain a regular exercise program. Some athletes, for example, will be more motivated to exercise when competing against a partner than by exercising alone. These athletes may, for example, exercise with a partner, enter into athletic contests such as races, or even just compare their current performance ability with a friend's.

BRIEF SUMMARY

Various aspects of the invention relate to the collection and display of athletic information. With some implementations of the invention, athletic data relating to a single person is collected and displayed so that the person can fully critique his or her performance. For example, a set of athletic data corresponding to athletic activity performed by a person over a first time period may be displayed as a graph. If the set of athletic data is generated from, e.g., a person running or walking, then the person's speed may be plotted against his or her distance over the time period for the activity. Alternatively or additionally, a number of steps performed or calories burned during walking or another step-related activity may be plotted against time. With some implementations, the set of athletic data can be analyzed, and the analysis results can be displayed simultaneously with the graph. For example, with a set of athletic data obtained from a person running, the data can be analyzed to determine the change in speed (i.e., acceleration or deceleration) between fixed distances (first mile, second mile, etc.). This information can then be displayed with the graph, so that the person can review when and how much he or she changed speed during the run. In another example, a set of athletic data obtained from a person walking may be analyzed to determine a pace with which the user is walking, a time of day the user is most active, a best workout in a period of a week and the like.

According to another aspect, athletic activity data may be visualized in a variety of ways. For example, an athletic activity chart may be represented by a bar graph having various textures, colors, patterns and the like. The various patterns, colors or textures may also be used to represent different information attributes such as a time of day or level of intensity of a particular set of activity data.

Athletic activity data may further be published in one or more outlets. For example, activity data may be published as a news entry on a user's social network page. Alternatively, the activity data may be published as a status entry on a user's social messaging site. The activity data may automatically be transmitted to the publication outlets based on a specified schedule or in response to certain triggers such as the completion of a goal or burning a certain number of calories. The user may further limit the types and/or amount of information publicly displayed.

In addition, some examples of the invention may allow a person to specify a goal related to an athletic activity. A person may, e.g., set a goal of running a specified total distance within a specified period of time. With these implementations of the invention, data from multiple sets of a person's athletic data may be aggregated and displayed in contrast with the person's specified goal. The goal may be displayed, for example, as an empty shape, like an oval. The aggregated data may then be displayed as fill within the empty shape. Thus, if the aggregated data shows that the person is within 80% of his or her goal, then the shape representing the goal will be displayed as 80% filled. In another example, a person may specify a goal to walk a certain number of steps or burn a number of calories by walking. Accordingly, the user's progress in burning the number of calories or walking the number of steps may be reflected in the visual appearance of a goal object such as a donut (e.g., for calories burned) or a building (e.g., for steps walked).

According to one or more aspects, a goal may be represented by a goal object that is visually relevant. For example, the goal object may be a food item representative of a number of calories the user must burn. In another example, the goal object may be a building representing a number of steps the user must walk. A series of goal objects may offer the user a sense of progression such that once a user completes a first goal, a second goal is offered to the user. Completion of each goal or all of the goals may correspond to an award. Certain goals and corresponding goal objects might not be available to a user for selection until the user has completed prerequisite or other goals.

Goals may be defined with a common thematic element. For example, goals may relate to various locations in the world. Thus, each location may have a series of goals that the user must accomplish prior to progressing to another location. The goals in each geographic location may be relevant or associated with that location. For example, in Paris, France, goals may include virtually walking up the Eiffel Tower (e.g., translating actual walking or running to virtually ascending the Eiffel Tower), burning a baguette's worth of calories and/or running a distance equal to the distance between the Arc De Triomphe and the Louvre. As with goals and goal objects, users might not be allowed to access certain locations in the world until completing goals and activity objectives in other locations. Users may further define custom themes by defining goals for the theme and specifying a progression of the goals.

With some implementations, sets of athletic data may be obtained from a plurality of different persons and displayed. For example, one or more sets of data from each of a plurality of different persons may be collected. Data from each person's data sets can then be aggregated and displayed to each person. For example, a set of athletic data can be generated for each run a person makes. For each person, data from his or her data sets, such as distance data, can be added up. An icon, such as a bar or line, can then be displayed for each person to represent the sum of the data from his or her data sets. A dimension of the icon, such as, e.g., its height, may correspond to the sum of the data added from each of a person's data sets.

According to yet another aspect, users may offer or accept challenges. Challenges may include one or more goals that are to be completed in a specified time frame. A challenge may be won by completing the challenge in the fastest time, performing the most steps in the allotted time and/or burning the most calories.

Still further, some examples of the invention may allow a person to "invite" one or more other persons to share athletic data corresponding to their athletic activities. With some implementations of the invention, for example, a user may send an invitation via electronic mail or a similar electronic medium to one or more other persons. Athletic data from only those invited persons may then be displayed simultaneously as noted above. This arrangement allows each invited person (including the inviting host, who inherently invites himself or herself and thus is considered an invitee as well) to compare his or her current athletic data with the other invitees.

For yet other implementations of the invention, the performance data collected from one or more users, details associated with one or more athletic performance goals or training programs, and the user interface associated therewith may be included in and/or displayed by a mobile device.

These and other features of the invention will become apparent from the following detailed description.

BRIEF DESCRIPTION OF THE DRAWINGS

FIGS. 40A-B illustrate example social networking outlets in which workout data may be published according to one or more aspects described herein.

FIGS. 42-47 illustrate user interfaces for progressing through and completing a themed workout plan according to one or more aspects described herein.

DETAILED DESCRIPTION OF THE INVENTION

Operating Environment
Overview

Aspects of the invention relate to the measurement, collection and display of athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person. Typically, an athletic information monitoring device will incorporate a sensor for measuring parameters relating to the person being monitored, and a computing device for processing the parameters measured by the sensor.

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some implementations of the invention may allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Figure 74:
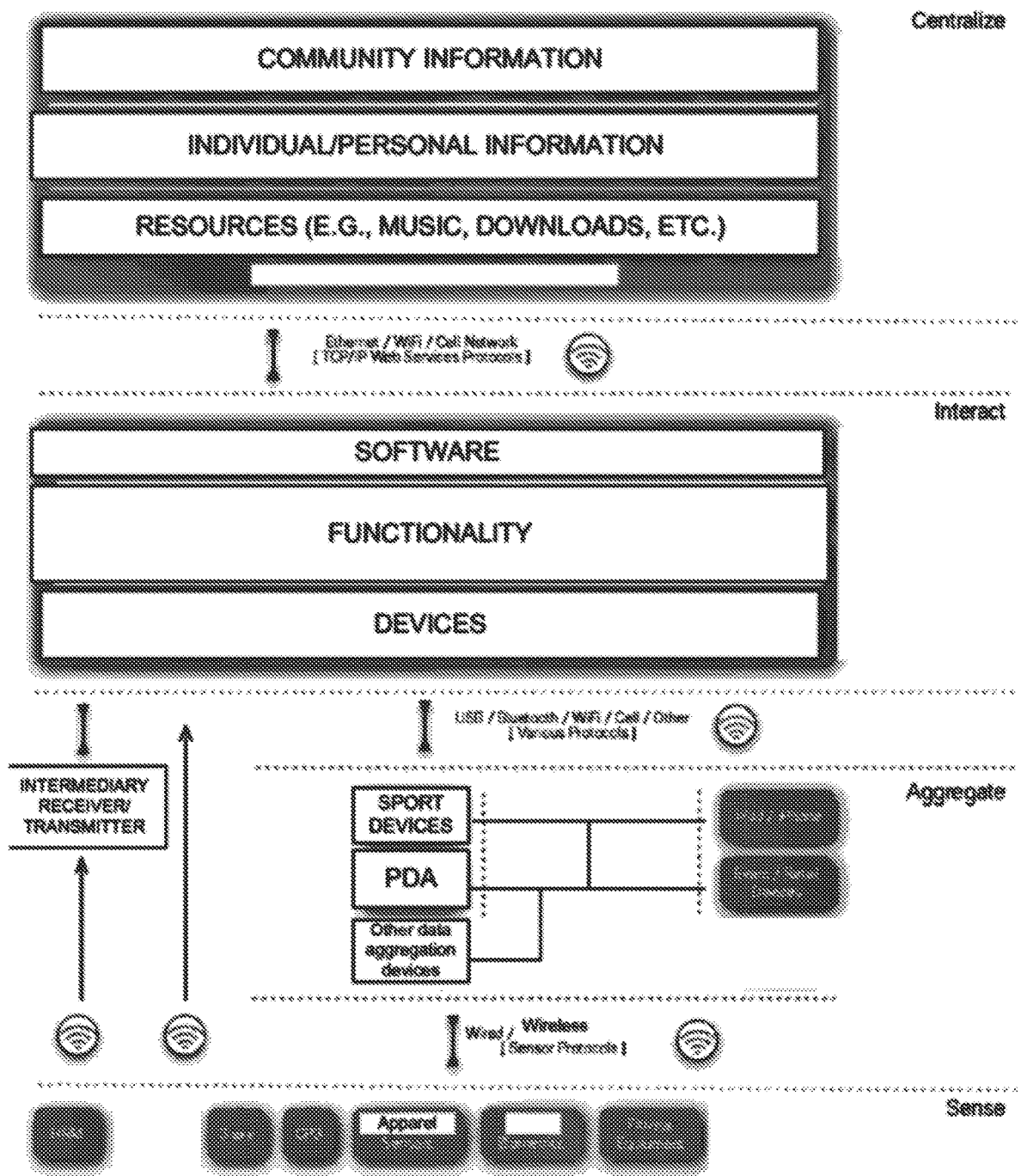
FIG. 74 illustrates a network environment in which various aspects described herein may be used.

FIG. 74 illustrates a data collection and monitoring network environment in which various aspects described herein may be used. For example, the network may include logical divisions such as between sensing devices, data aggregation devices, interactive devices for interacting with the data, other devices, one or more network sites and the like, and centralized sites and systems such as an athletic activity monitoring and tracking site. Sensing devices may include various types of sensors including pedometers, accelerometers, pressure sensors and the like. Sensing devices may be included in apparel such as clothing and shoes, in digital music players, other portable electronic devices, and the like. Alternatively, sensing devices may be standalone systems. Data from the sensors may either be transmitted to an application providing interactive functionality to view and explore workout data from a sensing device directly, through an aggregation device or through a third party receiver/transceiver. Aggregation devices may include a personal data assistant (PDA), sport specific devices, digital music players, smartphones, and the like. Aggregation devices may, in one or more arrangements, be configured to share data through, e.g., an ad-hoc network.

The interactive portion of the network may include a variety of software such as applications, browsers, widgets, mashups, daemons and embedded applications. The interactive portion may further include functionality (e.g., provided by the software) such as support, transfer, broadcast, share, view, convert, validate, cache, organize, identify and configure. For example, workout data may be broadcast using the functionality of the interactive portion of the network. According to one or more aspects, the interactive portion may be embodied in one or more interactive devices. Such devices may include desktop computers, laptop computers, mobile phones, media players, fitness equipment and the like.

Some functionality and software may include interfacing with a centralized athletic activity data monitoring and networking system. The system may offer a variety of services directed to communities, individuals and resources. Resources, for example, may include downloads, documents, music, web services, blogs/forums, help/support, and the like. Individual services may include a personal profile, purchase history, workout plan, trophies/records, friends, teams, geodata maps/trails, device profiles, performance history and/or combinations thereof. Additionally, the system may include community services or functions including challenges, teams/clubs, sharing capabilities, social networking, even calendars, community statistics and the like. Communications between each portion of the network may be performed through wired or wireless communications mechanisms and protocols including USB, BLUETOOTH, WiFi, Ethernet, TCP/IP and Web protocols.

The following represent examples of how athletic data may be collected and communicated:
Sensor(s)→wearable aggregator(s)→secondary mobile aggregator(s)→event/retail kiosk/desktop aggregator(s)/conduit(s)→central database server(s)→application server(s)→client/browser/mobile display(s)

Also all the various sensing, aggregating, databasing, and displaying components could be any combination of same or different devices, or possibly missing entirely. A good example is one of the simplest configurations using an iPhone:
Sensor→Communication Device ↔Athletic training and monitoring server. In this case, the communication Device both aggregates the sensor data before upload to the monitoring server and later displays the user experience from monitoring server.

Other embodiments may include a data flow as follows:
Sensor→Aggregation Device→Aggregation Application→Activity data server→Aggregation device
Aggregation device→Aggregation application→Activity data server→Aggregation device
Sensor→wearable aggregator→mobile multi-person aggregator→event-side upload kiosk→Activity data server→3rd party application server (e.g. Facebook)→client browser→activity display According to one or more aspects, athletic information may be received from one or more monitoring devices such as the sensor devices shown in FIG. 74 as well as one or more data entry devices (e.g. honor system entry of activities) such as one or more of the aggregation devices. In one example, clients may enter activity information into an activity based monitoring system (via server-to-server protocols) via an aggregation device as "fuel" to feed activity, challenges and goals. Another example would be a "log your activity" form directly on the activity monitoring and tracking site.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Figure 1:
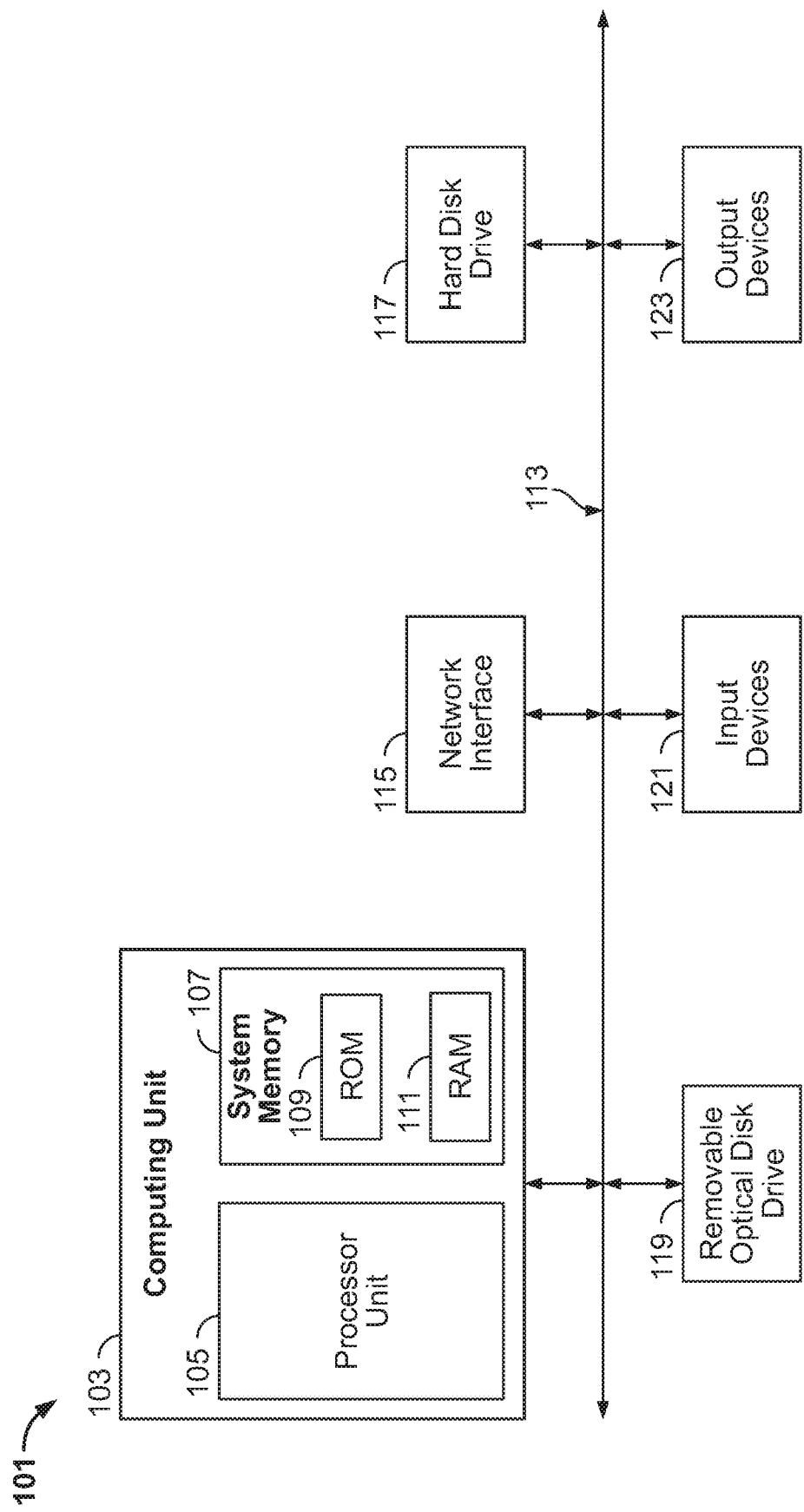
FIG. 1 illustrates a computing device that may be used to implement various examples of the invention.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). Network adapters may be wireless or wired or combinations thereof. These protocols are well known in the art, and thus will not be discussed here in more detail. An interface 127 may employ any suitable connection agent for connecting to a network, including, for example, a wireless transceiver, a power line adapter, a modem, or an Ethernet connection. Connection agents may similarly be wireless or wired or a combination thereof.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can serve as both an output device for a computer (e.g., outputting music from a sound file or pictures from an image file) and a storage device. In addition, this type of digital music play also can serve as an input device for inputting recorded athletic information, as will be discussed in more detail below. Connections and interfaces may be wireless, wired or combinations thereof.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data maintained may be synchronized.

Of course, still other peripheral devices may be included with our otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101, however. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
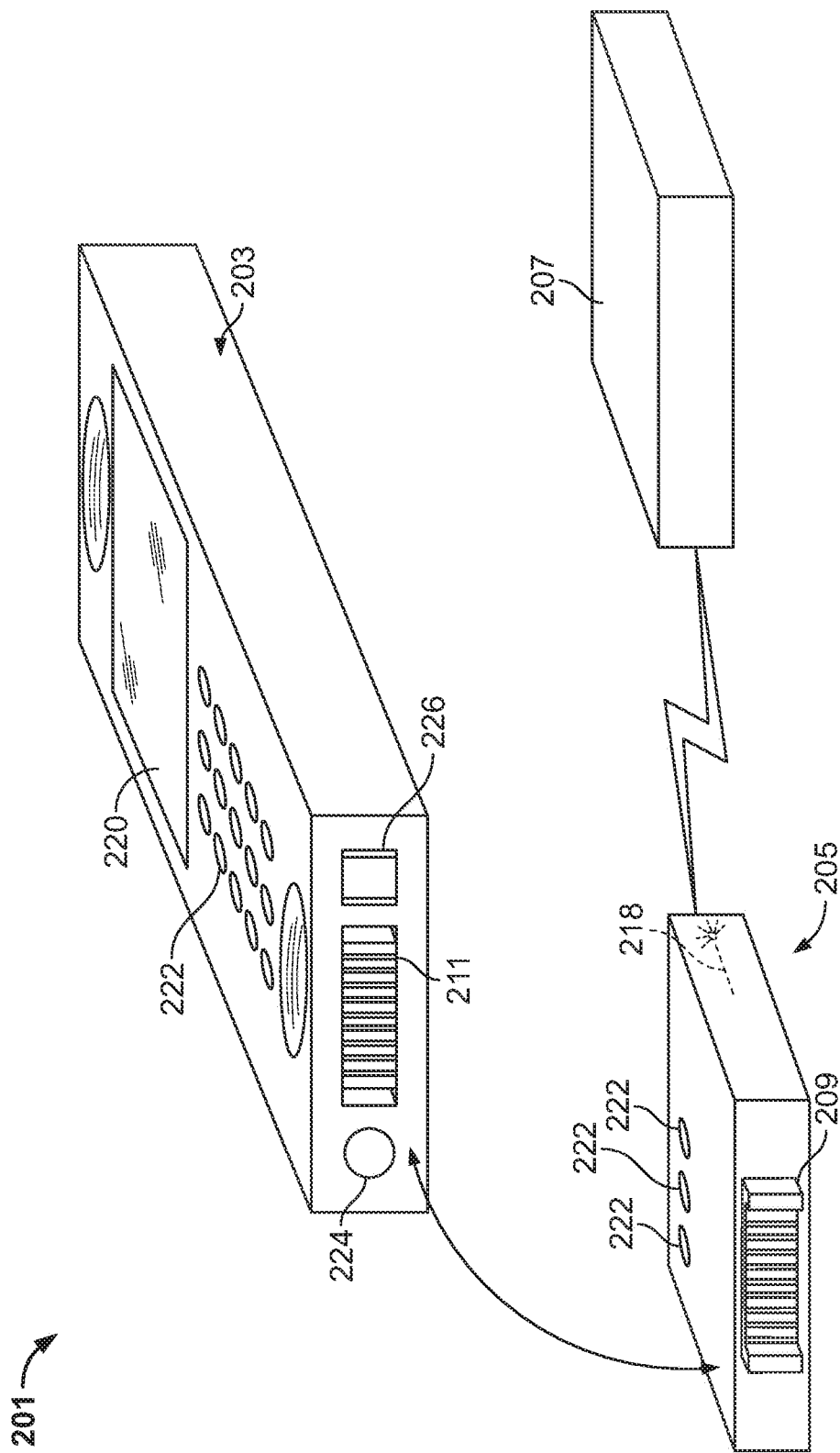
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207, and provides the received information to the digital music player 203.

Figure 3:
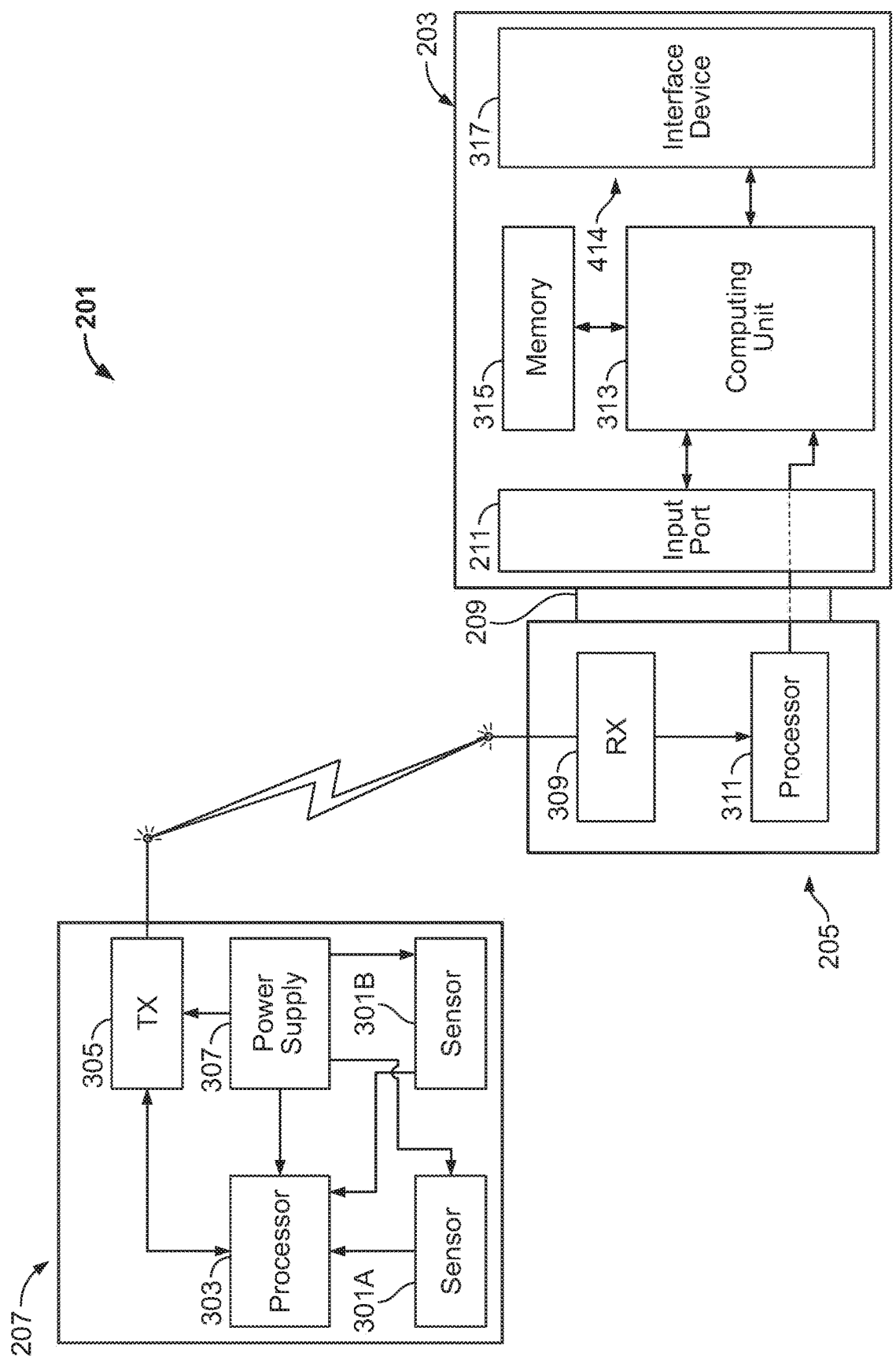
Figure 4:
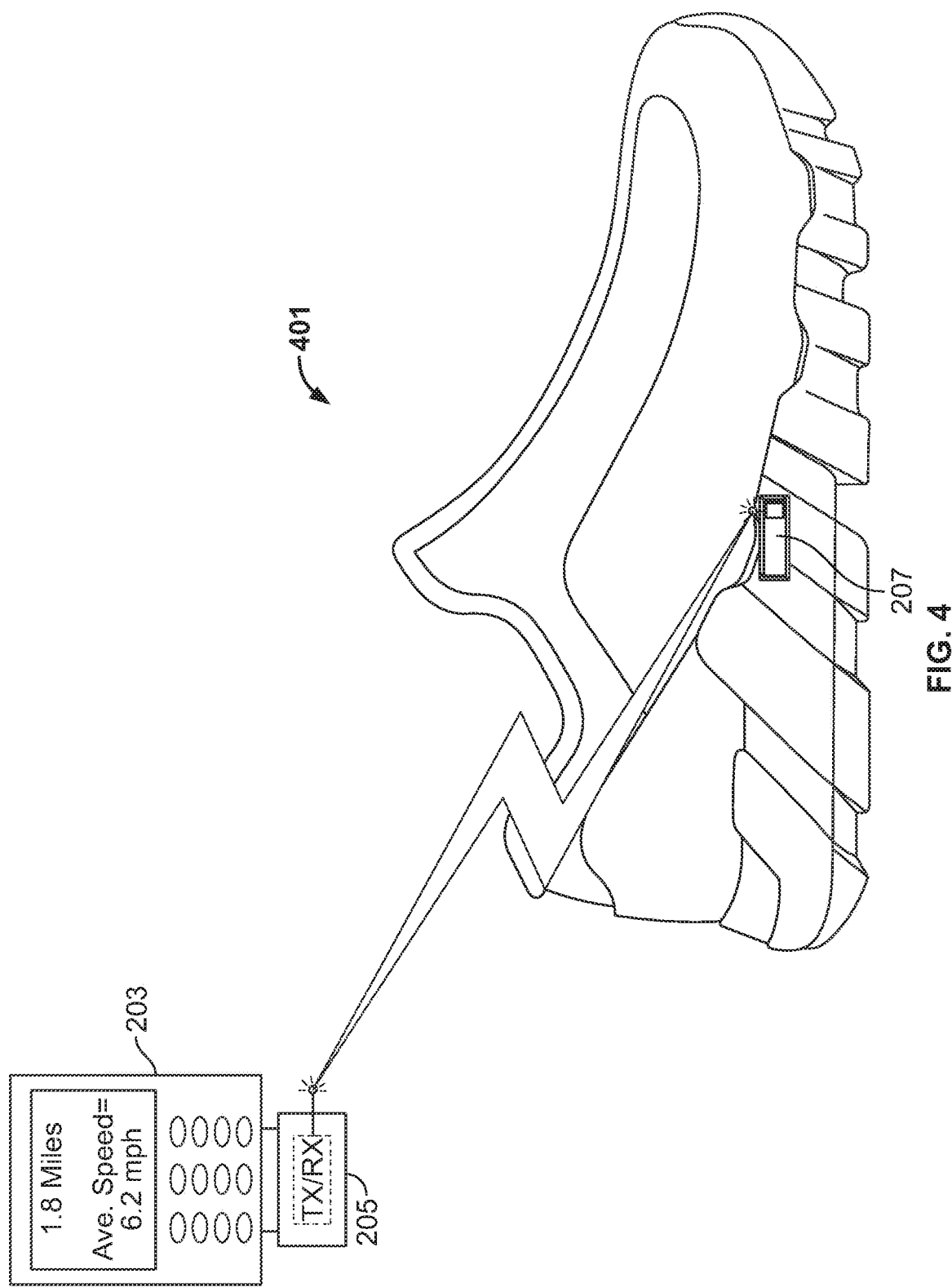
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user.

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 305. The athletic parameter measurement device 207 also includes a power supply 307, for providing power to the sensors 301, the processor 303, and the transmitter 305 as needed. The power supply 307 may be, for example, a battery.

According to one or more aspects, the athletic parameter measurement device 207 may include a fully or partially passive device such as a radio frequency ID (RFID) tag where the presence/absence or distance to that device is measured. For example, for a stair climbing exercise machine, an RFID sensor may be used detect when your foot is on the rise and approaches an RFID tag attached to some part of the exercise machine, allowing a very inexpensive way for counting steps performed on that machine. Another example is a wired or wireless sensor in close proximity to a bicycle wheel that detects an RFID, magnet, or other passive device attached to the wheel. In the wireless case, a battery powered detector would detect rotations and then periodically send a signal wirelessly to a receiver/aggregator that encodes how many rotations have been detected over a specific (or implied) period of time.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further Like the processor 303, the processor 311 may perform any desired operation on the processed signals, such as curve smoothing, noise filtering, outlier removal, amplification, summation, integration, or the like.

The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc.) The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the electronic interface device 205). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 303 provides the processed signals to the computing unit 313. The computing unit 313 may initially store the processed signals in the memory 315. Further, with some implementations of the invention, the computing unit 313 may operate on the processed signals provided by the athletic information monitoring device 201 to generate a set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 210 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, short-range wireless communications (e.g., short-range RF transmission technologies such as WiBree and BLUETOOTH), long-range wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, anther type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using short-range wireless transmission protocols (e.g., short-range RF transmission), long-range transmission protocols, wired transmission methods and/or combinations thereof. For example, short-range wireless methods may include BLUETOOTH wireless communication protocol, so that it can be employed with Bluetooth-capable mobile telephones, WiBree, personal digital assistants, watches or personal computers. WiBree generally refers to digital radio technology that provides short-range transceiver capabilities with low power consumption. In one or more arrangements, WiBree may complement other protocols such as Bluetooth. Of course, still other wireless or wired communication techniques could be employed while omitting the interface device 205. For example, a digital music player or mobile communication device (or combination thereof) may be configured to communicate directly with a sensor or measurement device 207 through short range wireless or wired methods.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance of a bicycle, the speed and/or work performed by a treadmill, rowing machine, elliptical machine, stationary bicycle, the speed and/or distance traveled by skis (water or snow), skates (roller or ice), or snowshoes or the like worn by the user, etc.

Also, while the athletic parameter measurement device 207 has been described as being separate for the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Athletic Collection and Display Tools

Figure 5:
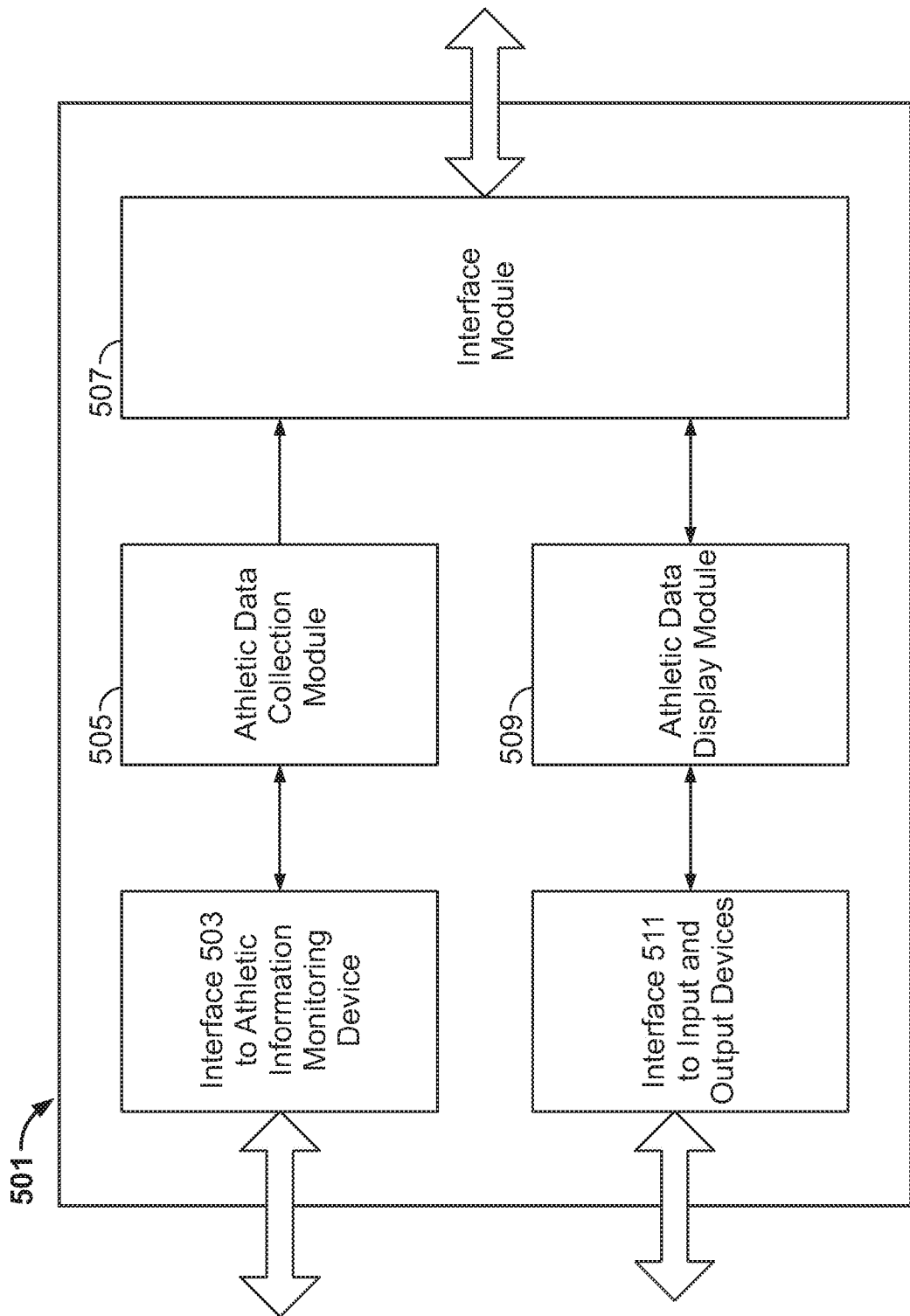
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503, establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 113 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6:
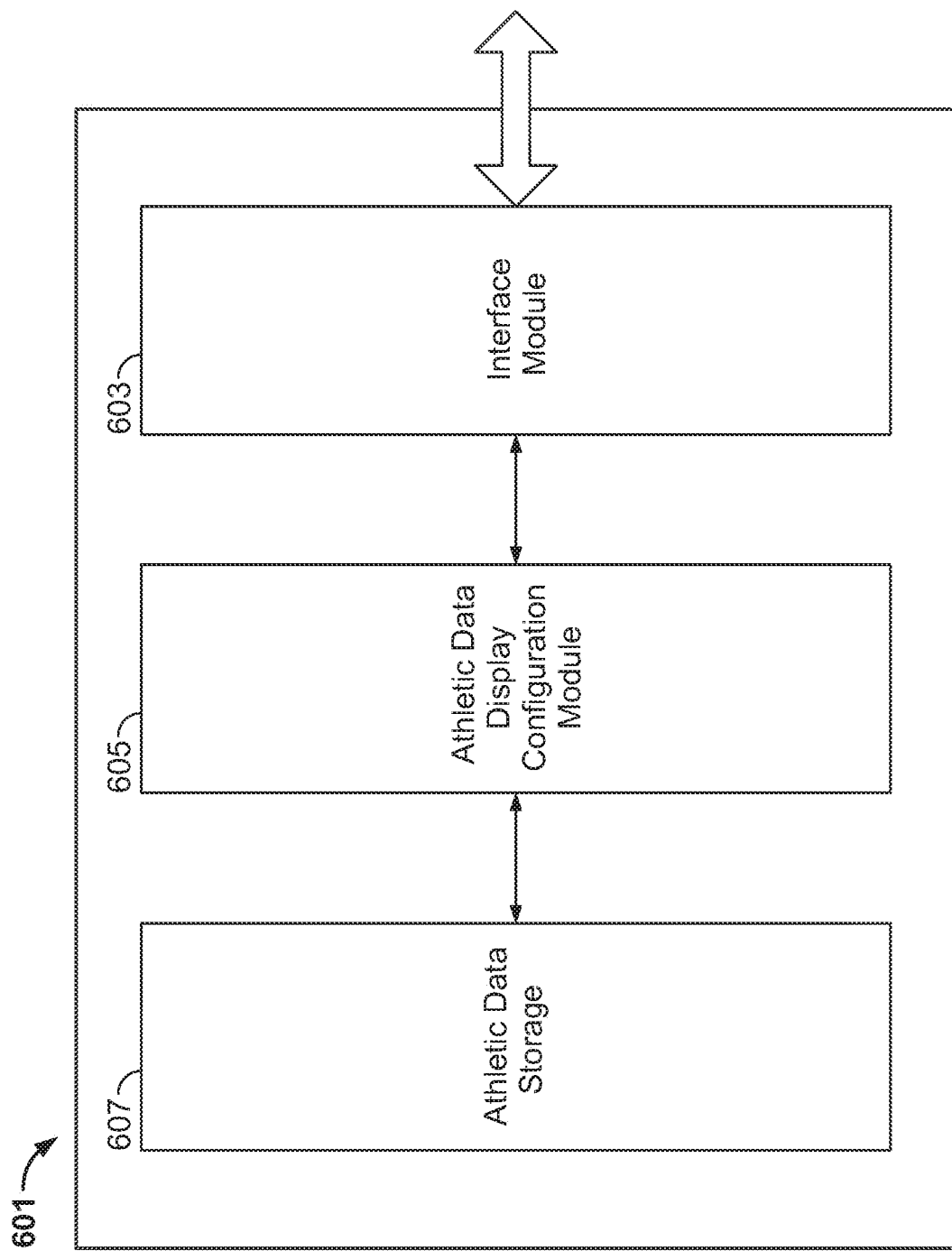
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 113. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented by, for example, a purpose-specific software tool for displaying athletic data.

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Figure 7:
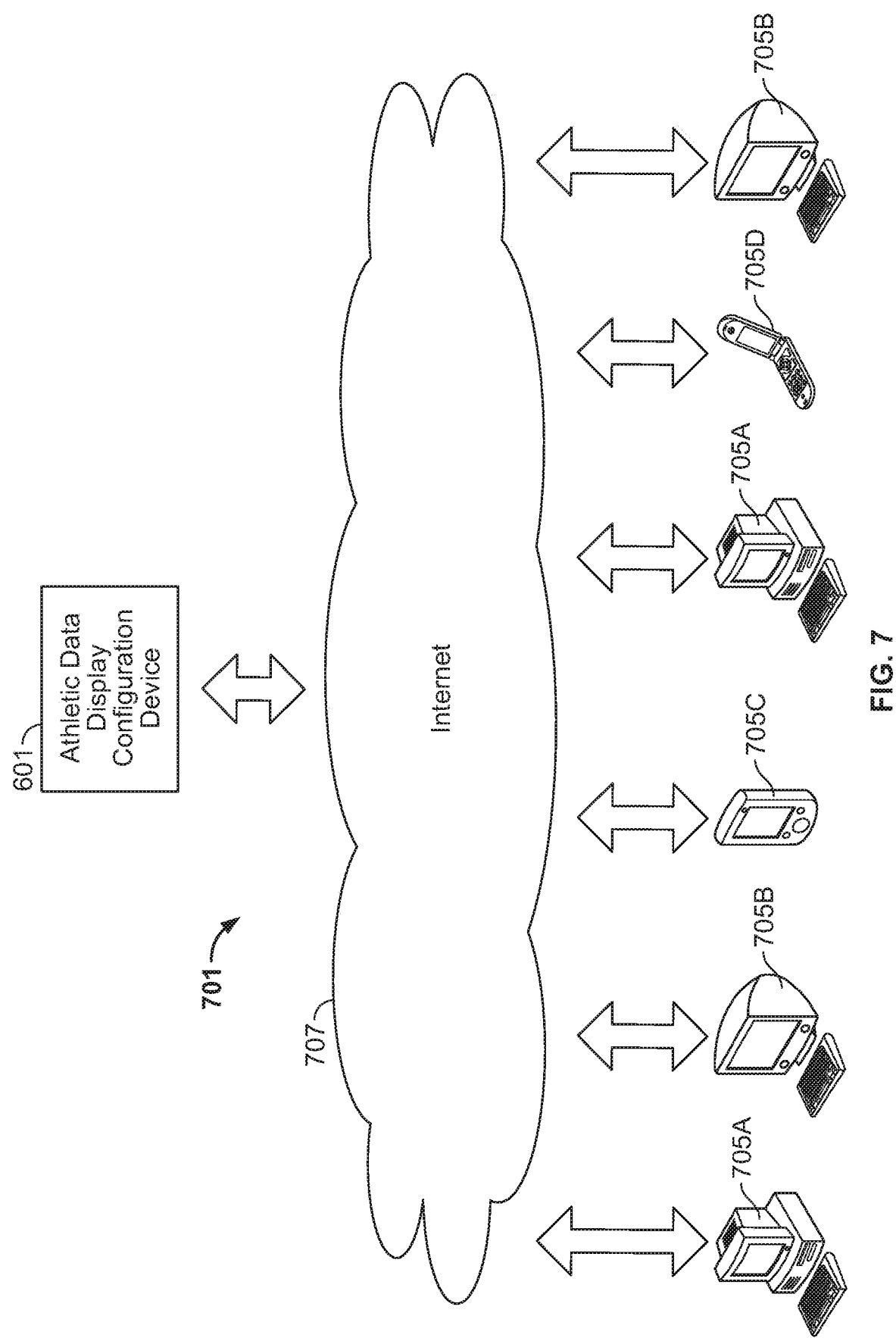
FIG. 7 illustrates a network including an athletic data display configuration device and a plurality of client devices of the type that may be employed according to various examples of the invention.

Typically, the athletic data display configuration device 601 will be implemented at a remote location from the athletic information collection and display device 501. The athletic information collection and display device 501 then may be connected to the athletic data display configuration device 601 through an electronic communication network, as previously noted. The electronic communication network may be a public network, such as the Internet, a private network, or include some combination of both. For example, FIG. 7 illustrates a network 701 including an athletic data display configuration device 601 and a plurality of client devices 705 for collecting and/or displaying athletic data. These client devices 705 may include personal computers 705A using some version of the Microsoft Windows operating systems available from Microsoft Corporation of Redmond, Wash., personal computers 705B using some version of the Apple operating system, personal digital assistants 705C and telephones 705D. Of course, various examples of the invention may alternately or additionally include any other desired electronic device that can be configured to collect and/or display athletic data as discussed above.

It should be appreciated that a client device 705 may perform an athletic data collection function, an athletic data display function, or both. That is, while the example of the athletic information collection and display device 501 described above is capable of both collecting and displaying athletic data, some client devices 705 may only collect athletic data. Further, some client devices may only display athletic data. For example, a user may employ a GPS-equipped smart telephone to collect athletic data and transmit the collected athletic data to the athletic data display configuration device 601. The user may then employ a personal computer equipped with only a conventional browser to subsequently download and display the collected athletic data.

Display Of User's Athletic Information
Display Of Athletic Activity Values

In response to receiving a request to review athletic information from a user via the athletic data display module 509, the athletic data display configuration module 605 will determine the user's identity. The athletic data display configuration module 605 will then retrieve the athletic data associated with the user from the athletic data storage 607. Next, the athletic data display configuration module 605 will prepare a user interface for displaying the requested athletic data, and transmit the user interface with the athletic data to the athletic data display module 509 for display to the user.

Figure 8A:
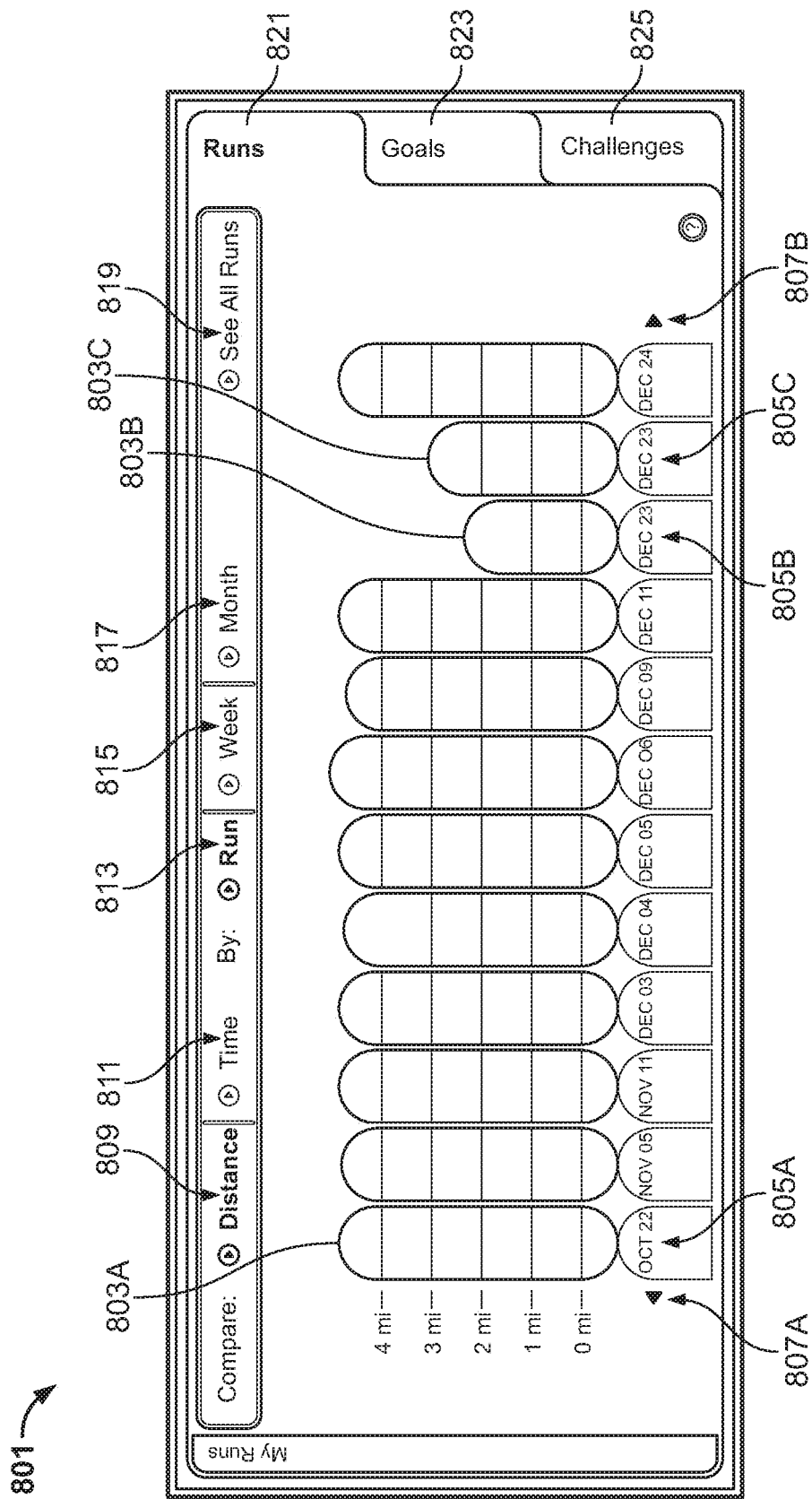
FIGS. 8A-8F, 9A and 9B illustrate examples of user interfaces that may be provided to display athletic data for a user according to various implementations of the invention.

FIG. 8A illustrates an example of an initial user interface that may be provided to a user according to various implementations of the invention. As seen in this figure, the user interface 801 includes a plurality of icons 803. Each icon 803 represents an athletic data value corresponding to an athletic activity performed by the user over a specified time period. More particularly, each icon 803 represents a distance value corresponding to athletic activity performed by a user. A calendar date field 805 associated with each icon 803 is shown at the bottom of each icon 803 to indicate the date on which the corresponding athletic activity was performed, as illustrated in FIG. 8. The user interface 801 also displays a number of control buttons 807-819 that allow the user to select what athletic data values will be displayed in the user interface as well as the time periods for which the athletic data values will be displayed. In addition, the interface 801 includes tabs 821-825, which will be discussed in more detail below.

As shown in FIG. 8A, the user has activated the "Distance" button 809 and the "Run" button 813. In response, the display 801 initially shows an icon 803 for the each of the most recent, e.g., twelve sets of athletic data collected by the server that corresponds to the user. As previously noted, each data set includes athletic data values generated from athletic information measured during a single, discrete athletic activity performed by a person over a particular time period. Further, the height of each icon 803 will correspond to the total distance value included in the set of athletic data represented by the icon 803. For example, on October 22, the user traveled a total distance of 4.05 miles during a run, whereas the user traveled a total distance of only 1.59 miles during a first run on December 23. Accordingly, the icon 803A corresponding to the athletic activity on October 22 will be proportionally larger than the icon 803B representing the athletic data collected for the user's first run on December 23, as shown in this figure. If the user wishes to view icons 803 for athletic activities performed before or after the athletic activities corresponding to the displayed icons 803, the user can view those additional icons 803 by activating the desired arrow buttons 807. The user interface 801 may further include, in one or more arrangements, data such as calories burned and steps taken or various representation thereof (e.g., a graph or chart).

Figure 8B:
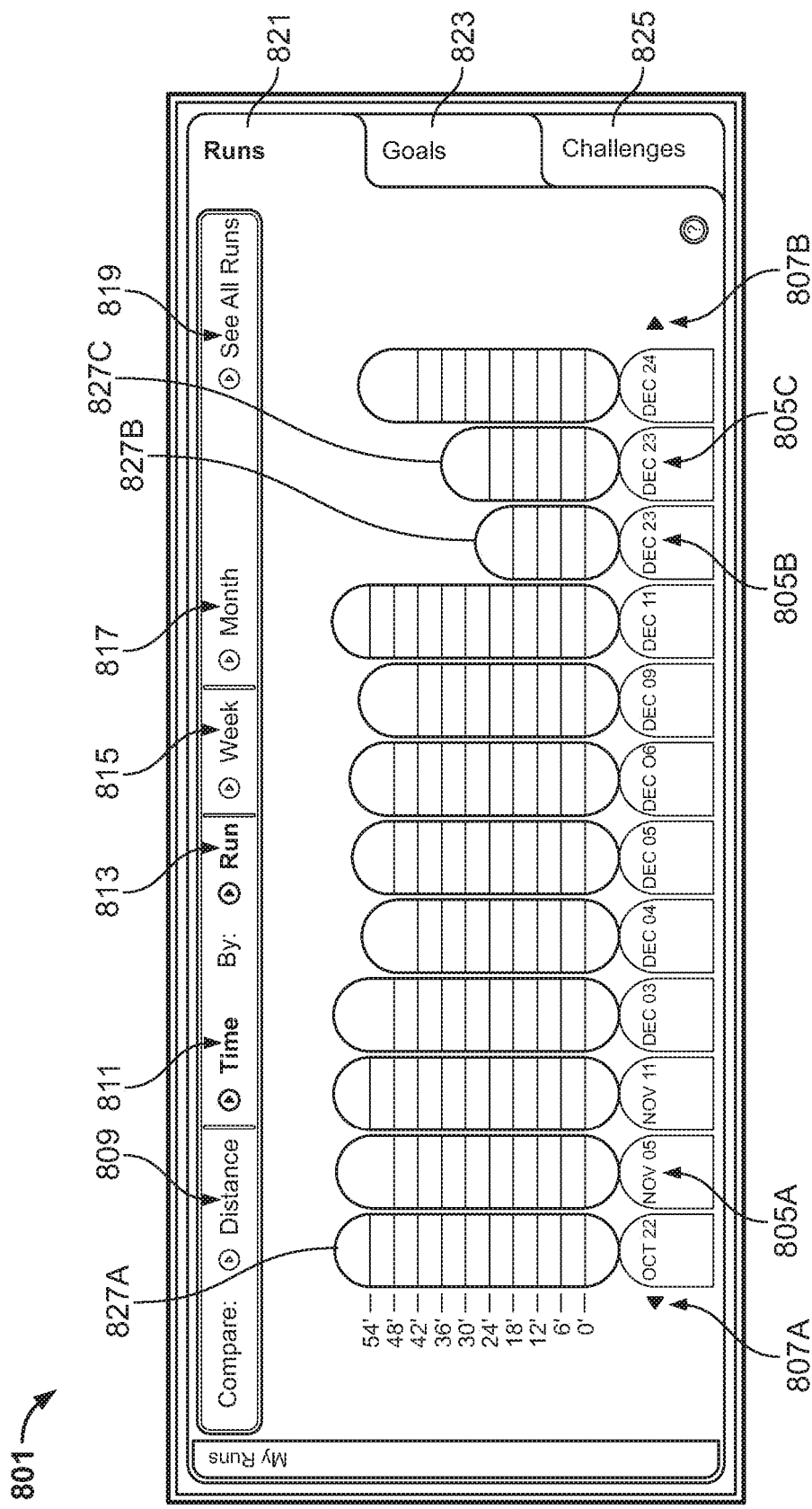

If a user subsequently selects the "Time" button 811, the athletic data display configuration module 605 will reconfigure the user interface 801 to display new icons 827 so that each icon 827 represents a total time value for each of the data sets. For example, as shown in FIG. 8B, the height of each icon 827 will correspond to the total time value in each represented data set. For example, if the length of the user's run on October 22 was 54 minutes, 2 seconds, whereas the duration of the user's first run on December 23 was only 18 minutes, 11 seconds, then the icon 827A corresponding to the athletic data set for October 22 will be proportionally taller than the icon 827B representing the athletic data set collected for the user's run on December 23.

In addition to displaying only distance and time information, the user interface 801 may optionally display additional information. For example, with some implementations of the invention, a user may employ a pointing device to select a specific icon 803 or 827. In response to the selection by, e.g. positioning a cursor over the icon, the user interface 801 may display additional information from the athletic data set represented by the selected icon. For example, the user interface 801 may use, e.g., a pop-up display (not shown) to display data values for the total distance, time, speed, and calories burned for the athletic activity represented by the selected icon 803 or 827. Still further, the user interface may use, e.g., color information to distinguish between the most-recently collected sets of athletic data and athletic data sets that were collected at an earlier time. Thus, the icons 803 or 827 representing data sets collected during the most recent download from an athletic information monitoring device 201 may be illustrated using, e.g., a light green color, while icons 803 or 827 representing previously-collected athletic data sets may be displayed with a dark green color.

Figure 9A:
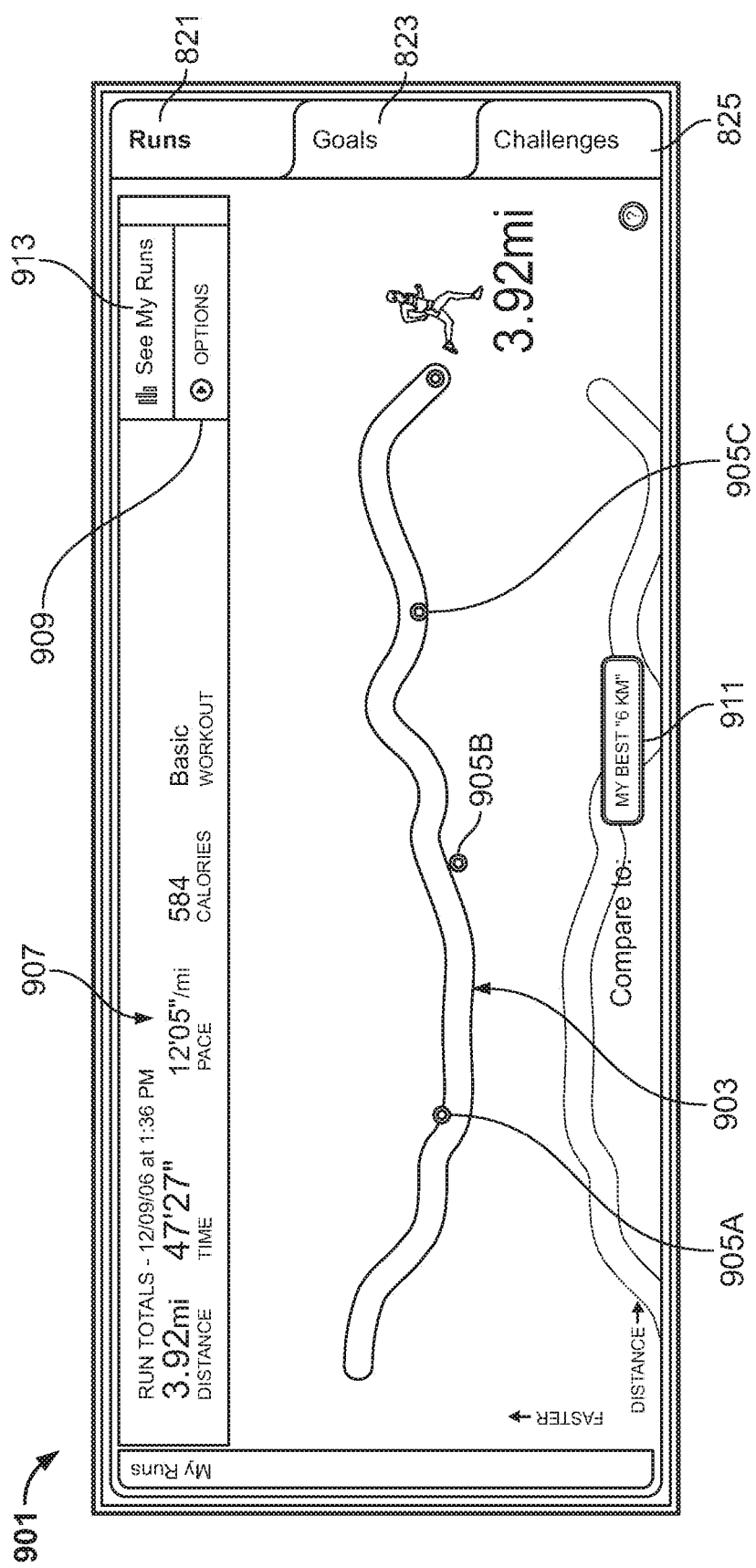

With some implementations of the invention, a user may obtain still more detailed information regarding an athletic data set by "activating" the icon 803 or 827 representing the athletic data set. For example, a user may position a cursor over a desired icon 803 or 827 using a pointing device, and then depress a selection button to activate the icon 803 or 827. In response, the athletic data display configuration module 605 will configure and provide a user interface graphically illustrating the data values in the corresponding athletic data set in more detail. For example, as illustrated in FIG. 9A, various implementations of the inventions may display a user interface 901 plotting a first type of data in the data set against a second type of data in the data set to provide a visual graph 903. More particularly, as illustrated in this figure, the athletic data display configuration module 605 will plot speed values in the athletic data set against distance values data in the athletic data set, providing the graph 903. In this manner, a user can view what his or her instantaneous speed was at various points during the run. In addition, the graph 903 may include other relevant information such as, for example, an icon showing the type of athletic activity (e.g., running) and an indication on of the total distance traveled.

With some implementations of the invention, the graph 903 also may include specific distance waypoints 905, which will show the particular speed value measured at the distance during the athletic activity represented by the position of the waypoint 905. For example, if the user employs a pointing device to move a cursor over waypoint 905A, the user interface 901 will display a pop-up window (not shown) indicating that the user had an average speed of 12 minutes, 12 seconds at the first mile. Similarly, if the user employs a pointing device to move a cursor over the waypoint 905B, the user interface 901 will display a pop-up window (not shown) indicating that the user had an average speed of 12 minutes, 17 seconds at the second mile. If the user then employs a pointing device to move a cursor over the waypoint 905C, the user interface 901 will display a pop-up window (not shown) indicating that the user had an average speed of 12 minutes, 3 seconds at the third mile.

The user interface 901 also may include a value field 907 indicating the total distance value, total time value, total average pace value, total calories burned value, and athletic activity type value corresponding to the represented athletic activity. It also may include an "Options" button 909. If the user activates the "Options" button 909, the interface 901 may display additional command buttons (not shown) that allow the user to name the selected athletic data set or delete the athletic data set. Still further, the interface may include a "Comparison" button 911.

If the user selects the "Comparison" button 911, the athletic data display configuration module 605 will determine a time or distance classification for the selected athletic activity. For example, if the total distance value collected for the selected athletic activity is approximately 6 kilometers, then the athletic data display configuration module 605 will classify the athletic data set corresponding to the selected athletic activity as a "6 kilometer" athletic data set. Similarly, if the total distance value collected for the selected athletic activity is proximal to another specified distance category (e.g., 1 mile, 10 kilometers, 15 kilometers, 10 miles, 26 miles, etc.), then the athletic data display configuration module 605 will classify the athletic data set based upon the relevant category.

Figure 9B:
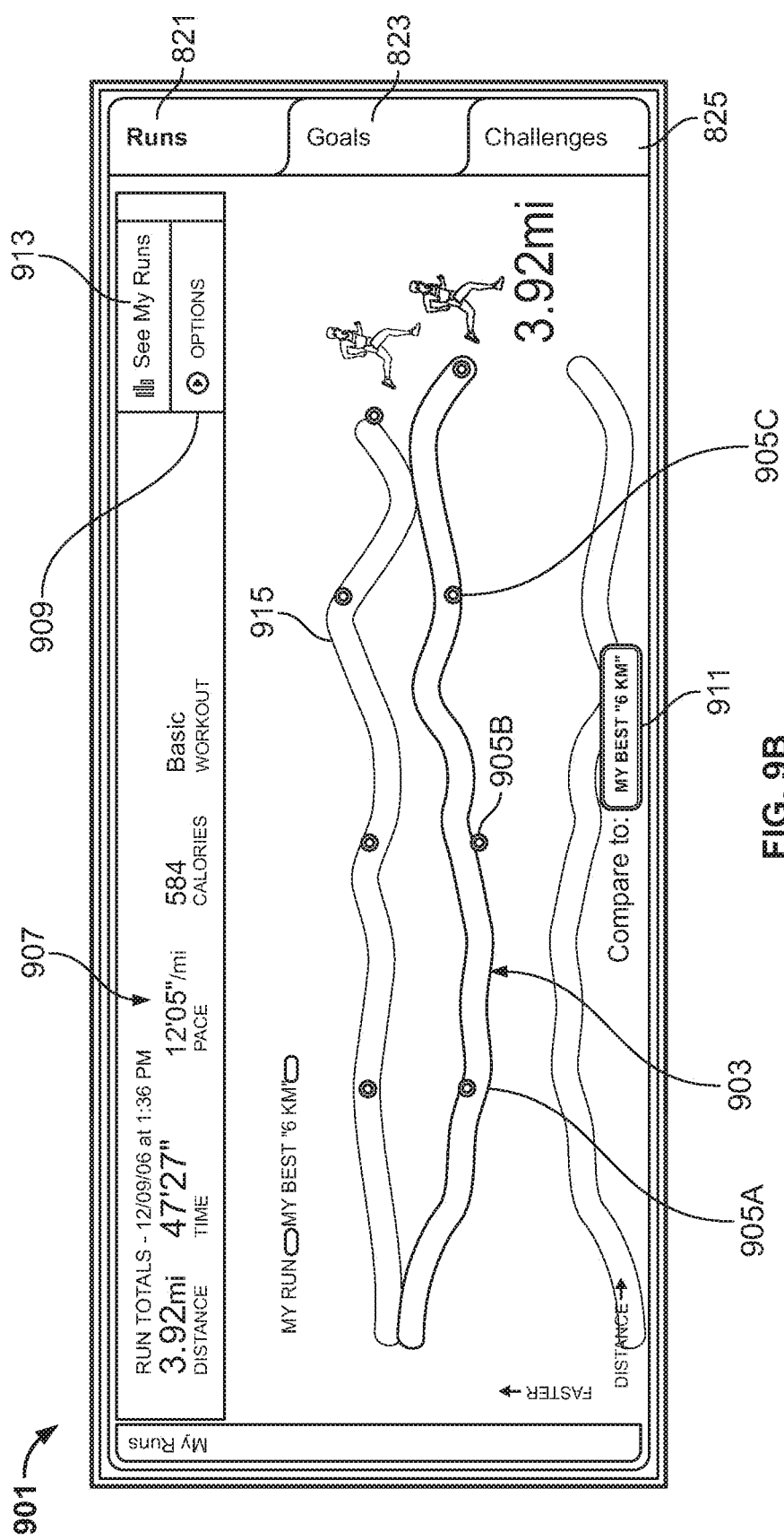

After the athletic data display configuration module 605 has classified the athletic data set, it examines the other athletic data sets in that classification to determine which athletic data set has the highest total distance value (or, if the classification is based upon time or speed, the lowest total time value or the highest average speed value). Once the athletic data display configuration module 605 identifies the "best" set of athletic data for the determined classification, it will then reconfigure the user interface 901 to include a graph of this "best" athletic data set as shown in FIG. 9B. As seen in this figure, the graph 915 may have the same characteristics and features as the graph 905 representing the selected athletic activity session.

If the user selects the "See My Runs" button 913, the athletic data display configuration module 605 will configure and provide the interface 801 for display, as shown in FIGS. 8A and 8B. Returning now to those figures, if the user selects the "Week" button 815 or the "Month" button 817, the athletic data display configuration module 605 will modify the user interface 801 to display one or more icons representing an aggregation of multiple sets of athletic data. More particularly, the athletic data display configuration module 605 will aggregate data values from each athletic data set based upon the designated time period.

Figure 8C:
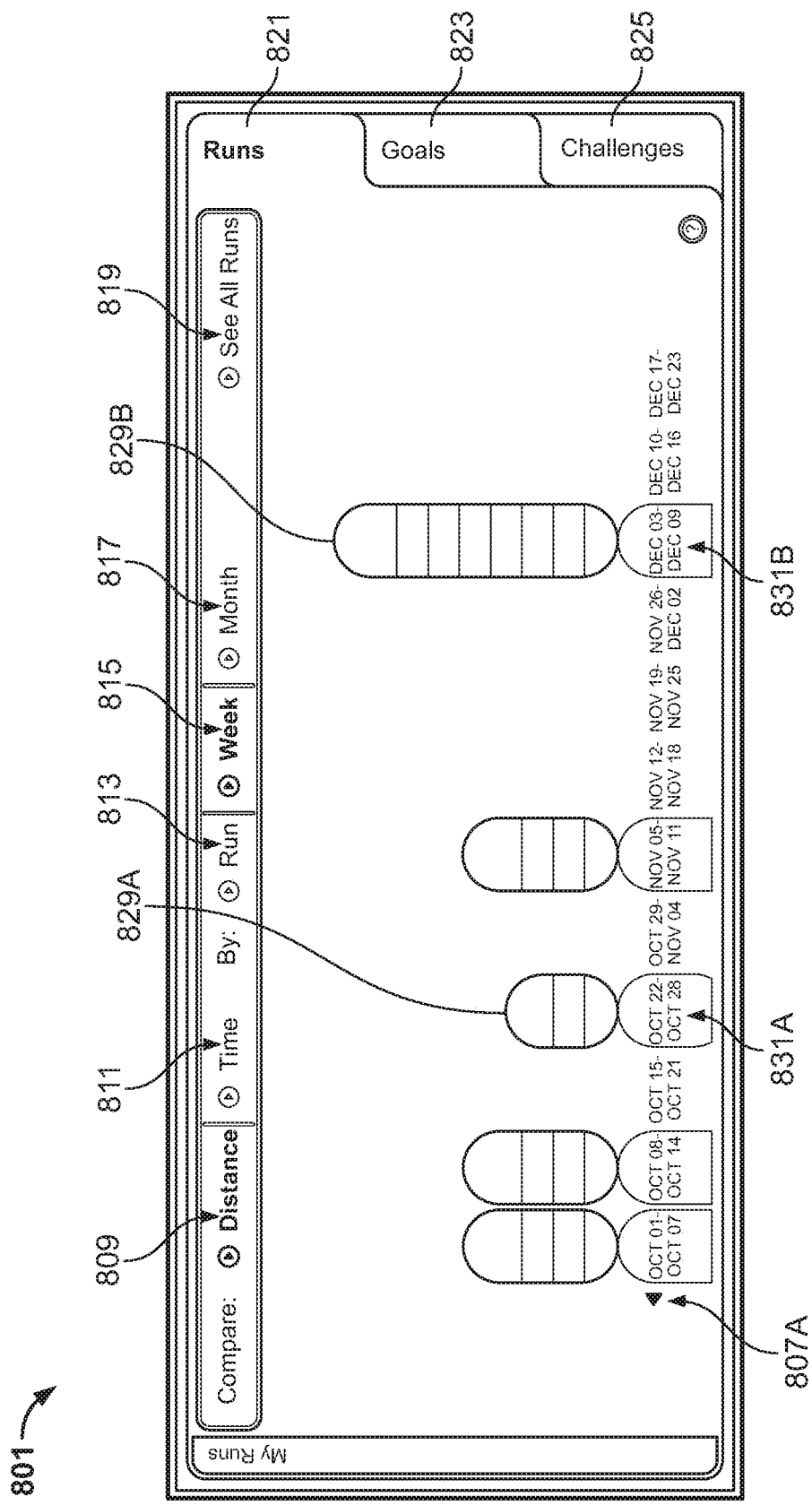

For example, if the user has selected the "Distance" button 809 in addition to the "Week" button 815, then the athletic data display configuration module 605 will add up the total distance data values for each set of athletic data corresponding to an athletic activity session occurring within a particular calendar week. The athletic data display configuration module 605 will then modify the user interface 801 to include icons 829, where each icon 829 graphically represents the sum of total distance values in the athletic data sets generated during a particular week. The athletic data display configuration module 605 may also modify the user interface 801 to include a calendar week field 831 specifying the calendar week to which each icon 829 is associated. As shown in FIG. 8C, the height of each icon represents the sum of the total distance values for each athletic data set for the specified week period. For example, the user may have run a total of 4.05 miles during the weekly period from October 22 to October 28. On the other hand, the user may have run a total distance of 20.25 miles during the week period of December 3 to December 9. Accordingly, the icon 829B representing the aggregated athletic data for the week of December 3 to December 9 will be proportionally larger than the icon 829A representing the athletic data aggregated from the athletic data sets obtained for the week of October 22 to October 28.

Figure 8D:
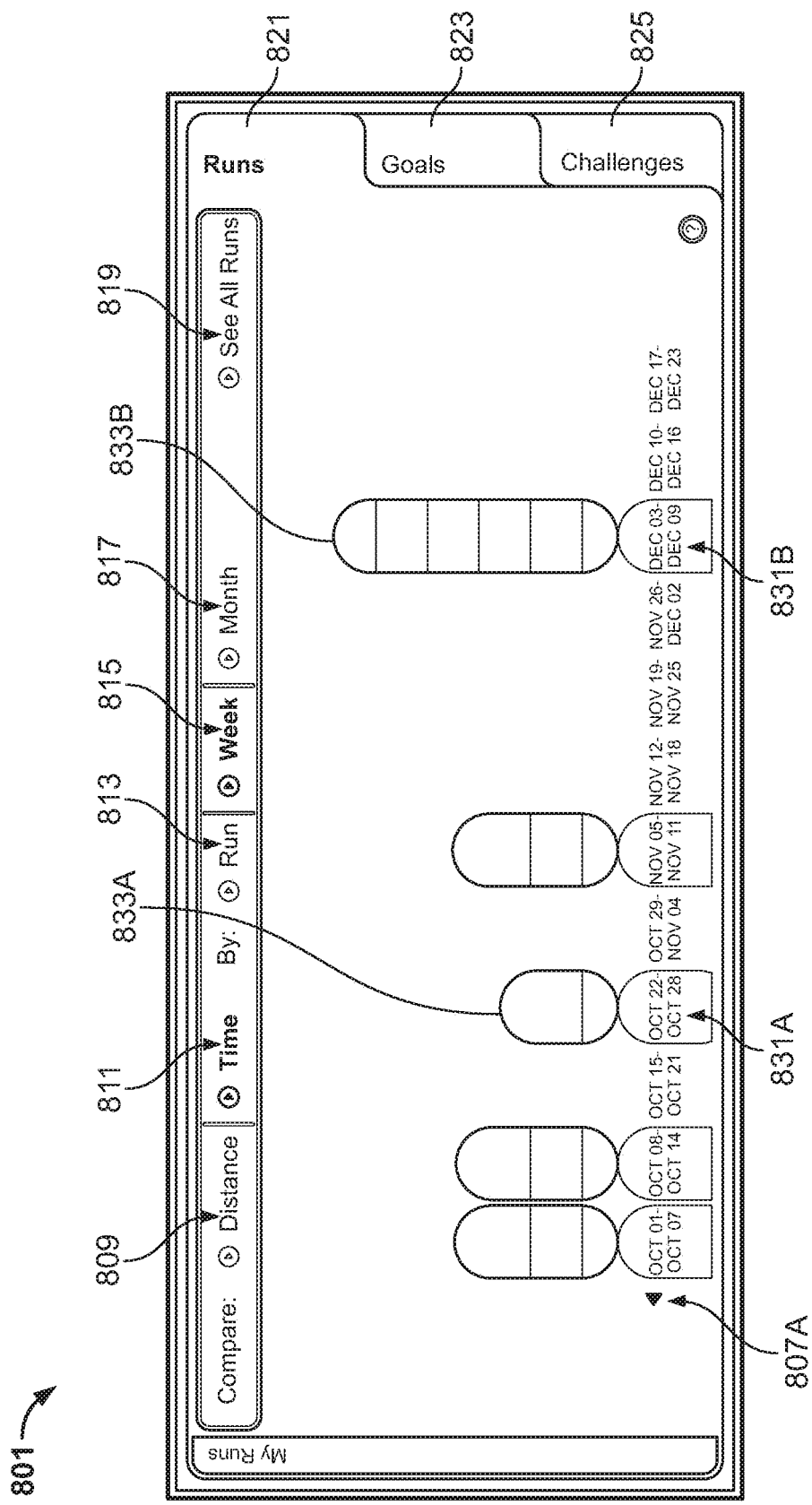

Similarly, if the user selects the "Time" button 811, the athletic data display configuration module 605 will modify the user interface 801 to display icons 833 that represent the sum of total time values for aggregated sets of athletic data. More particularly, as shown in FIG. 8D, a height of each icon 833 will represent the sum of the total time values for each athletic data set obtained during the corresponding weekly period. For example, if a user ran for a total time of 54 minutes 2 seconds during the week from October 22 to October 28, but ran for a total time of 4 hours 7 minutes and 24 seconds during the week of December 3 to December 9, then the icon 833B representing the aggregation of athletic data for the week of December 3 to December 9 will be proportionally larger than the icon 833A representing the aggregation of athletic data for the weekly period of October 22 to October 28.

Figure 8E:
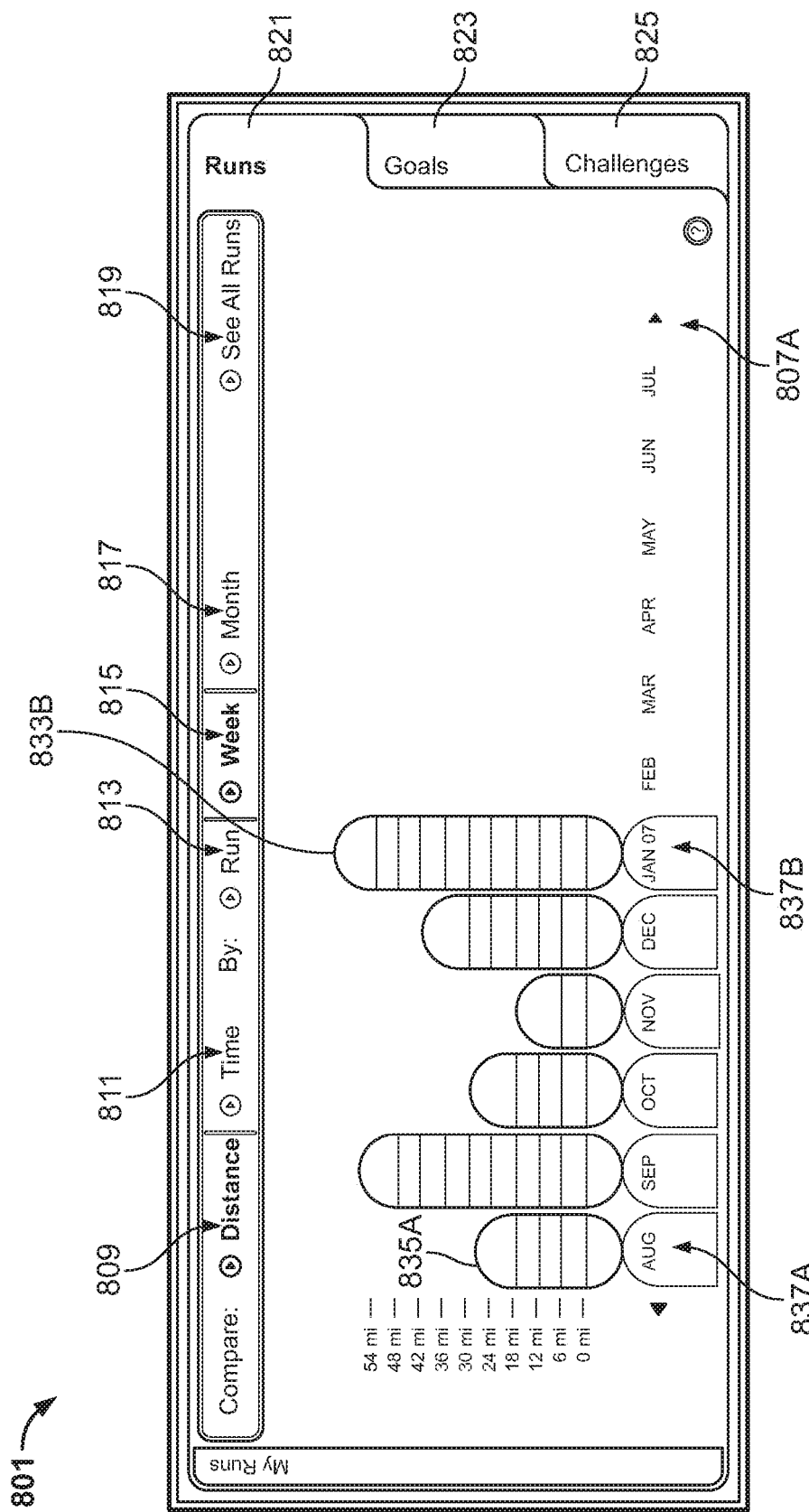

Similarly, if the user selects the "Month" button 817, the athletic data display configuration module 605 will modify the user interface 801 to display icons representing the aggregations of data values from athletic data sets obtained over each monthly time period. For example, if the user has selected the "Distance" button 809 as well, the user interface 801 may display an icon 835 representing the aggregation of total distance values from data sets obtained for athletic activity sessions performed during each calendar month, as illustrated in FIG. 8E. The user interface 801 also may include a calendar month field 837 specifying the calendar month to which each icon 835 is associated. As shown in this figure, the user interface 801 thus includes an icon 835A representing the aggregation of total distance values from data sets obtained for athletic activity sessions performed during the month of August, and another icon 835B representing the aggregation of total distance values from data sets obtained for athletic activity sessions performed during the month of January. The height of the icon 835A represents the sum of the total distance values for each athletic data set obtained for athletic activity sessions performed in August (i.e., 18.84 miles), while the height of the icon 835B correspond to the sum of each of the total distance data values for each athletic data set obtained for athletic activity sessions performed in January (i.e., 58.84 miles).

Figure 8F:
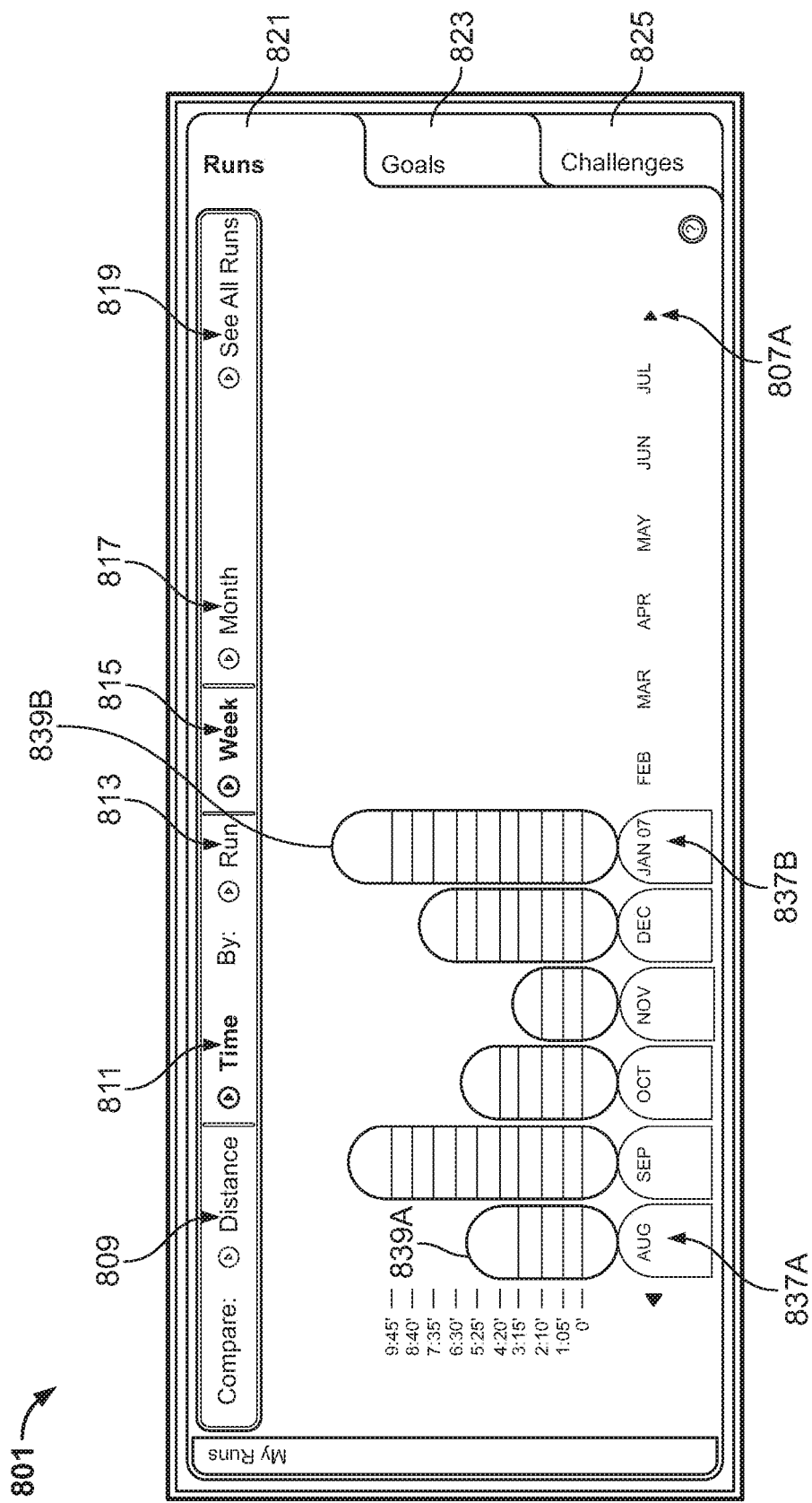

If, on the other hand, the user has selected the "Time" button 811, the user interface 801 may display an icon 839 representing the aggregation of total time values from data sets obtained for athletic activity sessions performed during each calendar month, as illustrated in FIG. 8F. As shown in this figure, the user interface 801 thus includes an icon 839A representing the aggregation of total distance values from data sets obtained for athletic activity sessions performed during the month of August, and another icon 839B representing the aggregation of total time values from data sets obtained for athletic activity sessions performed during the month of January. The height of the icon 839A represents the sum of the total time values for each athletic data set obtained for athletic activity sessions performed in August (i.e., 4 hours, 6 minutes, 1 second), while the height of the icon 839B correspond to the sum of each of the total time data values for each athletic data set obtained for athletic activity sessions performed in January (i.e., 10 hours, 47 minutes, 27 seconds).

In addition to displaying only distance and time information, the user interface 801 may optionally display additional information aggregated from multiple sets of athletic data. For example, with some implementations of the invention, a user may employ a pointing device to select a specific icon 829, 833, 835 or 839. In response to the selection by, e.g. positioning a cursor over the icon, the user interface 801 may display additional information from the aggregation of athletic data sets represented by the selected icon. For example, the user interface 801 may provide, e.g., a pop-up display (not shown) to display sum of total distance data values corresponding to the aggregation of athletic activity information represented by the selected icon, the some of the total time data values corresponding to the aggregation of athletic activity information represented by the selected icon, the average of the average speed data values corresponding to the aggregation of athletic activity information represented by the selected icon speed, and the sum of the calories burned data values data values corresponding to the aggregation of athletic activity information represented by the selected icon.

It should be noted that the athletic data display configuration module 605 (or, with some implementations of the invention, the athletic data display module 509) may aggregate data from multiple athletic data sets in advance of receiving a request to display aggregated athletic data from a user. Alternately, the athletic data display configuration module 605 (or, with some implementations of the invention, the athletic data display module 509) may aggregate data from multiple athletic data sets only in response to a specific request from a user to view the aggregated data.

Display of Goals

Figure 10:
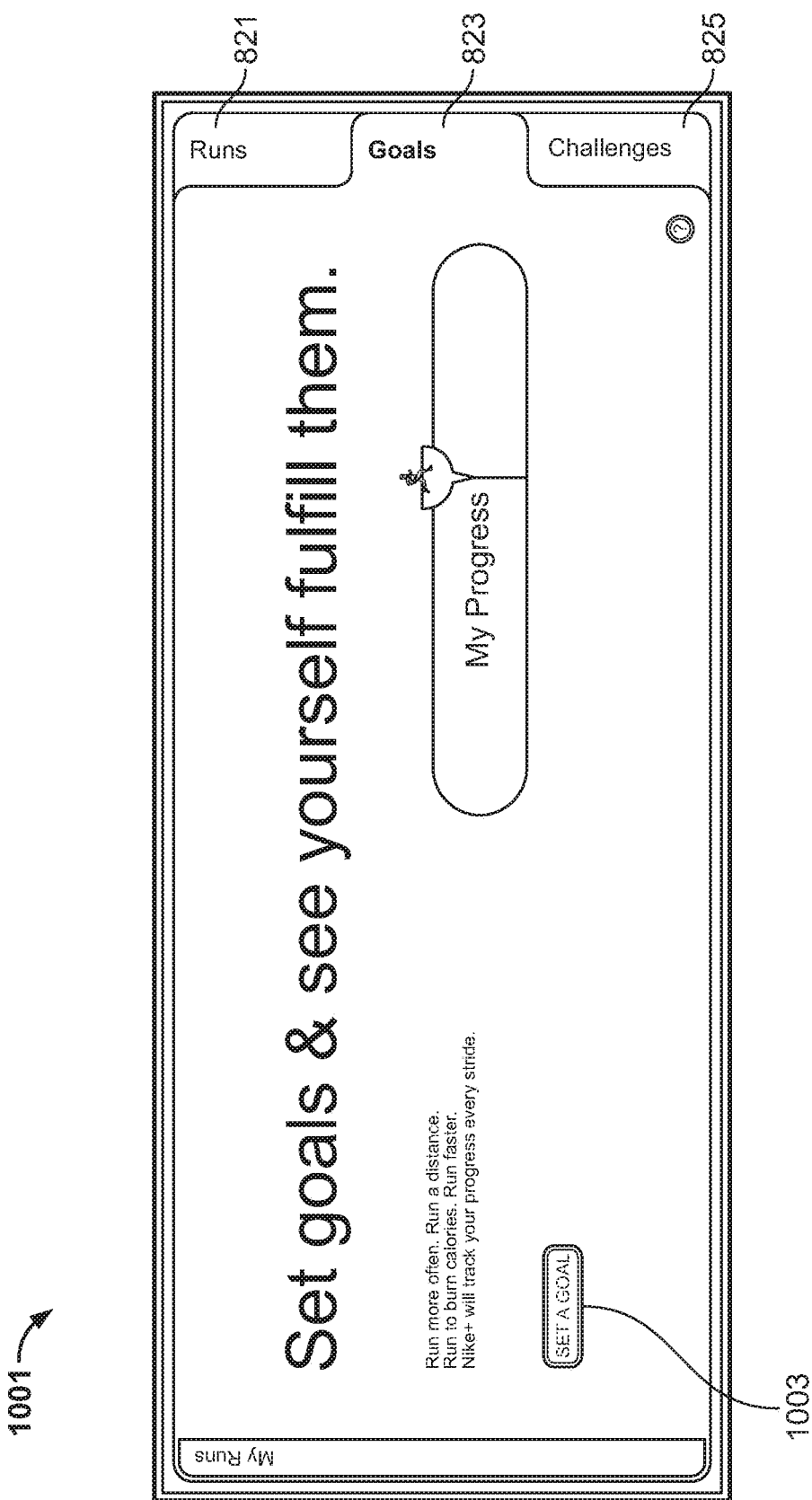
FIGS. 10 and 11A-11E illustrate examples of user interfaces that may be provided to select goals for a user according to various implementations of the invention.

In addition to displaying specific athletic data values or aggregates of athletic data values, various embodiments of the invention may alternately or additionally permit a user to set a goal relating to his or her athletic activities, and then view one or more images graphically illustrating the user's progress toward accomplishing those goals. For example, with the embodiments illustrated in FIGS. 8A-9B, a user can select the "Goals" tab 823 shown in these figures. In response, the athletic data display configuration module 605 may configure and provide the user interface 1001 illustrated in FIG. 10. As seen in this figure, the user interface 1001 includes a "Set A Goal" button 1003 prompting the user to select a desired goal relating to his or her athletic activities.

When the user activates the "Set A Goal" button 1003, the athletic data display configuration module 605 will configure and provide the user interface 1101 shown in FIG. 11. As seen in this figure, the user interface 1101 includes a "More Often" button 1103, a "Distance" button 1105, a "Burn More Calories" button 1107, a "Faster" button 1109, and a "Back" button 1111. As known in the art, activating the "Back" button 1111 will cause the athletic data display configuration module 605 (or, with some examples of the invention, the athletic data display module 509) to configure and display the previously displayed configuration of the user interface 1101, or if the currently displayed configuration of the user interface 1101 is its initial configuration, a previously shown user interface.

Figure 11A:
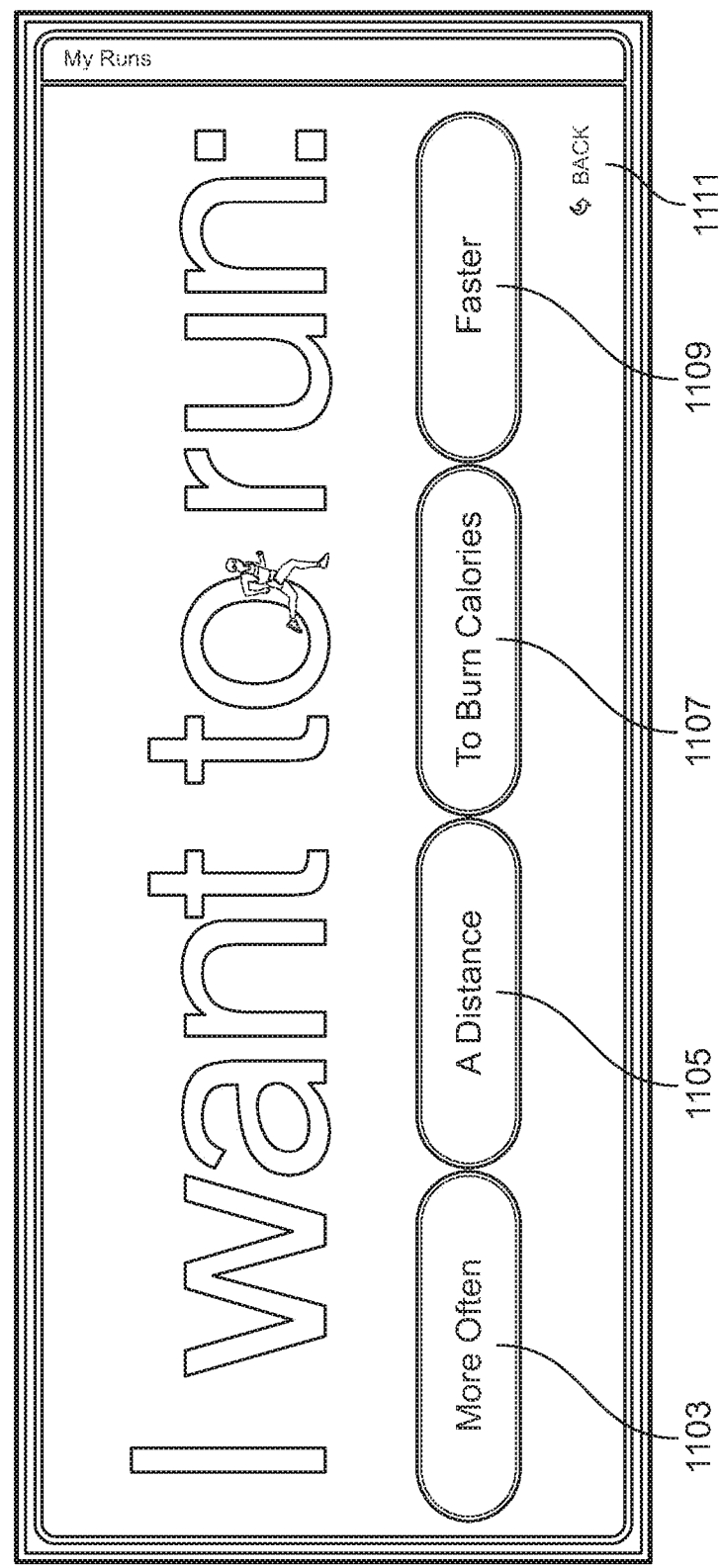
Figure 11B:
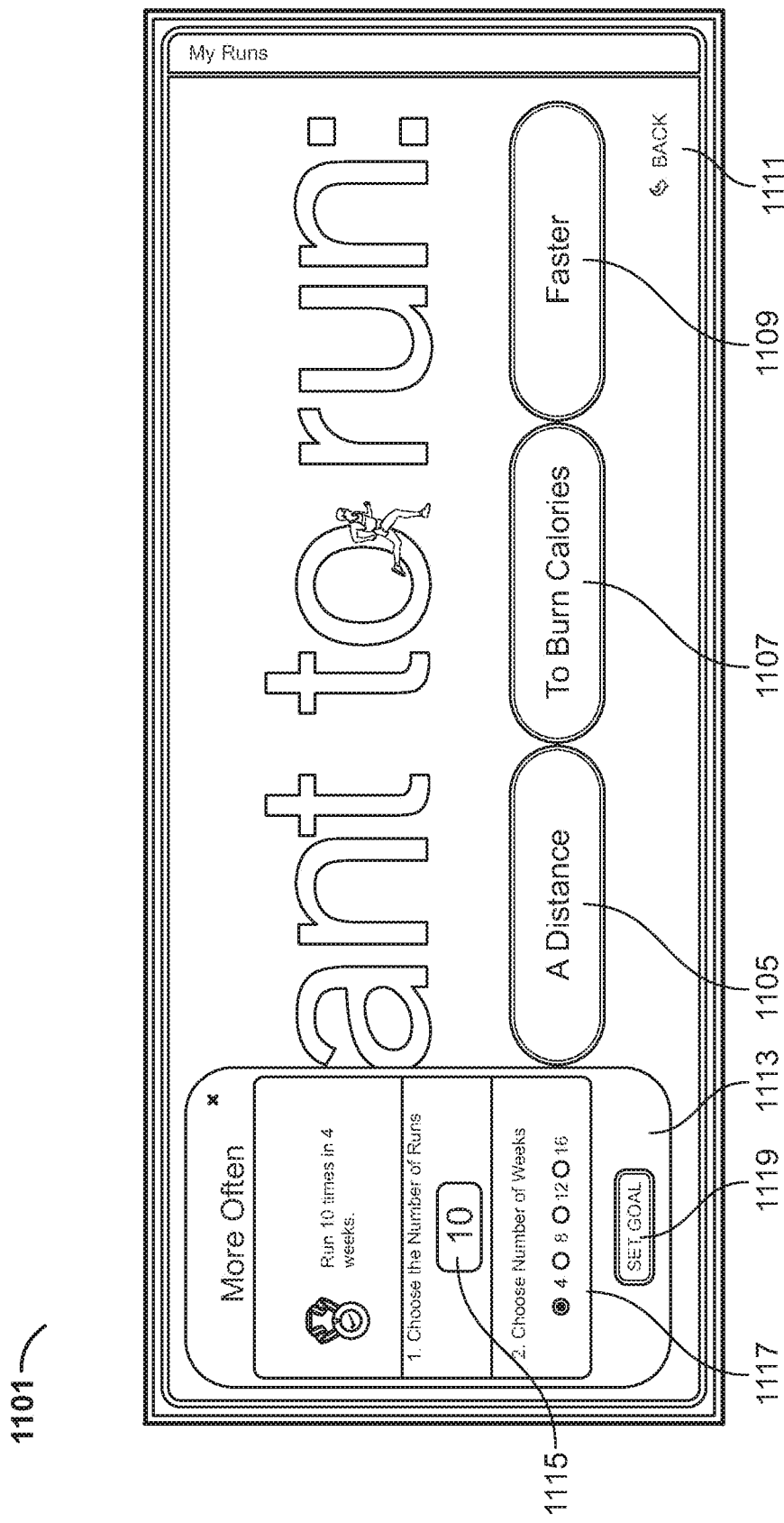

If a user wishes to perform the athletic activity more often, then the user activates the "More Often" button 1103. In response, the athletic data display configuration module 605 reconfigures the user interface 1101 to include a sub-interface 1113. As seen in FIG. 11B, the sub-interface 1113 includes a "Number Of Runs" control 1115, a "Number Of Weeks" control 1117, and a "Set Goal" button 1119. By employing the "Number Of Runs" control 1115, a user can specify the number of runs (or the number of times to perform some other athletic activity, if appropriate) he or she wishes to make within a desired time period. Similarly, by employing the "Number Of Weeks" control 1117, a user can specify the number of weeks making up the desired time period allowed to reach the desired goal. In the illustrated example, the "Number Of Runs" control 1115 is a field control (i.e., having a field in which a value can be typed in) while the "Number Of Weeks" control 1117 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1119.

Figure 11C:
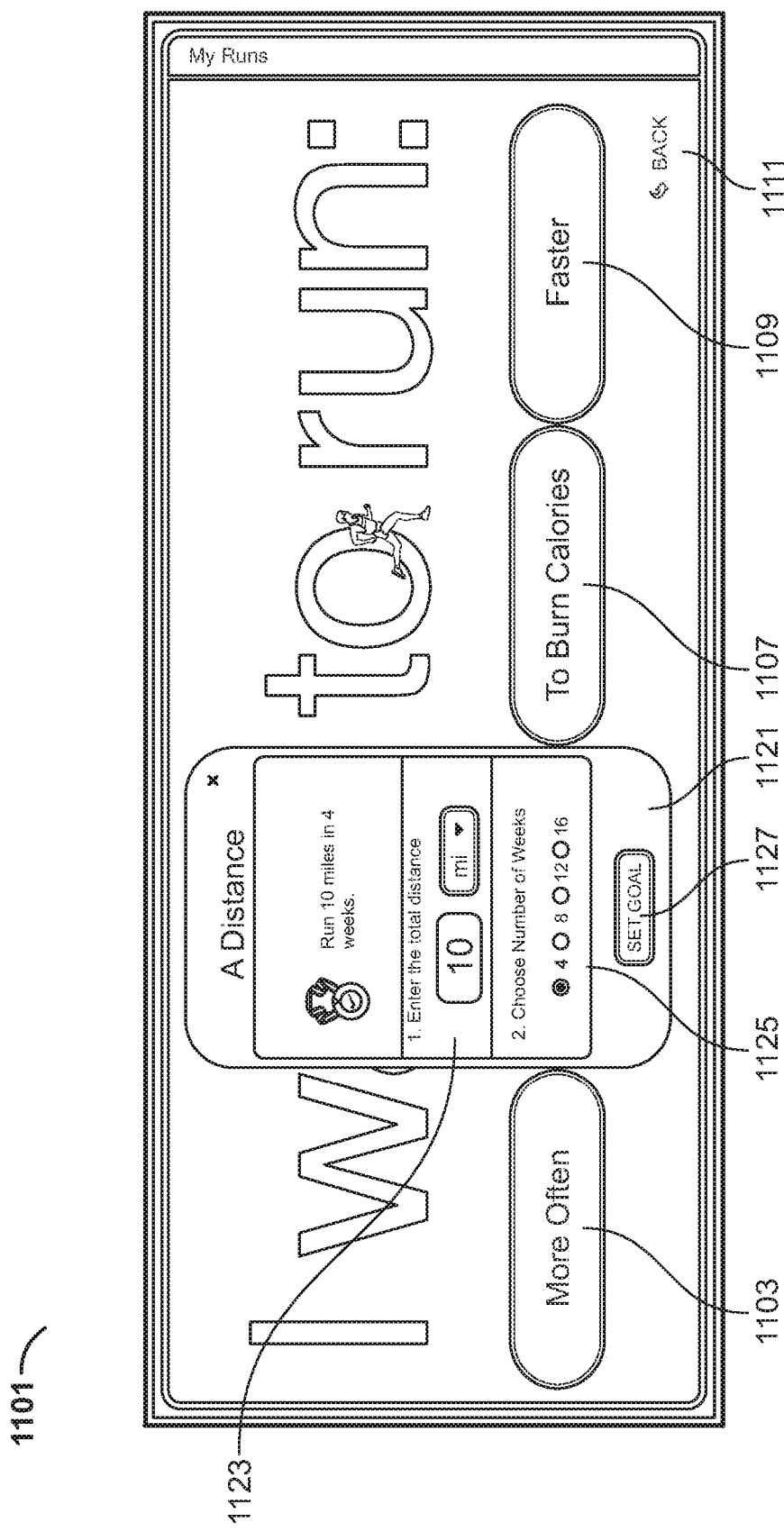

Similarly, if a user wishes to run a longer distance in a given time period, then the user activates the "Distance" button 1105. In response, the athletic data display configuration module 605 reconfigures the user interface 1101 to include a sub-interface 1121. As seen in FIG. 11C, the sub-interface 1121 includes a "Total Distance" control 1123, a "Number Of Weeks" control 1125, and a "Set Goal" button 1127. By employing the "Total Distance" control 1123, a user can specify the total distance he or she wishes to run within a desired time period. Similarly, by employing the "Number Of Weeks" control 1125, a user can specify the number of weeks making up the desired time period allowed to reach the desired goal. In the illustrated example, the "Total Distance" control 1123 is a combination control, with both a field control (i.e., a field in which a value can be typed) and a drop down menu control (i.e., to allow the user to select the units in which the distance would be measure). The "Number Of Weeks" control 1125 illustrated in FIG. 11C then is a radio control. Various examples of the invention, however, may employ alternate types of controls as desired. Once a user has specified the number of runs that must be made and specified the time period in which they must be made to meet a desired goal, the user can finalize the goal parameters by activating the "Set Goal" button 1127.

Figure 11D:
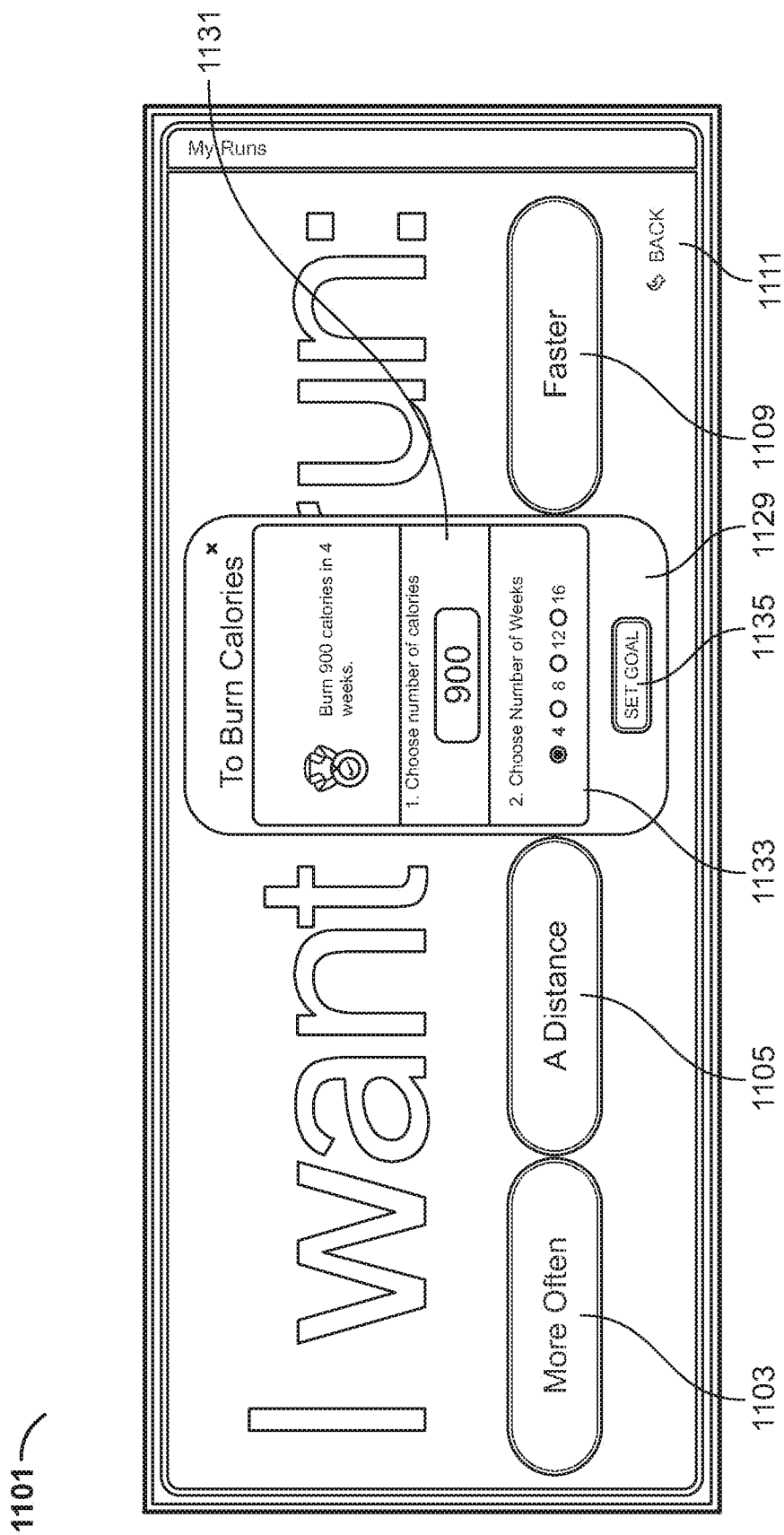

If a user wishes to burn more calories during a particular time period, then the user activates the "Burn More Calories" button 1107. In response, the athletic data display configuration module 605 reconfigures the user interface 1101 to include a sub-interface 1129. As seen in FIG. 11D, the sub-interface 1129 includes a "Number Of Calories" control 1131, a "Number Of Weeks" control 1133, and a "Set Goal" button 1135. By employing the "Number Of Calories" control 1131, a user can specify the number of calories he or she wishes to burn within a desired time period. Similarly, by employing the "Number Of Weeks" control 1133, a user can specify the number of weeks making up the desired time period allowed to burn the desired number of calories. In the illustrated example, the "Number Of Calories" control 1131 is a field control (i.e., having a field in which a value can be typed in) while the "Number Of Weeks" control 1133 is a radio control, but various examples of the invention may employ alternate types of controls as desired. Once a user has specified the number of runs that must be made and specified the time period in which they must be made to meet a desired goal, the user can finalize the goal parameters by activating the "Set Goal" button 1135.

Figure 11E:
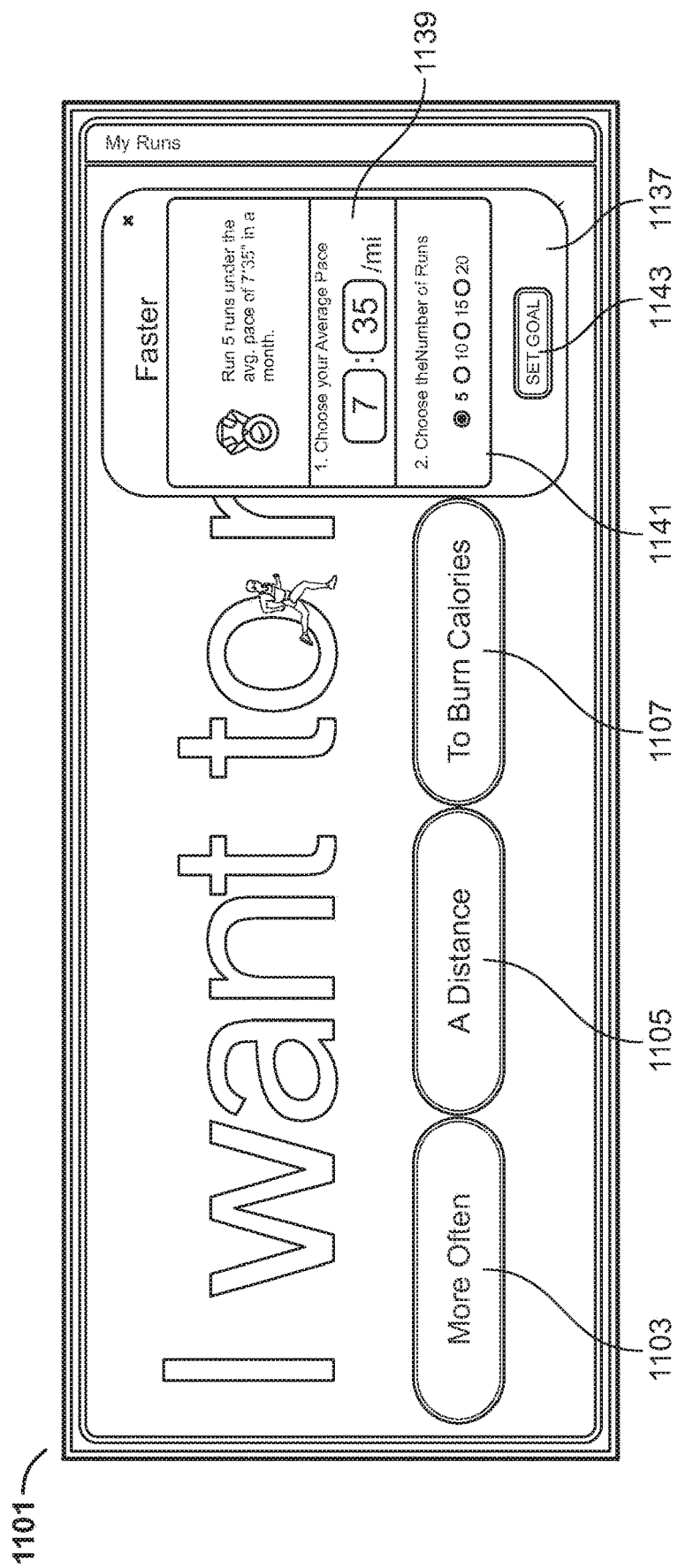

Lastly, if a user wishes to run faster for a desired number of runs, then the user activates the "Faster" button 1109. In response, the athletic data display configuration module 605 reconfigures the user interface 1101 to include a sub-interface 1137. As seen in FIG. 11E, the sub-interface 1137 includes an "Average Pace" control 1139, a "Number Of Runs" control 1141, and a "Set Goal" button 1143. By employing the "Average Pace" control 1139, a user can specify the minimum pace at which he or she wishes to travel for the desired number of runs. Similarly, by employing the "Number Of Runs" control 1141, a user can specify the number of runs for which the user wishes to run faster in order to reach the desired goal. In the illustrated example, the "Average Pace" control 1139 is a field control (i.e., having fields in which values can be typed) while the "Number Of Runs" control 1141 is a radio control, but various examples of the invention may employ alternate types of controls as desired. Once a user has specified the average pace and the number of runs for which he or she must run at or faster than the specified average pace to meet a desired goal, the user can finalize the goal parameters by activating the "Set Goal" button 1143.

Figure 12:
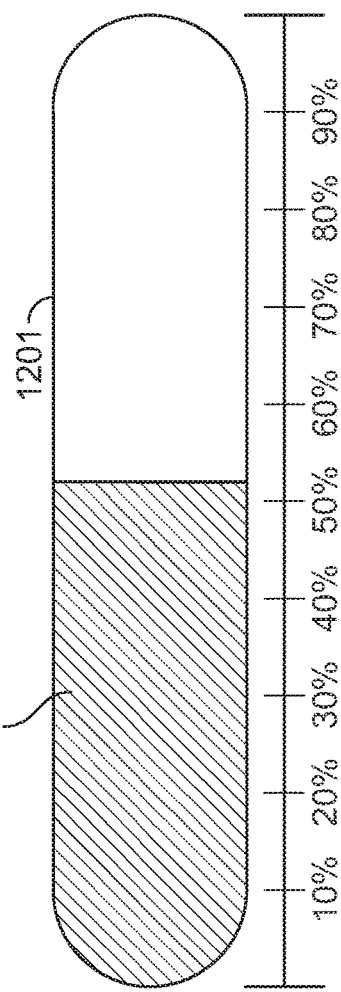
FIG. 12 illustrates an example of a user interface that may be provided to indicate a user's progress toward achieving an athletic activity goal according to various implementations of the invention.

After the user has specified a desired goal, the athletic data display configuration module 605 will monitor the athletic data collected by the athletic data collection module 505. When the user subsequently wishes to view his or her progress toward accomplishing the specified goals (by, e.g., selecting the "Goals" tab), then the athletic data display configuration module 605 will aggregate the relevant data from the collected athletic data set and configure a user interface graphically displaying the user's progress toward the specified goals. For example, with some implementations of the invention, the athletic data display configuration module 605 may configure a user interface displaying bar graph, such as the bar graph 1201 shown in FIG. 12. A portion of the bar graph corresponding to the user's progress is marked with fill 1203. Thus, in the illustrated example, the fill 1203 in the bar graph 1203 indicates that the user has accomplished more than 50% of the athletic activity required to complete his or her goal. Some implementations may simultaneously display a bar graph or other progress indicator for each goal set by the user. Still other implementations of the invention may provide controls to allow a user to select a single bar graph or other progress indicator for display in the user interface.

Display of Other User's Athletic Data

Challenges

Figure 13A:
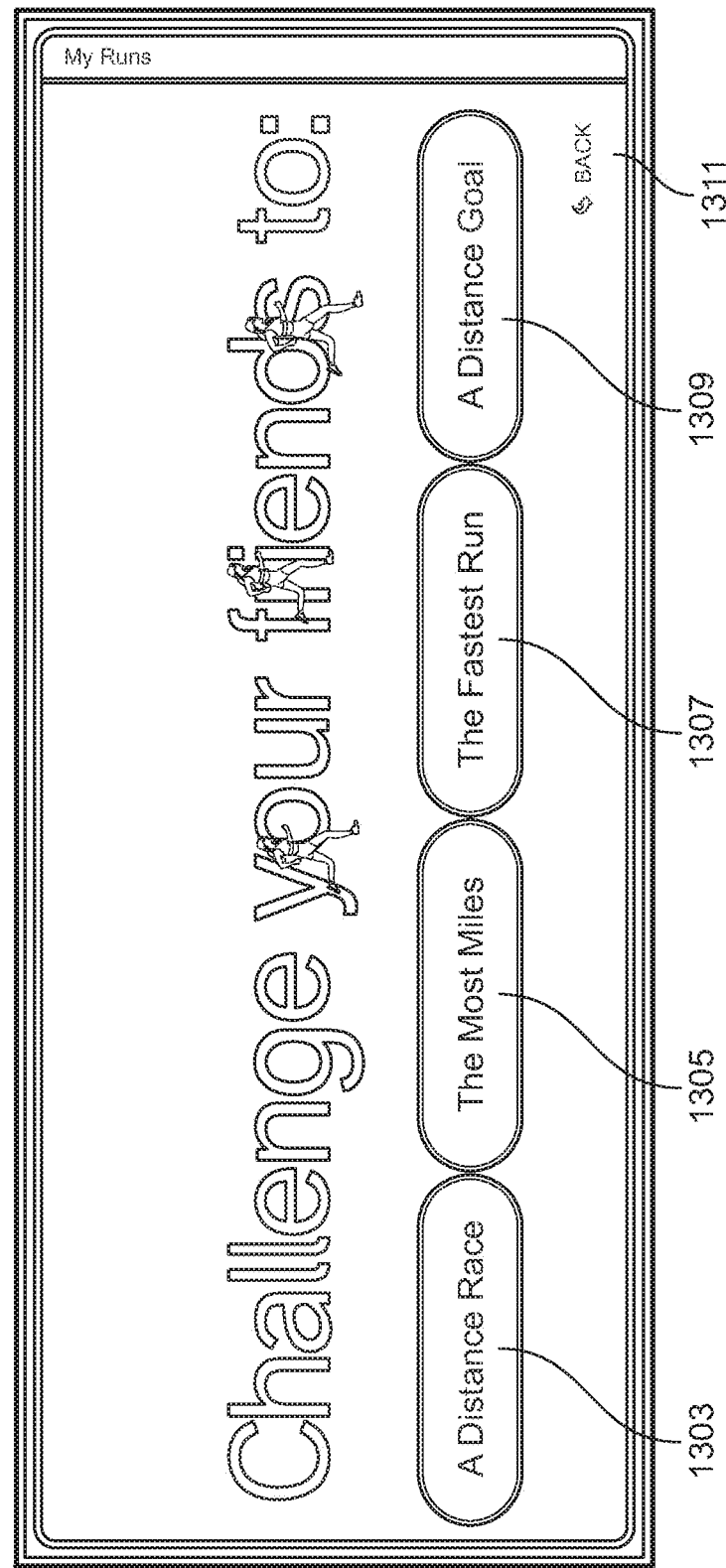
FIGS. 13A-13F illustrate examples of user interfaces that may be provided to create a challenge to other users according to various implementations of the invention.

Various examples of the invention may allow a user to "challenge" one or more other users (i.e., athletes employing embodiments of the invention) to a competition regarding athletic activities. With some implementations of the invention, for example, a user may issue a challenge to one or more other athletes by requesting the user interface 1301 shown in FIG. 13A. As seen in this figure, the interface 1301 includes a "Distance Race" button 1303, a "Most Miles" button 1305, a "Fastest Run" button 1307, a "Distance Goal" button 1309, and a "Back" button 1311. As known in the art, activating the "Back" button 1311 will cause the athletic data display configuration module 605 (or, with some examples of the invention, the athletic data display module 509) to configure and display the previously displayed configuration of the user interface 1301, or if the currently displayed configuration of the user interface 1301 is its initial configuration, a previously-shown user interface.

Figure 13B:
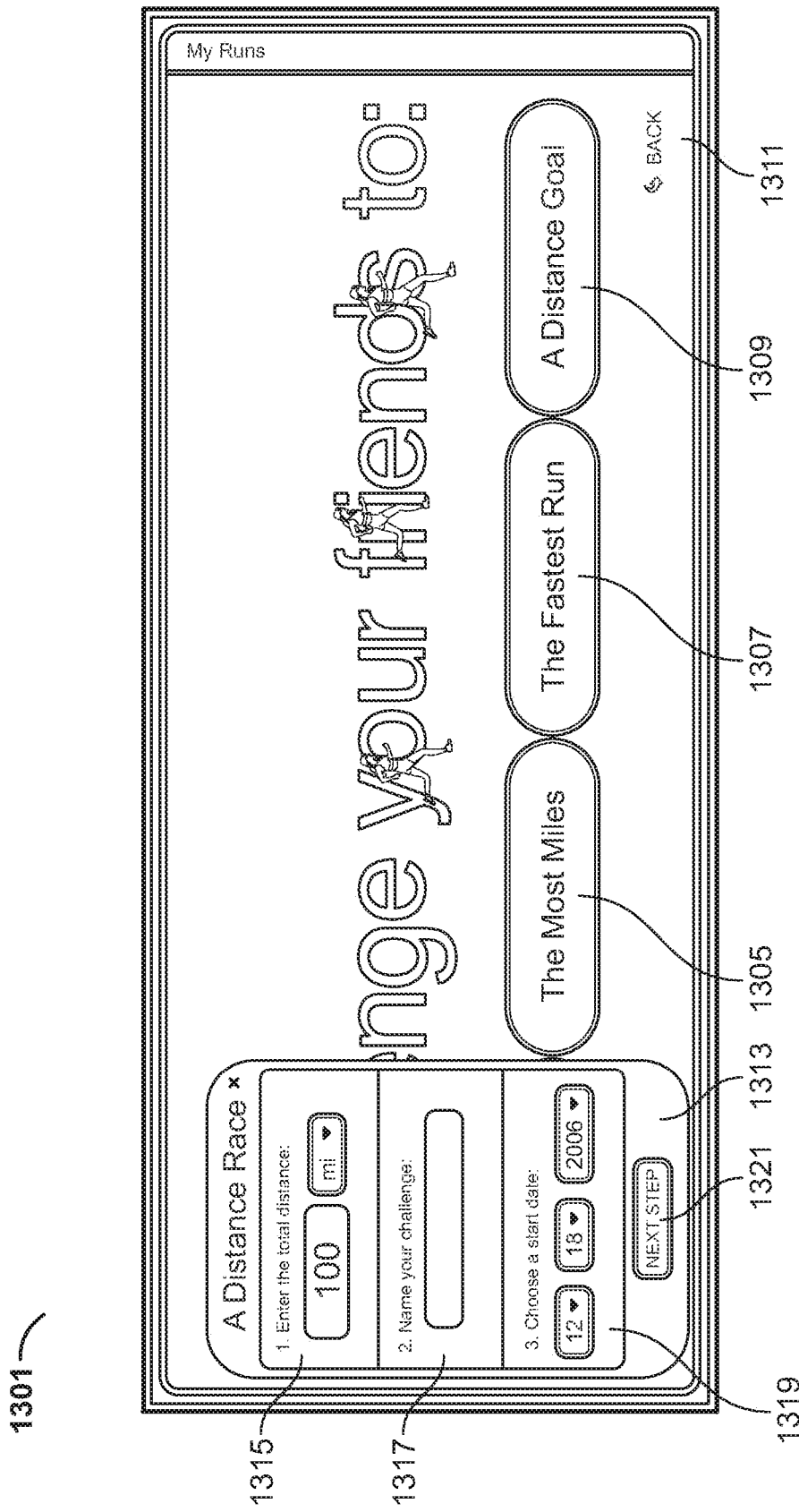

If a user wishes to establish a challenge regarding who can run a specified distance first, then the user activates the "Distance Race" button 1303. In response, the athletic data display configuration module 605 reconfigures the user interface 1301 to include a sub-interface 1313. As seen in FIG. 13B, the sub-interface 1313 includes a "Total Distance" control 1315, a "Challenge Name" control 1317, a "Start Date" control 1319, and a "Next Step" button 1321. By employing the "Total Distance" control 1315, a user can specify the total distance that a challenge participant must be the first to run in order to win the challenge. Next, the user can provide a specific name for the challenge using the "Challenge Name" control 1317. Naming each challenge allows an athlete to identify and keep track of a plurality of different challenges in which he or she may be concurrently participating. The user can then specify the starting date for the challenge using the "Start Date" control 1319. In the illustrated example, the "Total Distance" control 1315 and the "Challenge Name" control 1317 are each field controls (i.e., controls having a field in which a value can be typed), while the "Start Date" control 1319 is made up of a number of drop-down menus. It should be appreciated, however, that various examples of the invention may employ alternate types of controls as desired. Once a user has specified the parameters of the challenge, the user can begin the process of inviting specific athletes to participate in the challenge by activating the "Next Step" button 1321.

Figure 13C:
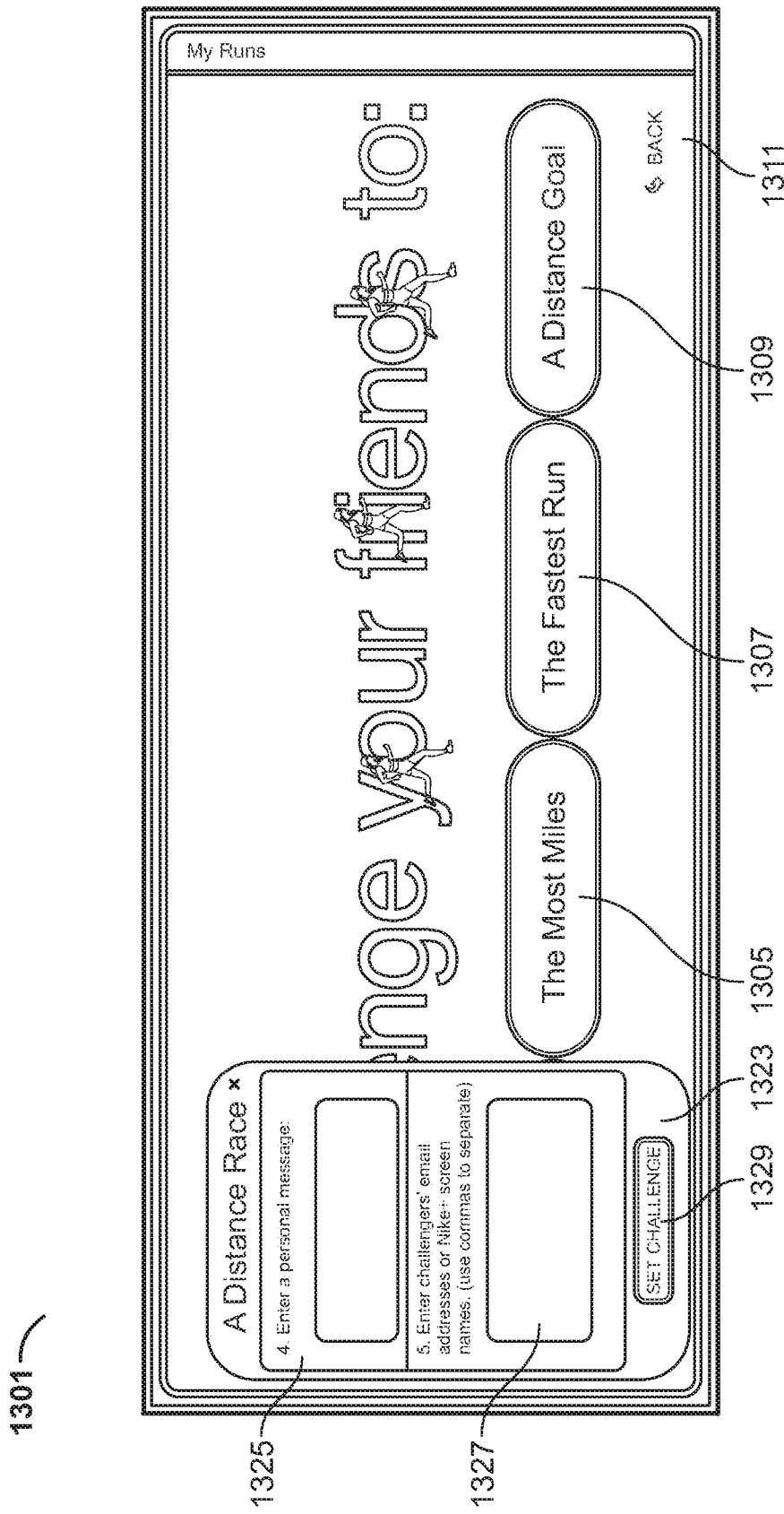

When the user activates the "Next Step" button 1321, the athletic data display configuration module 605 reconfigures the user interface 1301 to include a sub-interface 1323 in place of the "Distance Race" button 1303, as shown in FIG. 13C. As seen in this figure, the sub-interface 1323 includes a "Personal Message" control 1325, an "Email Address" control 1327, and a "Set Challenge" button 1329. The user can employ the "Personal Message" control 1325 to create a personal message to each athlete the user wishes to invite to participate in the challenge. Using the "Email Address" control 1327, the user can then specify the email address for each person he or she wishes to invite to participate in the challenge. In the illustrated example, the "Personal Message" control 1325 and the "Challenge Name" control 1317 are each field controls (i.e., controls having a field in which a value can be typed), but various examples of the invention may employ alternate types of controls as desired.

Once the user has provided the email address for each desired participant, the user can initiate the challenge by activating the "Set Challenge" button 1329. In response to the user activating the "Set Challenge" button 1329, the athletic data display configuration device 601 (or, with some implementations of the invention, the user's athletic information collection and display device 501) sends an email to each of the specified invitees. The email will contain the personal message and, e.g., an interactive prompt to join the challenge. If an invitee agrees to join the challenge by responding to the prompt, then the athletic data display configuration device 601 will be notified that the invitee has agreed to join the challenge. These types of email interactive prompts (such as the "voting" buttons provided in versions of the Outlook software tool available from Microsoft Corporation of Redmond, Wash.) are well known in the art, and will not be discussed here in detail.

After the athletic data display configuration device 601 has identified the participants in a challenge, it monitors the collected athletic data for each of the participants, and aggregates the relevant data values in the collected athletic data. For example, if the challenge is a race to determine who can be the first to run 100 miles, for each participant the athletic data display configuration device 601 will sum the total distance value in each athletic data set collected for that participant after the start date. When a participant has a sum of his or her total distance values that matches or exceeds the specified challenge distance (and is the first invitee to do so), then the athletic data display configuration device 601 will identify that participant as the winner of the challenge. In response, the athletic data display configuration device 601 will notify each participant of the winner. The athletic data display configuration device 601 may notify the participants using any desired technique, such as by sending an electronic mail message, by displaying a special-purpose interface when each participant connects to the athletic data display configuration device 601, etc. A variety of such notification techniques are well known in the art, and thus will not be discussed in detail.

With various examples of the invention, the athletic data display configuration device 601 may additionally provide updates regarding the status of a participant relative to the other participants. These updates also can be provided using any desired technique, such as by sending an electronic mail message, by displaying a special-purpose interface when each participant connects to the athletic data display configuration device 601, etc. For example, the athletic data display configuration device 601 may configure and provide a user interface showing each participant's progress toward the goal of the challenge using, e.g., bar graphs for each participant of the type previously described with regard to monitoring individual goals.

Figure 13D:
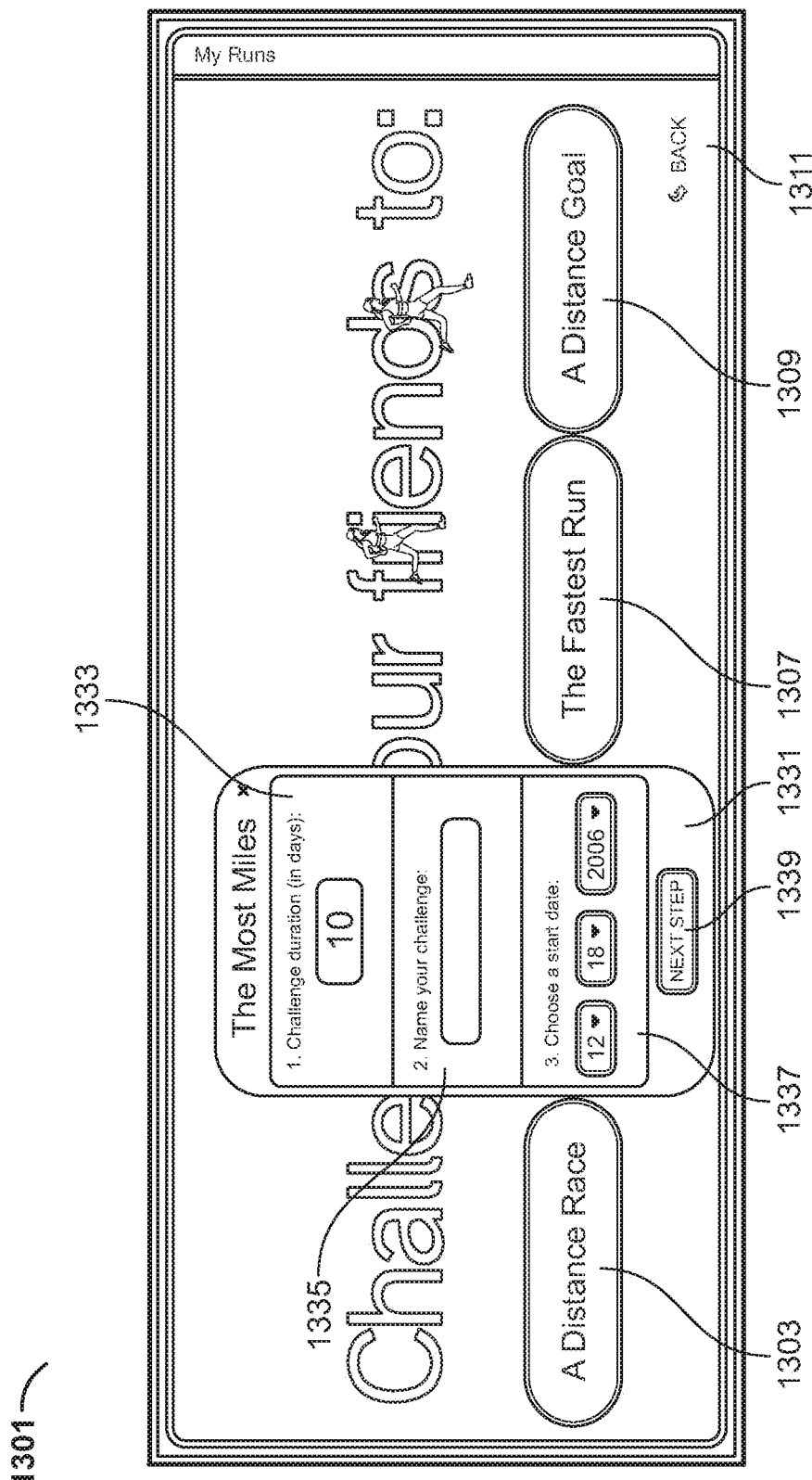

Returning now to FIG. 13A, if a user wishes to establish a challenge regarding who can run the most miles in a given period of time, then the user activates the "Most Miles" button 1305. In response, the athletic data display configuration module 605 reconfigures the user interface 1301 to include a sub-interface 1331, as seen in FIG. 13D. The sub-interface 1331 includes a "Challenge Duration" control 1333, a "Challenge Name" control 1335, a "Start Date" control 1337, and a "Next Step" button 1339. By employing the "Challenge Duration" control 1333, a user can specify the total amount of time for which a challenge participant has to run the greatest total distance in order to win the challenge. Next, the user can provide a specific name for the challenge using the "Challenge Name" control 1335. The user can then specify the starting date for the challenge using the "Start Date" control 1337. In the illustrated example, the "Challenge Duration" control 1333 and the "Challenge Name" control 1335 are each field controls (i.e., controls having a field in which a value can be typed), while the "Start Date" control 1337 is made up of a number of drop-down menus. It should be appreciated, however, that various examples of the invention may employ alternate types of controls as desired.

Once a user has specified the parameters of the challenge, the user can begin the process of inviting specific athletes to participate in the challenge by activating the "Next Step" button 1339. In response, the athletic data display configuration module 605 reconfigures the user interface 1301 to include the sub-interface 1323 in place of the "Most Miles" button 1305. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13E:
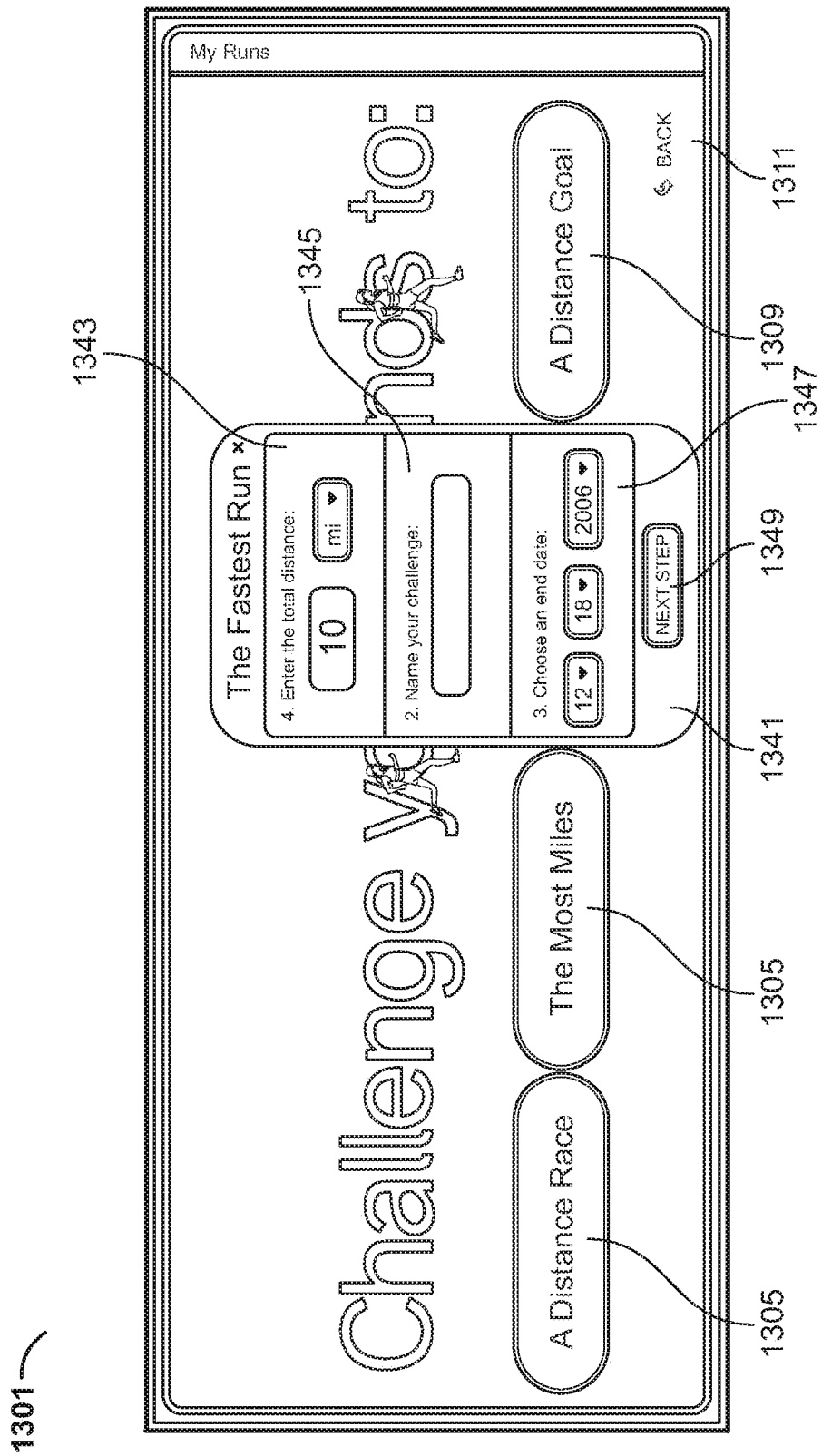

If a user wishes to establish a challenge regarding who can make the fastest run in a given period of time, then the user activates the "Fastest Run" button 1307. In response, the athletic data display configuration module 605 reconfigures the user interface 1301 to include a sub-interface 1341 as seen in FIG. 13E. The sub-interface 1341 includes a "Total Distance" control 1343, a "Challenge Name" control 1345, a "Start Date" control 1347, and a "Next Step" button 1349. By employing the "Total Distance" control 1343, a user can specify the total distance a user must run in order to have his or her run time eligible to win the challenge. Next, the user can provide a specific name for the challenge using the "Challenge Name" control 1345. The user can then specify the starting date for the challenge using the "Start Date" control 1347. In the illustrated example, the "Total Distance" control 1343 and the "Challenge Name" control 1345 are each field controls (i.e., controls having a field in which a value can be typed), while the "Start Date" control 1347 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1349. In response, the athletic data display configuration module 605 reconfigures the user interface 1301 to include a sub-interface 1323 in place of the "Fastest Run" button 1307. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Figure 13F:
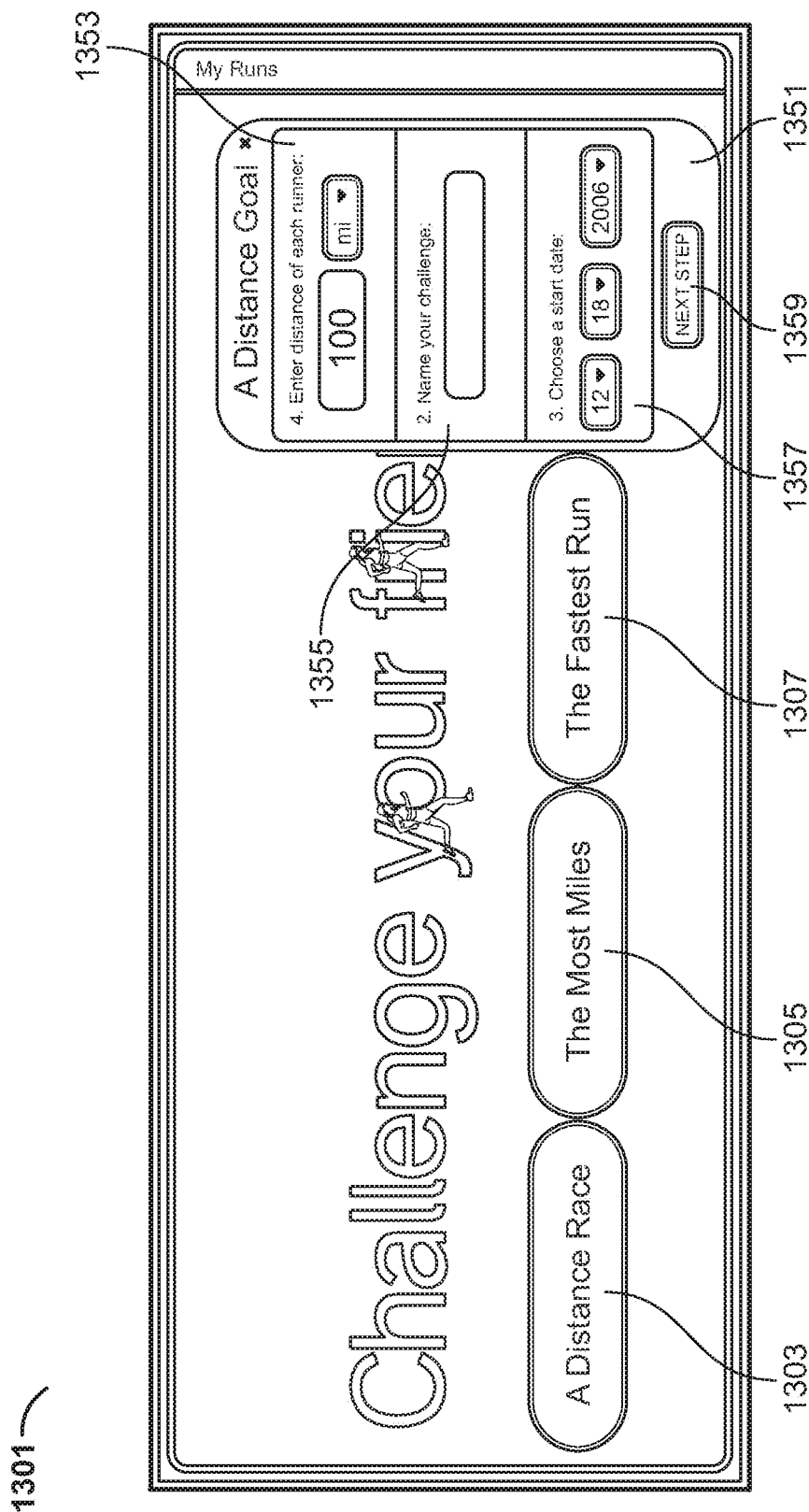

Lastly, if a user wishes to establish a challenge regarding who can run a specified distance in a given period of time, then the user activates the "Distance Goal" button 1309. In response, the athletic data display configuration module 605 reconfigures the user interface 1301 to include a sub-interface 1351. As seen in FIG. 13F, the sub-interface 1351 includes a "Total Distance" control 1353, a "Challenge Name" control 1355, a "Start Date" control 1357, and a "Next Step" button 1359. By employing the "Total Distance" control 1353, a user can specify the total distance a user must run over the specified time period in order to meet the challenge. Next, the user can provide a specific name for the challenge using the "Challenge Name" control 1355. The user can then specify the starting date for the challenge using the "Start Date" control 1357. In the illustrated example, the "Total Distance" control 1353 and the "Challenge Name" control 1355 are each field controls (i.e., controls having a field in which a value can be typed), while the "Start Date" control 1357 is made up of a number of drop-down menus, but various examples of the invention may employ alternate types of controls as desired.

Once a user has specified the parameters of the challenge, the user can begin the process of inviting specific athletes to participate in the challenge by activating the "Next Step" button 1359. In response, the athletic data display configuration module 605 reconfigures the user interface 1301 to include the sub-interface 1323 in place of the "Distance Goal" button 1309. (An example of sub-interface 1323 is illustrated in FIG. 13C.) As discussed in detail above, the user can employ the sub-interface 1323 to invite others to participate in the challenge, and ensure that the athletic data display configuration device 601 is informed of the participants in the challenge. As also previously discussed, the athletic data display configuration device 601 will monitor the collected athletic data for each participant, and aggregate the relevant data values from the collected athletic data to determine who wins the challenge. Still further, the athletic data display configuration device 601 can notify the participants of the winner of the challenge, and, with various examples of the invention, of the status of each participant during the challenge as described above.

Lists

As well as interactive comparisons of a user's athletic data with other users, such as the goals and challenges described in detail above, some implementations of the invention may alternately or additionally allow a user to passively compare his or her athletic data with other users. For example, some implementations of the invention may provide a ranking of where a user stands with respect to other users. The ranking may be based upon a simple comparison, or it may be limited to a specific demographic group, a particular geographic region, or some combination therefore.

Figure 14A:
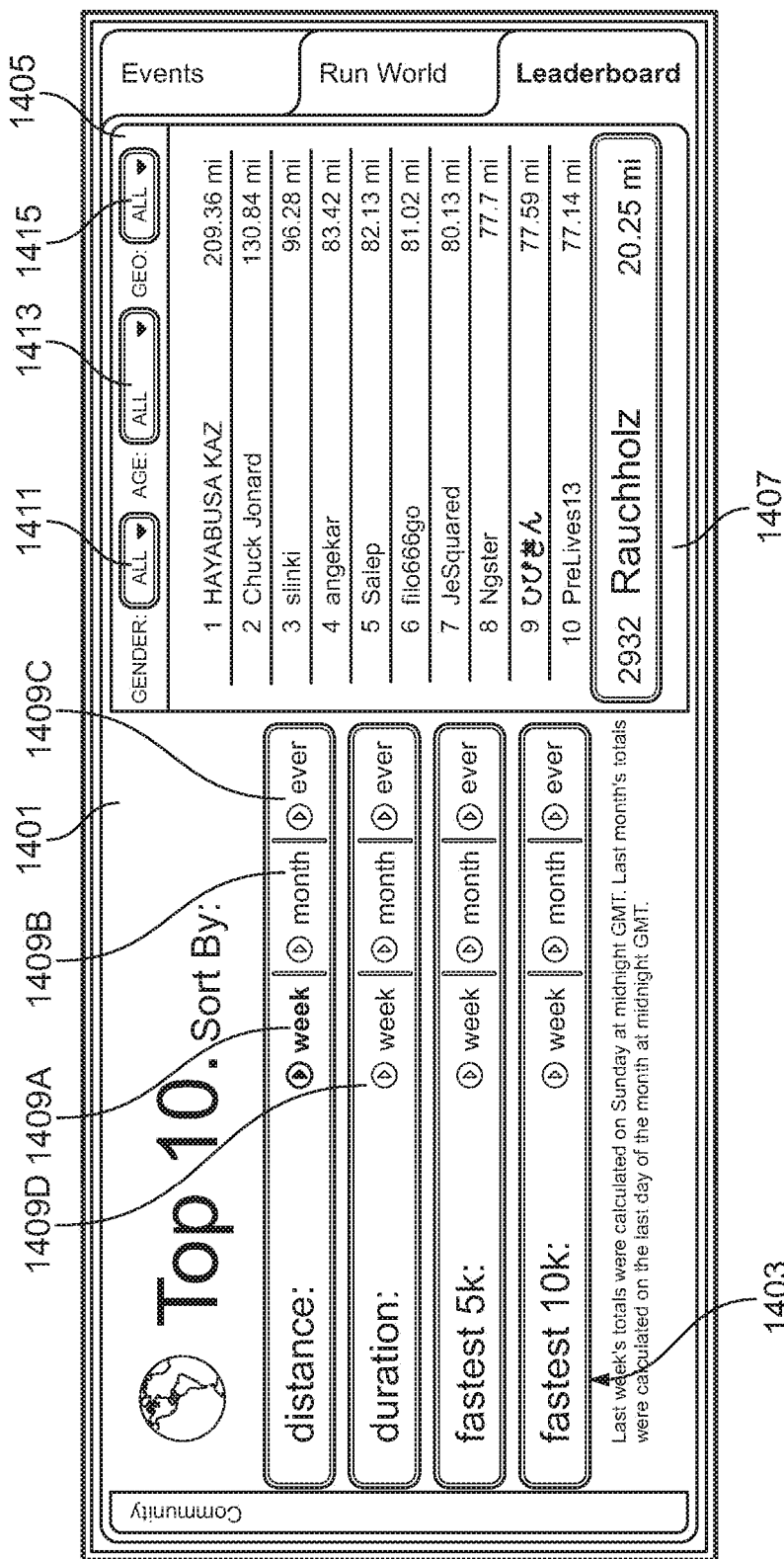
FIGS. 14A-14F illustrate examples of user interfaces that may be provided to compare a user's athletic data with the athletic data of other participating users according to various implementations of the invention.

For example, with some implementations of the invention, a user may request that the athletic data display configuration module 605 generate and display the user interface 1401 illustrated in FIG. 14A. As seen in this figure, the user interface 1401 includes a comparison criteria region 1403, a filter region 1405, and display region 1407. The comparison criteria region 1403 includes a plurality of "radio" style controls 1409, while the filter region 1405 includes a plurality of "drop-down" controls 1411-1413. The display region 1407 then displays user information based upon athletic data selected using the comparison and filter information selected using the controls 1409-1413.

More particularly, a user employs the "radio" style controls 1409 to specify the basic criteria according to which the athletic data display configuration module 605 will compare athletic data for a plurality of users. These controls 1409 are referred to herein as "radio" style controls because the selection of one of the controls (e.g., control 1409C) will automatically deselect a previously selected control, and only one control may be selected at any given time. Of course, it should be appreciated that other type of selection tools, including other types of controls, may be alternately or additionally employed with other implementations of the invention. Each control 1409 is associated with both a sorting criterion for sorting measured athletic data and a time criterion specifying a time period during which the athletic data being compared must have been measured. For example, each of controls 1409A-1409C is associated with total distance as a sorting criterion, while control 1409A is associated with a week time period, control 1409B is associated with a month time period, and control 1409C is associated with an unlimited time period. Control 1409D is then associated with a duration sorting criterion and a week time period.

With the example of the interface 1401 shown in FIG. 14A, each of the filter controls 1411-1415 are selected to "ALL," as will be discussed in more detail below. Further, the control 1409A is selected. Because the control 1409A is associated with the "distance" sorting criterion and the "week" time criterion, the athletic data display configuration module 605 will sort the aggregated distance data for participating users that was measured during the preceding week. It then lists the names of the participating users having the ten highest aggregated distance data values in the filter region 1405. In addition, the athletic data display configuration module 605 will display in the aggregated distance data values measured during the preceding week for each of the identified participating users. Still further, the athletic data display configuration module 605 will display the user's corresponding aggregated distance measured for the preceding week. With some implementations of the invention, the athletic data display configuration module 605 also may display the ranking of the user's corresponding aggregated distance information measured for the preceding week relative to those participating users having a greater aggregated distance measured for the preceding week. Thus, in the illustrated example, the user "Rauchholz" has a ranking of 2932 relative to other participating users.

With some implementations of the invention, the participating users will be any user who provides athletic data to the athletic data storage 607 (or to an affiliated athletic data storage). For still other implementations of the invention, however, the participating users may be a subset of the all of the users who provide athletic data to the athletic data storage 607 or to an affiliated athletic data storage. For example, the participating users may be only those users who agree in advance to have their data shared with other users, or those users who do not specifically indicate that they wish for their athletic data to be private. Of course, still other criteria may be used to determine which users will be treated as participating users.

Figure 14B:
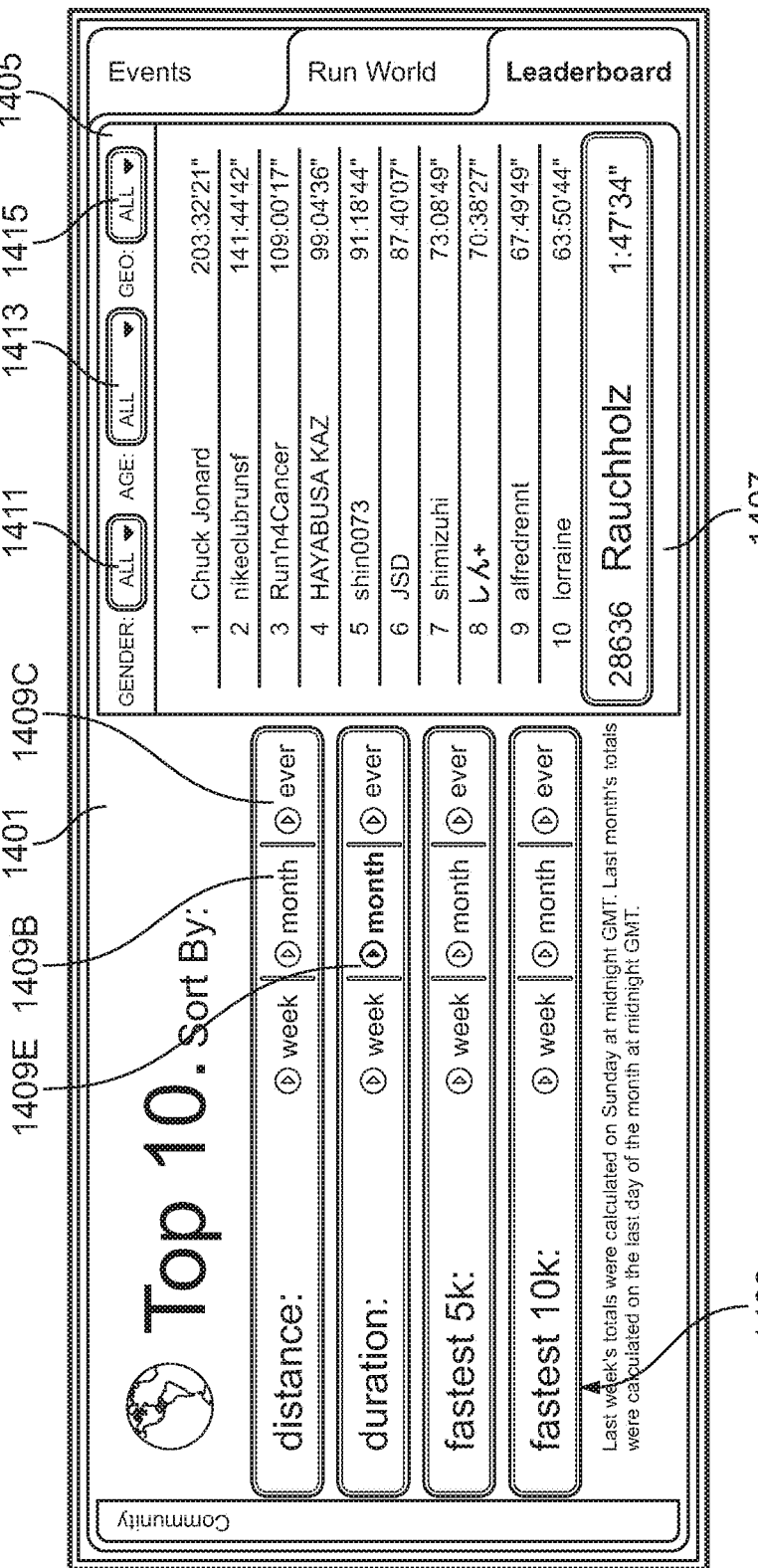

FIG. 14B illustrates another example of the interface 1401. Again, each of the filter controls 1411-1415 are selected to "ALL." Further, the control 1409E is selected, which is associated with the "duration" sorting criterion and the "month" time criterion. Accordingly, the athletic data display configuration module 605 will sort the aggregated running (or walking) duration data for participating users that was measured during the preceding month. It then lists the names of the participating users having the ten highest aggregated duration data values in the filter region 1405. In addition, the athletic data display configuration module 605 will display in the aggregated duration data values measured during the preceding month for each of the identified participating users. Still further, the athletic data display configuration module 605 will display the user's corresponding aggregated duration data measured for the preceding month. Again, the athletic data display configuration module 605 also displays the ranking of the user's corresponding aggregated duration data measured for the preceding month relative to those participating users having a greater aggregated duration value measured for the preceding month. Thus, in the illustrated example, the user "Rauchholz" has a ranking of 28636 relative to other participating users.

Figure 14C:
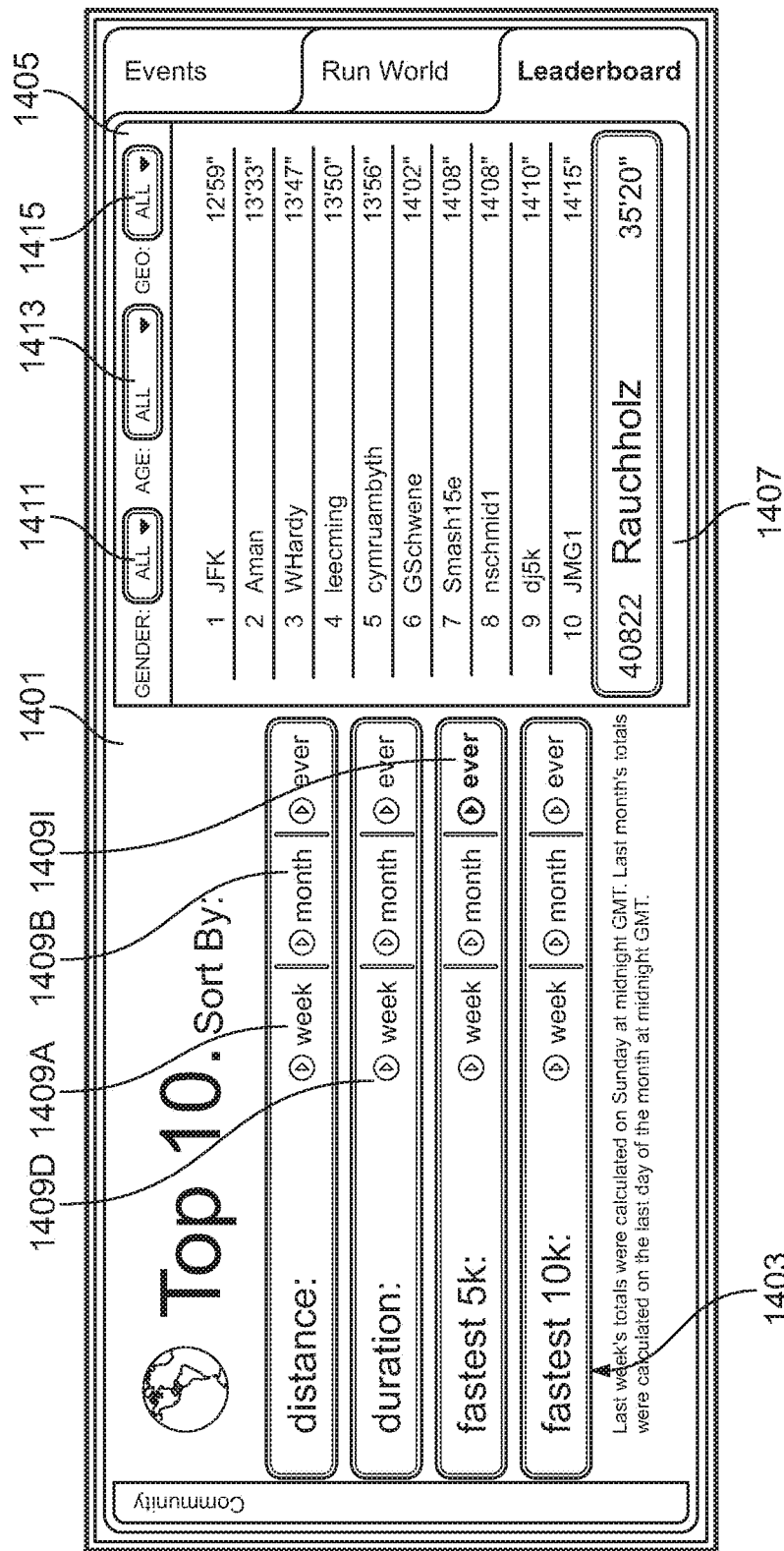

FIG. 14C illustrates yet another example of the interface 1401. Again, each of the filter controls 1411-1415 are selected to "ALL." Further, the control 1409I is selected, which is associated with the "fastest 5 k" sorting criterion and the "ever" time criterion. Accordingly, the athletic data display configuration module 605 will identify and display the participating users with the ten fastest travel times for a 5 k run that was measured at any time preceding the user's selection of the control 1409I. In addition, the athletic data display configuration module 605 will display in the fastest 5 k time value for each of the identified participating users. Still further, the athletic data display configuration module 605 will display the user's fastest measured time for a 5 k run, together with a ranking of that time relative to those participating users having a faster measured time for a 5 k run. Thus, in the illustrated example, the user "Rauchholz" has a ranking of 40822 relative to other participating users.

Figure 14D:
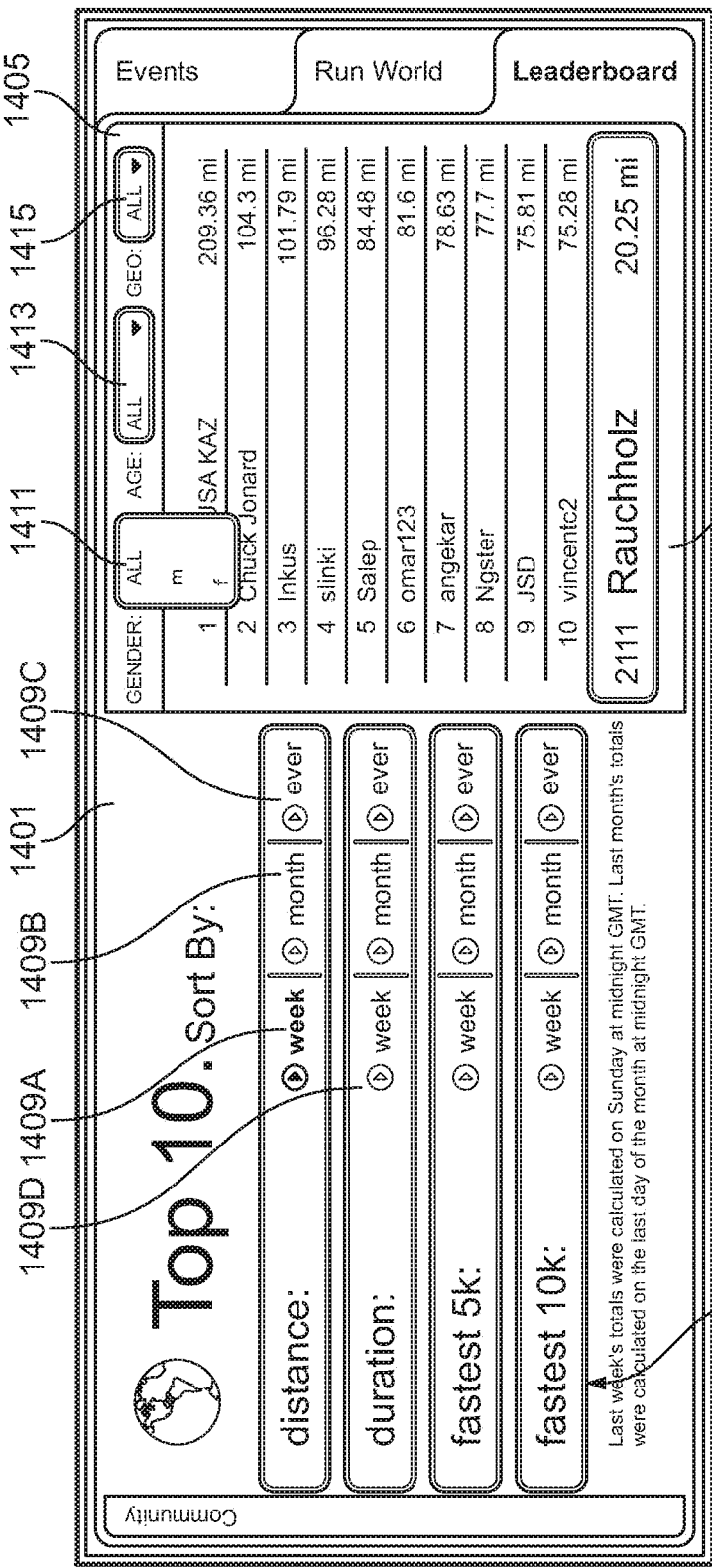
Figure 14E:
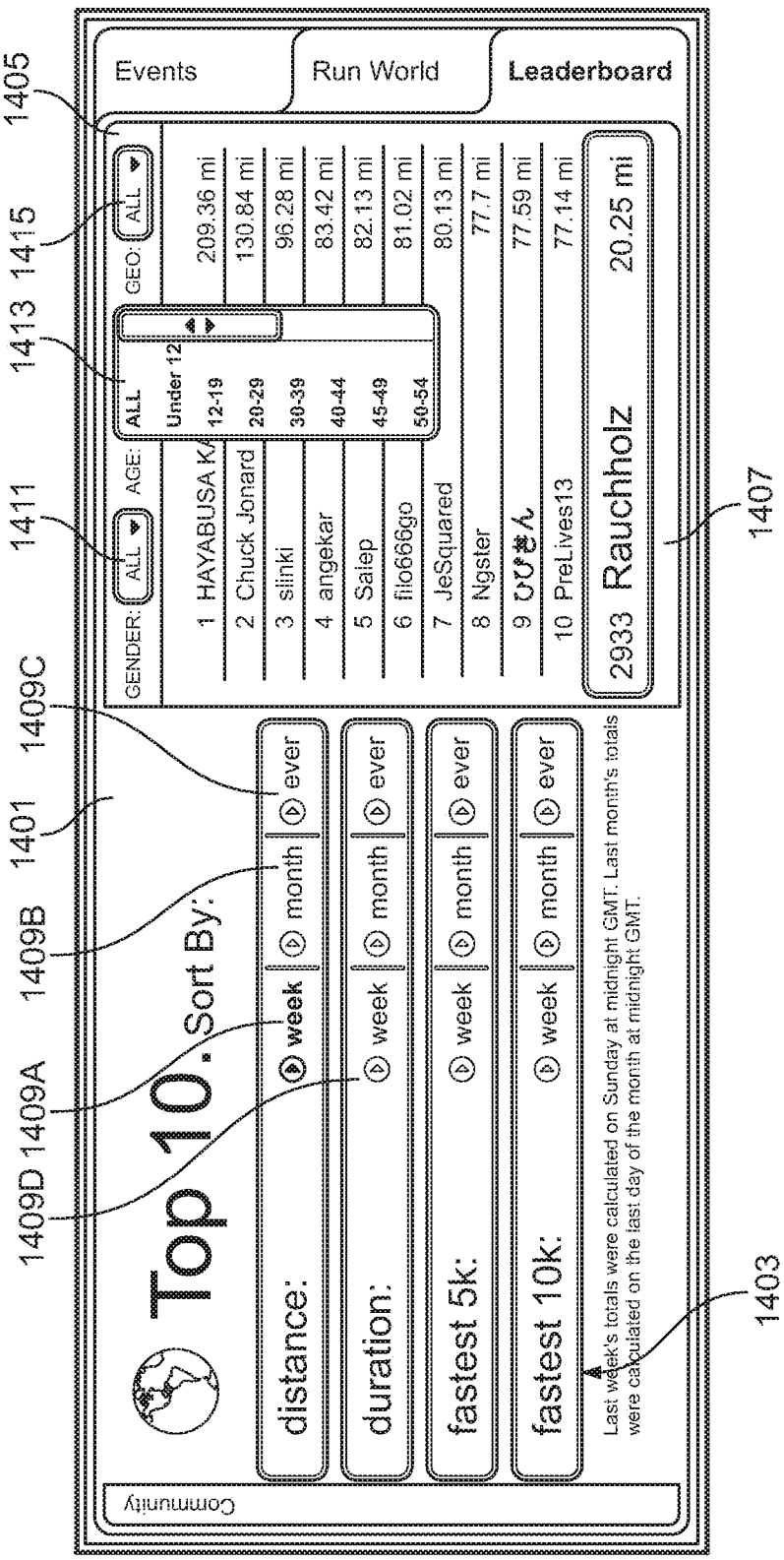
Figure 14F:
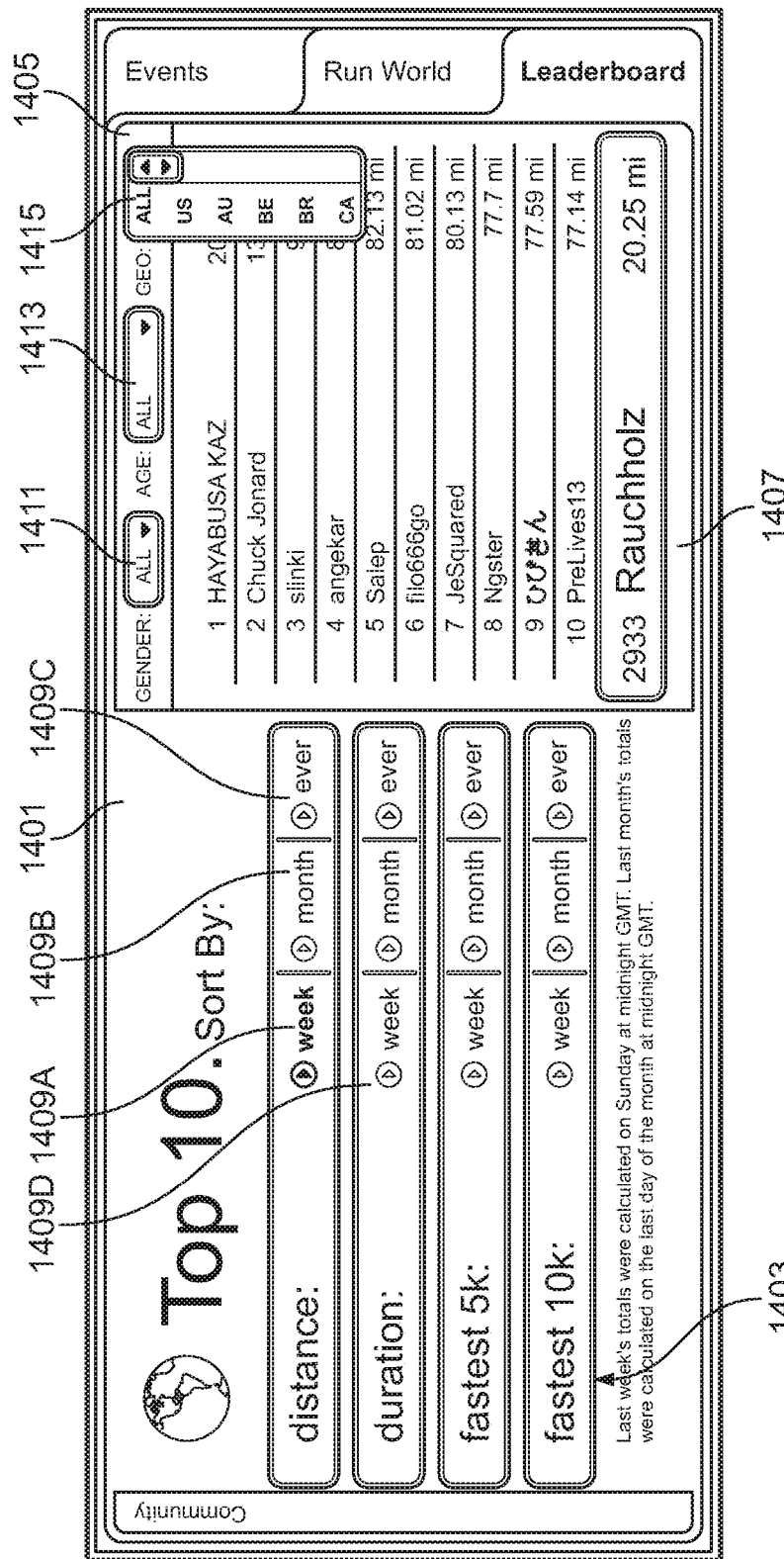

In some situations, a user may wish to limit the pool of participating users to whom the user will be compared. As previously noted, the filter region 1405 includes filter controls 1411-1415. These filter controls may be employed to limit the participating users that will be considered for a desired comparison. For example, as illustrated in FIG. 14D, a user can employ the filter control 1411 to select between including all participating users for comparison, only male participating users for comparison, or only female participating users for comparison. Similarly, as shown in FIG. 14E, a user can employ filter control 1413 to limit the comparison to only those participating users within a desired age group. Still further, as shown in FIG. 14F, a user can employ the filter control 1415 to limit the comparison to participating users within a geographic region.

It should be appreciated that, with some implementations of the invention, a user can employ each of the filters 1411-1415 simultaneously. For example, a user may employ the filter controls 1411-1415 to limit the participating users considered for comparison with the users' athletic data to only men between the ages of 40-44 residing in the United States. The information required to filter the participating users may be obtained from any available source. Conveniently, however, the information may be obtained by requesting the users to submit this information for a user profile during an initial registration process. Of course, while three specific filtering criteria have been disclosed, it should be appreciated that any desired type and/or combination of characteristics be employed as filters.

Step-Related Athletic Activity Data
Collection of Data

For some users, walking or other step-related activities such as stair-climbing may be preferable over exercises such as running. For example, athletes with an existing injury or condition may find walking more suitable for their condition than running or other activities that may have a higher likelihood of exacerbating the injury or condition. Accordingly, a system, method and apparatus for monitoring and tracking step-related activities may be provided for such users. Additionally, any of the aforementioned features, functions, devices and systems such as goal setting and tracking, challenges, display of activity data and the like may be used in conjunction with and/or to facilitate the collection and monitoring of step-related activities such as walking. Step-related or step activities as used herein may generally refer to activities that involve the detection of a number of steps taken below a threshold pace (e.g., a defined running pace).

In one or more arrangements, step activity data may be collected using a device such as digital music player 203 (FIG. 2) connected to parameter measurement device 207 (FIG. 2). For instance, parameter measurement device 207 may include a pedometer that is commonly used to measure a number of steps taken by a wearer. As illustrated in FIG. 2, the parameter measurement device 207 may be connected to digital music player 203 using an electronic interface device 205. Alternatively or additionally, parameter measurement device 207 may be connectable directly to the digital music player 203 or may be included within digital music player 203. Furthermore, and as noted herein, parameter measurement device 207 may be connected to other devices such as a mobile telecommunication device, a personal data assistant, athletic performance monitoring devices, athletic activity equipment and the like. For example, a step machine may include a step counting device configured to determine and record the number of steps taken by the user. In another example, a parameter measurement device 207 may be provided as a stand-alone device that is wearable and/or mobile.

Figure 15:
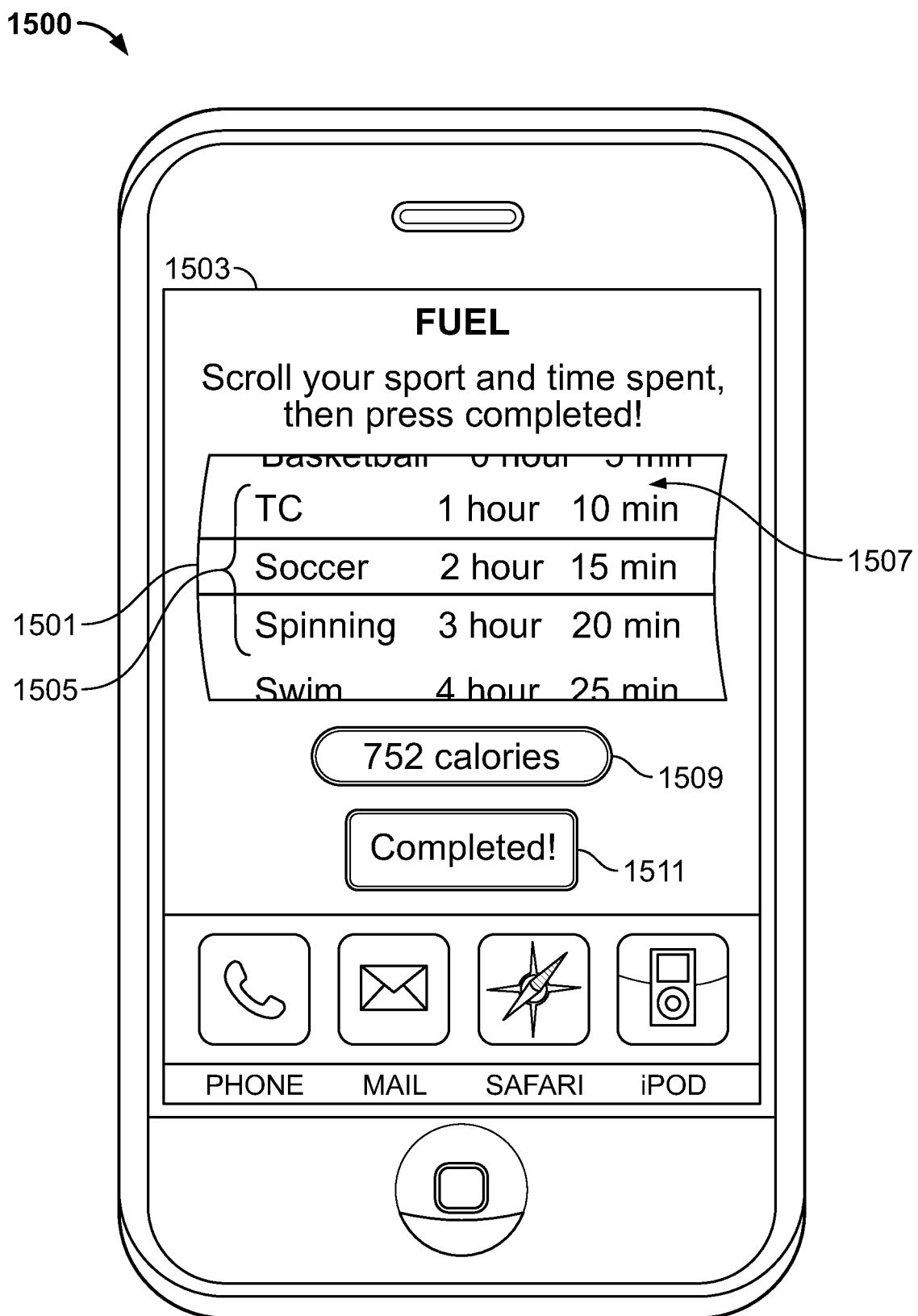
FIG. 15 illustrates a data collection device that may be used to manually enter workout data according to one or more aspects described herein.

According to one or more aspects, a user may self report data, such as a number of steps taken, a number of calories burned, a distance traveled, an amount of time spent performing an athletic activity and the like. FIG. 15 illustrates a mobile data collection and display device 1500 that may be used for self-reporting of athletic activity data. For example, display 1501 may display a user interface 1503 that includes a list of various athletic activities 1505 along with a list of times 1507. A user may scroll through lists 1505 and 1507 to select an activity performed and a length of time therefrom. Other athletic performance parameters may also be selected for entry of an athletic performance activity including average heart rate, distance, incline/decline and the like. Device 1500 may then estimate a number of calories burned based on the selections and display the estimate in portion 1509. Once the selection and entry of data is finalized, the user may select completed option 1511 to have the data entered into a database and/or transmitted to an athletic tracking and monitoring network site. Other devices may similarly be used to operate a display and software in which a user may enter athletic performance data. For example, users may perform data entry through a personal computer or a personal data assistant.

Figure 16:
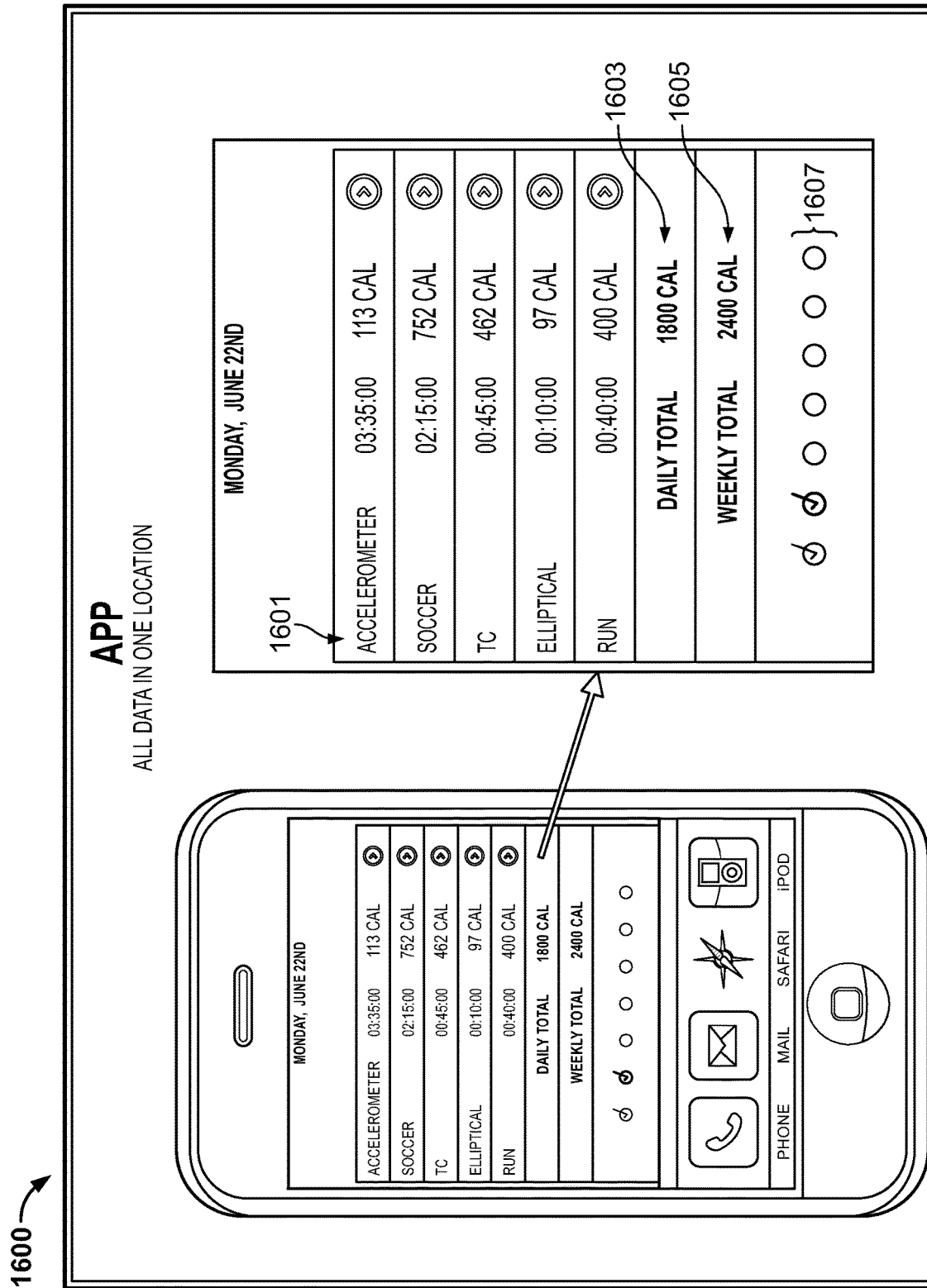
FIG. 16 illustrates a workout summary displayed on a data collection device according to one or more aspects described herein.

Additionally, device 1500 may be configured to display a summary of athletic performance data for a given time period. For example, FIG. 16 illustrates a user interface 1600 in which athletic activity performed on June $22^{nd}$ is summarized in list 1601 for the user. List 1601 may include the type of activity, the time spent performing the activity and a number of calories burned (actual or estimated). Further, a daily total of calories burned 1603 and a weekly total of calories burned 1605 may also be displayed. Markers 1607 corresponding to the days of the week may be provided to identify the days on which athletic activity was performed. The user may then switch to the various days by selecting different ones of markers 1607. The number of markers 1607 may be determined based on a specified time frame for the display of athletic performance data. The time frame may be user defined or may be configured based on a default (e.g., weekly).

Figure 17:
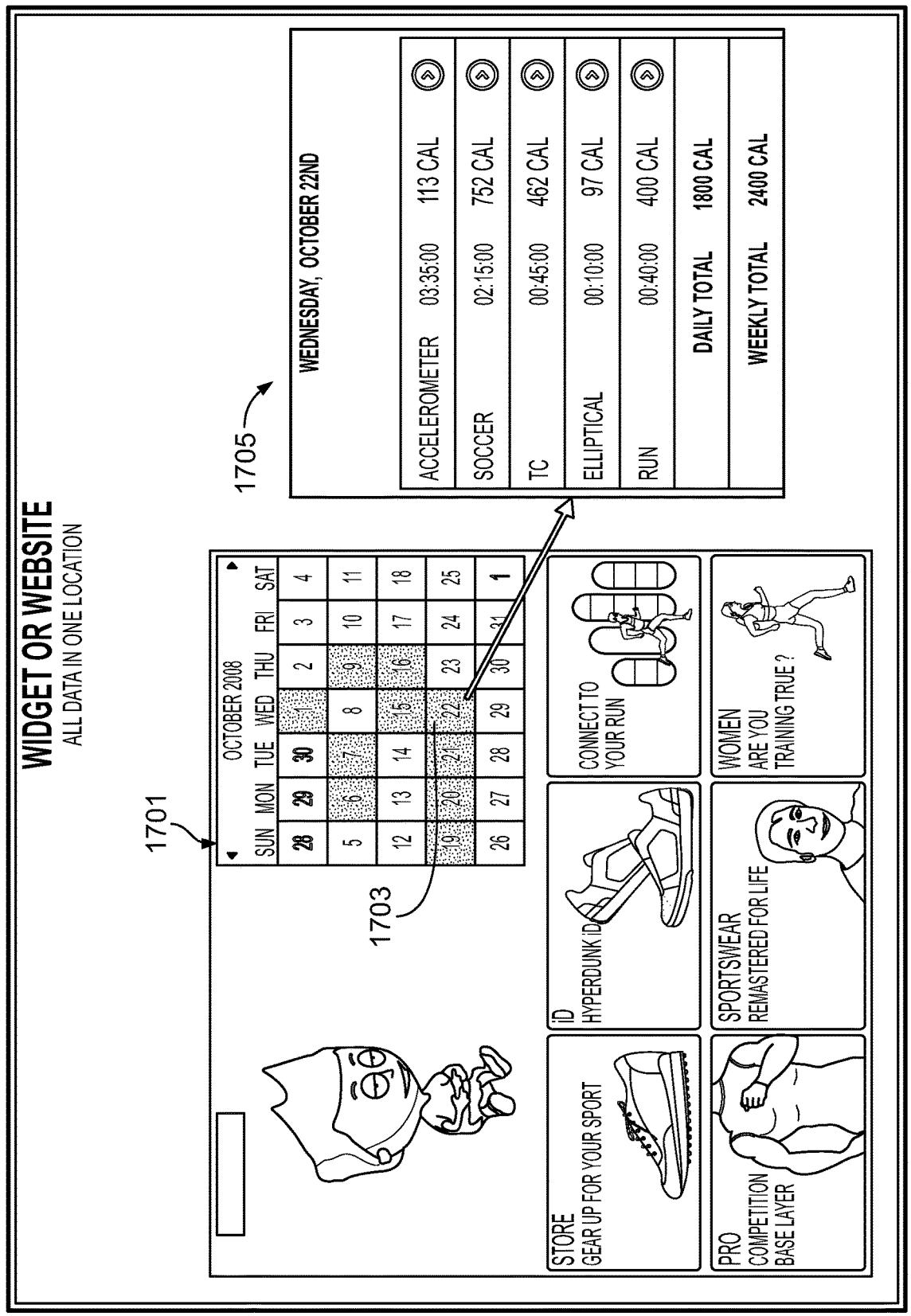
FIG. 17 illustrates a workout summary and interactive calendar that may be displayed as part of a widget or website according to one or more aspects described herein.

An athletic performance summary such as that provided in interface 1600 of FIG. 16 may also be configured as a widget or website. FIG. 17 illustrates a website function that allows a user to view a calendar 1701 of dates and select a particular date 1703 or week to view a corresponding athletic performance summary 1705. Days on which athletic activity was performed may have a different appearance as compared to days on which athletic activity was not performed. This allows the user to more easily identify days for which athletic performance information is available. In one or more configurations, the website function may be provided as a series of webpages, applets or combinations thereof.

Athletic activity data may be transmitted to a remote network site for storage, monitoring and tracking. In one example, athletic activity data stored in a digital music player may be transmitted through network access components included therein. However, in arrangements where the digital music player or other athletic activity data collection device does not include network access capabilities, the device may be connected to an intermediary device such as a personal computer or a mobile communication device that does have network access.

Figure 18:
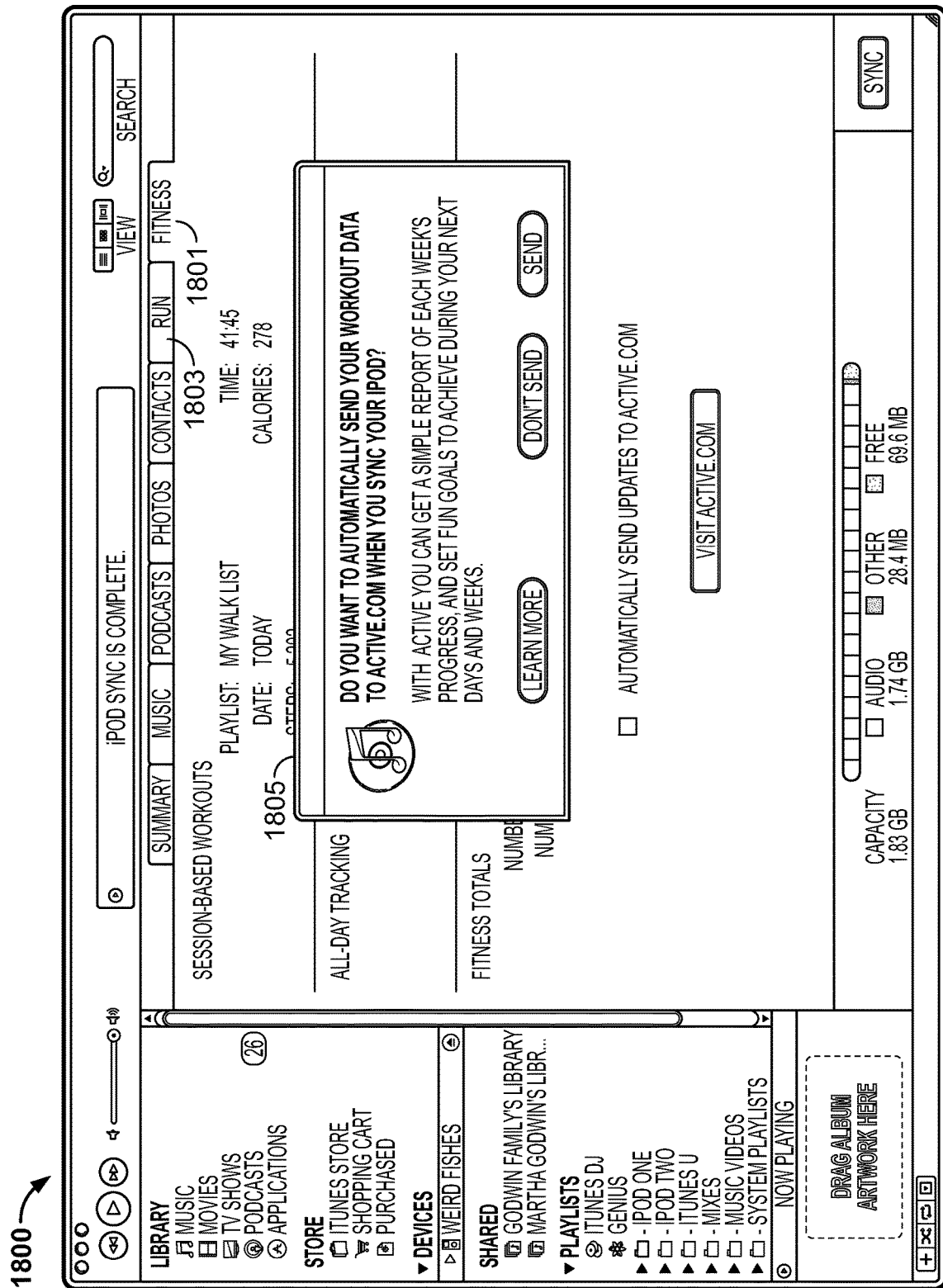
FIG. 18 illustrates an interface for synchronizing workout data with an athletic activity tracking and monitoring site according to one or more aspects described herein.
Figure 19:
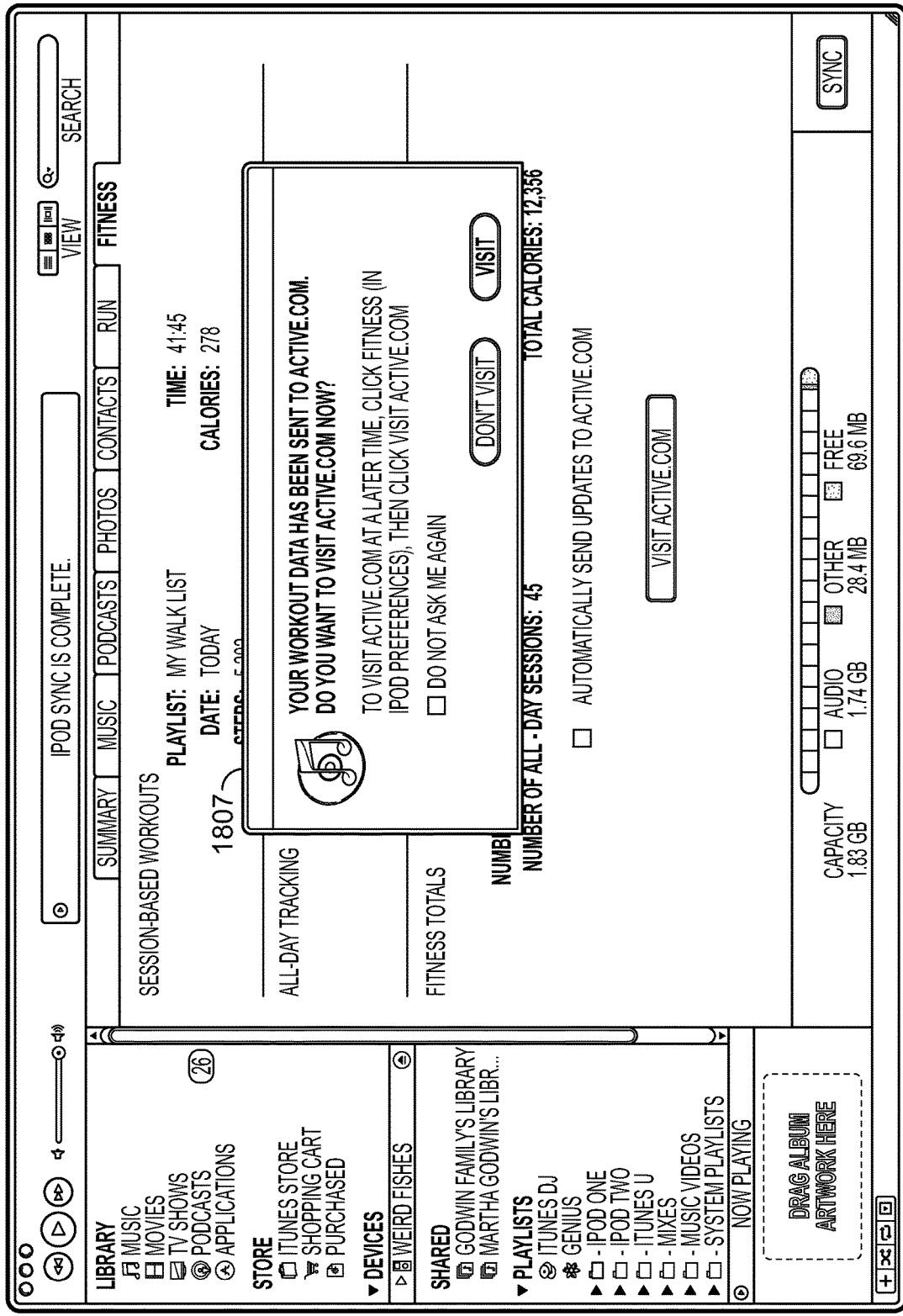
FIG. 19 illustrates an interface for directing a user to an athletic activity tracking and monitoring site according to one or more aspects described herein.

FIGS. 18 and 19 illustrate an interface 1800 through which athletic activity data for step-related activities may be detected and transmitted to a remote network site separately from other types of activity data. Interface 1800 may be displayed on a device separate from the athletic performance data collection device or module. For example, interface 1800 may be displayed on a personal computer upon connecting an athletic performance data collection device to the personal computer. Interface 1800 may include a tab for step-related activities 1801 and a tab for running activities 1803. Depending on the tab selected or on which activity focus currently resides, interface 1800 may prompt 1805 the user to determine whether the user wants to send workout data to the remote network site. Prompt 1805 might only be provided in response to detecting workout data or new workout data. Alternatively, the tabs 1801 and 1803 may be automatically selected based on the type of data detected. If multiple types of data are detected, interface 1800 may separately prompt the user to send each type of data in sequence. In some arrangements, interface 1800 may include additional functionality including music or video purchasing and downloading, music and video playback and the like.

If the user requests transmission of the athletic performance data to the network site, interface 1800 may further prompt 1807 the user to visit the network site, as shown in FIG. 19. In one or more instances, the network site may be specific to the type of athletic activity performed. For example, prompt 1807 may ask the user to visit a site dedicated to tracking and monitoring step activity rather than one related to a running activity. If the user does not currently wish to visit the site, prompt 1807 may provide additional information on how to access the site at a later time.

Figure 20A:
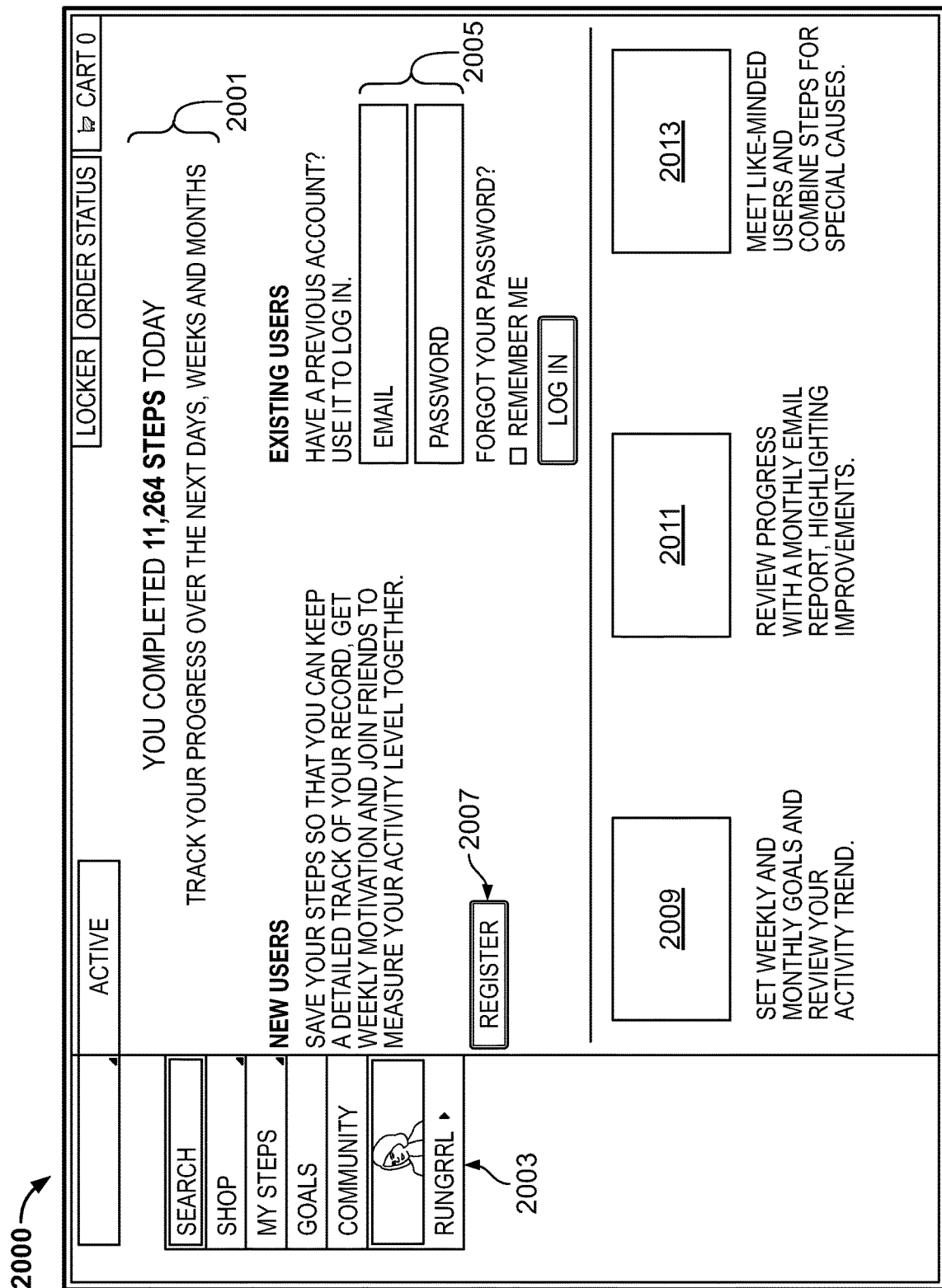
FIGS. 20A-D illustrate example soft login interfaces displaying workout data for a user according to one or more aspects described herein.

FIG. 20A illustrates a soft login interface for an athletic performance tracking and monitoring site. Soft login interface 2000 may provide a limited amount of data about the user including information 2001 about the received athletic performance data and a username 2003. However, more detailed information such as a graph of athletic performances, goals achieved, activities performed, account settings, user identification information and the like might not be accessible until the user logs in via login 2005 or registers via registration option 2007. Accordingly, selecting options that are user-specific such as setting goals 2009 and reviewing progress 2011 may lead the user to a login interface or registration interface if the user is not already logged in. Interface 2000 may, in one or more arrangements, be specifically directed to step-related activities. Option 2013 may be provided allowing the user to engage in a team effort with one or more other athletes to meet a goal.

Figure 20B:
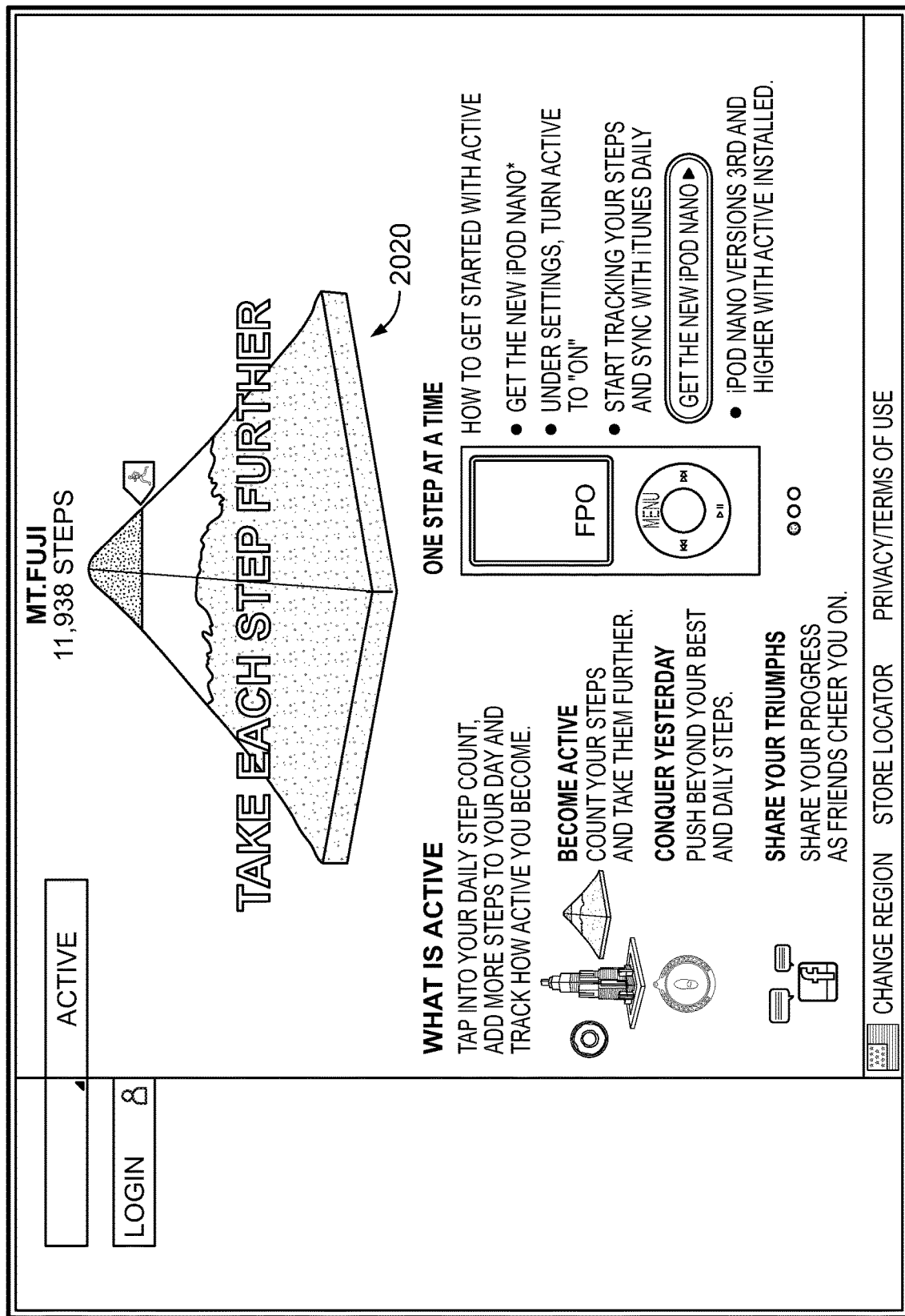
Figure 20C:
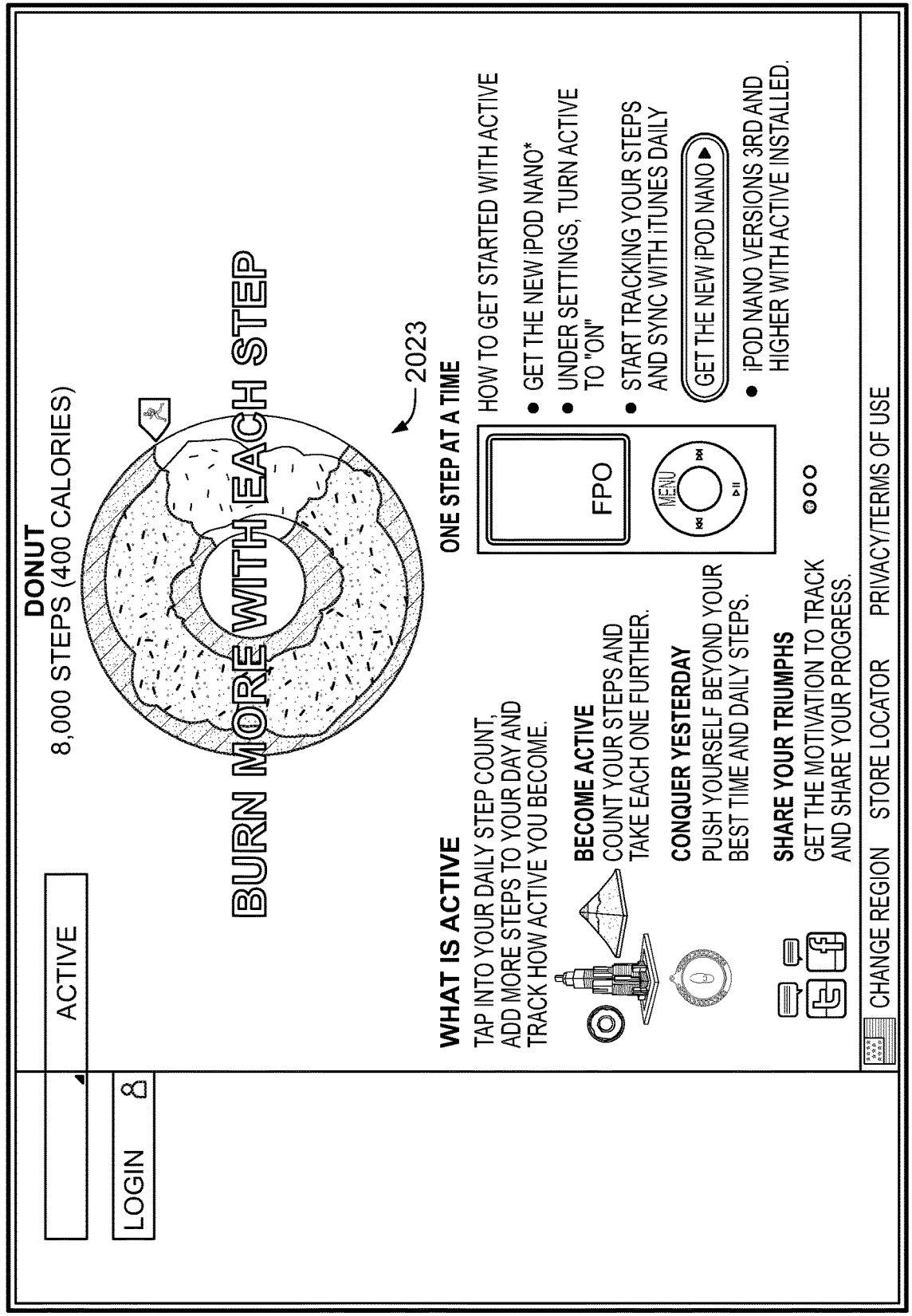
Figure 20D:
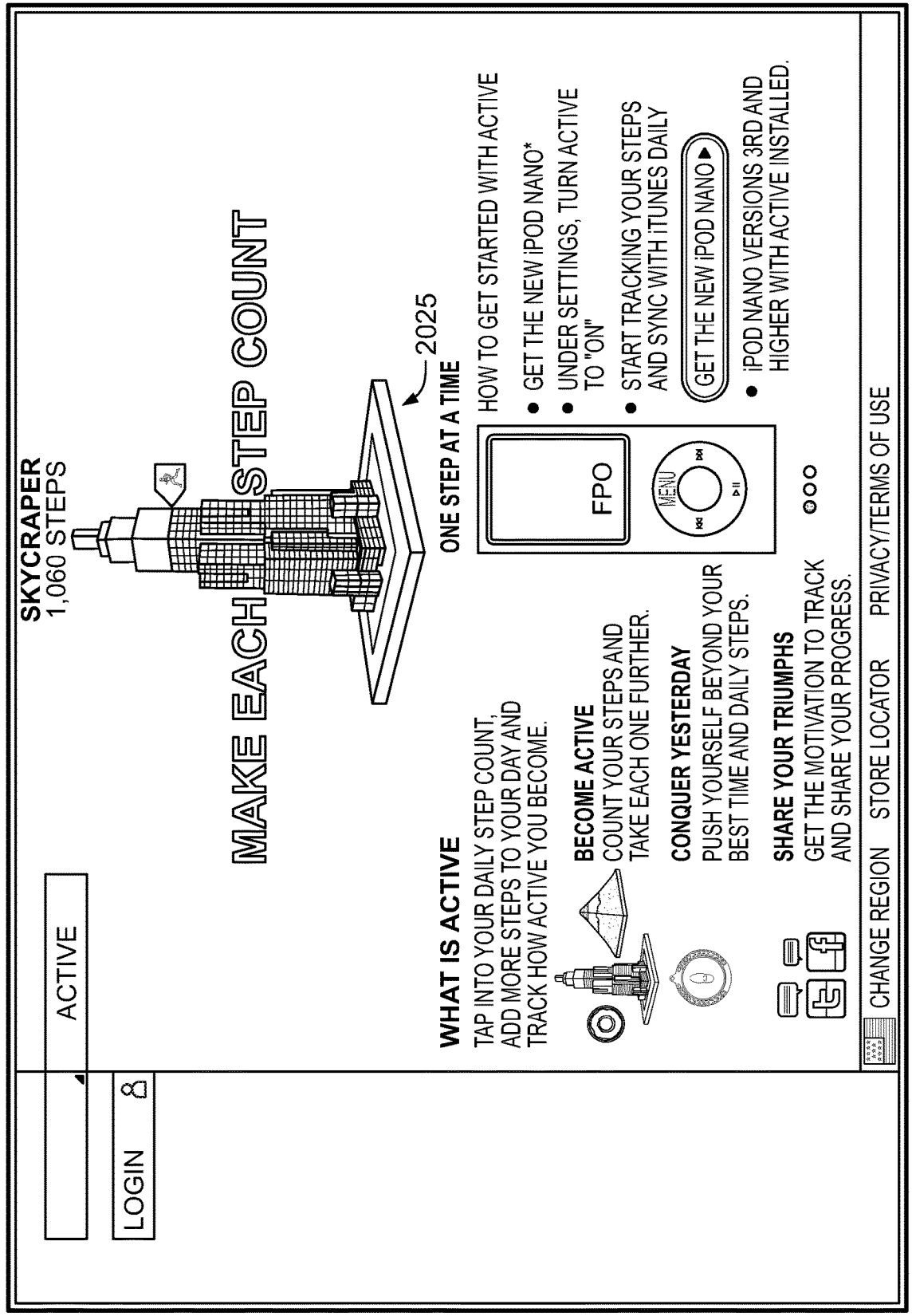

FIGS. 20B-D illustrate alternate embodiments of a soft login interface where the user's synchronized workout data (e.g., number of steps performed and/or calories burned) are applied toward a goal object such as objects 2020 (FIG. 20B), 2023 (FIG. 20C) and 2025 (FIG. 20D). Goal objects and the appearance thereof in conjunction with the user's workout activities are further described herein.

Figure 21A:
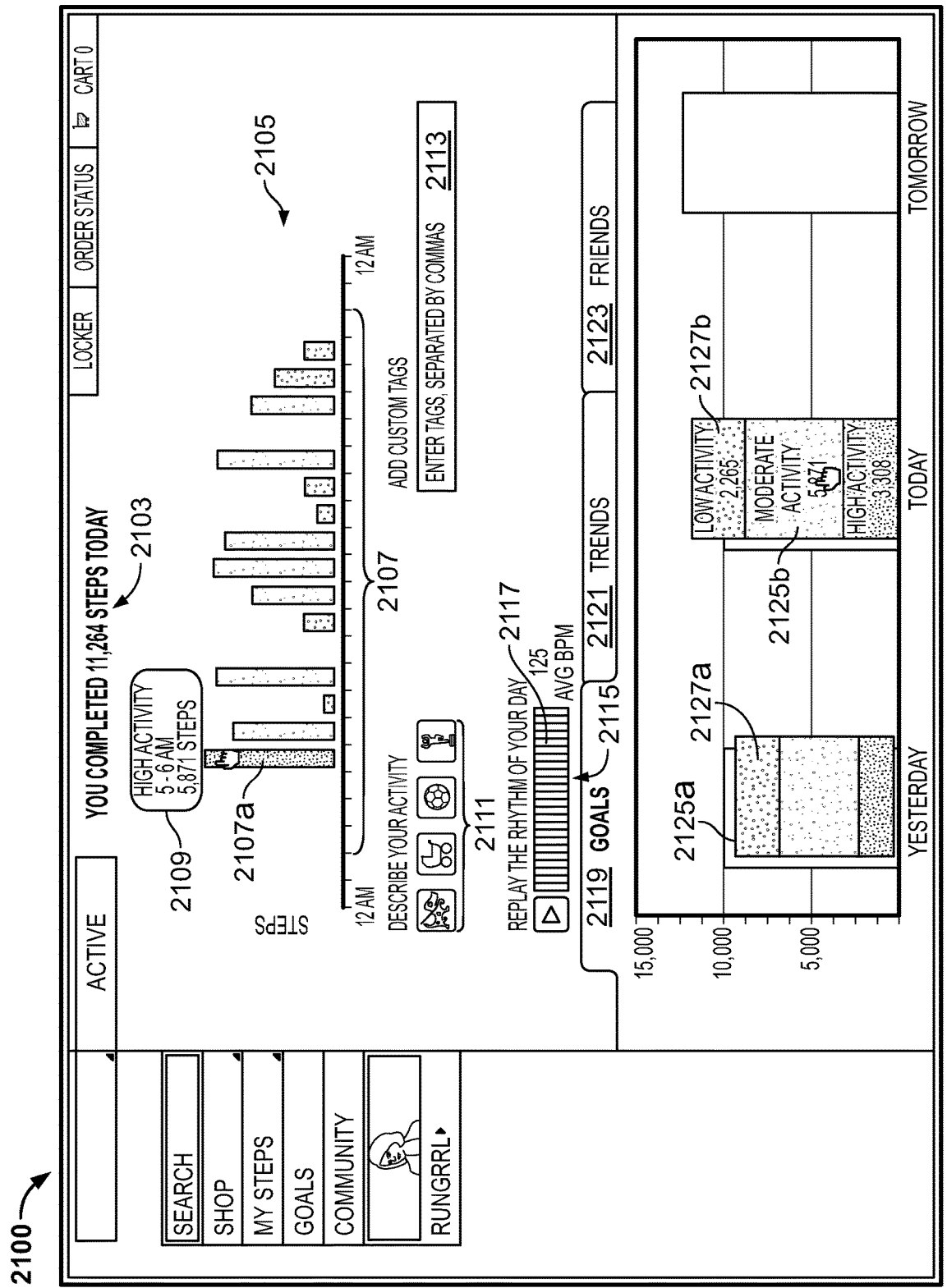
FIGS. 21A-C illustrate example user account pages displaying detailed workout information according to one or more aspects described herein.

Once the user has logged into the site via either existing user login or new user registration, the network site may provide a more detailed interface such as interface 2100 of FIG. 21A. In addition to an indication 2103 of a number of steps performed today, interface 2100 may provide a step tracker 2105 that tracks the number of steps taken on an hourly basis. The step tracker 2105 may be configured to display the number of steps taken on other time scales such as per minute, per 30 minutes, per 2 hours, per day and the like. Hovering over one of athletic performance bars 2107 of step tracker 2105 may trigger interface 2100 to display details about that particular segment of athletic activity. For example, hovering or otherwise interacting with bar 2107a may cause interface 2100 to display detail bubble 2109. Detail bubble 2109 may indicate that the bar 2107a corresponds to a high level activity between 5-6 am including 5,871 steps. The user may further be provided with an option to provide further details on the activity performed by selecting from activity types 2111 and/or adding a custom tag 2113. Custom tag 2113 may be provided so as to allow a user to enter customized notes and information.

Interface 2100 may further provide a replay function 2115 that displays the user's average heart rate throughout the day based on the activity performed and recorded in tracker 2105. The heart rate may be estimated based on a variety of information including user-specific characteristics and general approximations. For example, an estimated heart rate of an individual may be calculated based on weight, age, rate of steps taken (e.g., number of steps per hour) and the like. One visualization includes meter 2117 being filled and emptied based on the changes to the user's estimated heart rate throughout the day.

Other features of interface 2100 may include goals 2119, trends 2121 and friends 2123. Goals 2119 may be used to display a user's level of activity as compared to a defined goal. Goals may be represented by blocks 2125 while a user's actual level of activity may be represented by blocks 2127. Blocks 2127 may further display a breakdown of the level of activity performed including low, moderate and high activity. The level of activity may be determined based on a specified type of activity performed and/or a number of steps taken over a specified amount of time. Trends feature 2121 may be used to graph a user's athletic performance over longer periods of time than what is shown in step tracker 2105. Friends feature 2123, on the other hand, may be provided so that a user may quickly link to or view the athletic performance data, social activity, messages, status updates and other information of his or her friends registered with the network site.

Figure 21B:
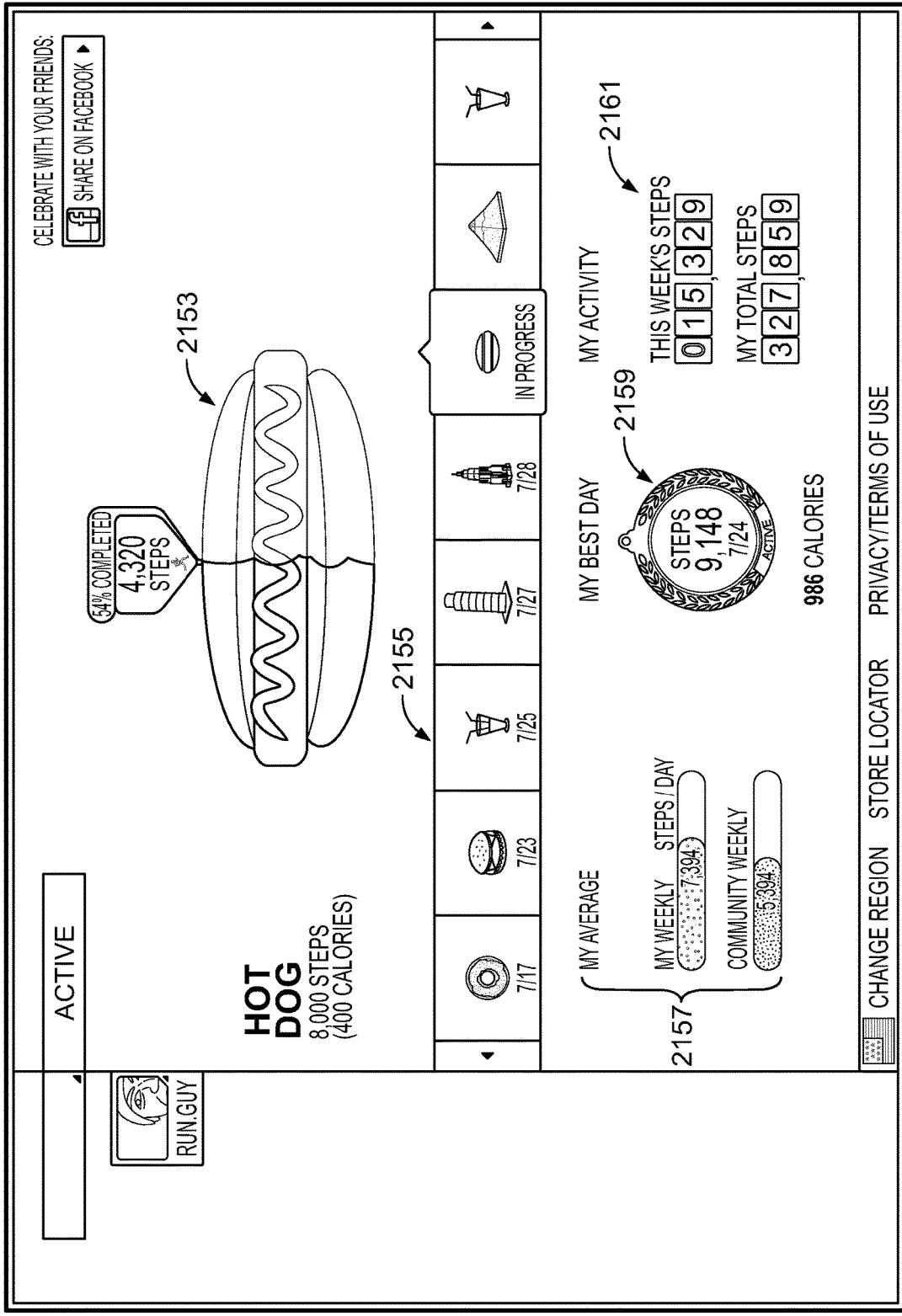

FIG. 21B illustrates an alternative user detail interface that may be displayed upon user login. Interface 2150 includes goal object 2153 that may be used to visually represent and indicate a user's progress. Additionally, a goal tracker bar 2155 may be displayed showing the various goals that may be achieved or that have already been achieved. If a goal has been achieved, the date on which the goal was achieved may be displayed in tracker bar 2155. Additionally, a workout average summary 2157 is displayed with a weekly steps/day average for the user in comparison with a weekly steps/day average for a community (e.g., friends, a group in which the user is a member, all members of the site). Interface 2150 may further display workout details for the user's best day 2159 for a given period of time (e.g., a week, a month, a year). An activity summary section 2161 may further display a number of steps performed this week as well as a total number of steps performed. The total number of steps performed may correspond to a total number of steps recorded in an athletic data collection device.

Figure 21C:
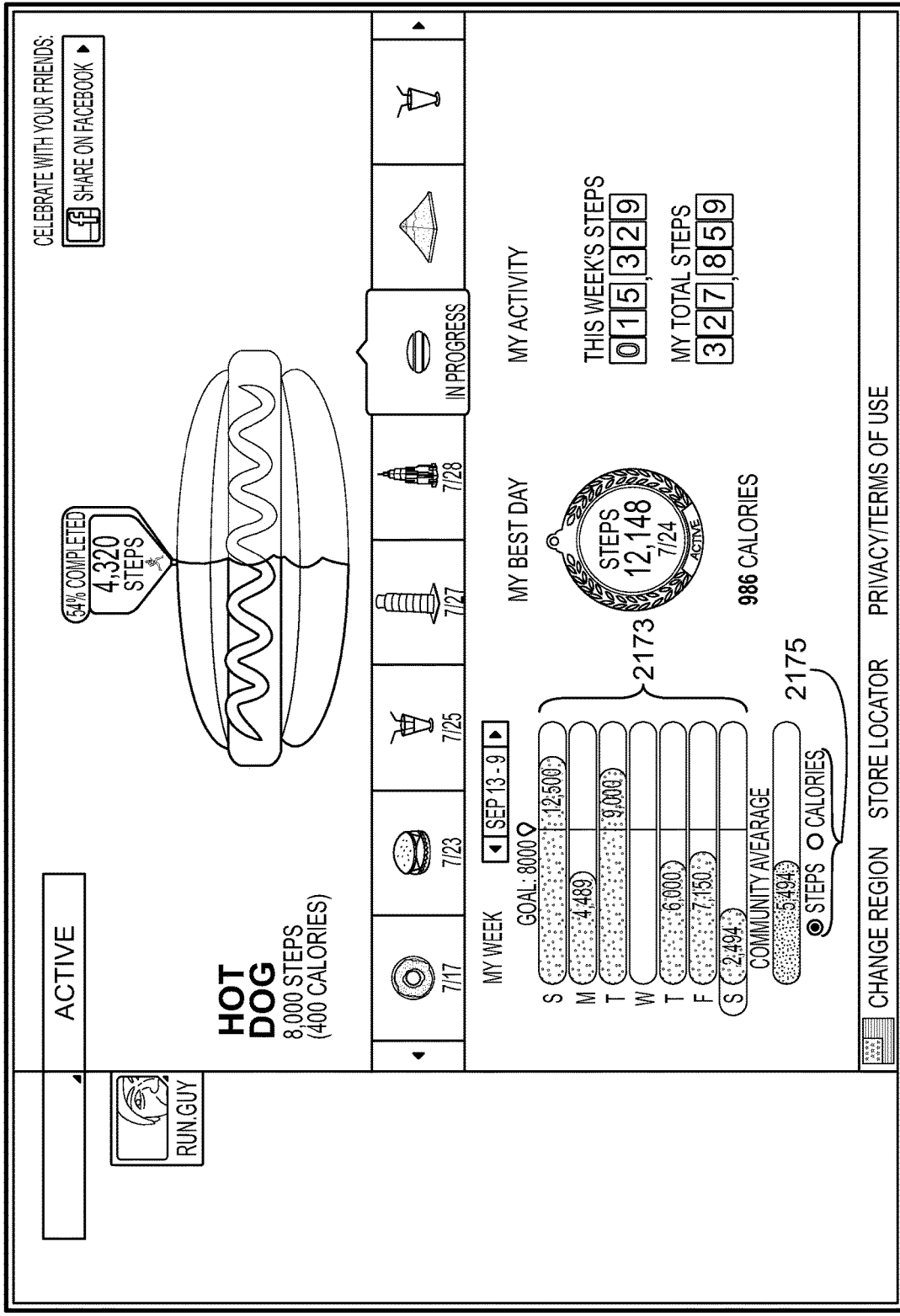

FIG. 21C illustrates another user detail interface similar to that of interface 2150. However, instead of a workout average summary, interface 2170 may display a breakdown 2173 of steps performed for each day of an entire week. The user may also be able to switch the breakdown 2173 between steps and calories using option 2175. In one or more arrangements, the user may also switch between an average summary 2157 (FIG. 21B) and breakdown 2173.

Figure 22:
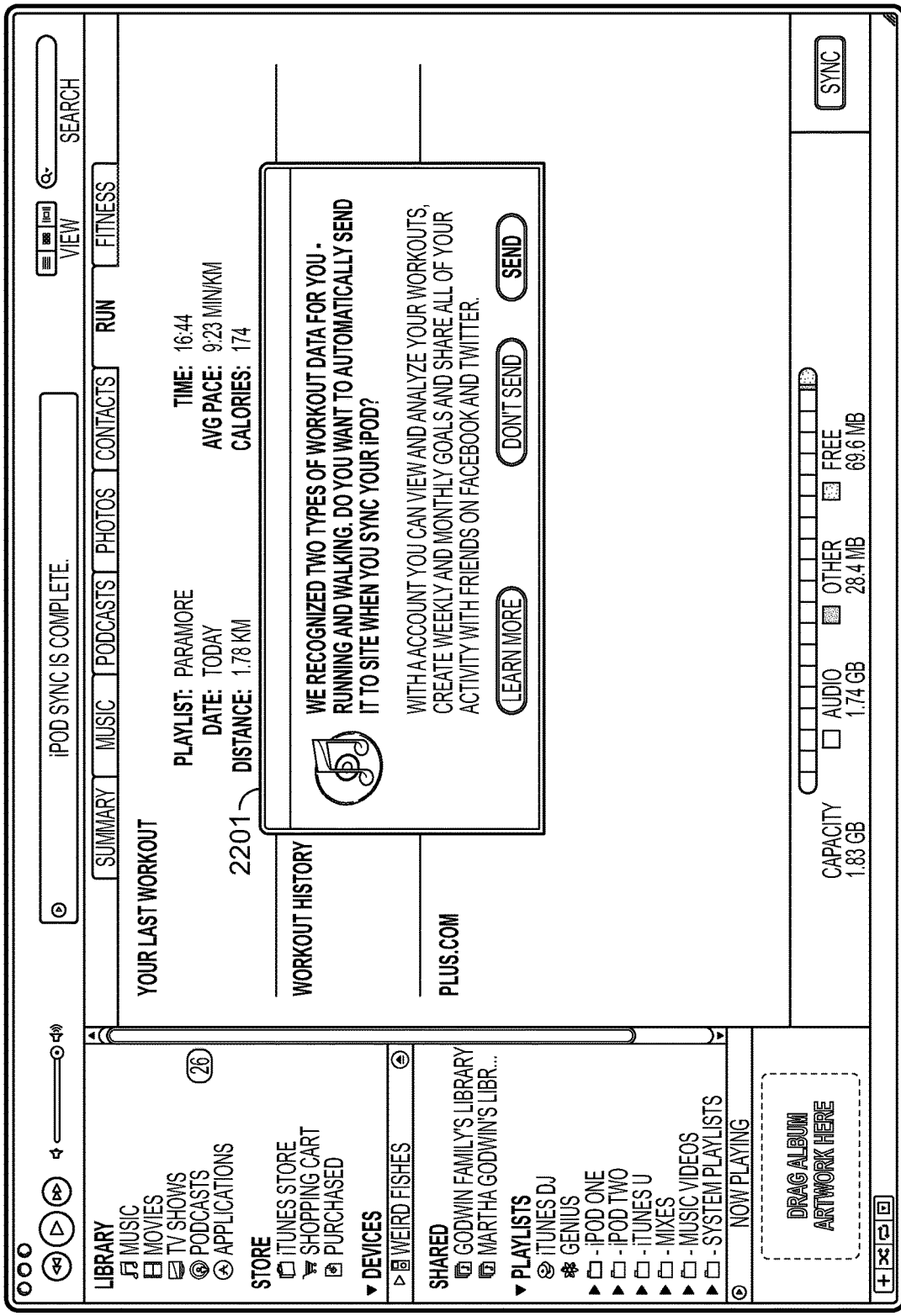
FIGS. 22-24 illustrate example user interfaces for synchronizing one or more of walking data and running data according to one or more aspects described herein.
Figure 23:
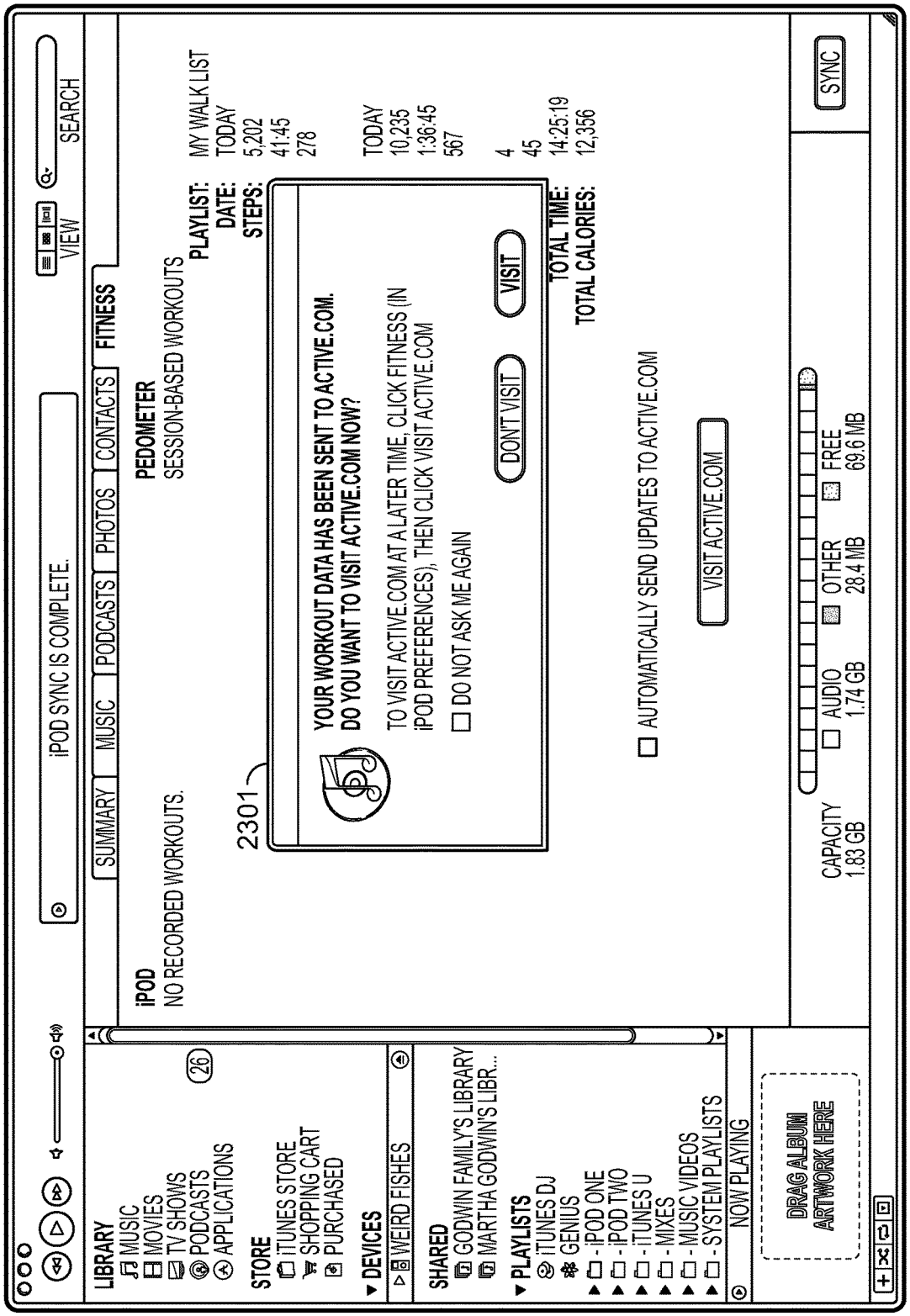
Figure 24:
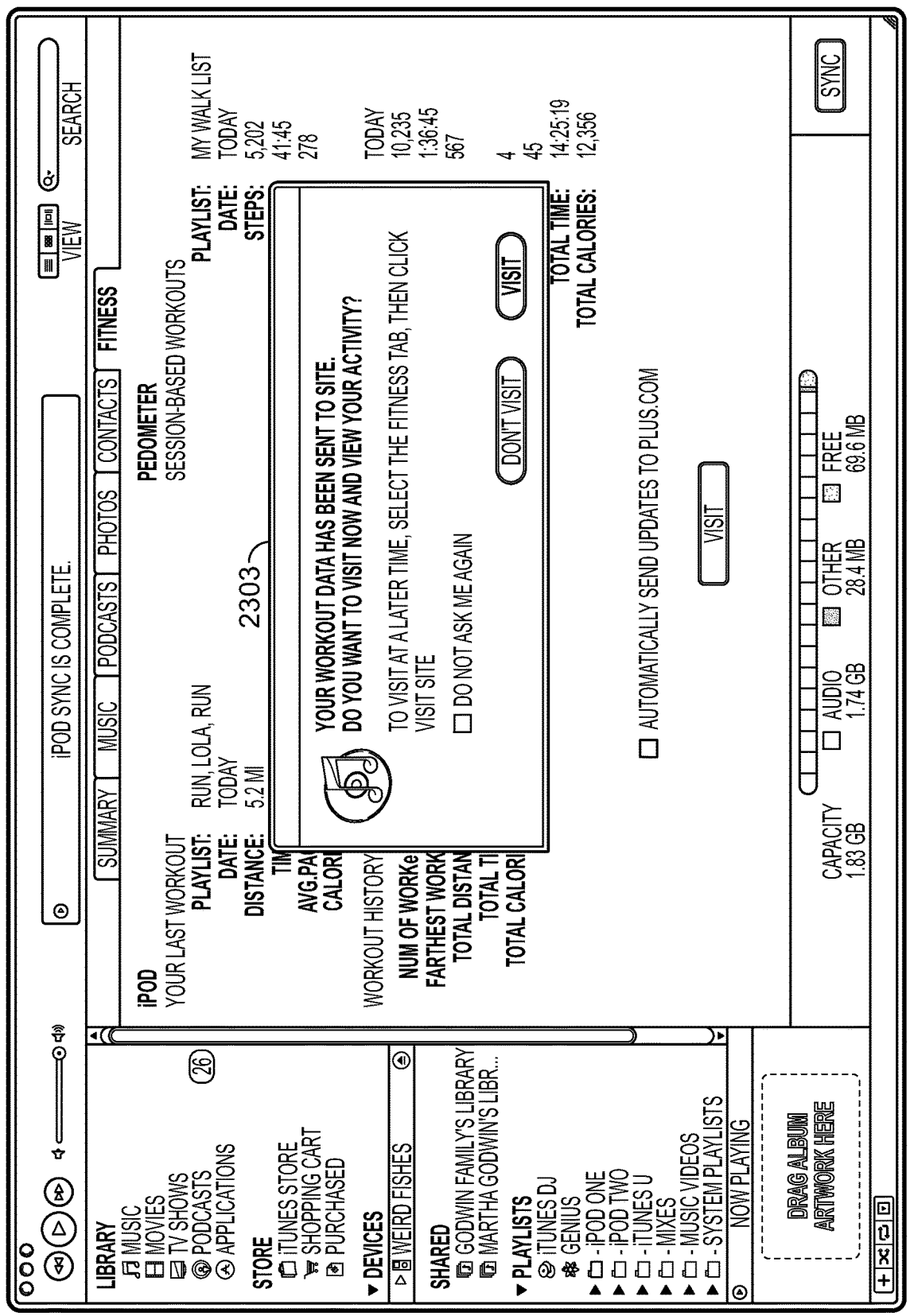

FIGS. 22-24 illustrate alternative interfaces through which athletic activity data may be transmitted to a network site. FIG. 22, for example, illustrates an interface 2200 where the different types of athletic activity may be recognized and transmitted together. For example, prompt 2201 indicates that both running and walking workout data was recognized and asks whether the user wants to send the data to the network site.

Alternatively, in FIGS. 23 and 24, interface 2300 may selectively determine a site to which the data is to be sent based on the type of data detected. For example, in FIG. 23, prompt 2301 asks whether the user would like to visit a walking specific network site based on recognizing and transmitting only step-based workout data. FIG. 24, on the other hand, illustrates a prompt 2303 that asks the user whether the user would like to visit a general workout site when the workout data includes both running and walking athletic activity data.

Figure 25:
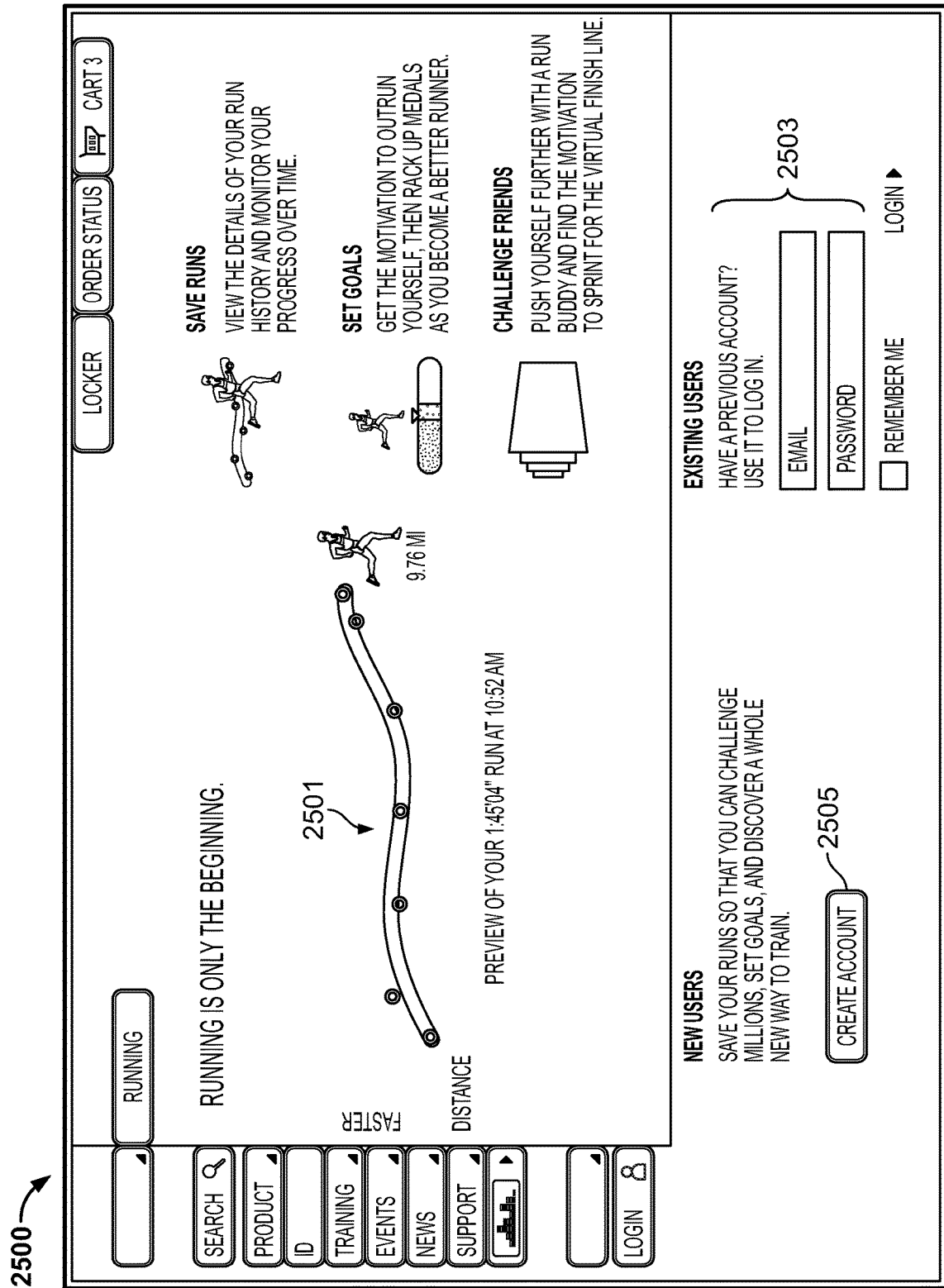
FIG. 25 illustrates an example soft login when running data is synchronized with an athletic activity tracking and monitoring site according to one or more aspects described herein.

FIGS. 25-28 illustrate various pages of a network site that is configured to monitor and track a variety of workout data types. FIG. 25 illustrates a soft login page 2500 that is focused on running, but provides support for other types of workouts such as walking and other step-based activity. Page 2500 may provide a visual summary 2501 of a current or planned workout as well as a login interface 2503 and an opportunity 2505 to create an account. As noted herein, user details and more detailed activity information might not be available until the user has logged into an account. Once the user has logged in, additional athletic activity information and user-specific data may be displayed for browsing.

Figure 26:
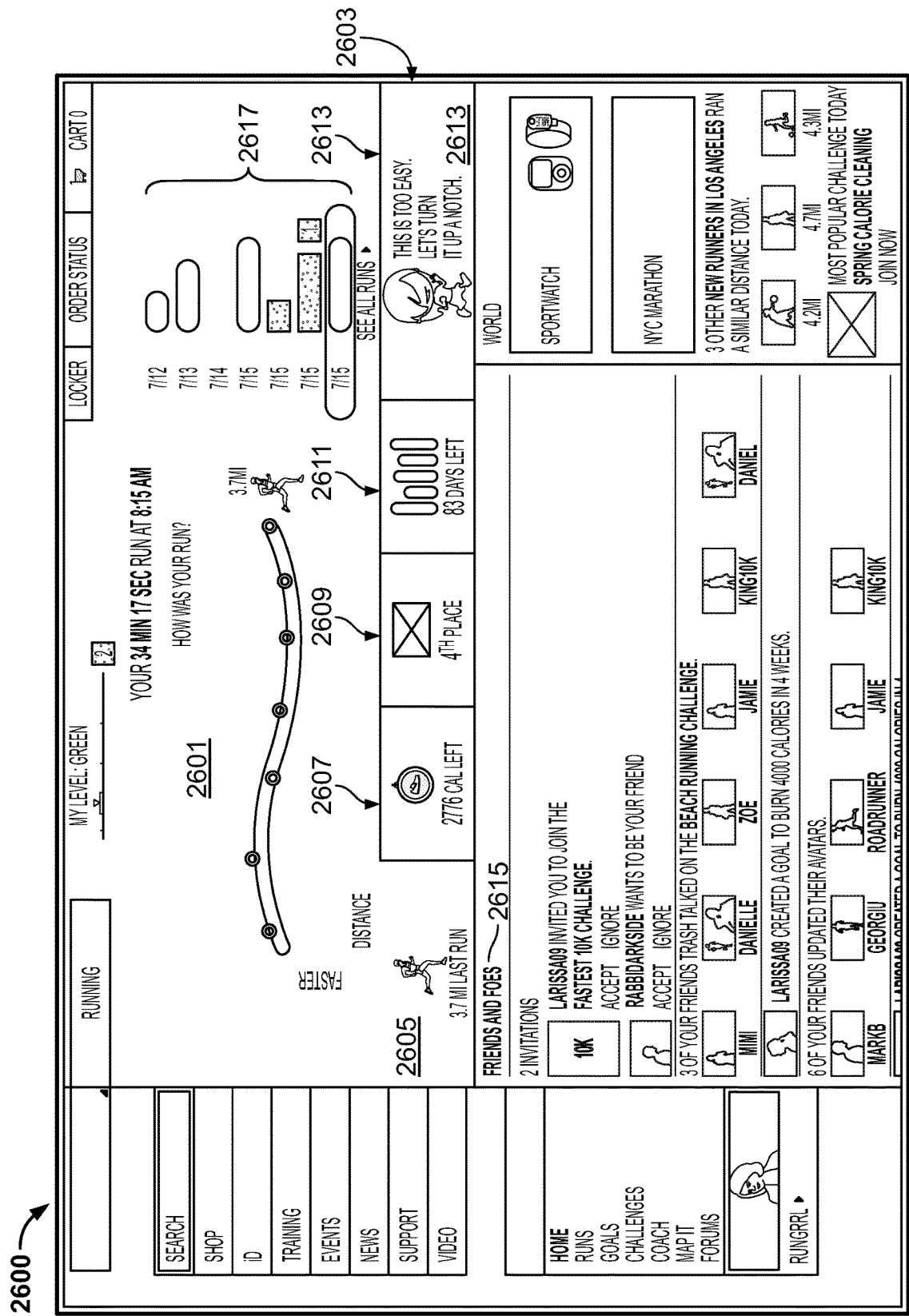
FIGS. 26-28 illustrate user account pages having interfaces that allow a user to switch between viewing running data and walking data according to one or more aspects described herein.

FIG. 26 illustrates a user's account page where a summary of a run on July 15 is visually summarized in section 2601. The user's run is depicted by a line graph plotting pace over time. Section 2601 may provide an indication of the amount of time spent performing the activity as well as a time the activity occurred and total distance run. Page 2600 may further include summary and goal tracking information in tracker bar 2603. For example, tracker bar 2603 may provide a summary 2605 of a most recent run, a number of calories left to burn 2607, a position 2609 in a race, challenge or other competition, a number of days left 2611 to achieve a goal, finish a competition or the like and/or a workout recommendation 2613. Workout recommendation 2613 may provide the user with the option to modify their planned workout to increase or decrease the level of difficulty depending on the user's past performance. Additionally, a friends and foes section 2615 is provided in interface 2600 to display messages from or about friends or adversaries (e.g., friendly competitors) in a social network. Social networks may be built around a particular athletic activity, a particular challenge, a goal, an area, athletic level and the like.

Multiple activities performed on the same day may be tracked and recorded separately from one another to provide a distinct breakdown 2617 of a user's day. In one example, workouts may be separated based on type of activity, whether the workout is a session workout or a daily workout and the like. In one or more configurations, step activity data may be monitored and tracked separately from running data. For example, a distance or pace a user walked might not be counted towards running distances and levels and vice versa. Instead, a separate distance and/or pace tracker may be provided for each of running activities and walking activities. Accordingly, multiple workouts may be recorded and displayed for a single day (e.g., July 15 includes 4 different workouts).

Figure 27:
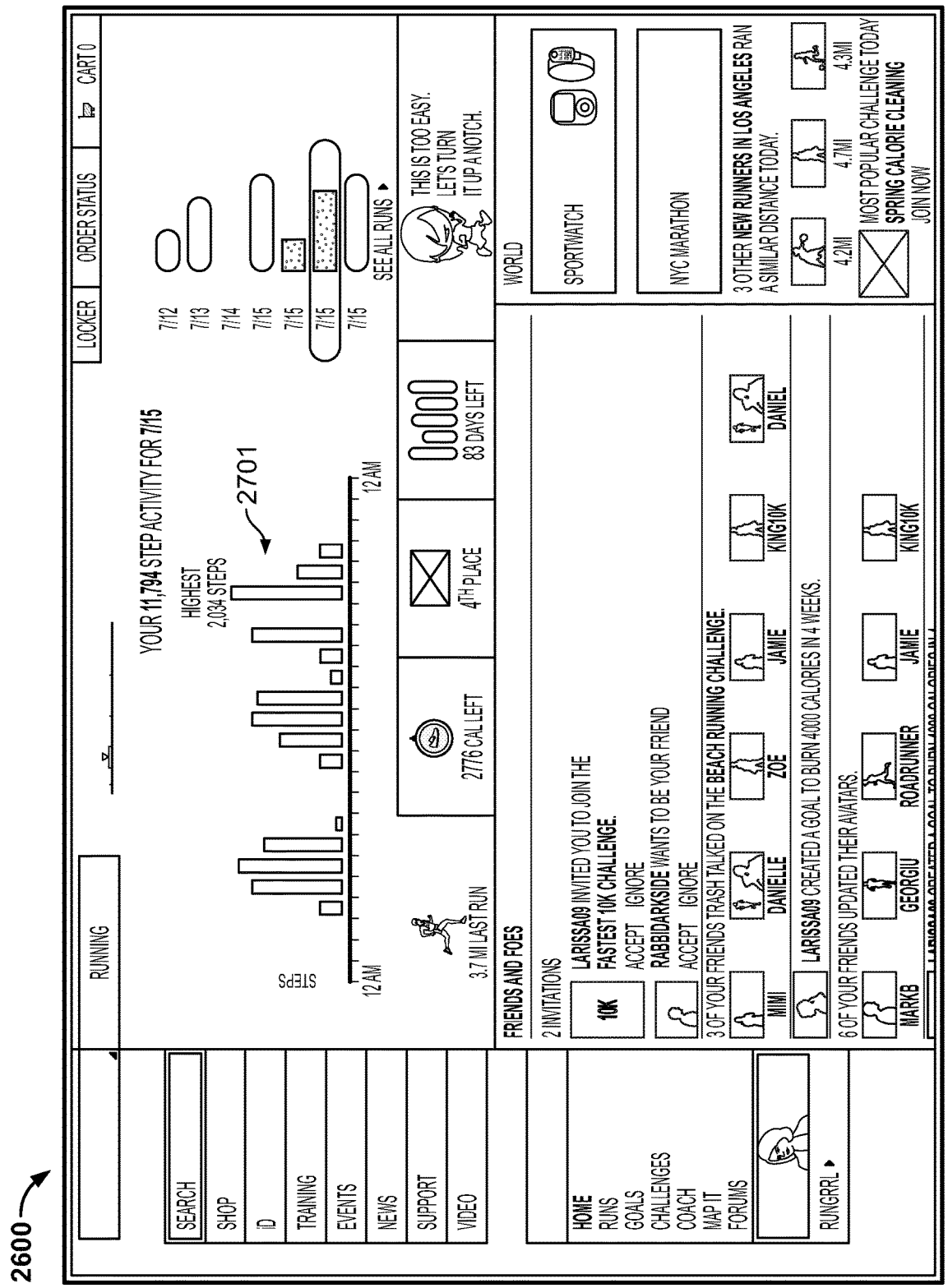
Figure 28:
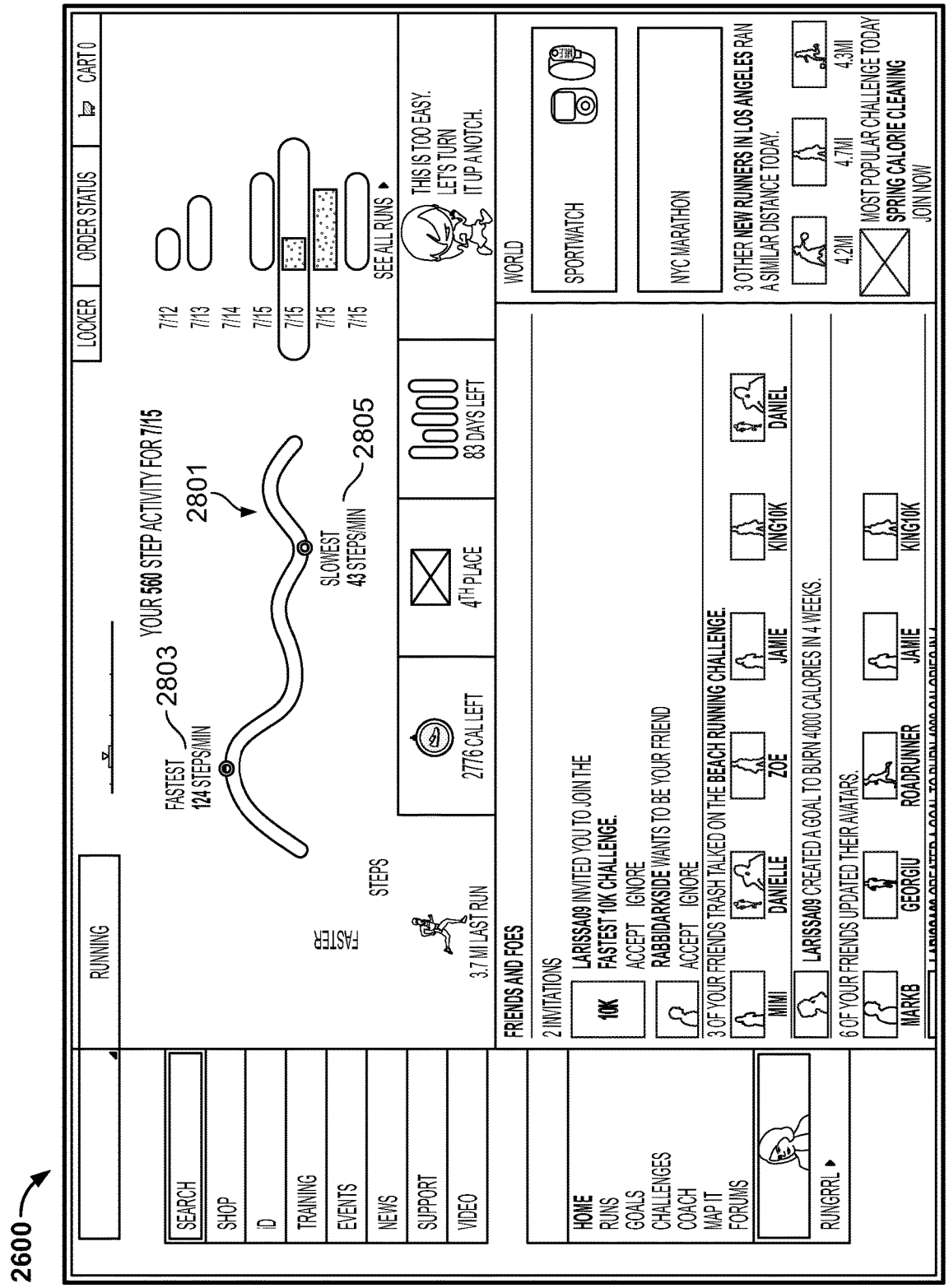

FIGS. 27 and 28 illustrate interface 2600 where summaries for two different step activities performed on the same day, i.e., July 15, are displayed. In particular, FIGS. 27 and 28 provide two different types of visualizations for the step activity data. For example, FIG. 27 illustrates a bar graph 2701 charting the number of steps performed against the time of day. FIG. 28, on the other hand, illustrates a line graph 2801 charting the pace of the user versus time. Pace may be expressed in terms of steps/min, steps/hour, calories burned/min, calories burned/hour and the like. The fastest pace 2803 and the slowest pace 2805 may be identified on the line graph. Other points and/or benchmarks may be identified such as an average pace line. In one or more arrangements, the way in which athletic activity is visualized may be changed using one or more visualization options (not shown) as further described herein.

Figure 29:
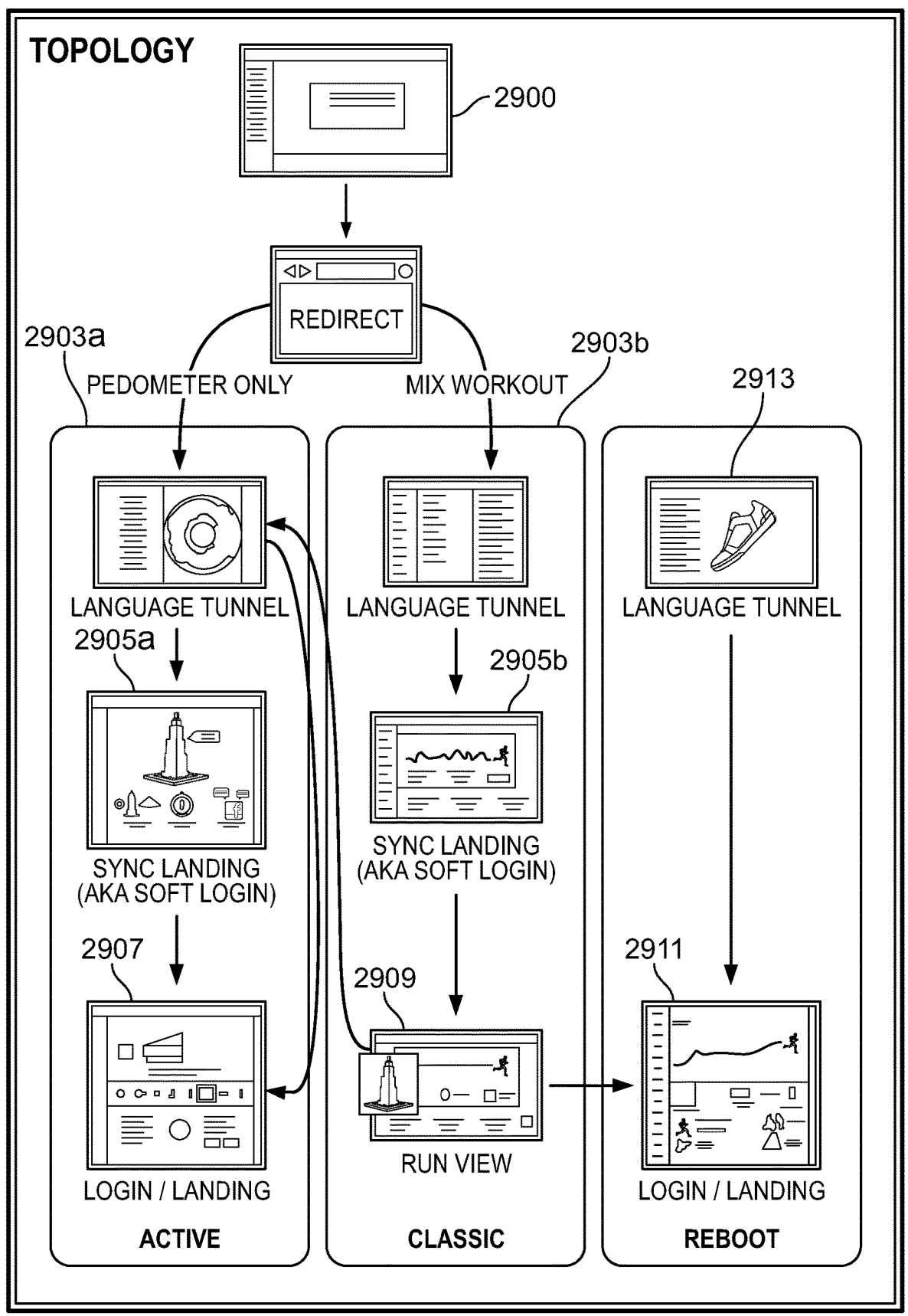
FIG. 29 illustrates a navigation topology for synchronizing workout data and visiting an athletic activity tracking and monitoring site receiving the workout data according to one or more aspects described herein.

FIG. 29 illustrates a navigation topology whereby athletic activity data may be collected by an application 2900 and transmitted to a network site. Application 2900 may then be configured to direct the user to one of two sites depending on the type of athletic activity data detected and collected. For example, if only step-based activity data is detected, application 2900 may redirect the user to a step-specific network page (e.g., page 2100 of FIG. 21). Alternatively, if both step-based and run workout data is detected or if only run workout data is detected, the user may be redirected to a running activity network page (e.g., page 2600 of FIG. 26). In one or more examples, the network page to which a user is redirected may include a series of pages including language selection pages 2903 and soft login pages 2905.

In a step-based network site, a user may be redirected to a user-specific detailed workout page 2907 for tracking and monitoring the user's walking or other step-related activity. In examples where a user is redirected to a run-based network site, the user may be redirected to a user-specific general view page 2909 that may display summaries for both run workouts and walking or step-based workouts. Upon selection of a run workout, the user may then be redirected to a user-specific run workout page 2911 for tracking the user's run activities. Alternatively, if the user elects to view walking activities, the user may be redirected to language selection page 2903a and subsequently to user-specific detailed workout page 2907, bypassing the soft login page 2905a (since the user already logged in at soft login page 2905b). Various reconfigurations of the topology may be performed based on user or client preferences for navigation. For example, if a user elects to view walking or step-related workouts from general view page 2909, the user may be directed to detailed workout page 2907 based on the language selected from language selection page 2903b thereby bypassing selection page 2903a.

Alternatively or additionally, a user may directly access run-specific workout page 2911 by manually navigating to a corresponding network site address for page 2911. The user may be asked to choose a language from language selection page 2913 prior to entering the site. In one or more arrangements, a user may be directed to a login page (not shown) prior to being allowed to access user-specific run workout page 2911. In yet another arrangement, application 2901 may redirect the user automatically to language selection page 2913 upon detecting only run based workout data.

Figure 30:
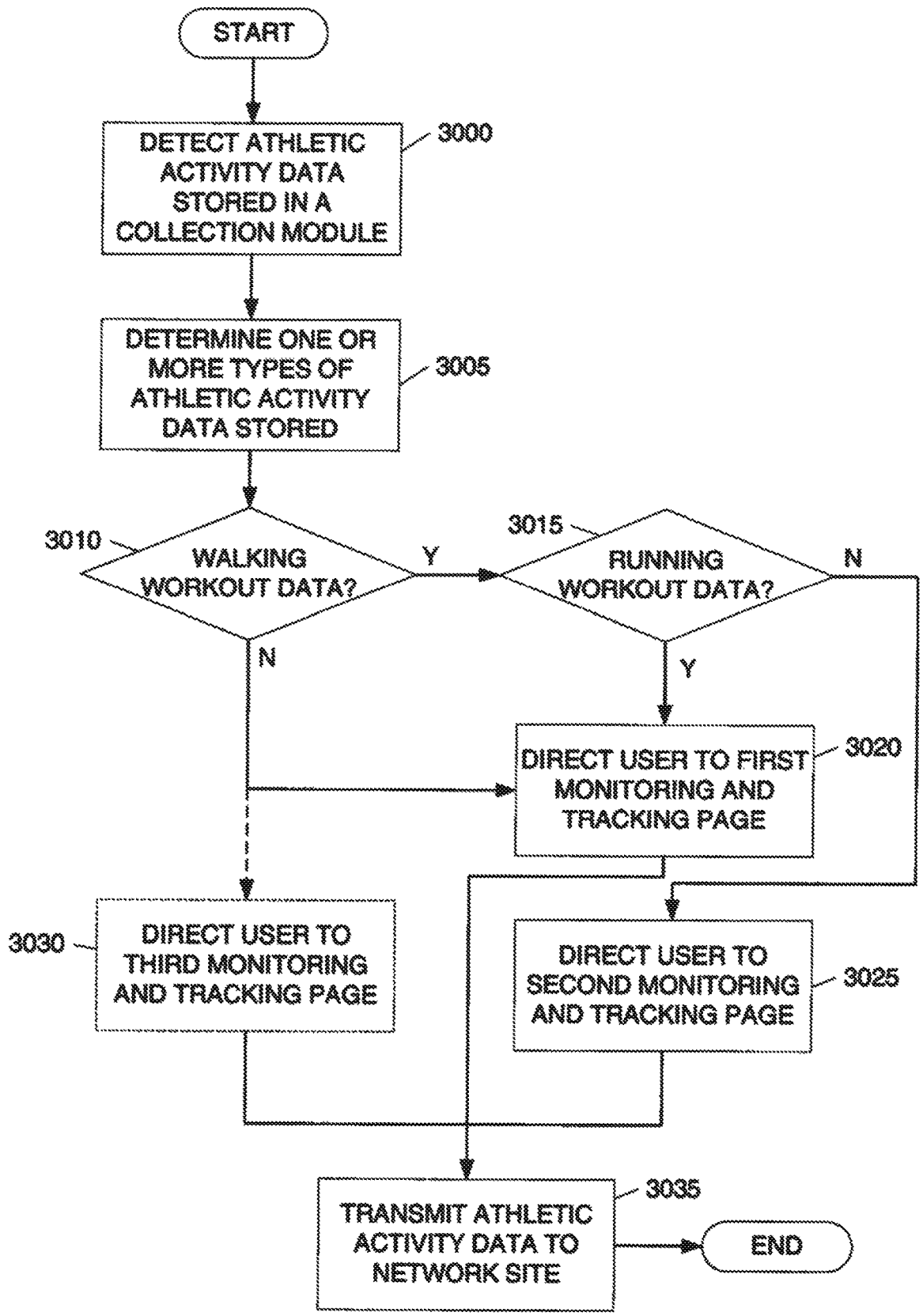
FIG. 30 is flowchart illustrating an example method for selecting a page or site to direct a user based on workout data types detected according to one or more aspects described herein.

FIG. 30 illustrates a method by which a user may synchronize workout data from a workout information collection device with an athletic activity monitoring and tracking system. In step 3000, a system may detect athletic activity data stored in a data collection module. The system may include software, hardware and/or combinations thereof that are configured to provide data collection modules that may be connected either through wired means or wireless means (e.g., short-range or long-range protocols such as WiBree, BLUETOOTH, Ethernet, IP). In one example, the system may detect athletic activity data only if new data has been collected since a previous synchronization. The system may determine if new data exists by comparing the data stored in the collection module with data stored by the system. Alternatively, the system may detect if any athletic activity data exists regardless of whether the data was previously synchronized.

Upon detecting athletic activity data stored in the collection module, the system may, in step 3005, determine the types of athletic activity data stored. Such a determination may be performed by examining data identifiers stored in association with the data. For example, data entries for workout data may include tags that specify the type of activity performed or a unit in which the data was collected. Thus, in one or more examples, walking or step activity may be identified by the unit steps while running activity may be identified by units such as miles per hour, miles or other distance unit and the like. In step 3010, the system may determine whether the athletic activity data includes walking workout data. If not, the system may determine that the data only includes running data and direct the user to a first monitoring and tracking page of a remote network site that is configured to monitor and track both running and walking activities in step 3020. Alternatively, the user may be directed to another monitoring and tracking page that is configured to monitor and track only running activities in step 3030 in response to determining that the data includes only running data.

If the detected activity data does include walking data, the system may subsequently determine whether the data also includes running data in step 3015. If so, the user may be directed to the monitoring and tracking page that is configured to monitor and track both running and walking workouts as described in step 3020. If however, the data only includes walking data, the user may be directed to another monitoring and tracking page that may, in one or more arrangements be specific and dedicated to walking workouts, as shown in step 3025.

In any of the above cases, the athletic activity data detected from the collection module may further be transmitted to a remote network site associated with the monitoring and tracking page to which the user is directed in step 3035. According to one aspect, the same remote network site may provide the different monitoring and tracking pages. In another arrangement, different sites may provide the different pages.

Data Monitoring and Tracking

Figure 31:
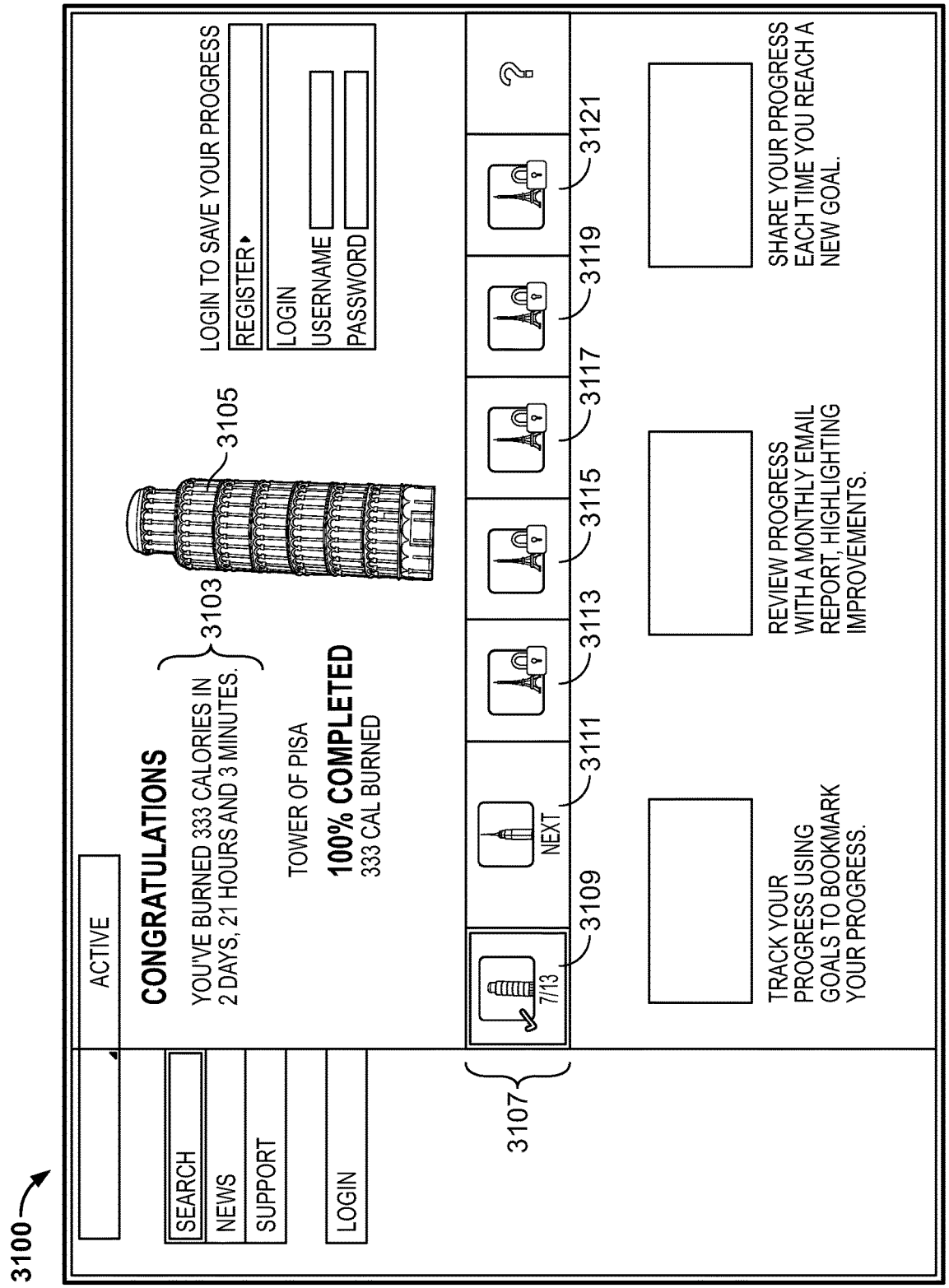
FIG. 31 illustrates a soft login interface in which a user is shown a plurality of goals that may be achieved according to one or more aspects described herein.

FIG. 31 illustrates an example soft login page 3100 that may be provided with limited workout and user specific data prior to the user logging in to the corresponding athletic activity tracking and monitoring site. Soft login page 3100 may include a summary 3103 of the workout data received or collected including a number of calories burned, the amount of time spent workout out and a percentage of a goal completed. The goal may be represented by an object such as a building, a food item, a road, an energy meter and the like. For example, an energy meter may fill up as the user reaches a specified goal. In another example, a building may be used to visually represent a number of calories to be burned or steps to be walked while a food item may be used to visualize a number of calories to be burned or a corresponding number of steps that must be walked to burn those calories. Soft login page 3100, for example, uses the Tower of Pisa building 3105 to represent the goal to be achieved. In particular, the number of calories to be burned or the number of steps to be performed may approximately equal the number of calories burned walking to the top of building 3105 or the number of steps required to walk to the top of building 3105, respectively. Building 3105 may be shaded, colored or otherwise modified appearance-wise depending on the progress of the user. Thus, if the user has only completed 33% of the goal, building 3105 may be shaded 33% of the way to the top. Alternatively, if the user has completed the entire goal (as illustrated), building 3105 may be entirely shaded.

Soft login page 3105 may also include a goal tracker bar 3107 displaying a series of goals that may be completed in a specified order. For example, once a user has completed goal 3109 corresponding to building 3105, a user may progress to a subsequent goal 3111. In some arrangements, a user might only be able to view and/or select goals 3113-3121 upon the user completing the immediately preceding goal, a number of goals and/or earning an amount of virtual currency/credits. As illustrated, goal 3113 is locked (represented by the lock icon) or hidden (e.g., a generic or grayed out image of a goal) since the user has not completed goal 3111. Goal 3111 is viewable and selectable because the user has completed present goal 3109, as indicated by the check mark. Other completion indicators may also be used.

Figure 32:
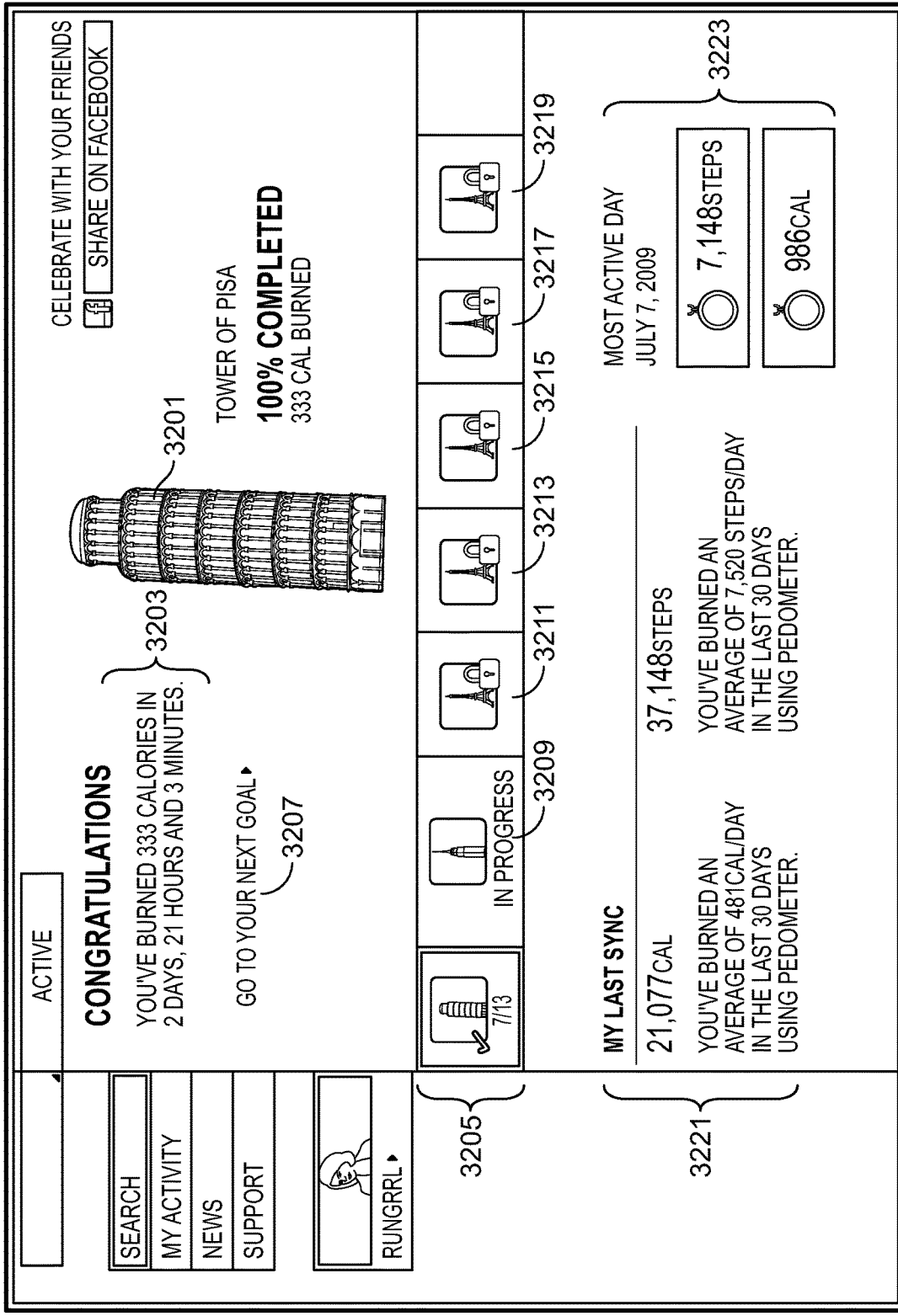
FIGS. 32-36 illustrate interfaces for a user-specific account page in which the user may progress from goal to goal and view information of the various goals according to one or more aspects described herein.

FIG. 32 illustrates an athletic activity monitoring interface 3200 that may appear once a user has logged into the athletic activity monitoring and tracking network site. Interface 3200 may include some similar elements to page 3100 of FIG. 31. For example, interface 3200 may include goal object 3201, goal summary information 3203 and goal tracker bar 3205. Interface 3200 may further include an option 3207 that allows the user to progress from current goal 3209 to the next goal, e.g., goal 3211. Additional goals 3213-3219 may be hidden or locked until a previous goal has been completed. Interface 3200 may further include a synced data section 3221 that provides a summary of calories burned and/or steps performed from a most recent synchronization. Synchronization may include an upload, comparison and reconciliation of athletic workout data between an athletic activity data collection device and the network site. Synchronization may be performed for all data stored in an athletic activity data collection device and/or data stored for a specified period of time. In addition to synchronized data, interface 3200 provides a most active day section 3223 that displays the date of and the athletic activity data such as calories burned and steps performed for the user's most active day.

Goal objects such as goal object 3201 may be automatically or user selected. For example, goal object 3201 may be selected based on an estimated number of calories burned or steps required to achieve some result with respect to the object. In a particular example, a building such as the Tower of Pisa may be chosen based on a determination that 1000 steps are required to reach the top of the building. In another example, a food item such as donut may be used to represent a goal. A network site may then determine a number of calories corresponding to eating the donut and a number of steps needed to burn off that number of calories. In one or more arrangements, a number of calories burned may be approximated based on a default set of user characteristics or on user-specific attributes such as weight, height, age and the like. Goal objects may be positioned in goal tracker bar so as to represent a progression from a less difficult goal to a more difficult goal. Additionally, if a user manually selects a number of calories to burn or steps to perform, the network site may automatically determine and select a goal object based on the user-specified goal parameters (i.e., number of calories or steps). Alternatively, a user may define goals by selecting the goal object. The network site may then determine the goal parameters based on the selected goal object.

Figure 33:
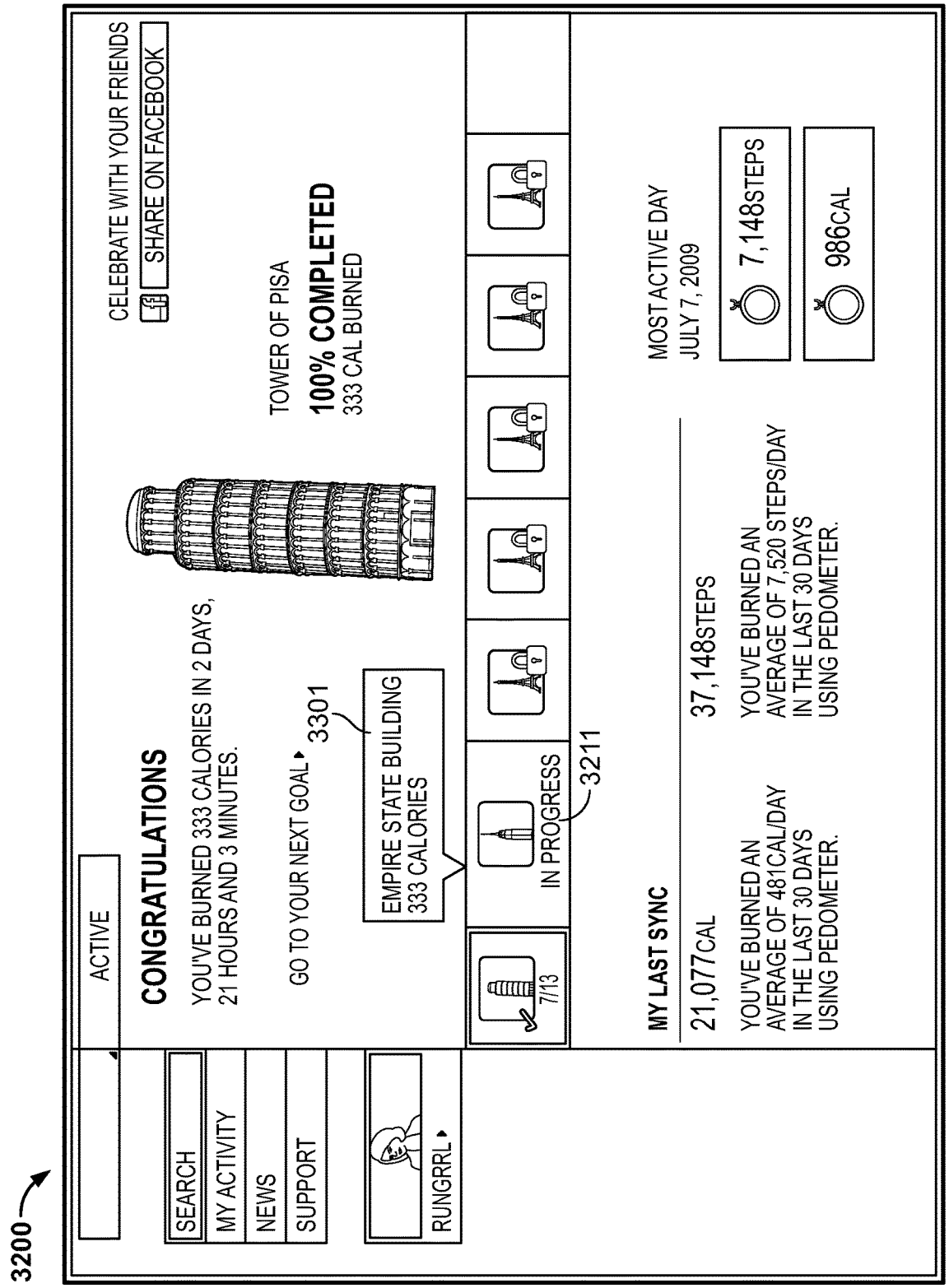

FIG. 33 illustrates interface 3200 upon the user hovering a cursor or other control element (not shown) over new goal 3211. Upon hovering over or otherwise interacting with new goal 3211 in goal tracker bar 3205, a detail bubble 3301 may be displayed. Detail bubble 3301 may display details regarding goal 3211 including a name of the goal object and a number of calories to be burned.

Figure 34:
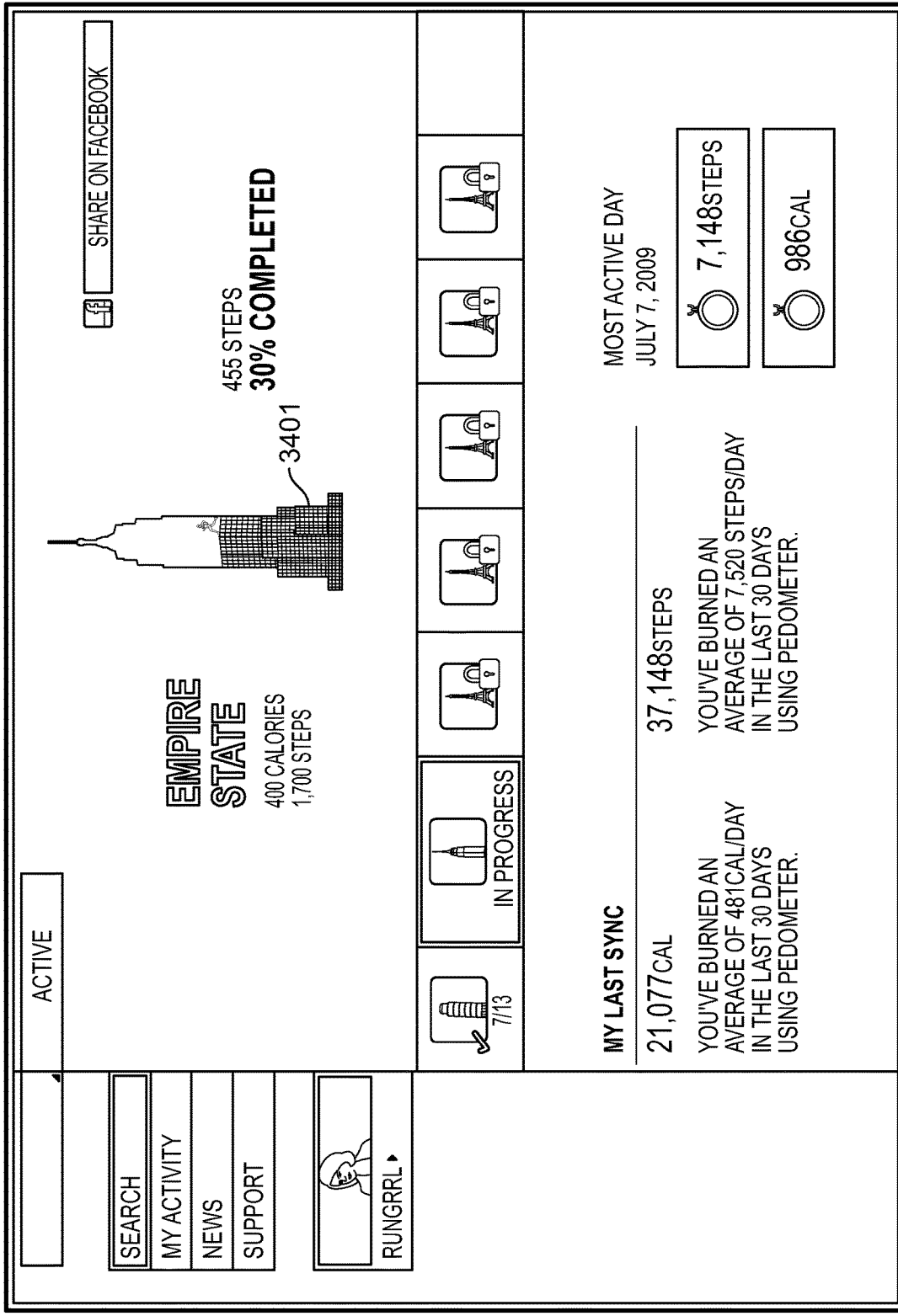

FIG. 34 illustrates interface 3200 upon the user selecting next goal option 3207. Interface 3200 includes the new goal object 3401, i.e., the Empire State Building, along with a target number of calories to be burned and a target number of steps. New goal object 3401 may indicate progress toward completing the goal. The progress may be based on steps or calories burned already completed in excess of the previous goal. Accordingly, the network site may roll over calories burned and steps performed exceeding the required amount to complete a previous goal. For example, if 1500 steps are required to complete goal 3209 and the user performs 1955 steps, the extra 455 steps may be applied to new goal object 3401. Alternatively, excess steps or calories burned might not be carried over. Thus, regardless of the number of steps taken or calories burned in achieving goal 3209, for example, the user may be required to start at 0% completion with new goal object 3401 corresponding to new goal 3211 in tracker bar 3205.

Figure 35:
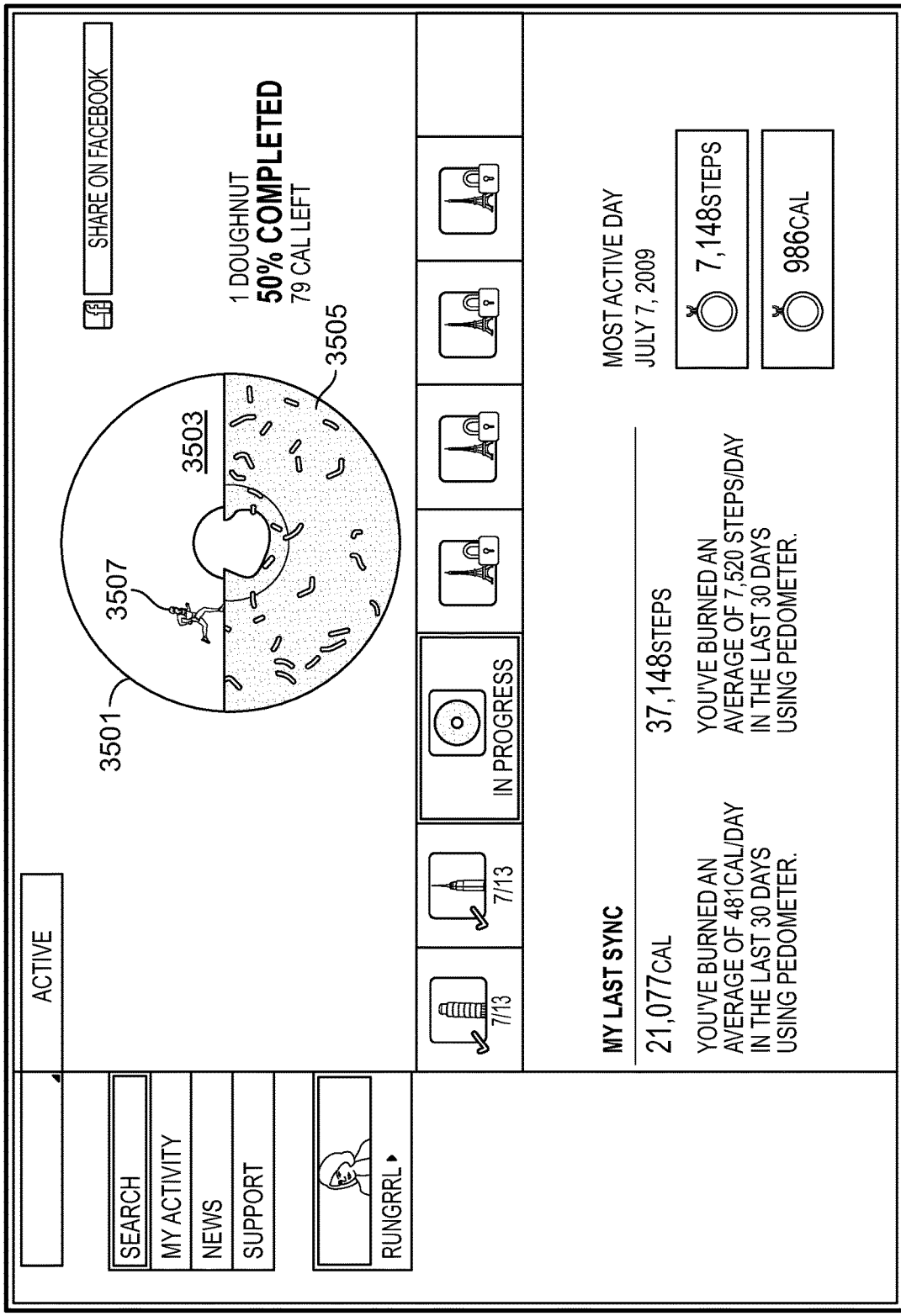

FIG. 35 illustrates interface 3200 displaying subsequent goal object 3501 which, in this illustrative example, is a food item upon a user completing goal 3211. The amount of progress the user has achieved toward completion of the goal may be visualized by displaying an outline of the food item 3501 for the uncompleted portion 3503 and displaying the foot item image or texture for the completed portion 3505. According to one or more aspects, an icon 3507 representative of the user may be displayed in or on goal object 3501 to mark the current level of progress.

The type of object selected for a goal may depend on the type of goal the user is attempting to achieve. For example, if a user wishes to burn a certain number of calories, the network site or system may select a food or beverage object since food and beverages are commonly associated with calories. Alternatively, if the user wishes to take or perform a specified number of steps, the system may select a building, location, path or the like that is conceptually more aligned with performing steps.

Figure 36:
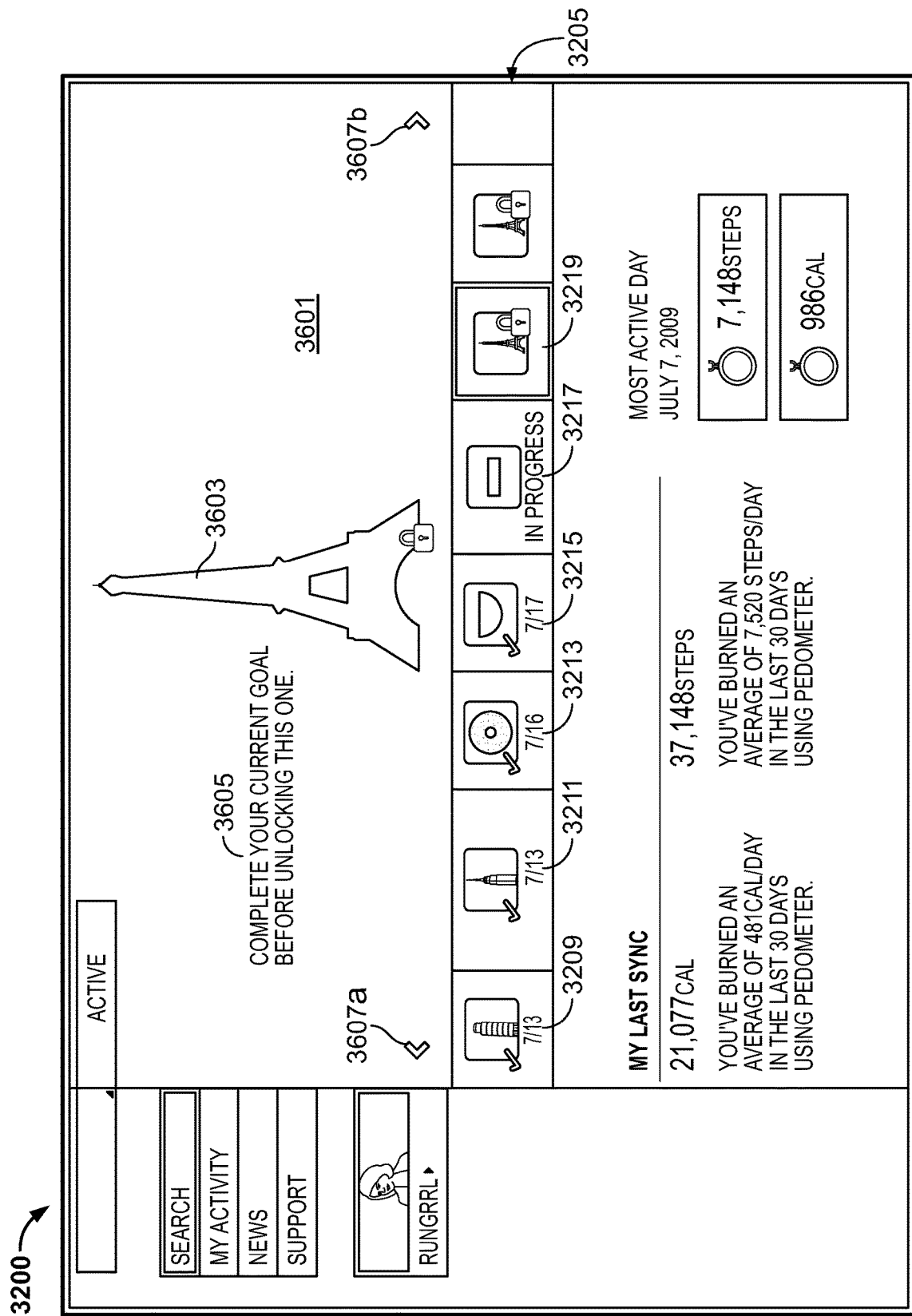

FIG. 36 illustrates interface 3200 where a user has completed goals 3209-3215 and is the process of completing goal 3217. The user may select a subsequent goal such as goal 3219 in tracker bar 3205 to view what lies ahead. However, if the user has not completed the immediately preceding goal, i.e., goal 3217, display section 3601 might display a generic image 3603 that does not reveal or otherwise keeps hidden the new goal object. Message 3605 may indicate to the user that he or she must complete the current goal 3217 prior to unlocking the selected goal 3219 and corresponding goal object 3603.

If the number of goals that a user wishes to achieve cannot all be displayed simultaneously on goal tracker bar 3205, goal tracker bar 3205 may include scroll buttons 3607 that are configured to scroll goal tracker bar 3205 in one or more directions. According to one or more configurations, scroll buttons 3607 may have a first appearance (e.g., a color, shade, shape) if no additional non-displayed goals are present on the goal tracker bar 3205 in the direction corresponding to the scroll buttons 3607a and/or 3607b. If, on the other hand, additional non-displayed goals are present on the goal tracker bar 3205, the scroll buttons 3607a and/or 3607b may have a second appearance.

Figure 37:
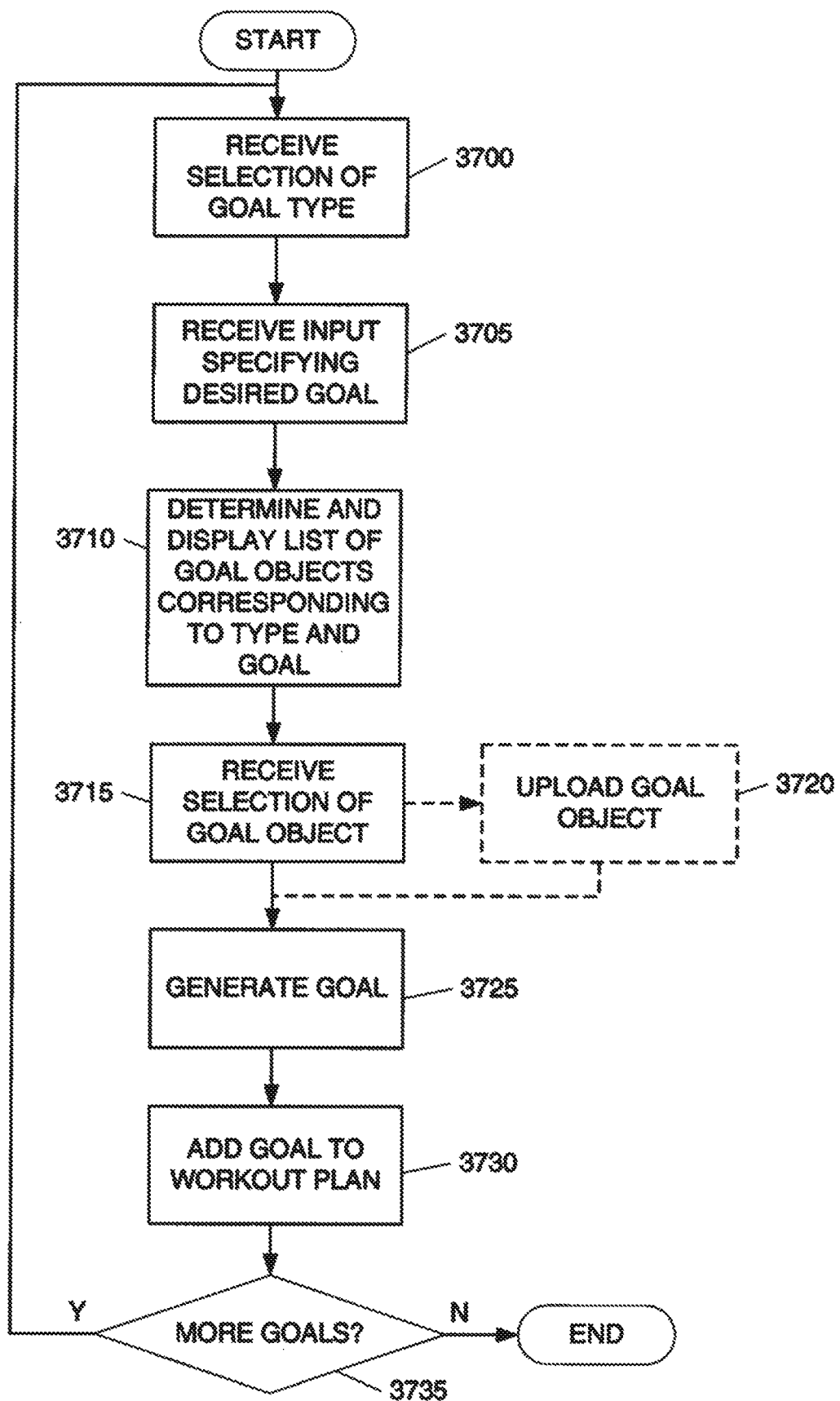
FIG. 37 is a flowchart illustrating an example method for creating a goal and/or workout plan according to one or more aspects described herein.

FIG. 37 illustrates a method by which a user may create and/or define goals and create a workout plan. In step 3700, an athletic activity tracking and monitoring system may receive a user selection of a goal type. The selectable goal types may include steps, calories, pace and the like. The user may select the goal type from a web page prompt or through an application based interface. In step 3705, the system may prompt for and receive input specifying the desired goal corresponding to the selected goal type. For example, if a user selects calories to burn, the user may enter 500 calories as the goal. On the other hand, if the user selects steps, the user may enter 1500 steps as the user's goal. In step 3710, the system may determine and display a list of available goal objects corresponding to the selected type and goal. The goal object is generally configured to visually represent a user's intended goal. Thus, if a user wishes to burn calories, a picture of a food item or beverage may be used. Alternatively if a user's goal is to walk a certain number of steps, a building, park, or the like may be used as the goal object. Accordingly, the system may identify goal objects that are associated with the goal type and also the goal. For example, if the user's goal is to burn 500 calories, the system may select a goal object that is approximately equal to 500 calories such as two donuts, a small milk shake and the like. On the other hand, if the user's goal is to walk a number of steps, the system may identify objects such as buildings that would approximately require that number of steps to traverse (e.g., reach a top floor, finish a trail).

In step 3715, the system may receive a user selection of a goal object from the displayed list of goal objects. Optionally, receiving the user selection of the goal object may be accompanied by the system uploading the goal object from a remote location in step 3720. For example, if a user wishes to use an image that is not already stored in the system, the user may upload the image from his or her computer or refer the system to a particular webpage or network site. The system may then generate the goal by specifying the entered parameters in association with the goal object in step 3725. For example, the image of the goal object may be stored in association with the user specified goal and the user's account in a goal or user database. In step 3730, the goal may be added to a workout plan consisting of a single goal or a series of goals. In one or more arrangements, the user may further be permitted to specify an order in which goals in a workout plan are arranged and presented to the user for completion. In step 3735, the system may determine whether the user wishes to enter more goals. If so, the process may return to step 3700. If not, the process may end.

Figure 38:
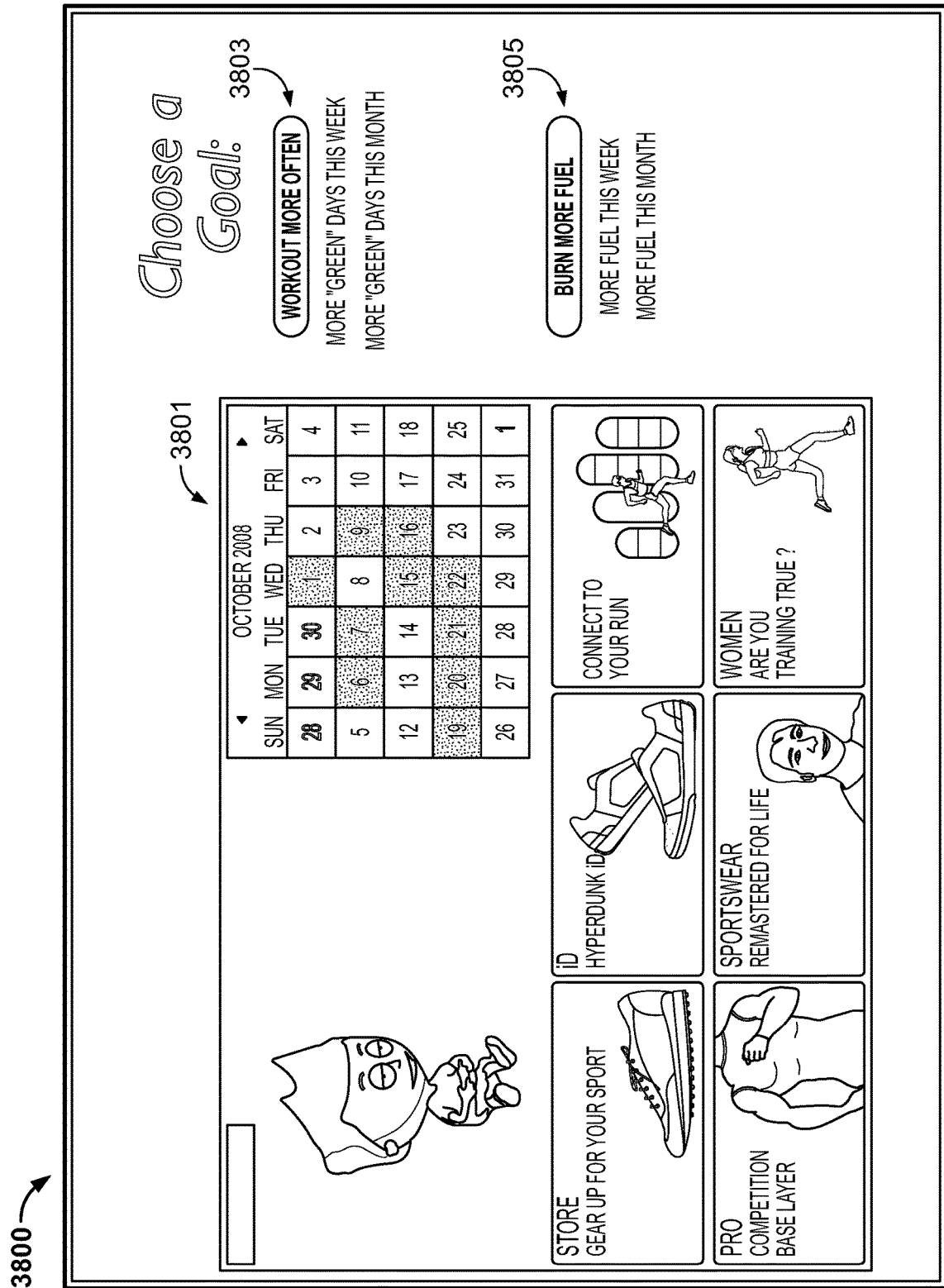
FIG. 38 illustrates an example interface from which the user may choose a goal according to one or more aspects described herein.

FIG. 38 illustrates an example user interface through which a user may select a goal on which a workout plan may be created. Interface 3800 may include calendar 3801 displaying the days on which a user worked out for a given month. Two sets of options 3803 and 3805 are provided to allow a user to select a goal based on frequency or intensity (e.g., burning more calories/fuel). Based on the goal selected, a workout plan may be generated as described above with respect to FIG. 37.

Data Publishing and Sharing

Figure 39:
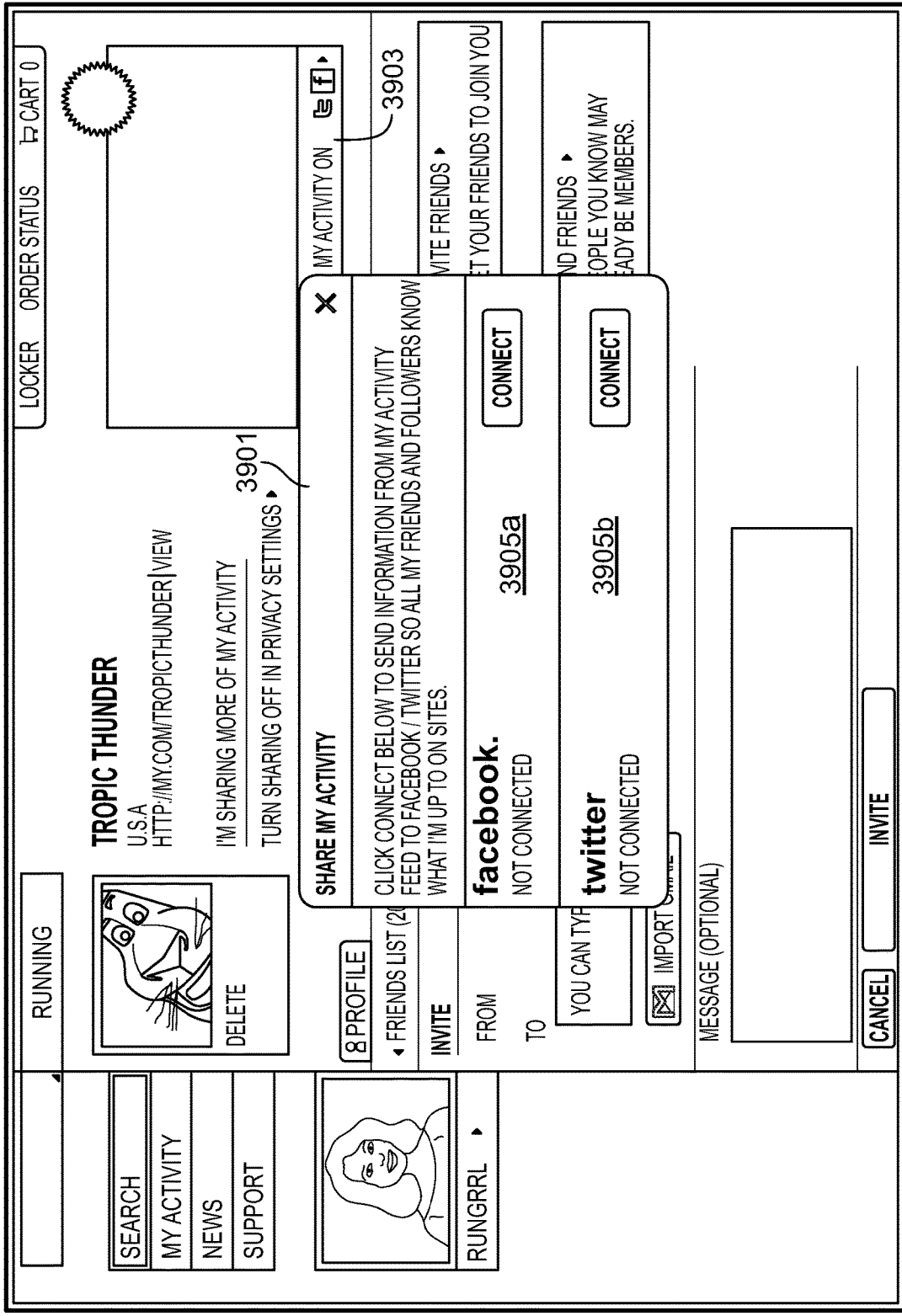
FIG. 39 illustrates an interface through which a user may share workout activity data through one or more social networking outlets according to one or more aspects described herein.

FIG. 39 illustrates an activity sharing option menu 3901 that may be displayed through a user account page 3900. Activity sharing option menu 3901 may be displayed as a pop-up window upon a user selecting a share option 3903 from page 3900. Menu 3901 may include multiple options 3905 for different publication outlets. For example, option 3905a may allow a user to publish athletic activity data and progress on a social networking site such as FACEBOOK while option 3905b may be used to publish information through a status broadcast system such as TWITTER. Activity data may be transmitted to the social networking site or status broadcast system based on a periodic or aperiodic schedule, upon detecting a triggering event (e.g., completion of a goal, reaching a 50% point). Upon selecting one of options 3905a or 3905b, the user may be presented with a login page to enter user identification information for accessing the user's account on the social network site or status broadcast system.

Figure 40A:
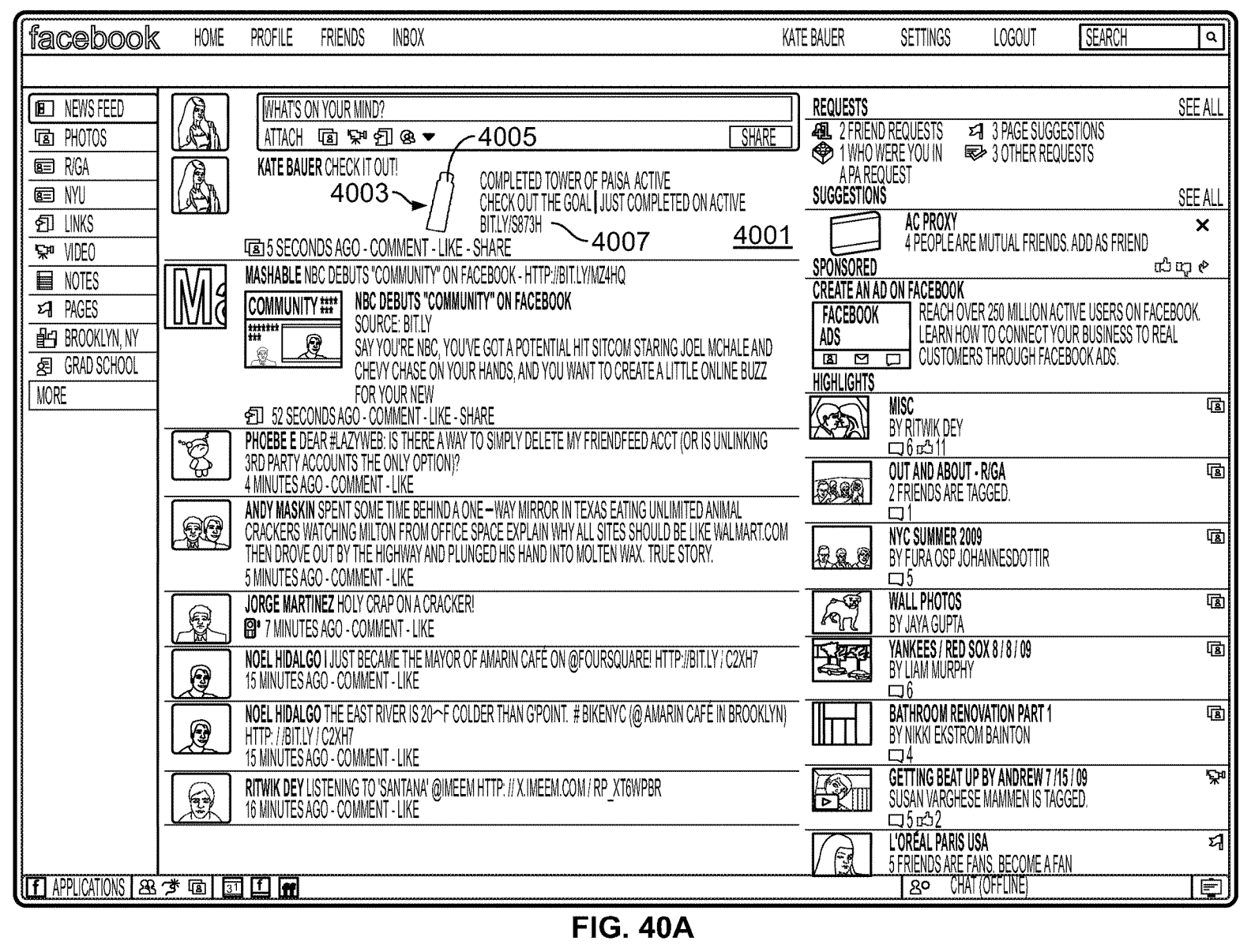
Figure 40B:
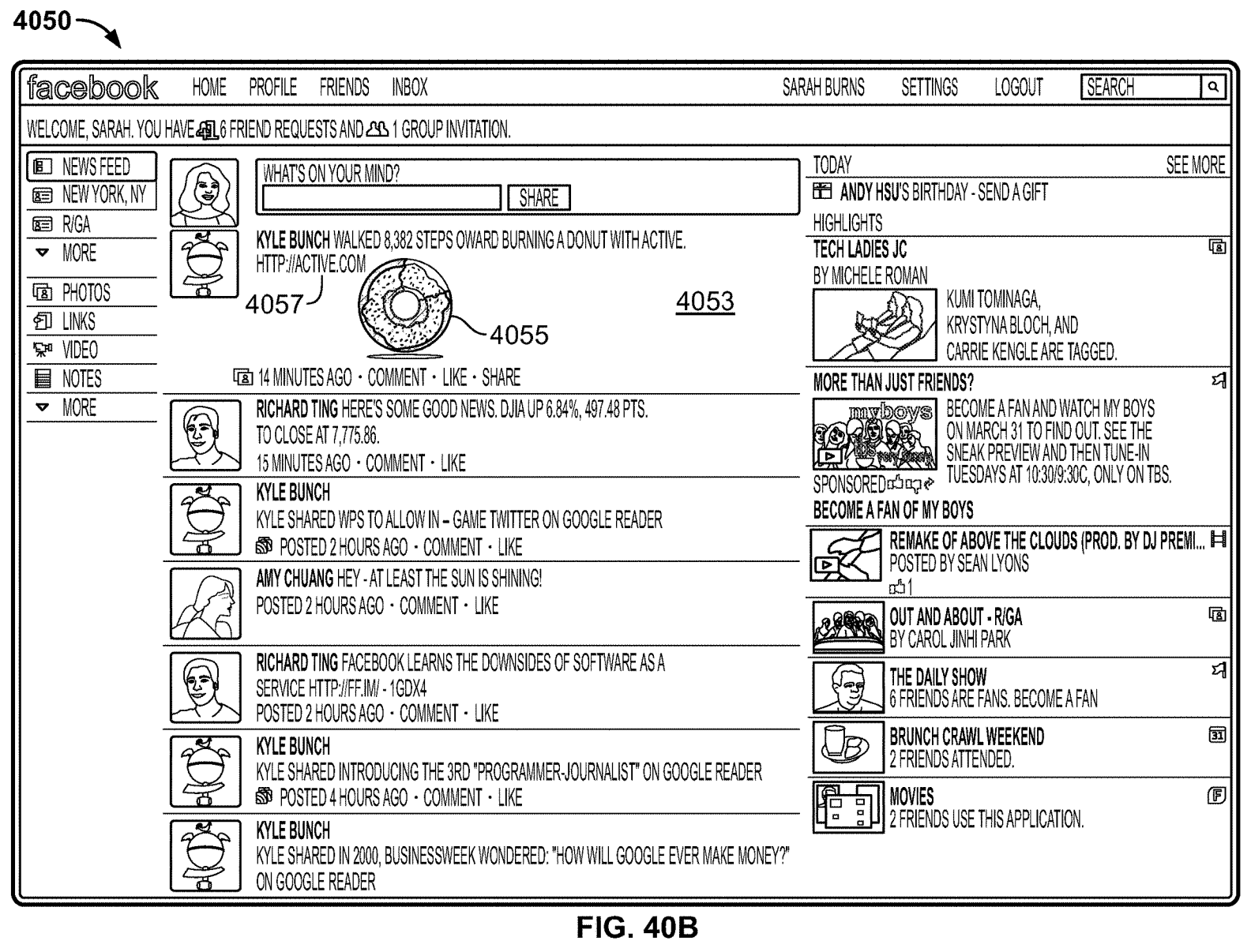
Figure 41A:
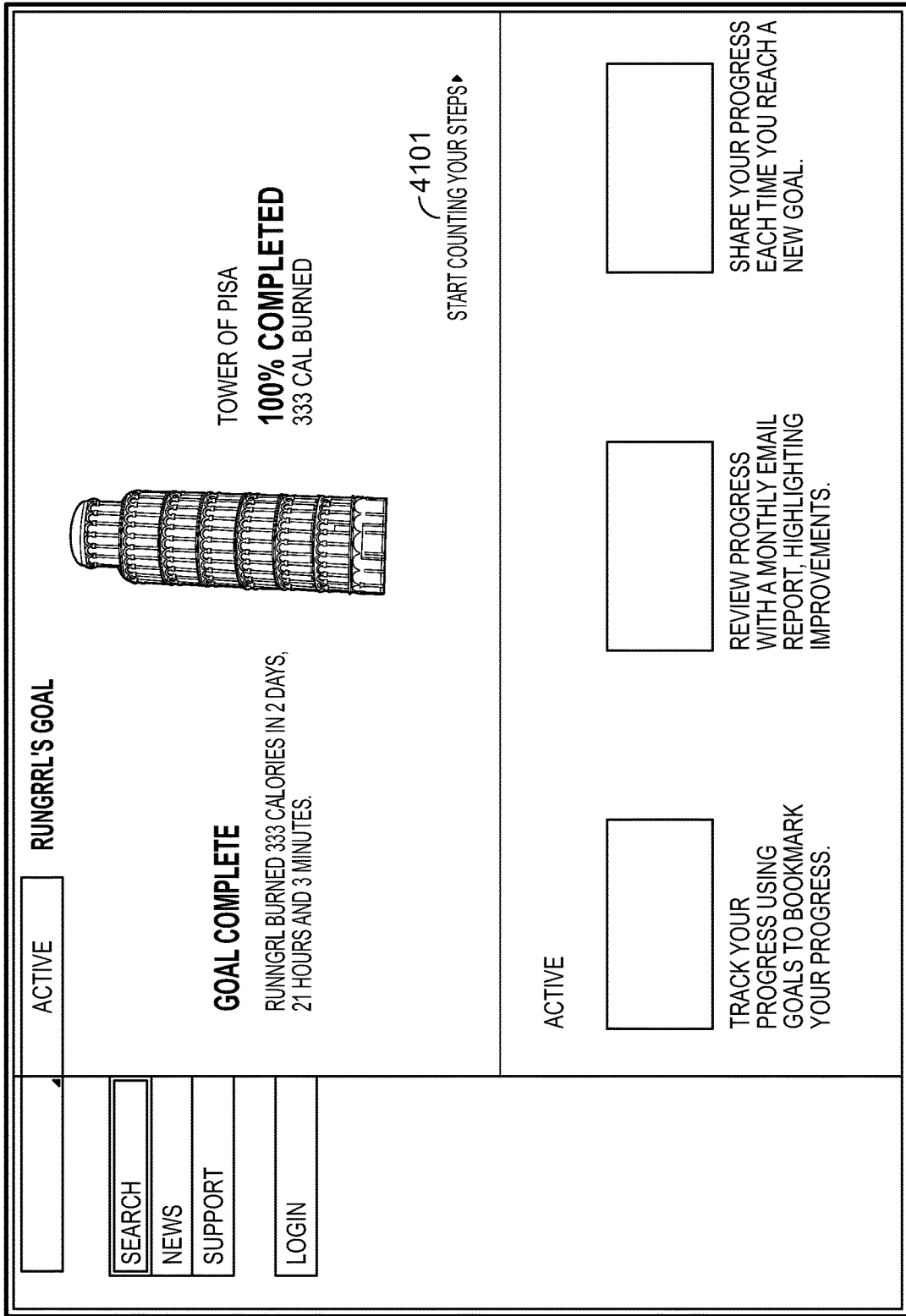
FIGS. 41A-B illustrate example public pages for a user displaying limited workout data and information about the user according to one or more aspects described herein.
Figure 41B:
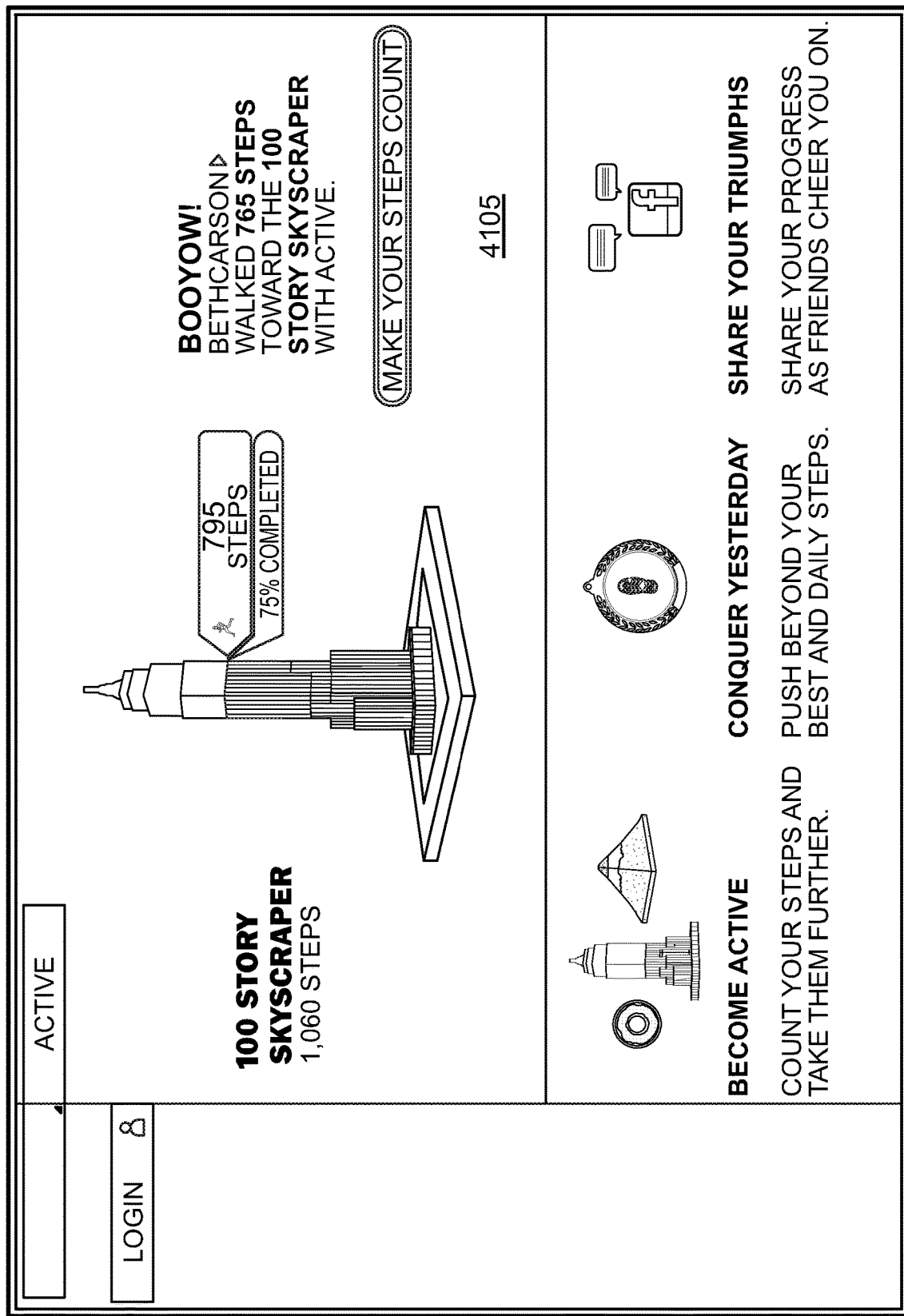

FIGS. 40A and 40B illustrate various embodiments of a social networking site page for a user. FIG. 40A, for example, illustrates that the user's athletic activity data may be published as an entry 4003 on the user's publicly viewable forum 4001. Entry 4003 may indicate an amount of progress made toward a specified goal. For example, entry 4003 indicates that the user has completed the Tower of Pisa goal. An image 4005 of the goal object is also displayed. Entry 4003 further includes a link 4007 to the athletic activity tracking and monitoring site and, in particular, a user's publicly accessible page thereon. For example, upon selecting link 4007, a friend or other visitor may be directed to page 4100 of FIG. 41A or page 4105 of FIG. 41B. A user may control the type and amount of information displayed on public pages 4100 (FIG. 41A) and 4105 (FIG. 41B). Page 4100, for example, may further include link 4101 that encourages the visitor or viewer to begin tracking and monitoring their own athletic activity by, for instance, registering for an account with the network site.

FIG. 40B illustrates another social networking page 4050 that also includes a workout entry 4053. The entry may include a workout object 4055 that is partially filled indicating a level of progress into a corresponding goal. The entry 4053 may further include link 4057 for accessing a public profile of the user's goal or workout activity.

Thematic Workout Plans and Goals

Figure 42:
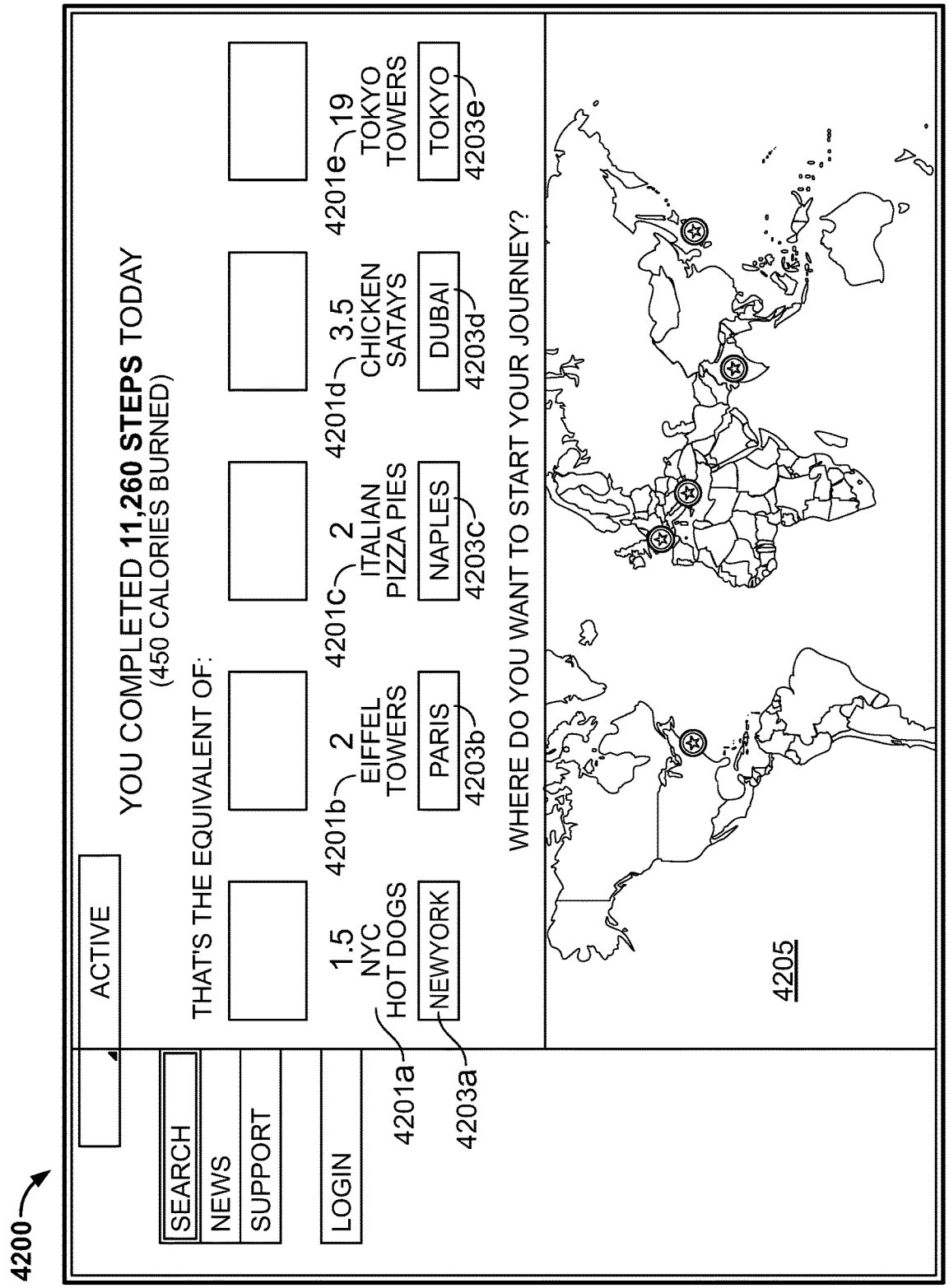

FIG. 42 illustrates an athletic tracking and monitoring interface 4200 that provides goals or a series of goals that correspond to a particular theme. In the illustrated example, the theme corresponds to real-world geographic locations where a user is invited to virtually complete goals in each of multiple cities or locations 4203 to complete a workout plan or routine. A user may select a starting location based on an initial workout. For example, if a user completes 11,260 steps in his or her initial workout, the site may convert that accomplishment into location-specific achievements 4201 such as 1.5 New York City hot dogs 4201a, 2 Eiffel Tower 4201b, 2 Italian Pizza Pies 4201c, 3.5 chicken satays 4201c (corresponding to the city of Dubai) and 19 Tokyo Towers 4201d. Below or in association with each of achievements 4201, interface 4200 identifies the corresponding geographical locations 4203. Map 4205 is further provided so the user may visualize the locations 4203 of the location themed workout plan. The user may then select from map 4205, achievements 4201 or locations 4203 to specify a location in which the user wishes to begin the thematic workout plan. A user might only be offered a subset of all geographic defined locations in a workout plan for selection based on the user's level of fitness. Accordingly, a user might only be able to select beginner level locations based on a level of fitness of the user determined based on the user's previous workouts. A user may thus take a virtual journey through locations 4203 by completing the workouts associated with each of locations 4203. Other themes may also be used to create workout plans including food categories, types of vehicles, movies, competitions with sports icons and the like. For example, a user may participate in a workout plan that progresses between categories of food including vegetables, meats, dairy, fruits and the like. Each category may include one or more food goal objects that correspond to a number of calories, a distance to run, a number of steps to walk and the like. The number of calories, distance run or steps to walk may correspond to an estimated amount necessary to compensate for (e.g., burn off) eating that particular food item.

Figure 43:
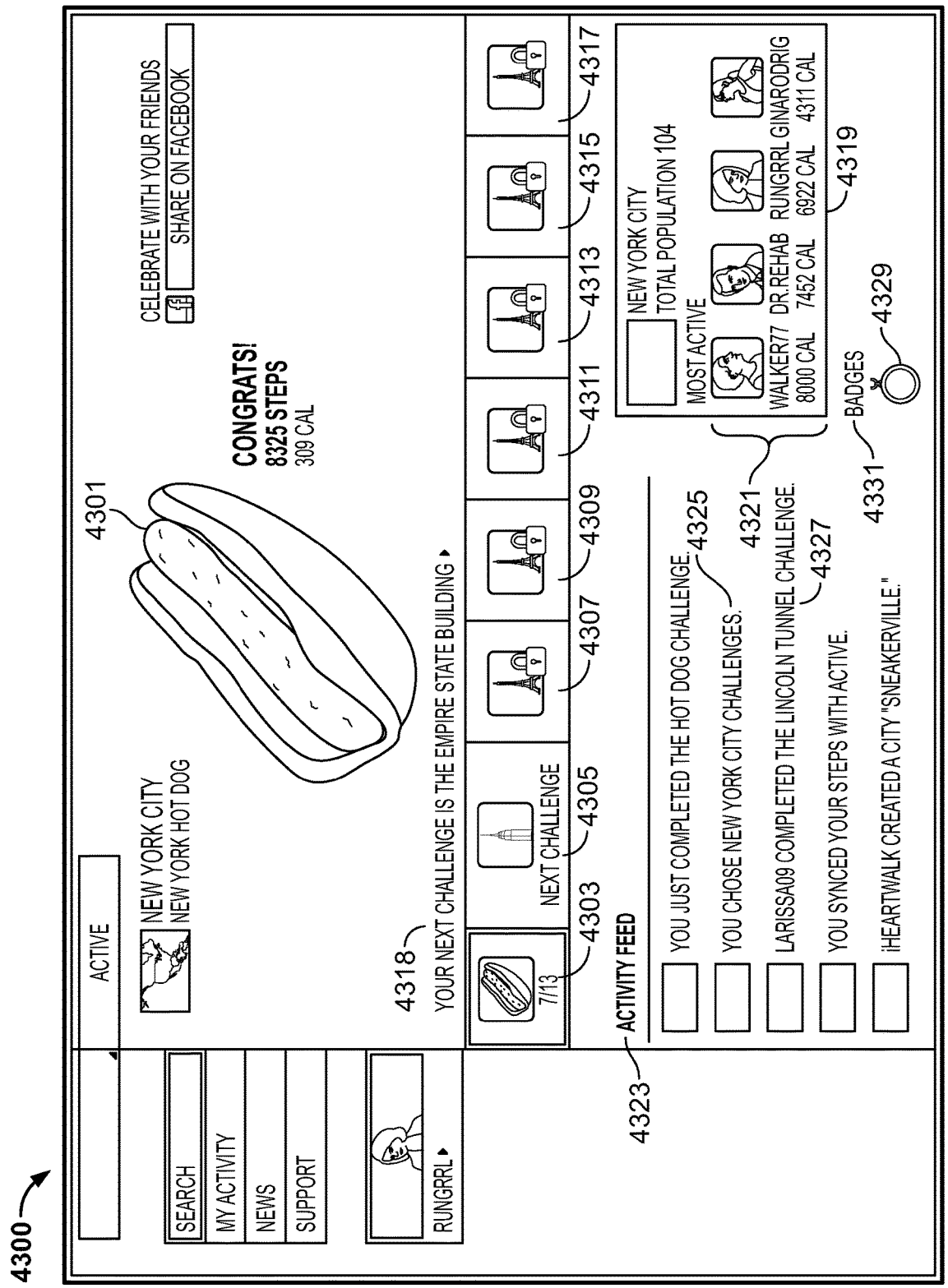

FIG. 43 illustrates location themed workout interface 4300 that may be displayed upon a user selecting New York City as a start location. The first objective 4303 may be to perform a number of steps and/or burn a number of calories corresponding to a New York City hot dog. Goal object 4301 may be displayed to help the user visualize his or her accomplishment. Goal objects for a particular location may correspond to landmarks or location-specific items. For example, the Statue of Liberty, the Empire State Building, Museum of Modern Art (MoMA), and/or a hot dog may all be considered symbolic of or particularly representative of New York City. Upon completion of objective 4303, message 4318 may be displayed indicating that the next objective 4305 is the Empire State Building. Objectives 4305-4317 may be locked and/or hidden until a required number of other objectives have been completed, an amount of athletic activity has been performed and/or an immediately preceding objective has been completed. In one or more arrangements, the number or intensity of workout objectives 4305-4317 may correspond to the size of the location (e.g., population, area). For example, a greater number or intensity of workout objectives may be included in New York City than in Melbourne, Australia by virtue of New York City being larger in population. The size of a location may be determined based on population, land area, wealth, tourism popularity and the like.

Location information box 4319 may be used to indicate a number of users currently working on objectives in the selected location, i.e., New York City. City information box 4319 may further display the top X number of athletes 4321 and the number of calories burned and/or number of steps performed by each. Activity feed 4323 of interface 4300 includes information about the user as well as other athletes and their progress, actions and accomplishments. For example, activity entry 4325 specifies that the user chose the New York City challenge while entry 4327 indicates that athlete Larissa09 completed the Lincoln Tunnel Challenge. Various other messages may be provided in activity feed 4323 depending on user preferences, default settings, system or site requirements and the like. According to one or more configurations, feed 4323 might only display information for groups, organizations or individuals with which the user is connected (e.g., confirmed friends, within 1, 2, 3 or 5 degrees of separation, confirmed member of an organization).

Badges may be awarded by the athletic activity tracking and monitoring site based on various achievements. For example, in the location themed workout plan, users may be awarded badges for each location that the user completes. Badge 4329 may be displayed in an outline or broken line form to indicate that the badge is available but has not yet been achieved. In one or more arrangements, only those badges that are achievable in the present location and/or badges that have already been achieved may be displayed in badges section 4331. Badges may be defined for other types of achievements as well. For example, a badge may be awarded for a user completing 3 goals in 3 consecutive days, completing 2 goals in a single day, being the first to complete a particular goal and the like. Upon being awarded a badge, the badge may be displayed in an alternate appearance. For example, the badge may be displayed in solid line form, with color, with writing, with texture and the like.

Figure 44:
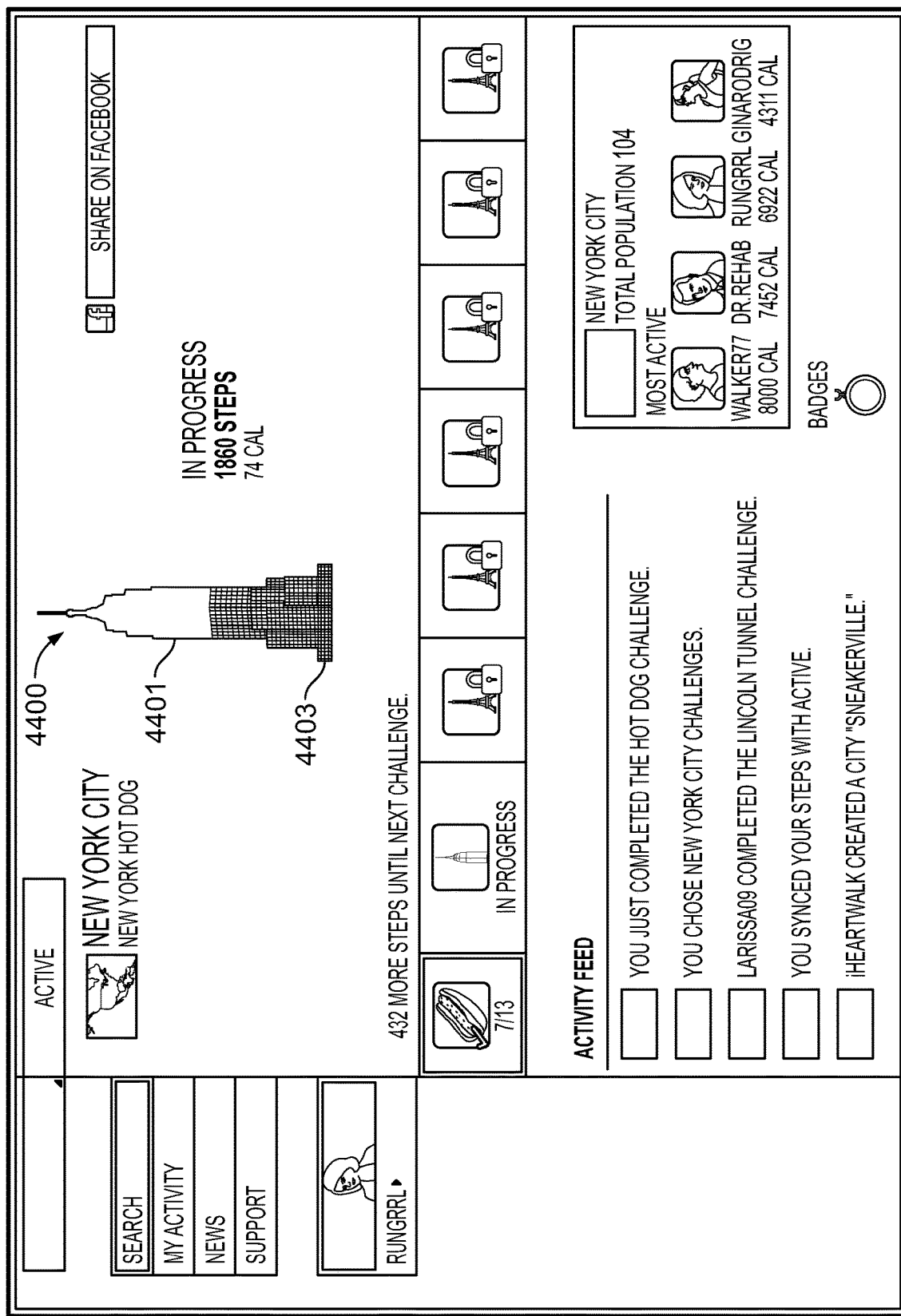

FIG. 44 illustrates a user's progress in completing objective 4305. As noted herein, an uncompleted portion 4401 of goal object 4400 corresponding to objective 4305 may be displayed in a first appearance format while completed portion 4403 may be displayed according to a second appearance format. This permits the user to differentiate and visualize an amount completed and an amount of objective 4305 remaining.

Figure 45:
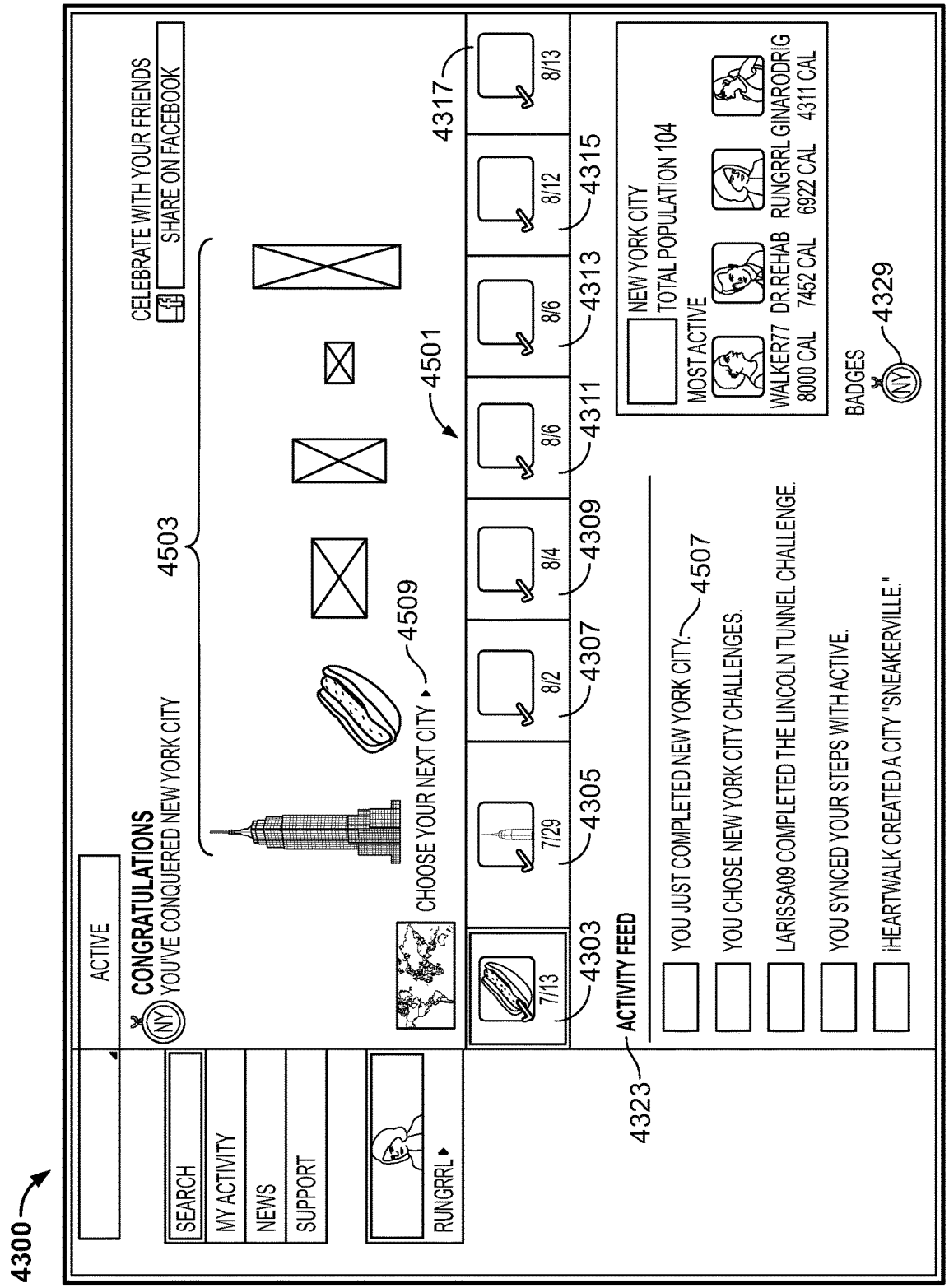

FIG. 45 illustrates interface 4300 once the user has completed all objectives 4303-4317 in a particular location. Badge 4329 is displayed in solid line form with the letters "NY" indicating completion of all workouts in the New York City portion of the workout plan. Goal tracker bar 4501 may further include the dates on which each of objectives 4303-4317 were completed. The various goal objects 4503 completed may also be displayed. The user may further be allowed to choose a new city to continue the virtual workout journey using option 4509. Interface 4300 further includes a new feed message 4507 in activity feed 4323 indicating that the user has completed all the workouts in the selected location.

Figure 46:
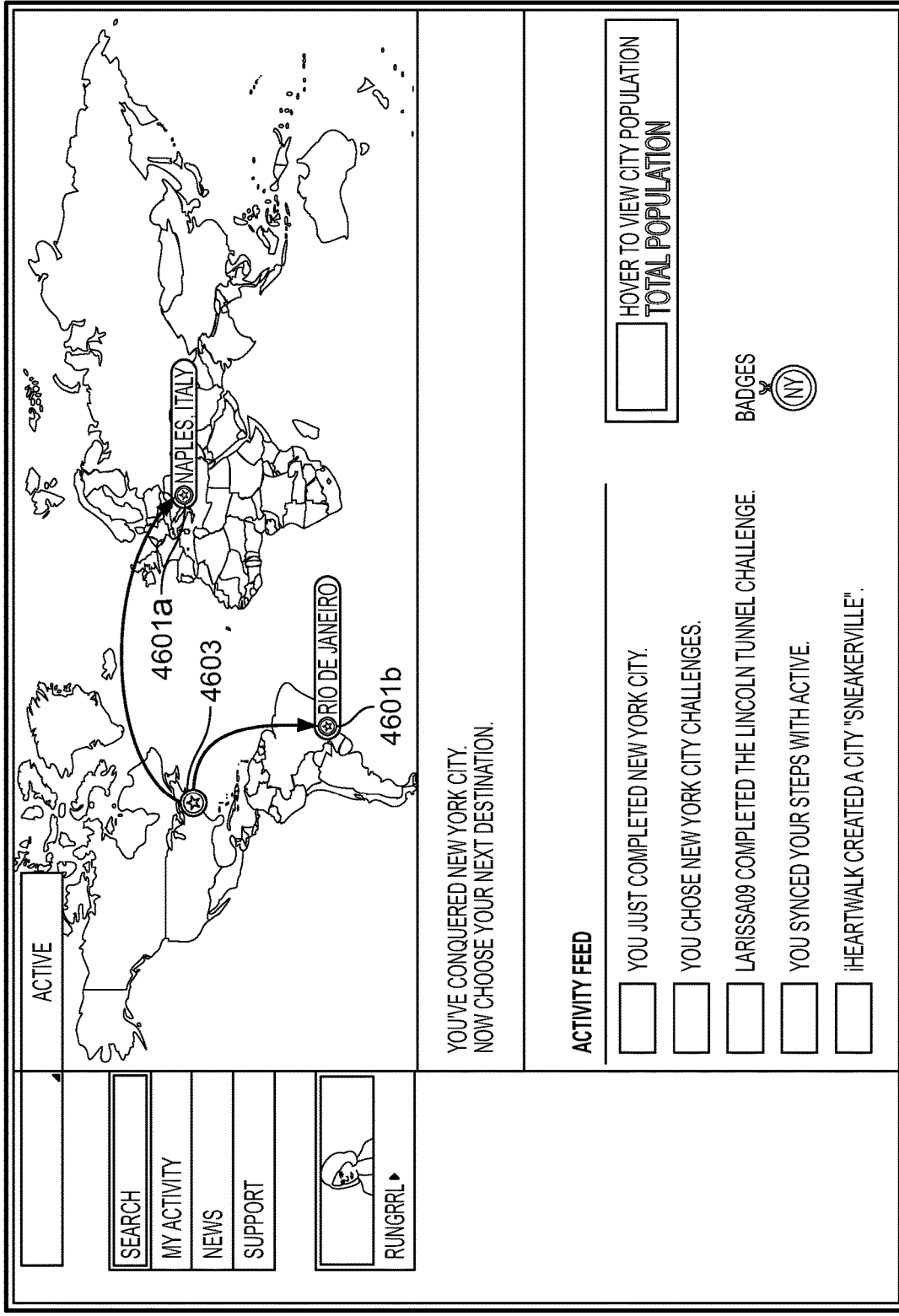

FIG. 46 illustrates a location selection map 4600 that displays subsequent locations 4601 (e.g., Naples, Italy and Rio de Janeiro, Brazil) from which the user may choose. The network site may restrict or limit the locations 4601 from which a user may choose based on a variety of factors including a geographic distance from a current location 4603, a number of workouts in each of locations 4601 and 4603, the locations of other users and the like. For example, the network site may only allow the user to choose from locations in which the number or intensity of workout objectives is greater than that of the workout objectives just completed in the user's current location 4603. In another example, the network site may restrict the user from choosing locations that may be too crowded (i.e., locations in which too many users are currently working on objectives). In yet another example, the network site might only allow the user to select from the next two geographically closest locations. In other examples, the network site may require the user to progress through the locations in a certain sequence. Accordingly, a user may be required to choose from locations in a predetermined sequence. The sequence may be defined based on a gradually increasing level of difficulty in one arrangement. Combinations of factors may also be used in providing location options to the user. A user may further hover over or otherwise interact with the locations indicated on map 4600 to view a population (site population or actual population) and other details relating to that location.

Figure 47:
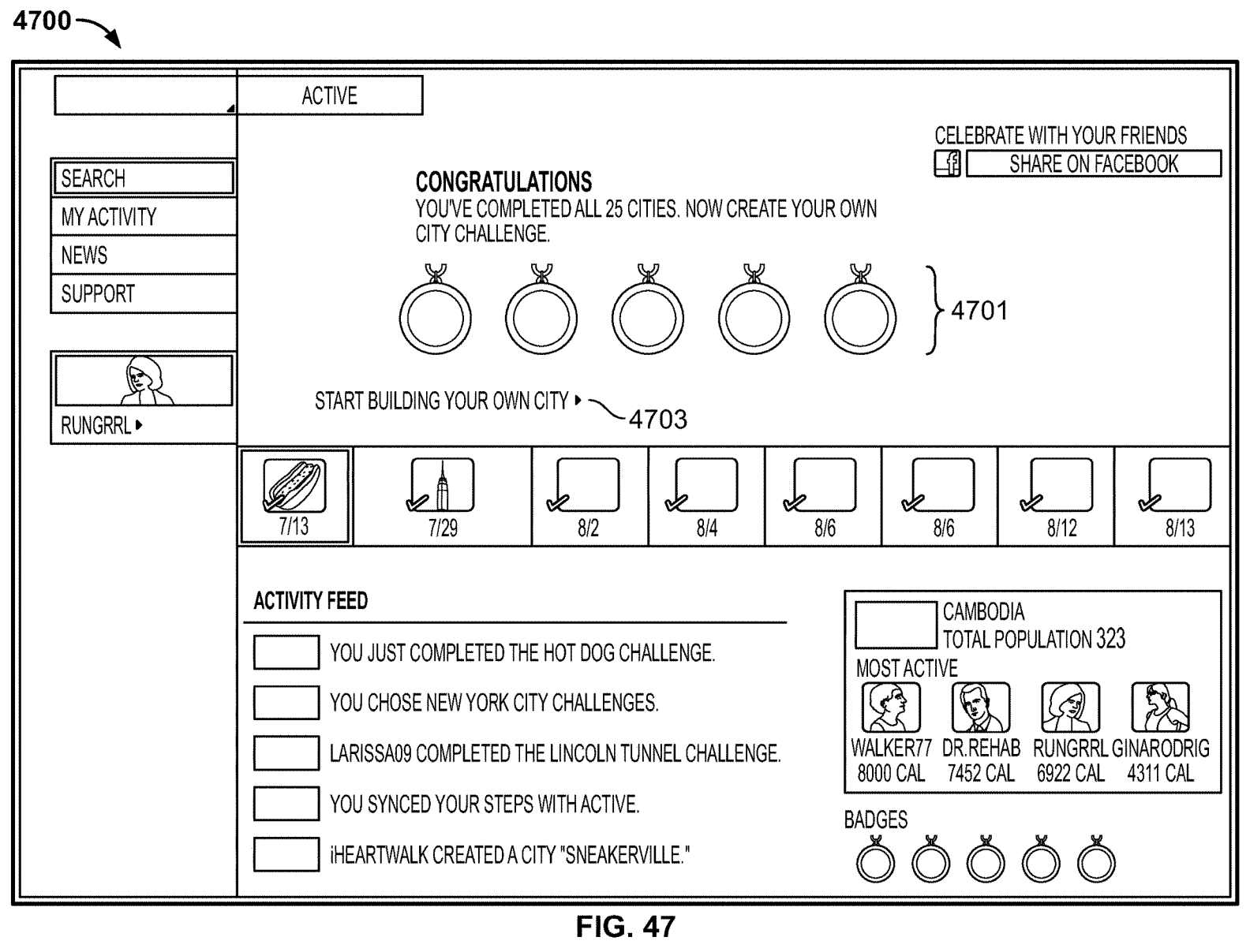

FIG. 47 illustrates an interface 4700 that may be displayed upon a user completing an entire location-themed workout plan consisting of workouts in multiple locations. Badges 4701 may correspond to each of the locations in which the user completed workouts. Option 4703 may be provided in interface 4700 allowing a user to create their own location-themed workout plan. For example, the user may select one or more locations and define one or more workouts in those locations to formulate a workout plan others may use.

Figure 48:
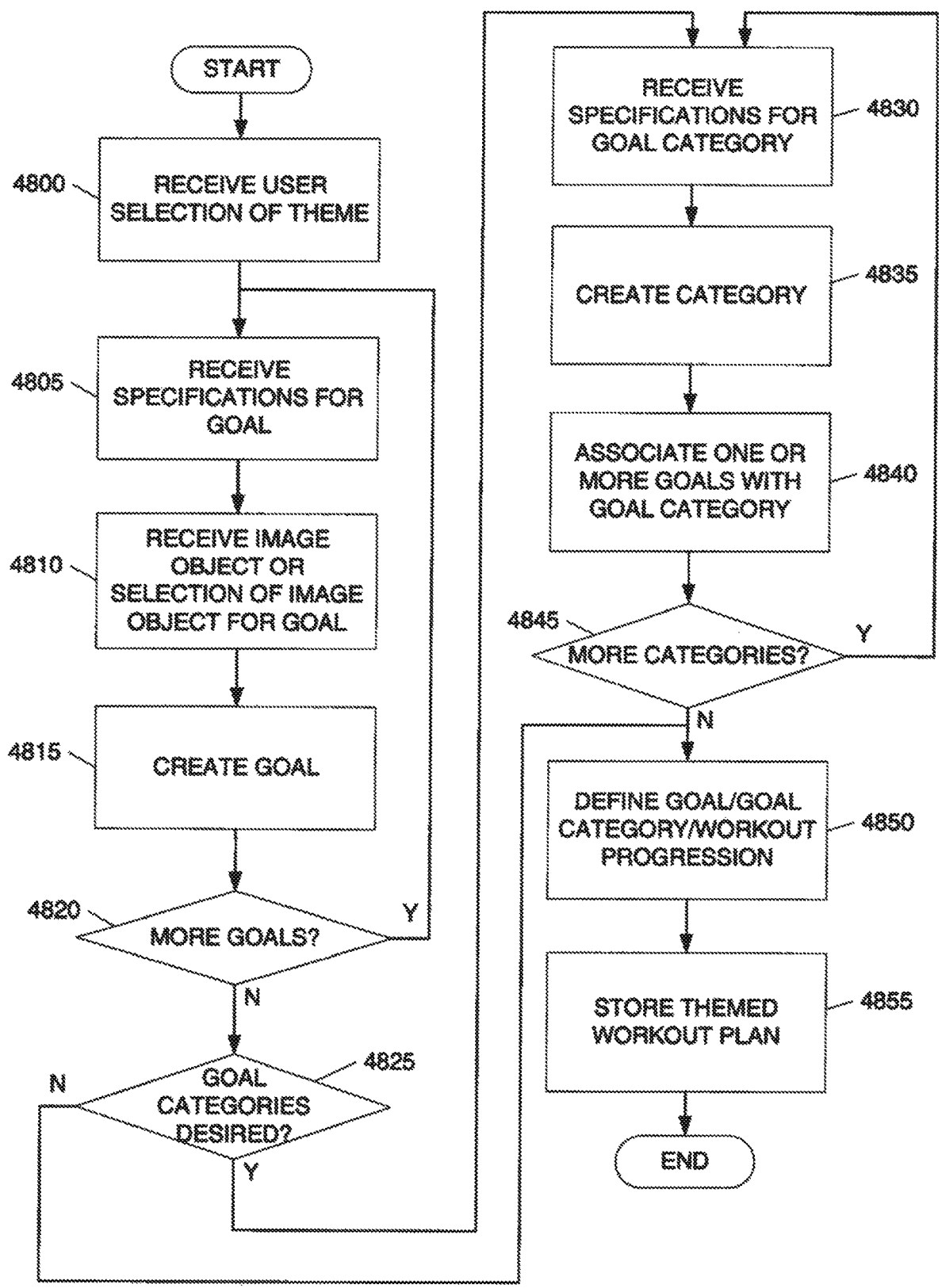
FIG. 48 is a flowchart illustrating an example method for creating a themed workout plan according to one or more aspects described herein.

FIG. 48 illustrates an example method for creating a themed workout plan. In step 4800, a workout creation system may receive a user selection of a theme. Selection of a theme may include selection of goal types, theme colors, a name of the workout plan, author information and a name of the theme. In step 4805, the system may receive specifications for a first goal in the themed workout plan. A goal may be described as discussed above with respect to FIG. 37. In step 4810, the system may receive an image object from the user or another system or receive a selection of a pre-stored image object. For example, if the user wants to use a custom image object, the user may specify the address of the image object (e.g., on the user's computer or on another website/computer system). Alternatively, the user may select an image object that is already stored and available in the system. In step 4815, the system may create the goal. A user may continue to add additional goals based on determination 4820 made by the system or if the user is finished with adding goals, determine whether goal categories are desired as illustrated in step 4825.

Goal categories may be used to add an additional level of hierarchy to the goals. As described herein, a location themed workout plan may include goal categories corresponding to various cities with one or more goals defined for each city. If goal categories are desired, the system may receive specifications for a goal category in step 4830. Goal category specifications may include a name of the category, imagery, text or sounds to be provided when a user has selected the category, achievable badges for that category, a level of difficulty and the like. In step 4835, the system may create the category based on the specifications. In step 4840, the system may associate one or more defined goals with the goal category. The association may be performed automatically, manually or a combination thereof. For example, a user may manually specify which goals should be stored in association with the category. Alternatively, the system may automatically add goals based on a user parameter. For example, the user may instruct the system to associate all goals with the word "donut" in the name or description with the created category.

In step 4845, the system may determine whether the user wants to add more categories. If the user would like to add more categories, the process may return to step 4830. If not, the process may proceed to defining an order or progression of the goals and goal categories in step 4850. The order or progression may define the sequence in which goals are accessible and achievable. The order or progression may be defined manually or automatically. For example, the system may automatically order the goals based on the magnitude of the goal or magnitude of all goals in a goal category (e.g., increasing based on calories burned or steps walked). Alternatively, a user may wish to manually define the order in which the goals are to be completed by the user and/or the order in which goal categories may be completed. Once the progression has been defined for the themed workout plan, the plan may be stored by the system in step 4855.

Figure 75A:
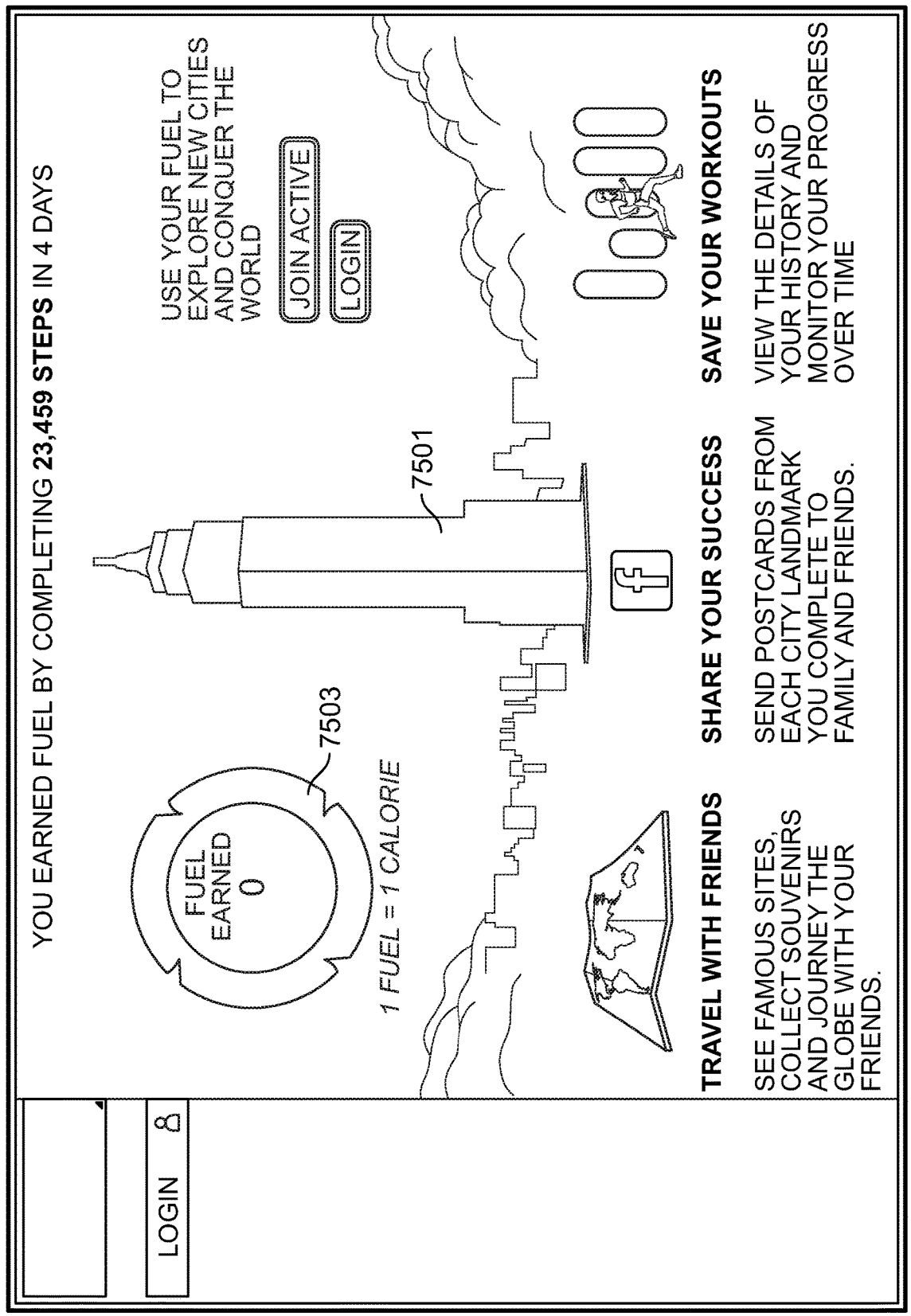
FIGS. 75A-82G illustrate example interfaces for tracking and monitoring user athletic activity progress in completing one or more athletic activity goals.
Figure 75B:
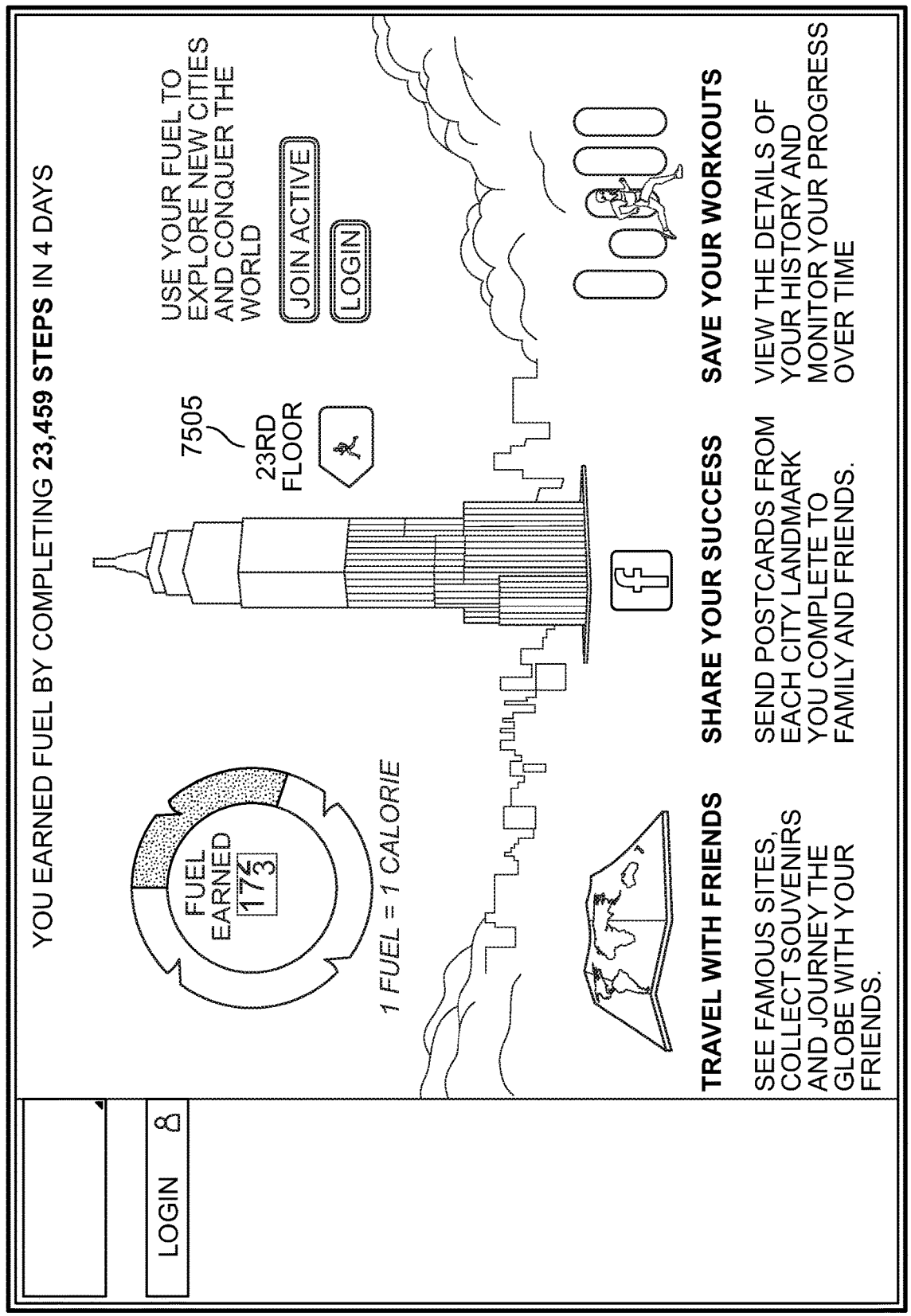
Figure 75C:
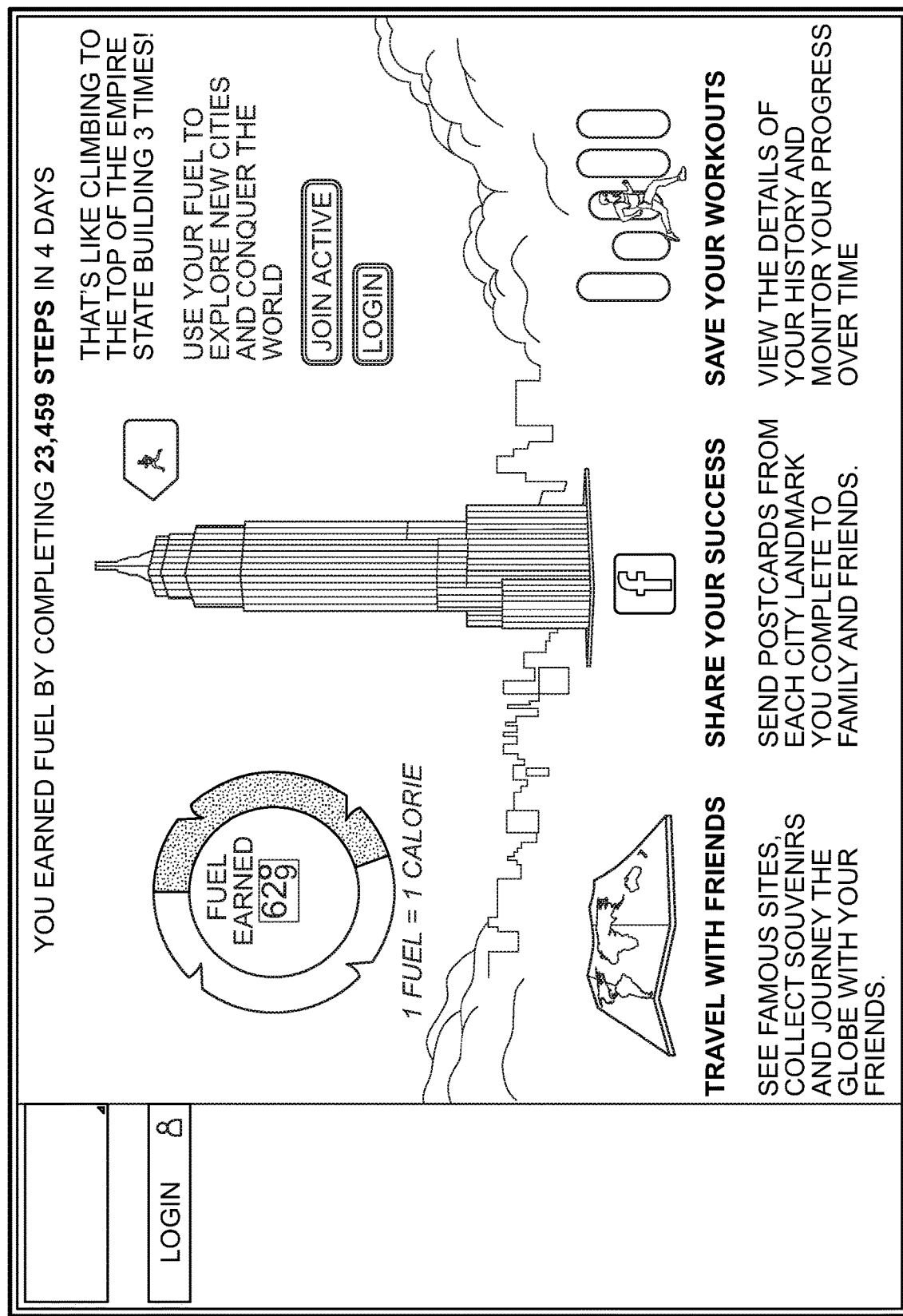

FIGS. 75A-C illustrate a series of user interfaces in which a user's progress is tracked using both a visualization object such as building 7501 and a fuel tracker 7503. In the illustrative example, 1 fuel may be equal to 1 calorie. Accordingly, as a user completes an athletic activity such as walking or running, the building 7501 may begin to fill with a color or other visual details (instead of simply an outline or transparent shell). Additionally, fuel tracker 7503 may also begin to change in appearance to reflect an amount of fuel earned. FIGS. 75B and 75C illustrate the filling of building 7501 and of fuel tracker 7503. Fuel tracker 7503 may further display an amount of fuel earned, while an indicator 7505 may be displayed in association with building 7501 to identify the current level or progress (e.g., floor of the building) achieved by the user.

Figure 76:
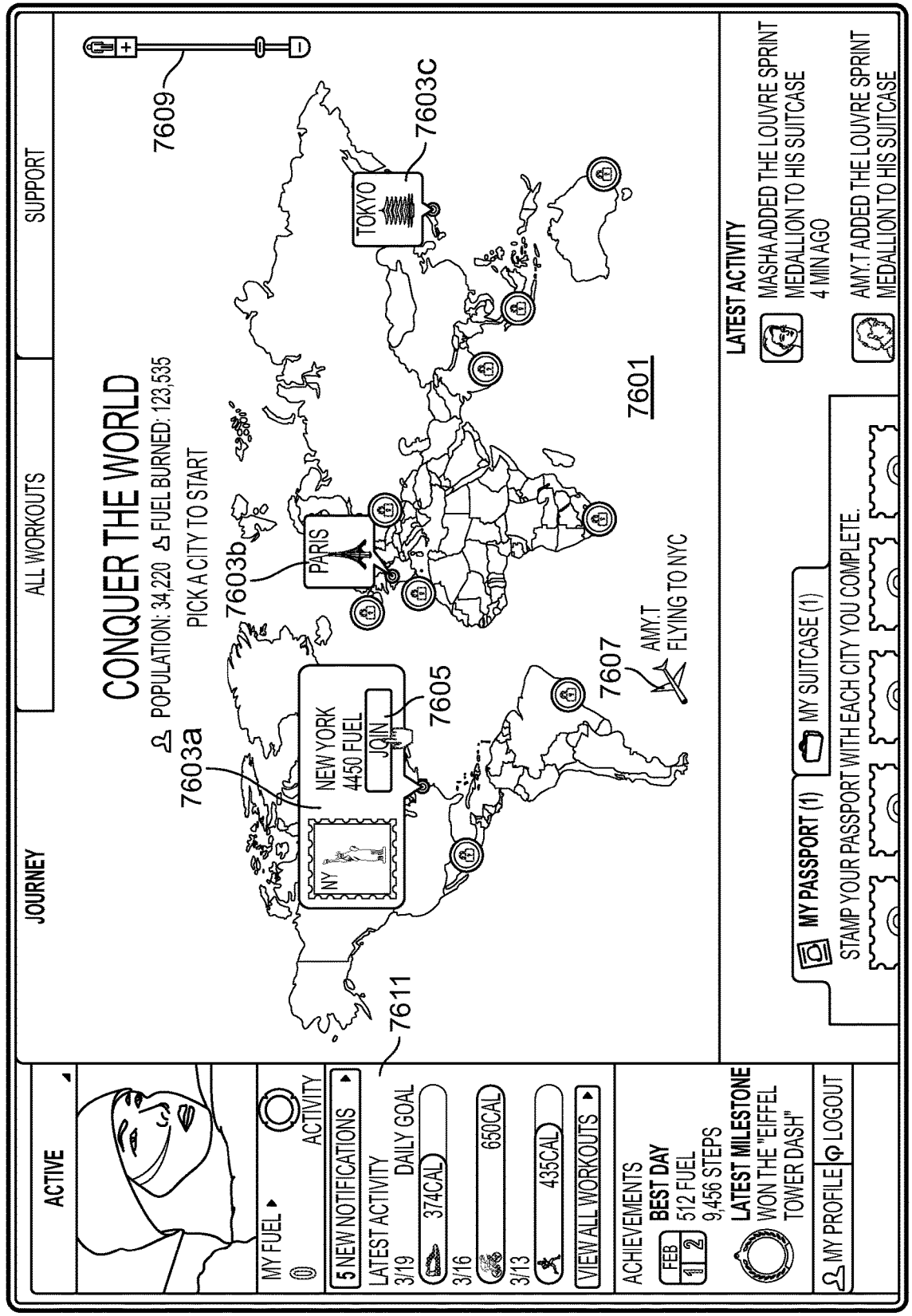

FIG. 76 illustrates another example map 7601 through which a user may view multiple location themed goals and track his or her progress through the goals. In one or more arrangements, some goals or locations may initially be locked, and might only be unlocked for use or selection upon reaching a predefined activity threshold. For example, a user may be required to complete 2 cities before being allowed to select goals in South Africa. Completing a location (e.g., a city) may include completing all goals in the location and/or earning a specified number of fuel points. The unlocked cities, e.g., cities 7603a-c, may be displayed along with an icon representing that city. For example, in FIG. 76, the icon may include a landmark representative of the city. Hovering over or otherwise interacting with one of the icons may cause further details, options and information to be displayed. For example, New York City prompt 7605 may be displayed in response to a user moving a cursor over a previously displayed New York City icon (not shown). New York City prompt 7605 may include an image of a New York City landmark, the name of the location and an amount of fuel (e.g., virtual currency or common activity measure) that may be earned through completing the New York City goals or tasks. Prompt 7605 may further include a join option to allow a user to begin working on the goals or tasks defined for the New York City location. In one or more arrangements, icons such as icon 7607 may identify the location and/or progress of friends or other users. For example, icon 7607 may indicate that a friend is (virtually) flying to New York City to begin one or more goals or objectives at that location. In one or more arrangements, icon 7607 may indicate a physical location of the friend or may reflect that the friend is joining the virtual New York City goal location. Hovering over or otherwise interacting with an icon of another individual (e.g., icon 7607) may provide progress details about that individual. For example, progress details may include a number of locations completes, a number of goals completes, awards receives, badges acquires, milestones and achievements reaches and the like.

In one or more arrangements, friends may post messages or provide encouraging messages or rewards upon the user reaching a certain point in a workout plan. For example, a friend may indicate that a message is to be displayed to a user upon the user completing the first goal in a particular goal location in a location themed workout plan. Alternatively or additionally, a friend or other user may ask the system to provide a reward, trophy, encouraging message and/or combinations thereof upon the user completing a specified amount of athletic activity (e.g., based on calories burned, miles run, steps taken, weight lifted, etc.). Messages from other users and triggering such messages based on athletic performance may keep the user motivated in continuing his or her athletic activity regimen.

Zoom bar 7609 allows a user to view locations in greater detail and in larger format. In some arrangements where multiple goal locations may be in close proximity to one another, zooming in may be necessary to more distinctly view the individual goal locations. At a zoomed-out level, the multiple goal locations in close proximity to one another may be grouped into one icon, tab or other indicator. Hovering over the grouped icon or tab may reveal a list of goal locations represented by the icon or tab.

FIG. 76 further illustrates an activity status bar 7611 that displays an amount of fuel earned, an activity level (e.g., low, average, medium, high). Status bar 7611 may further display a number of new notifications (e.g., for messages, new achievements, locations unlocked, etc.), a list of the user's latest athletic activity and a list of most recent achievements earned.

Figure 77A:
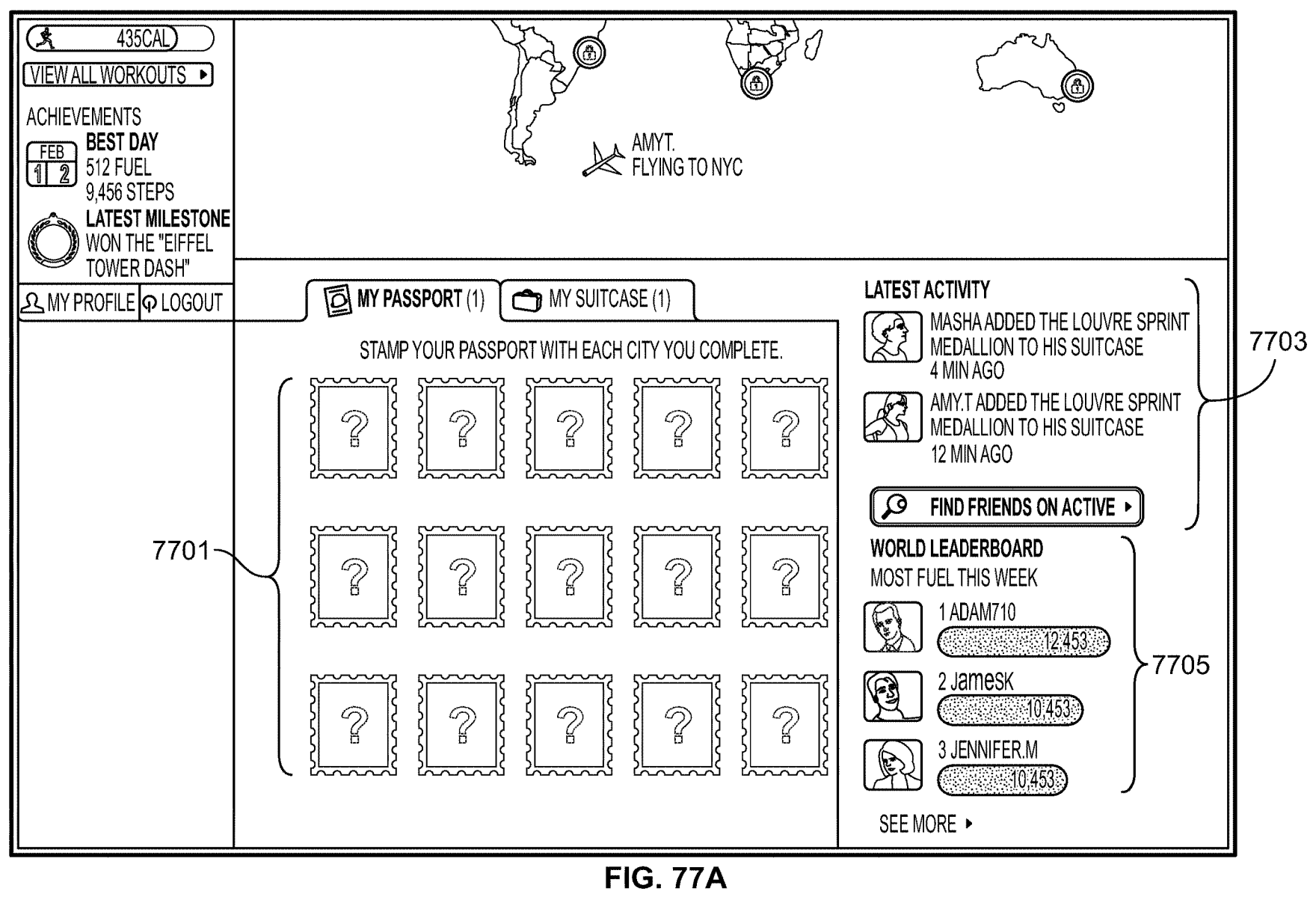

To track a multitude of activity goals and goal locations, a virtual activity passport may be provided. FIG. 77A illustrates an example virtual activity passport in which stamps, icons or other visual indicia may be displayed to indicate the goals and/or goal locations the user has completed. Accordingly, if a user completes the New York City goals, the user may be awarded with a New York City stamp. Prior to completion, stamp outlines 7701 may be displayed. Activity stream 7703 may be also be provided to specify the latest activity performed by various individuals (e.g., friends, people working on goals in the same goal location, individuals in the same network, users in the same category of fitness level). Additionally, a leaderboard 7705 may be displayed to identify individuals having earned the most fuel or other activity metric over a specified time period (e.g., a week, a month, a day, etc.).

Figure 77B:
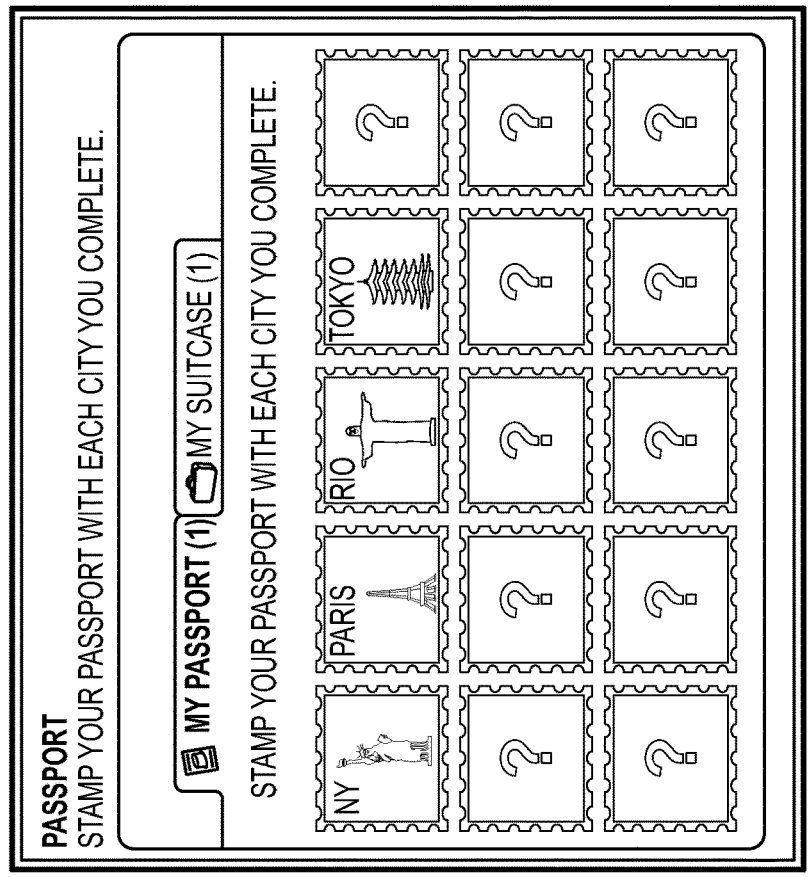
Figure 77C:
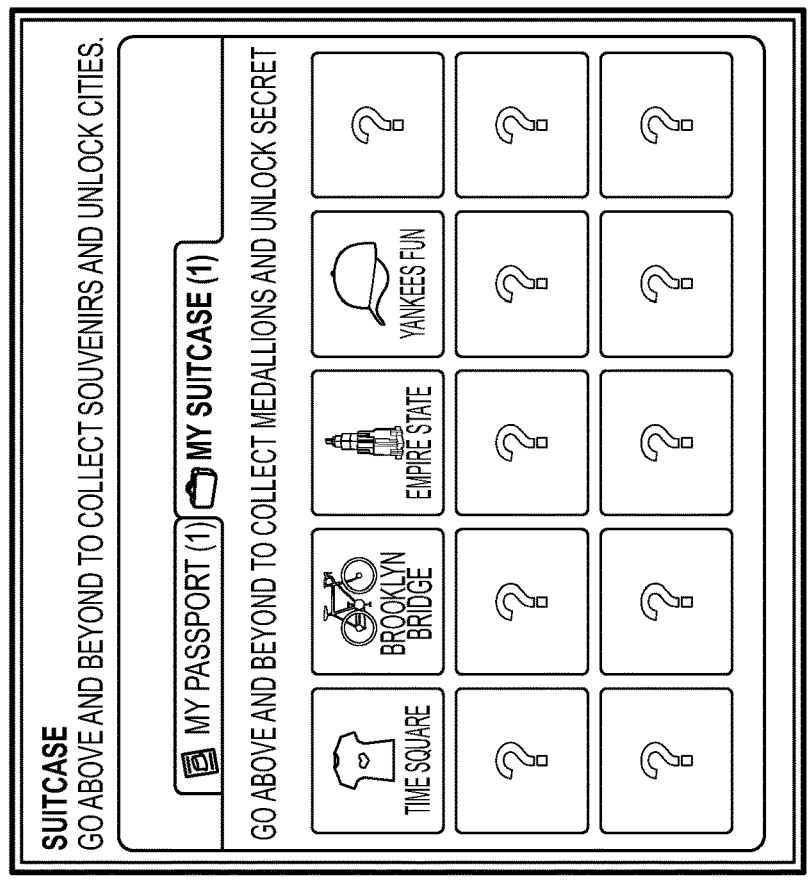

FIGS. 77B and 77C illustrate example stamps and trophies/medallions, respectively, that may be collected by a user by completing goals in a goal location and meeting the requirements of various achievements.

Figure 78A:
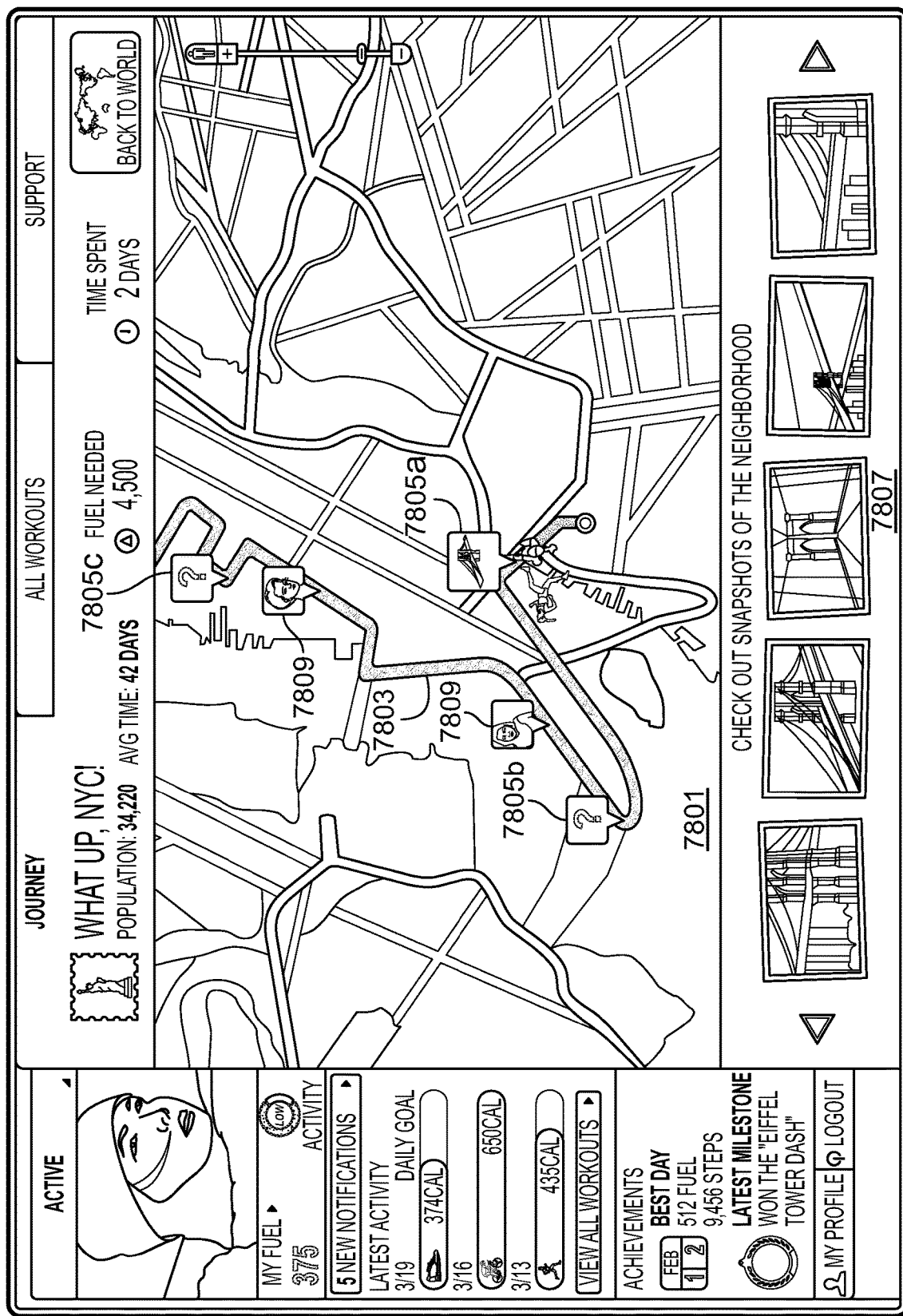

FIG. 78A illustrates a map 7801 displaying an activity goal location such as New York City. Map 7801 may display a virtual path 7803 that represents a user's athletic activity progress by a distance traveled through the location. A user may be required to perform an amount of athletic activity to move along the virtual path 7803. For example, a specific amount of athletic activity may be required to move between goals 7805a and 7805b. In another example, each inch, pixel, foot or other metric of map 7801 and path 7803 may correspond to an amount of athletic activity (e.g., 1 inch=100 calories). A completed portion of path 7803 may be displayed in a first color or with a first appearance while an incomplete portion of path 7803 may be displayed in a second color or with a second appearance different from the first. In one or more arrangements, map 7801 may display indicators corresponding to friends or other users participating in the workout plan. Hovering over or otherwise interacting with such indicators may provide detailed information specifying the other user's progress in completing a goal object, the location or the overall workout plan (e.g., a number of goal locations completes, a number completed goals out of all goals defined for the workout plan).

Additionally, various goals, landmarks or tasks such as goals 7805a, 7805b and 7805c may be displayed along path 7803. Further, the user's progress along path 7803 may be animated in one or more configurations (e.g., the user's avatar or icon may be moved along path 7803 or a color of path 7803 may change gradually representing the user's progress). A goal might not be revealed until an immediately preceding goal or a previous number of goals have been completed. Interface 7800 may further display images, video, text and/or audio in area 7807 of a current location of the user. Accordingly, if the user is running by or along the Brooklyn Bridge, pictures of the Brooklyn Bridge may be displayed in snapshots area 7807. The location may be a virtual location of a user in the progress map or an actual physical location of the user. Other users progressing through the same location may be identified along path 7803 using icons 7809. This allows the user to track their progress relative to his or her own progress. Interacting with icons 7809 may allow a user to contact and/or view details about the other users.

Figure 78B:
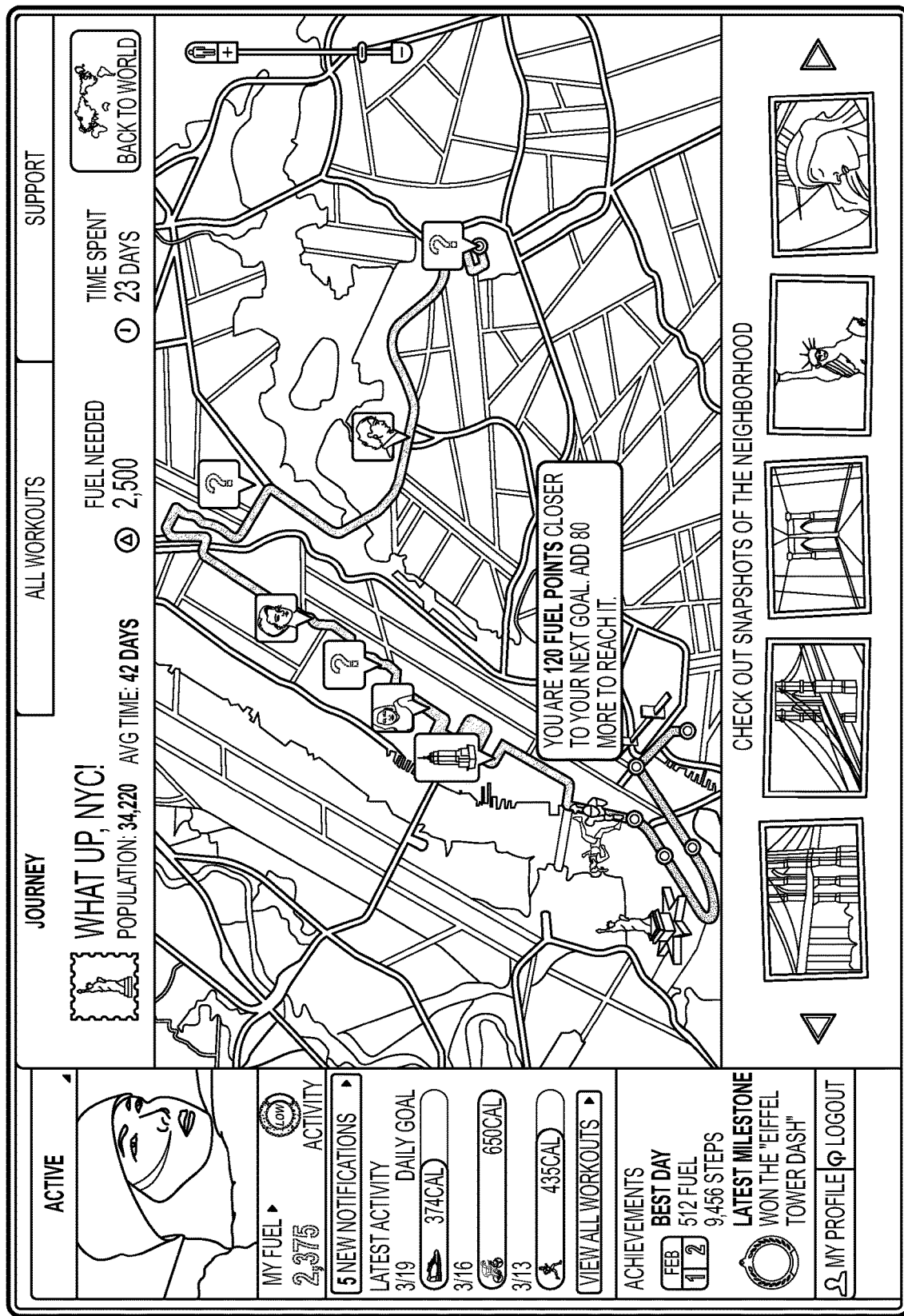

FIG. 78B illustrates another example progress tracking map. In this example, the map may display messages to encourage the user to progress further. For instance, if a user has just earned 120 fuel points, the map may indicate the progress made and encourage the user to reach a next goal by indicating the number of fuel points that must be earned to reaching the next goal.

Figure 78C:
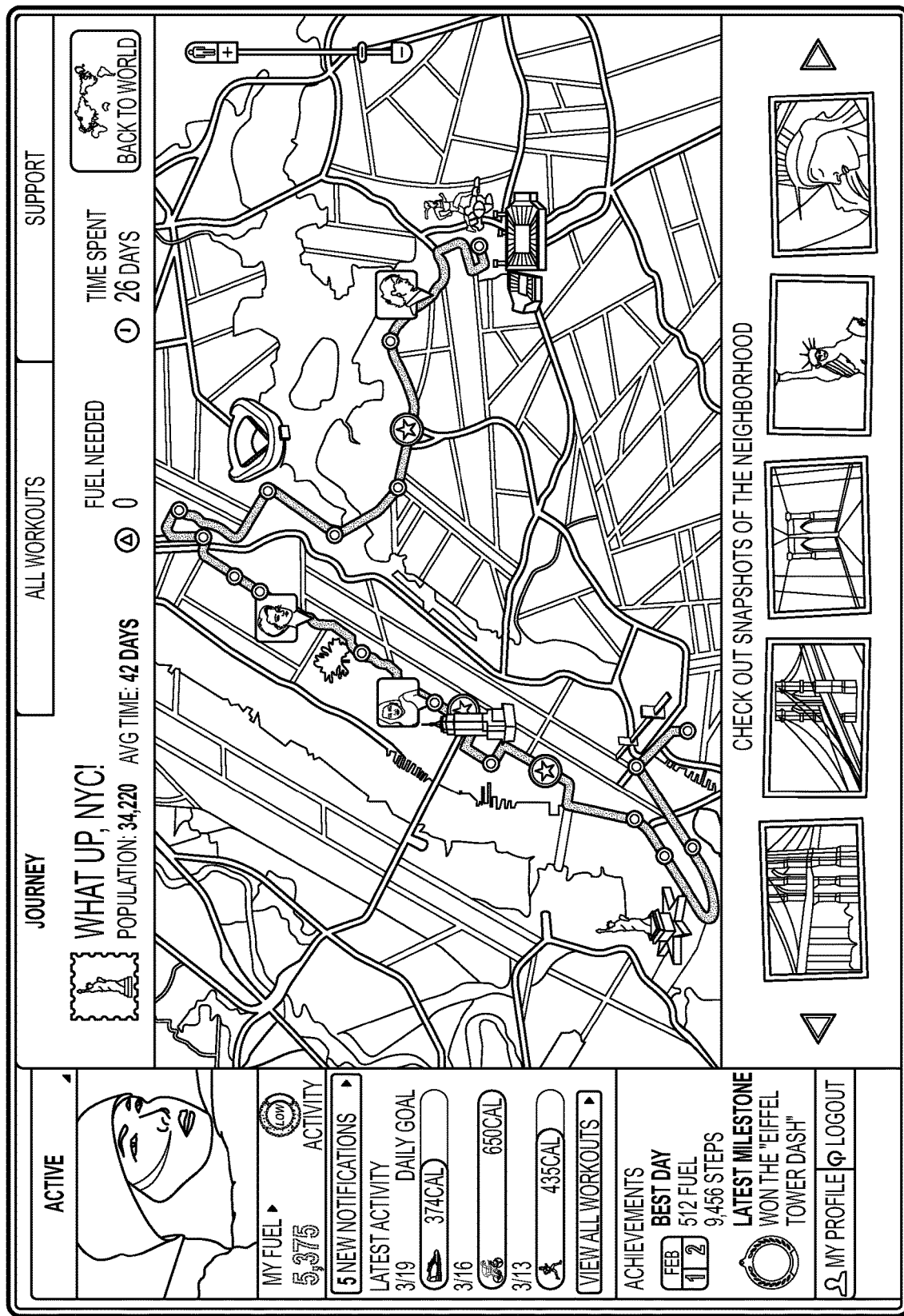

FIG. 78C illustrates an example progress tracking map showing completion of all goals in a particular goal location.

Figure 79A:
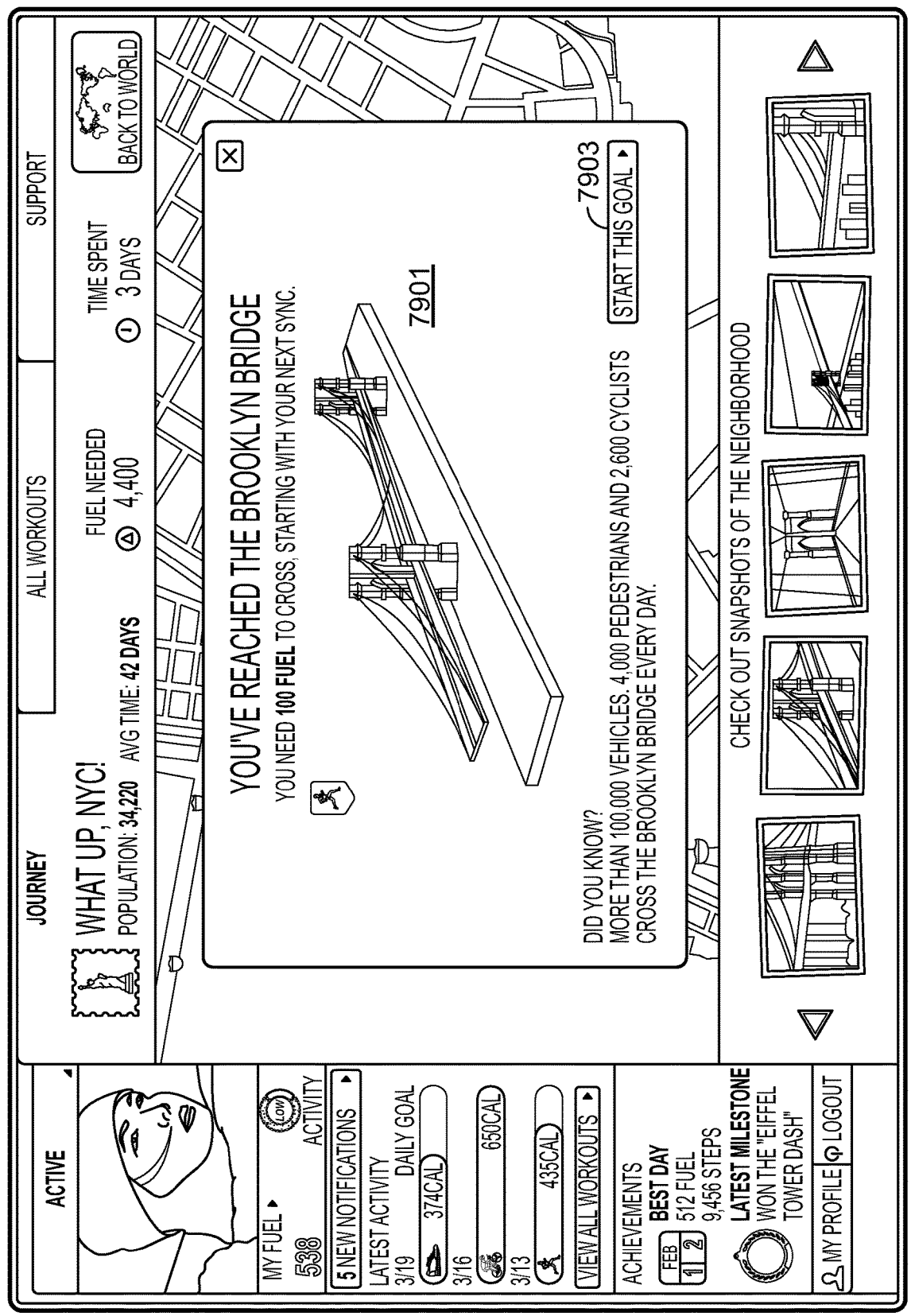

Upon reaching a goal, task or objective in a goal location, a tracking interface may display goal information and ask if the user wants to begin working on the goal. FIG. 79A illustrates prompt 7901 displaying a goal (e.g., the Brooklyn Bridge) and an option 7903 for starting the goal. Prompt 7901 may display the amount of fuel or other athletic activity metric required to complete the goal. For example, a user may need 100 fuel to cross the Brooklyn Bridge. The fuel or other athletic activity metric may correspond to an actual amount of athletic activity required for performing an athletic activity with the goal object (e.g., calories burned to cross the bridge) or may be an estimated, representative or virtual amount. Once a user selects option 7903, the user's athletic activity and progress in completing the goal may be tracked by the system and be reflected in the appearance of the goal object.

Figure 79B:
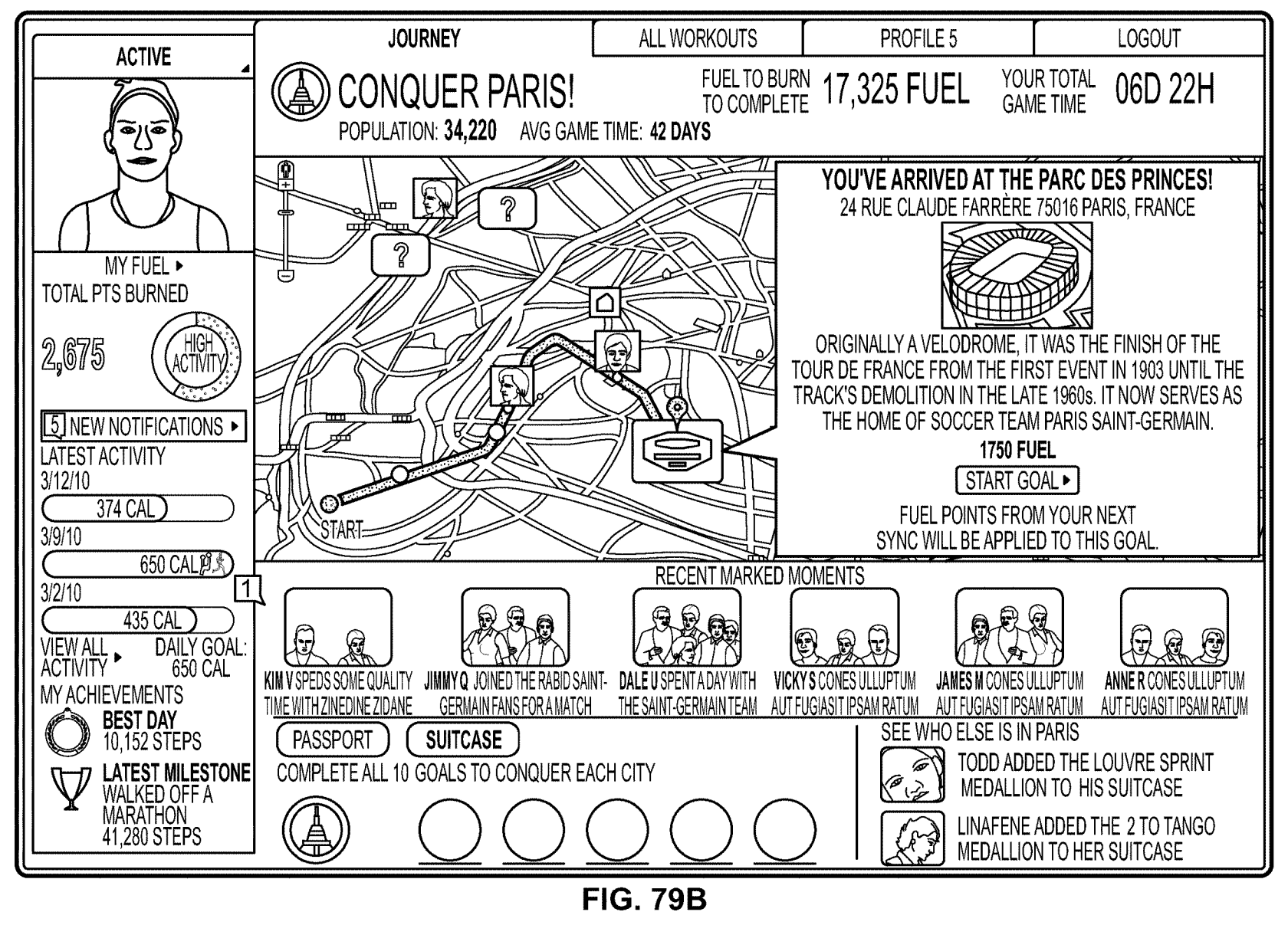

FIG. 79B illustrates another example in which a user is prompted to begin a goal upon reaching the goal on the progress map.

Figure 80A:
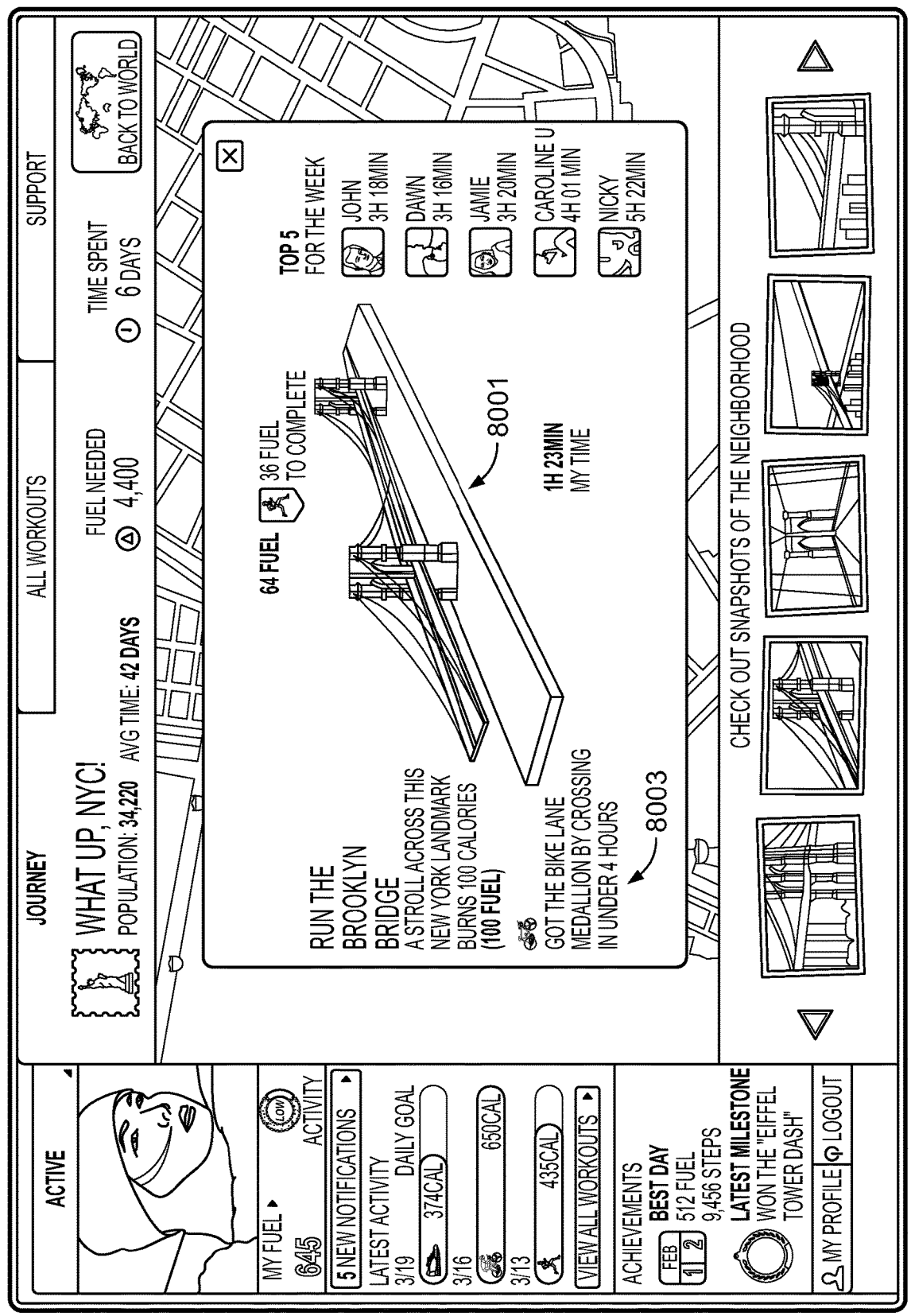
Figure 80B:
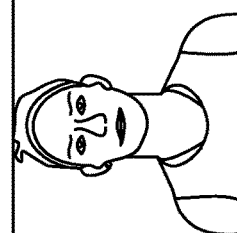
Figure 80C:
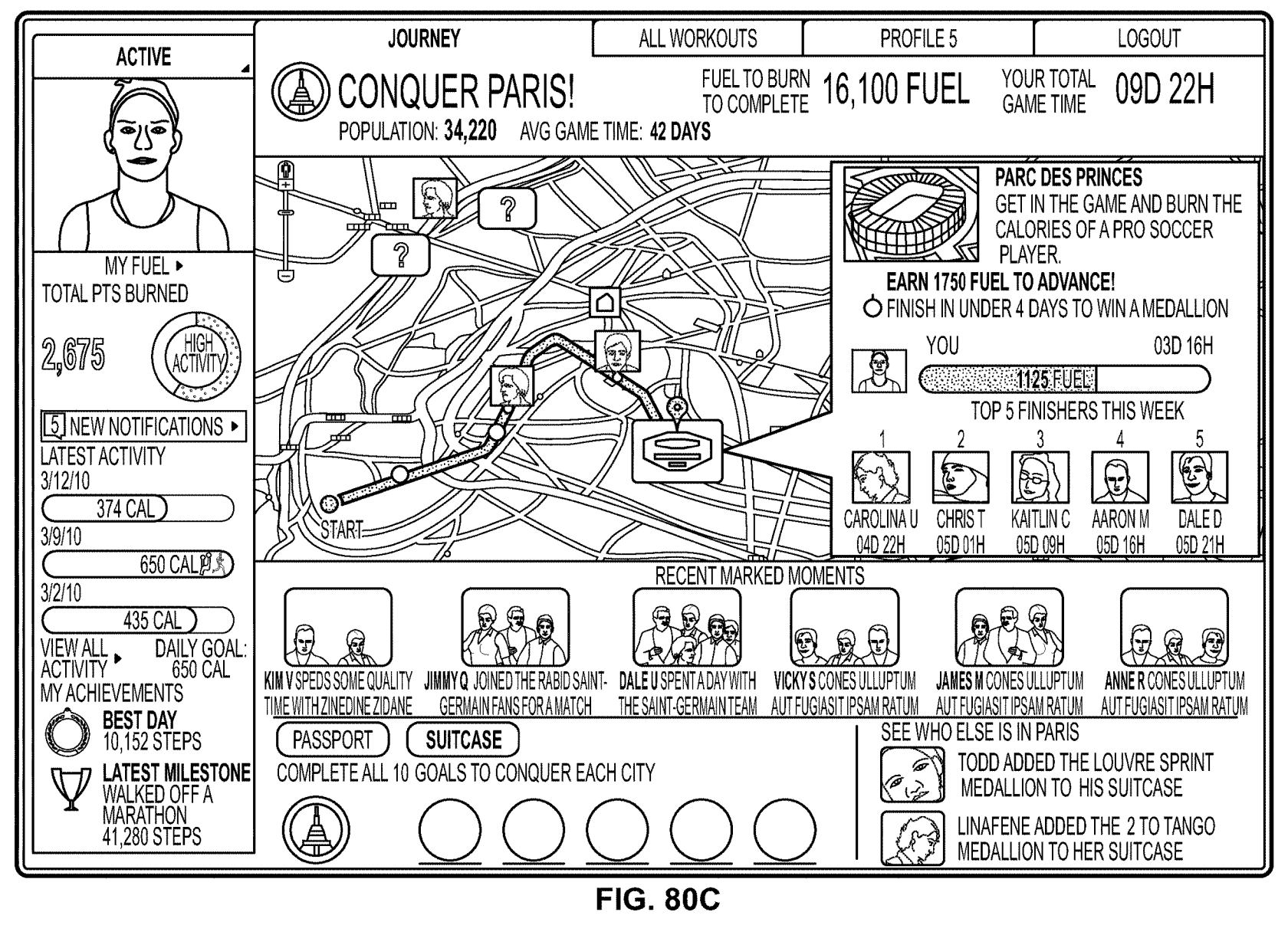

FIG. 80A illustrates goal object 8001 when a user has completed 64% of the goal (e.g., earned 64 of 100 fuel). In the illustrated embodiment, goal object 8001 may initially be displayed as an outline with no color. As a user progresses through the goal, portions of goal object 8001 may be displayed with color and/or additional details. A user's progress may also be specified by indicating an amount of time currently spent in progressing through the goal. The amount or portions of goal object 8001 displayed in color and/or with additional details may be proportional to the amount of the goal completed. Achievements may include a condition that a user may satisfy in completing a goal. Thus, a user may complete a goal even though the achievement has not been earned. An achievement 8003 associated with the goal may be specified in a portion of the screen as well. Achievement 8003, for example, indicates that the user may earn a bike lane medallion for crossing the bridge in under 4 hours. Accordingly, the achievement may be separate from the overall goal of crossing the bridge. Additionally or alternatively, a list of users that completed the goal in the fastest time may be displayed. The list of users may be organized and selected to reflect other metrics as well (e.g., heart rate, steps taken, distance run). The list of users may also be dependent on whether a user has any friends registered with the system. If so, the list of users might include only friends. If the user does not have any friends, the list may be generated from a field of all users.

Figure 80D:
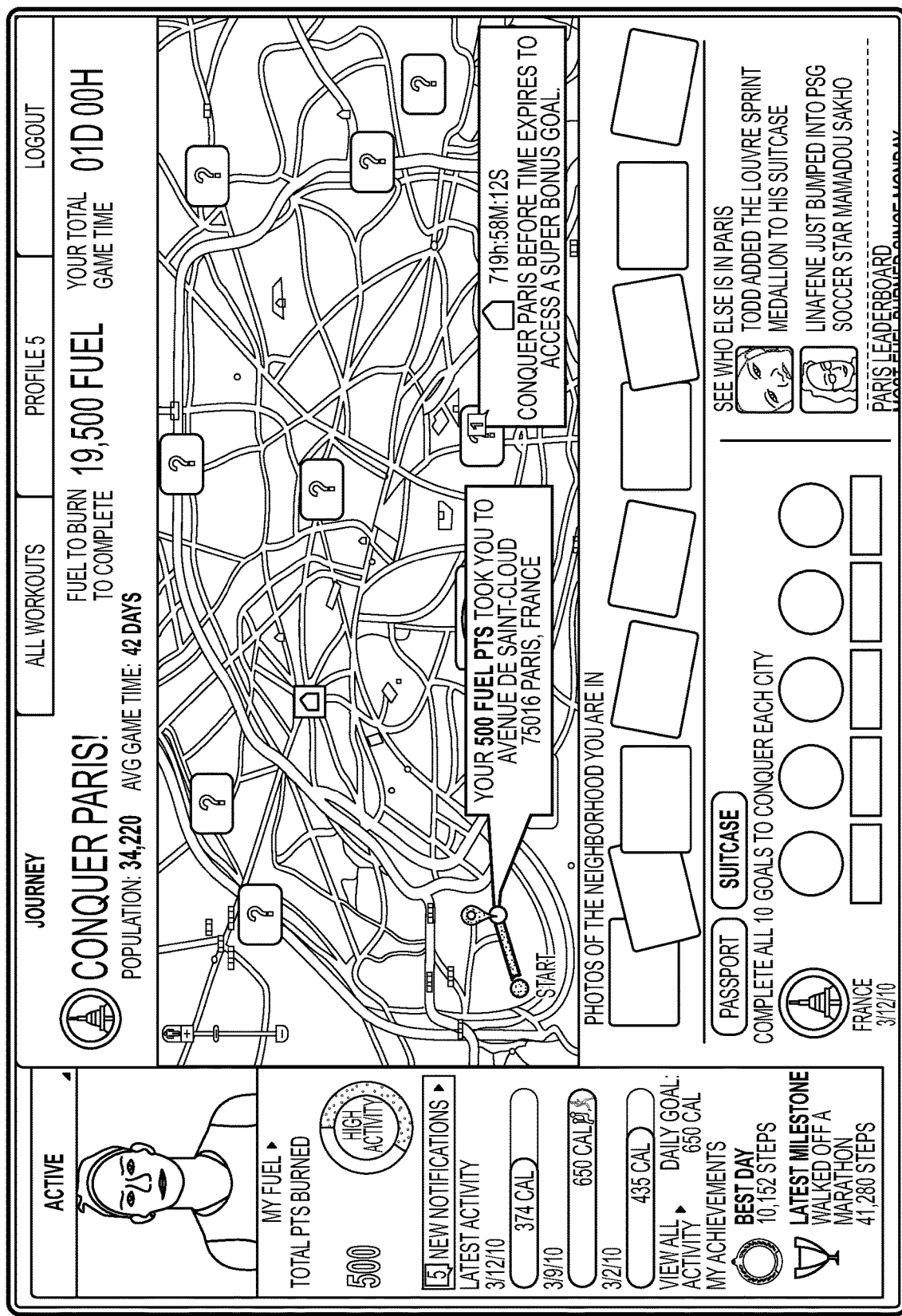
Figure 80E:
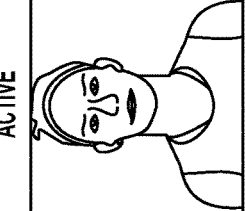

FIGS. 80B-E illustrate further example interfaces for tracking a user's progress in completing a goal. In FIG. 80D, the user may be provided with a timer for a time-based goal. For example, the user may be required to complete all goals in the goal location within a certain amount of time. In one or more arrangements, the time-based goal might not be required for completing the goal location. Instead, the time-based goal may be a bonus task or objective that may be rewarded in some way (e.g., virtual currency, virtual items for an avatar, celebrity postcards) if completed. In other arrangements, the time-based goal may be required for successful completion of the goal location.

Figure 81A:
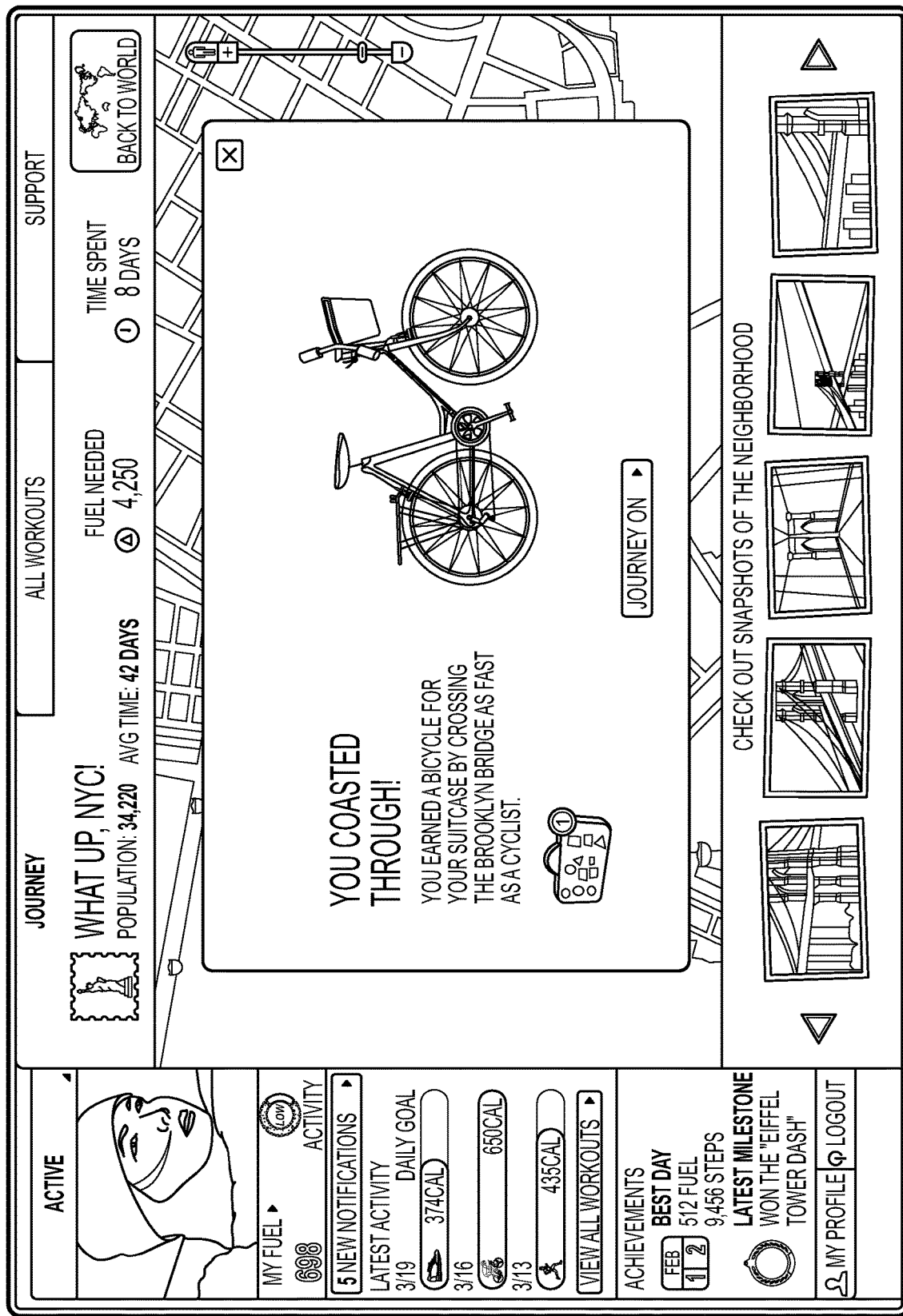
Figure 81B:
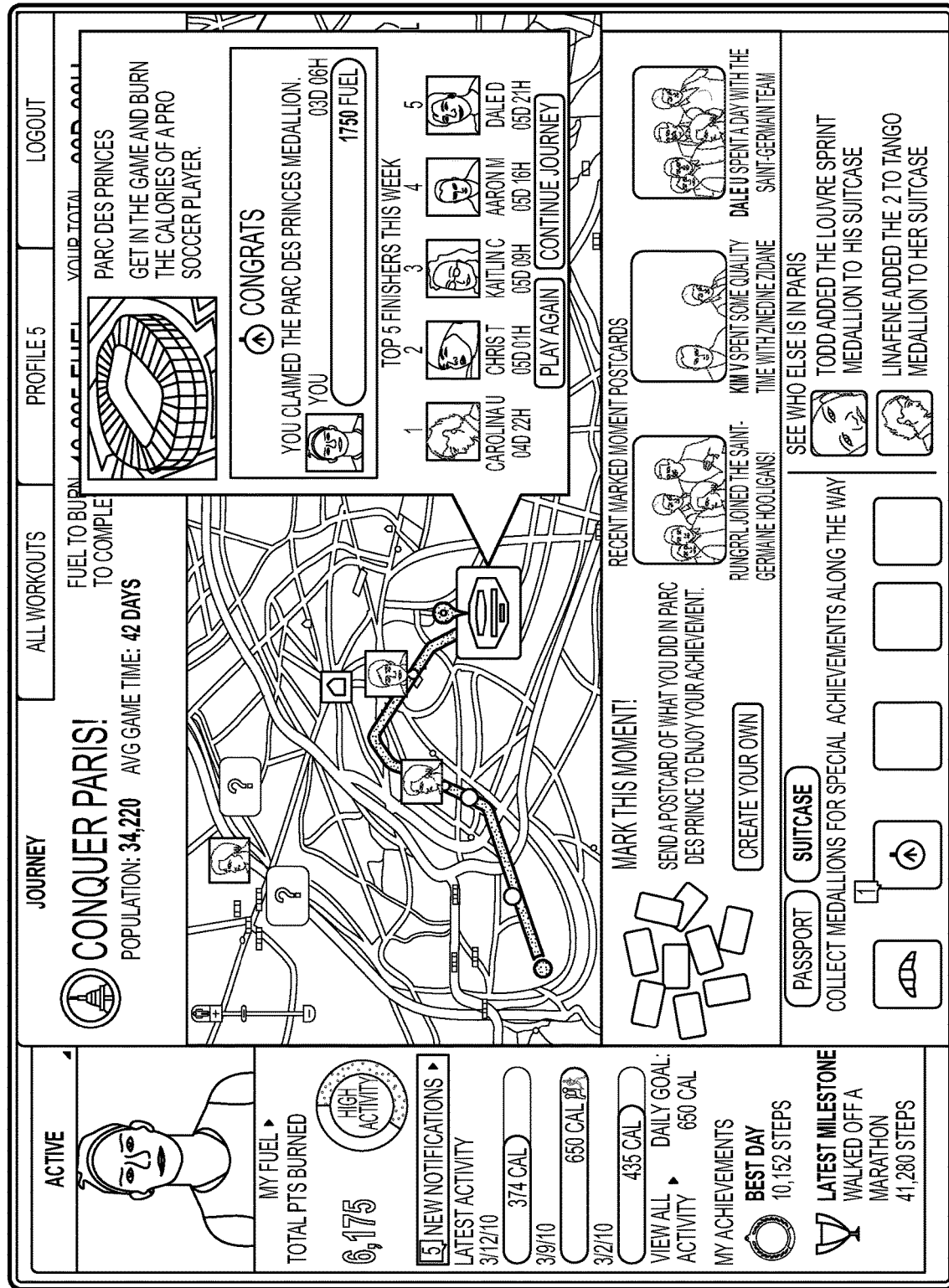
Figure 82A:
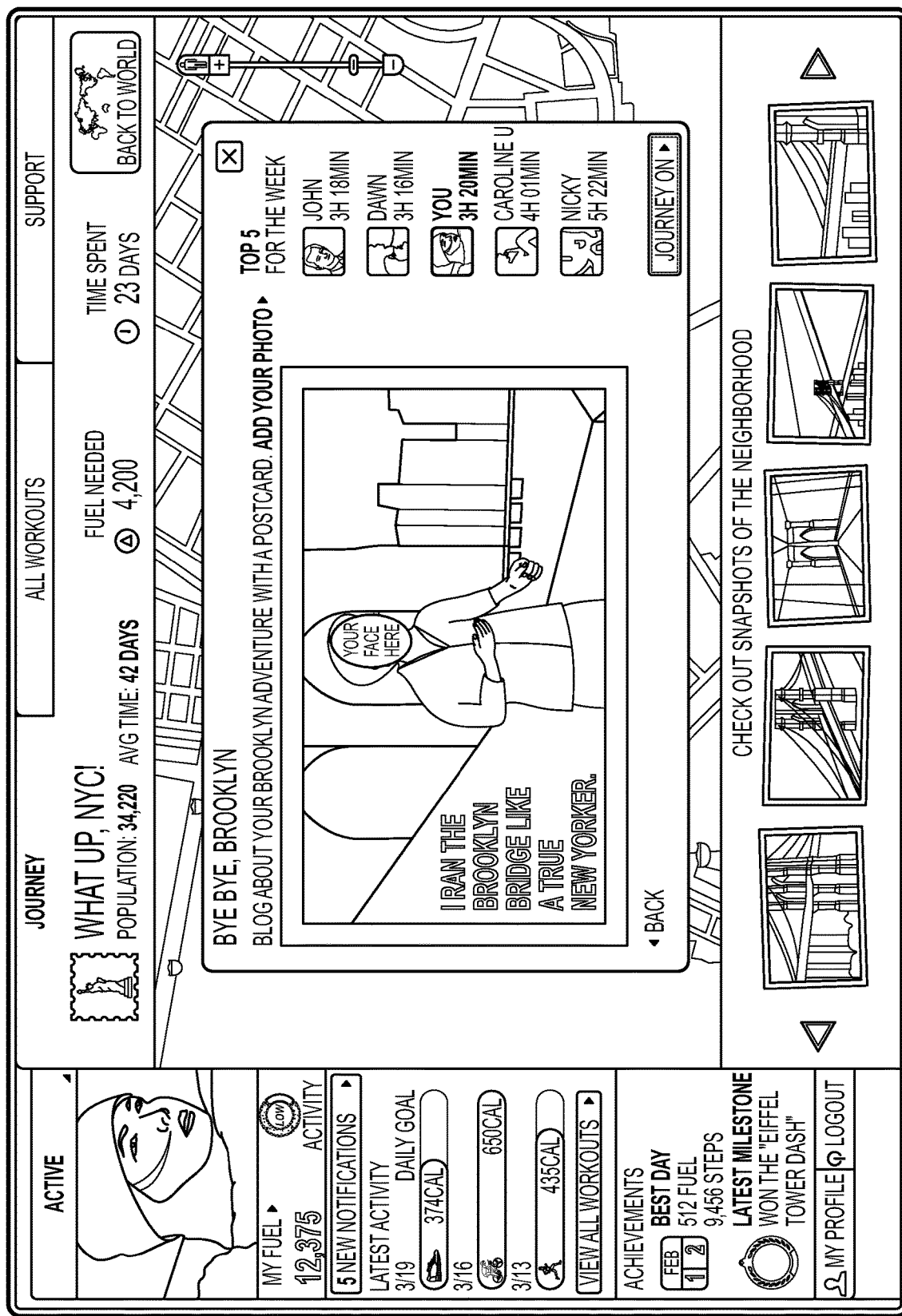
Figure 82B:
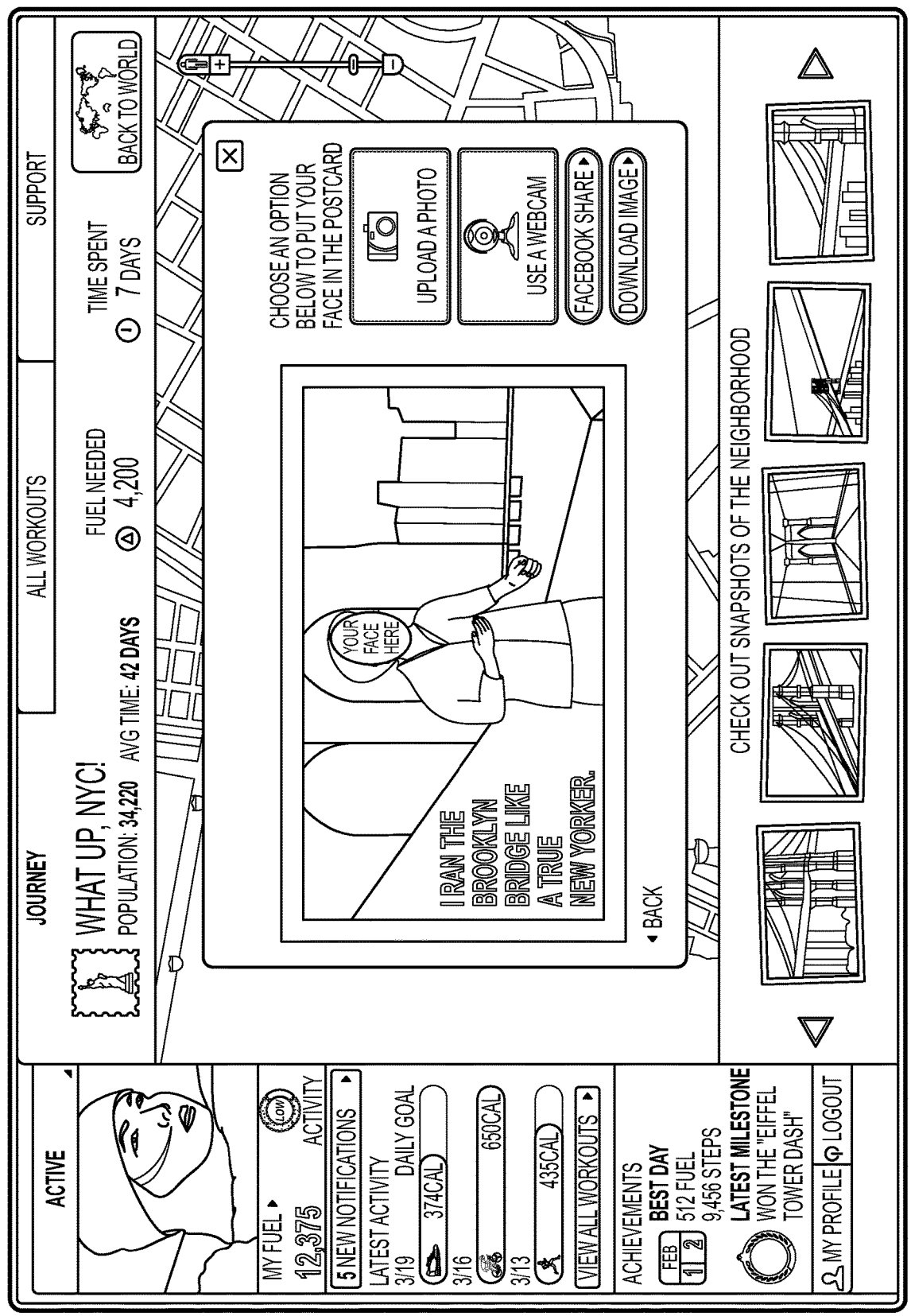
Figure 82C:
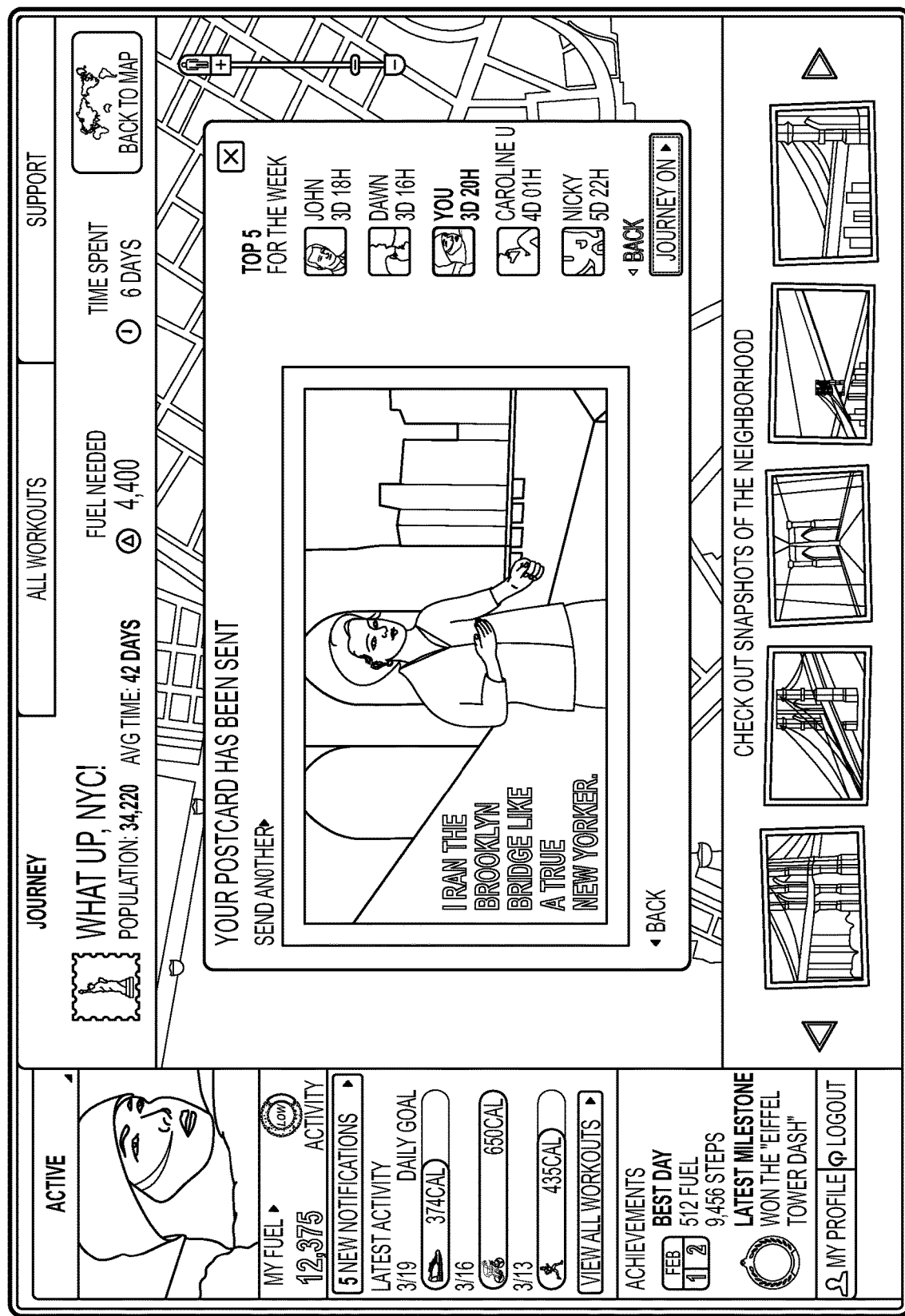
Figure 82D:
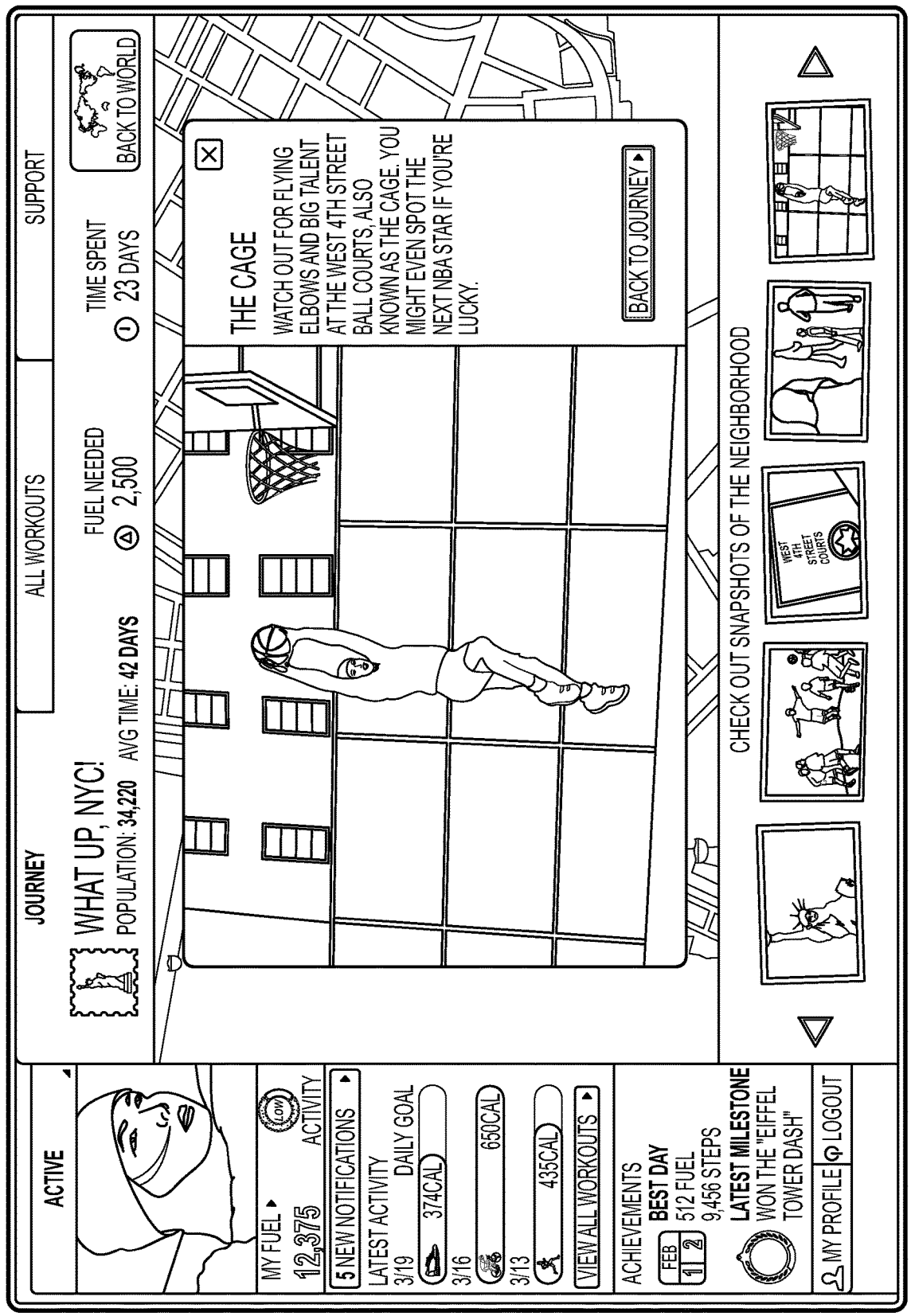
Figure 82E:
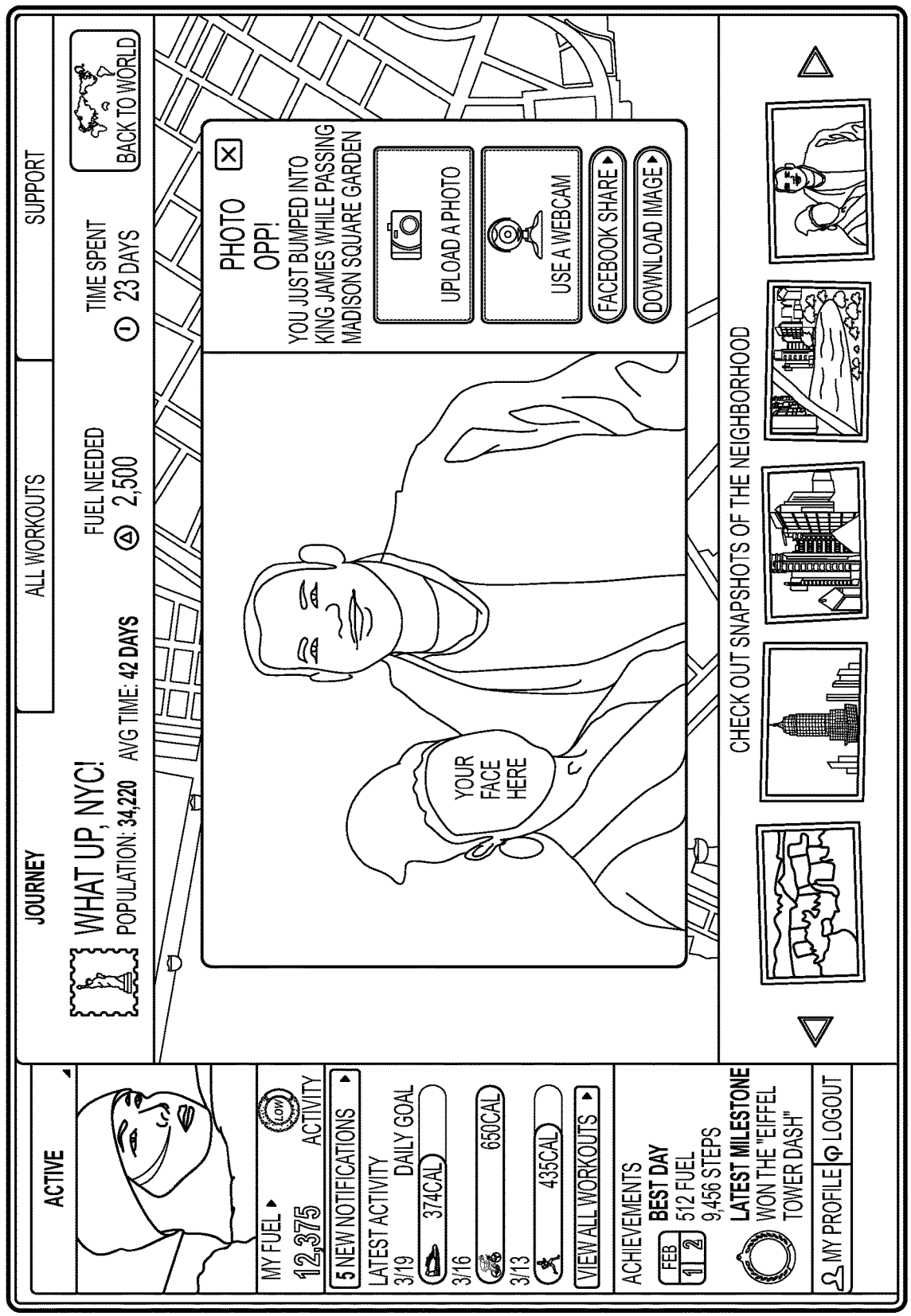
Figure 82F:
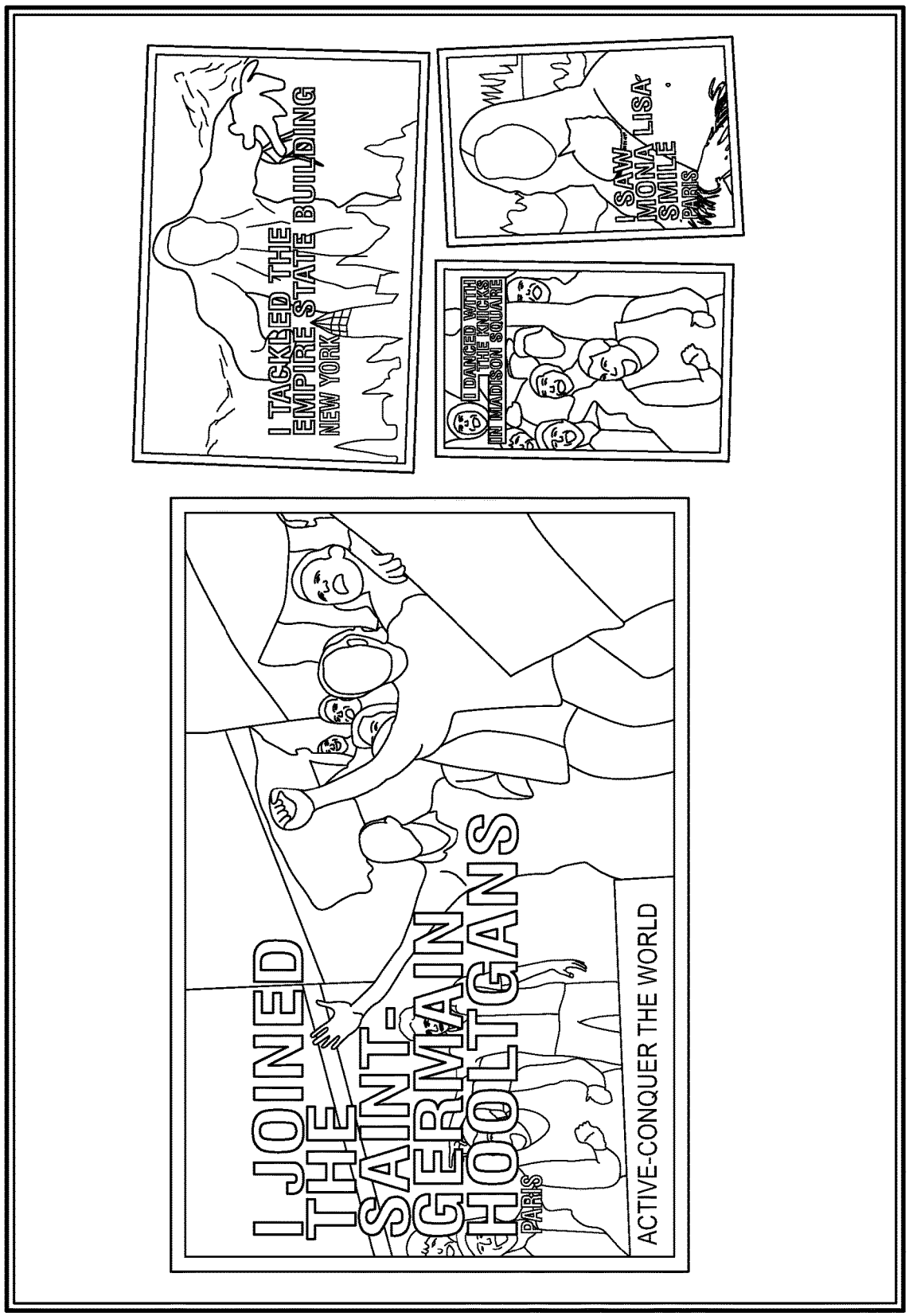

If the user completes the goal and satisfies the requirements or conditions of a specified achievement, the user may be awarded with a trophy or medallion reflecting the achievement. FIGS. 81A and 81B illustrate such awards.

FIGS. 82A-F illustrate various types of messages or postcards that a user may send to other users upon reaching a particular goal, reaching a location in a location themed workout plan, completing a goal, completing all goals in a goal location, satisfying requirements of an achievement, reaching a milestone and the like. For example, upon completing a goal or reaching a certain point in a goal location, the user may be prompted with the opportunity to send a postcard. The user may select a postcard from a list of postcards. Some postcards may be available by default and some may be earned through athletic activity. In one example, the postcard may display a runner with the runner's face missing. The interface may allow the user to upload or use a webcam to provide a picture of the user's face to be inserted onto the runner's body. In addition to being able to transmit the postcard or message, the user may also be allowed to post the postcard or to download the postcard as an image or other format.

Figure 82G:
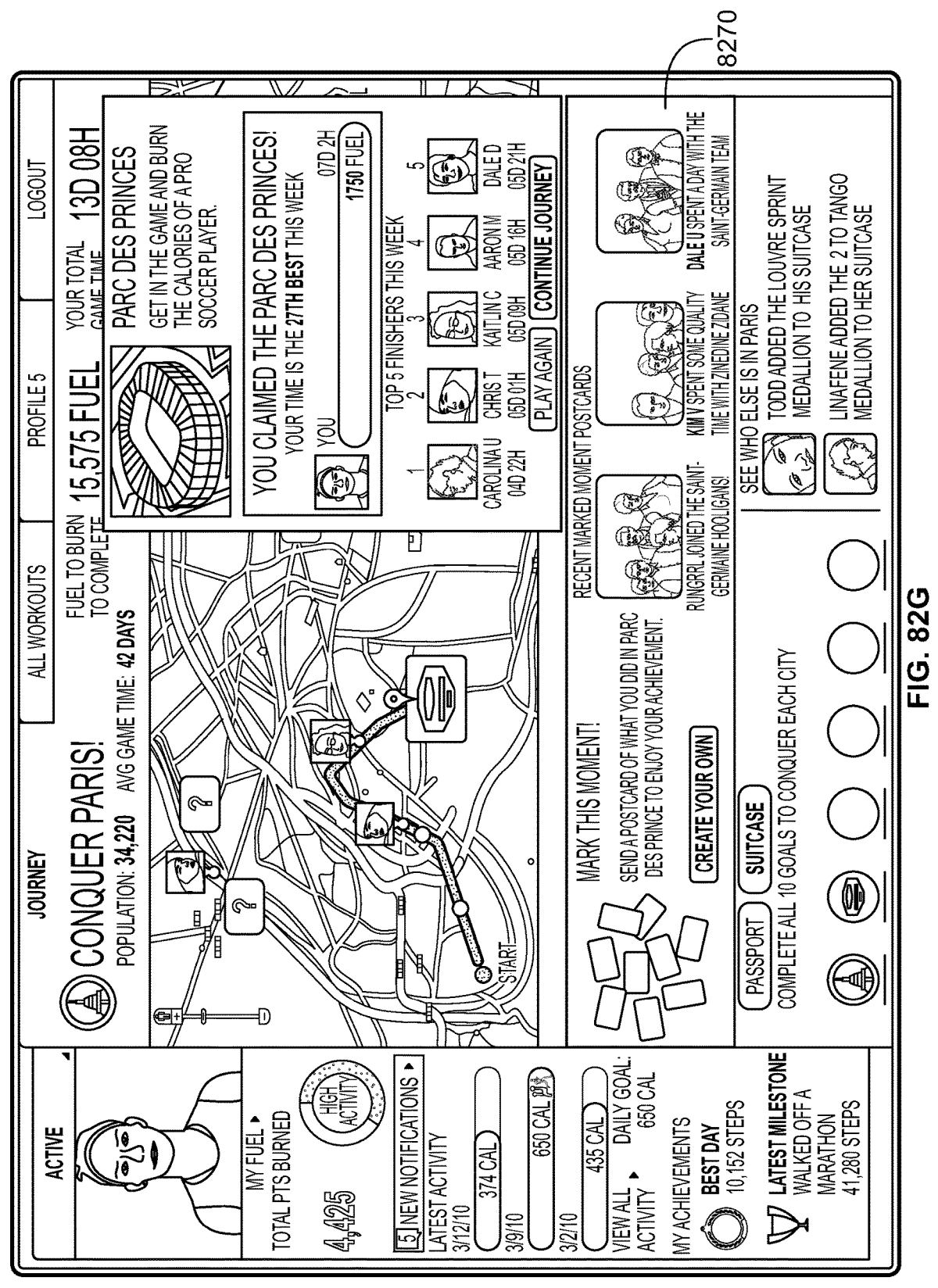

In one or more arrangements, postcards may be displayed in a user's progress interface. For example, in FIG. 82G, a postcard created by a user may be displayed in area 8270 to represent particularly memorable moments in a user's workout history. Selecting the postcard from area 8270 may allow the user to view details of that moment, achievement or accomplishment.

Figure 83:
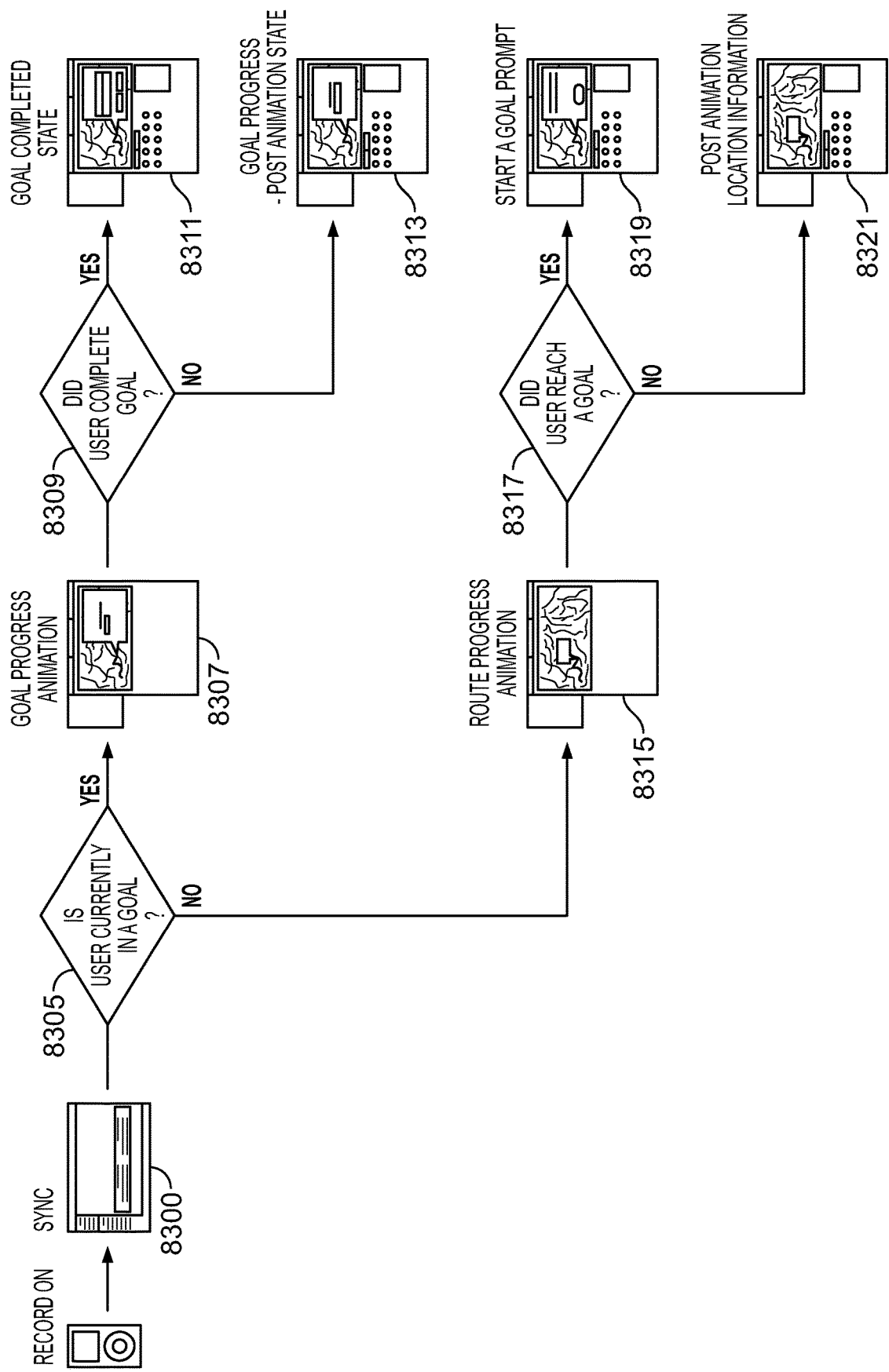
FIG. 83 is a flowchart illustrating a method for displaying athletic activity tracking and monitoring information.

FIG. 83 illustrates an example flowchart for determining a display state of a tracking and monitoring system. In step 8300, for example, athletic activity data recorded may be synchronized with the tracking and monitoring system. Synchronization may be performed through a network or through a direct local connection. In step 8305, the system may determine whether the user is currently in a goal. If so, the system may display a goal progress animation in step 8307. That is, the system may display an animation of the user's progress from a starting point (or a point at which the user left off in a previous workout session) to a current progress level or point. In one example, the animation may comprise the filling of a progress meter, animating a user icon along a path, filling of a goal object (e.g., the Statue of Liberty, the Eiffel Tower) and the like. The system may further determine whether the user completed the goal in step 8309. If so, a goal completed display may be provided in step 8311. If, however, the user has not completed the goal, the user may be provided with a goal progress interface in step 8313.

If the user is not currently in the process of completing a goal, a route animation representing the user's progress through the goal location and between goals may be displayed instead in step 8315. In step 8317, the system may determine whether the user has reached a goal. If so, the system may display a goal prompt to ask the user whether he or she wishes to start the goal (e.g., prompt 7901 of FIG. 79). If, however, the user has not reached a goal, the system may instead display information about a current location in the progress map (e.g., an amount of fuel earned, distance to next goal, fuel to next goal, fuel distance from previous goal).

Figure 84:
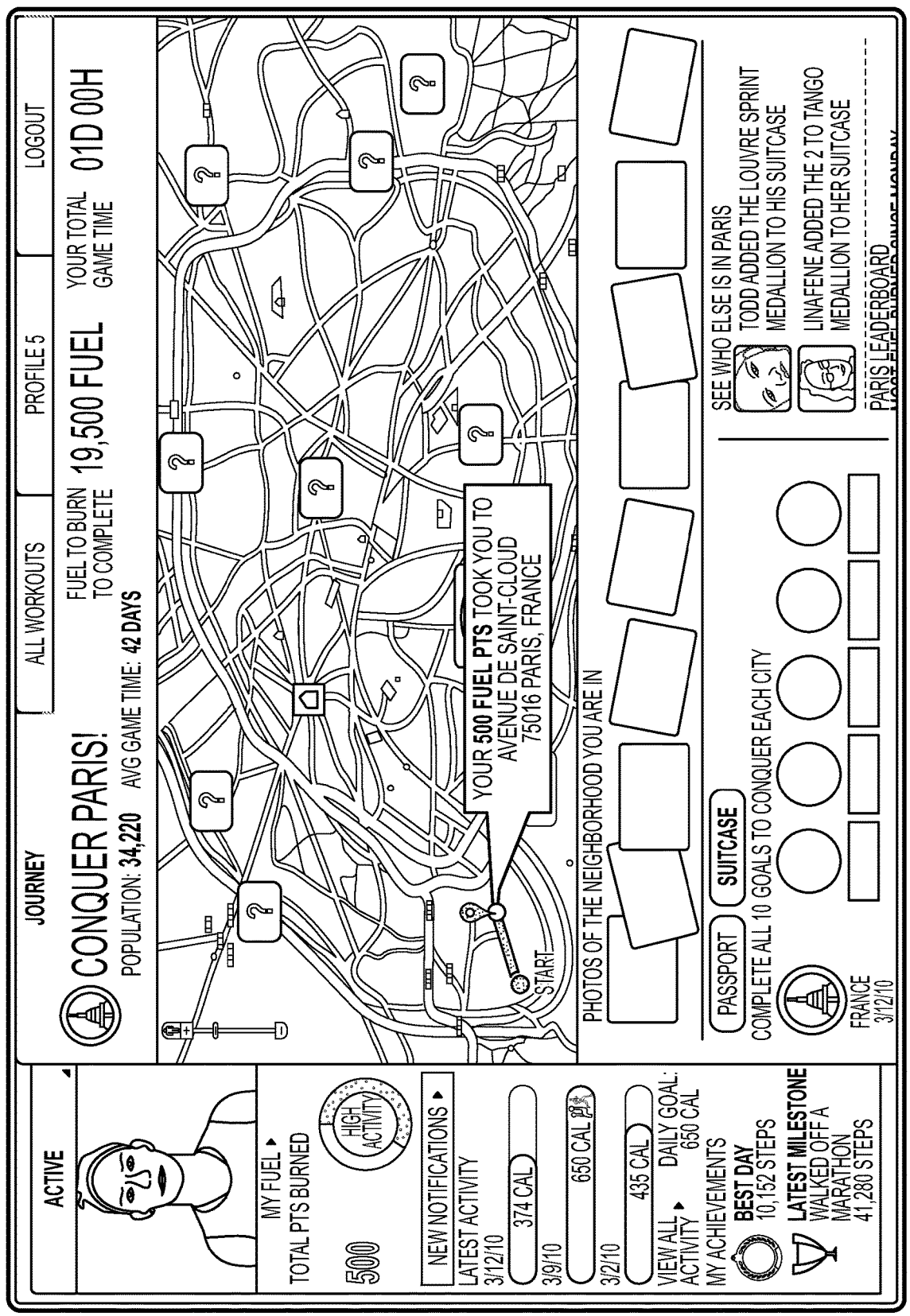
FIGS. 84-91 illustrate additional example interfaces for tracking and monitoring user athletic activity information.

FIG. 84 illustrates an example progress map in which location information is displayed for a non-goal endpoint or location. For example, the information prompt indicates that the user has earned 500 fuel points and has arrived at Avenue de Saint-Cloud.

Figure 85:
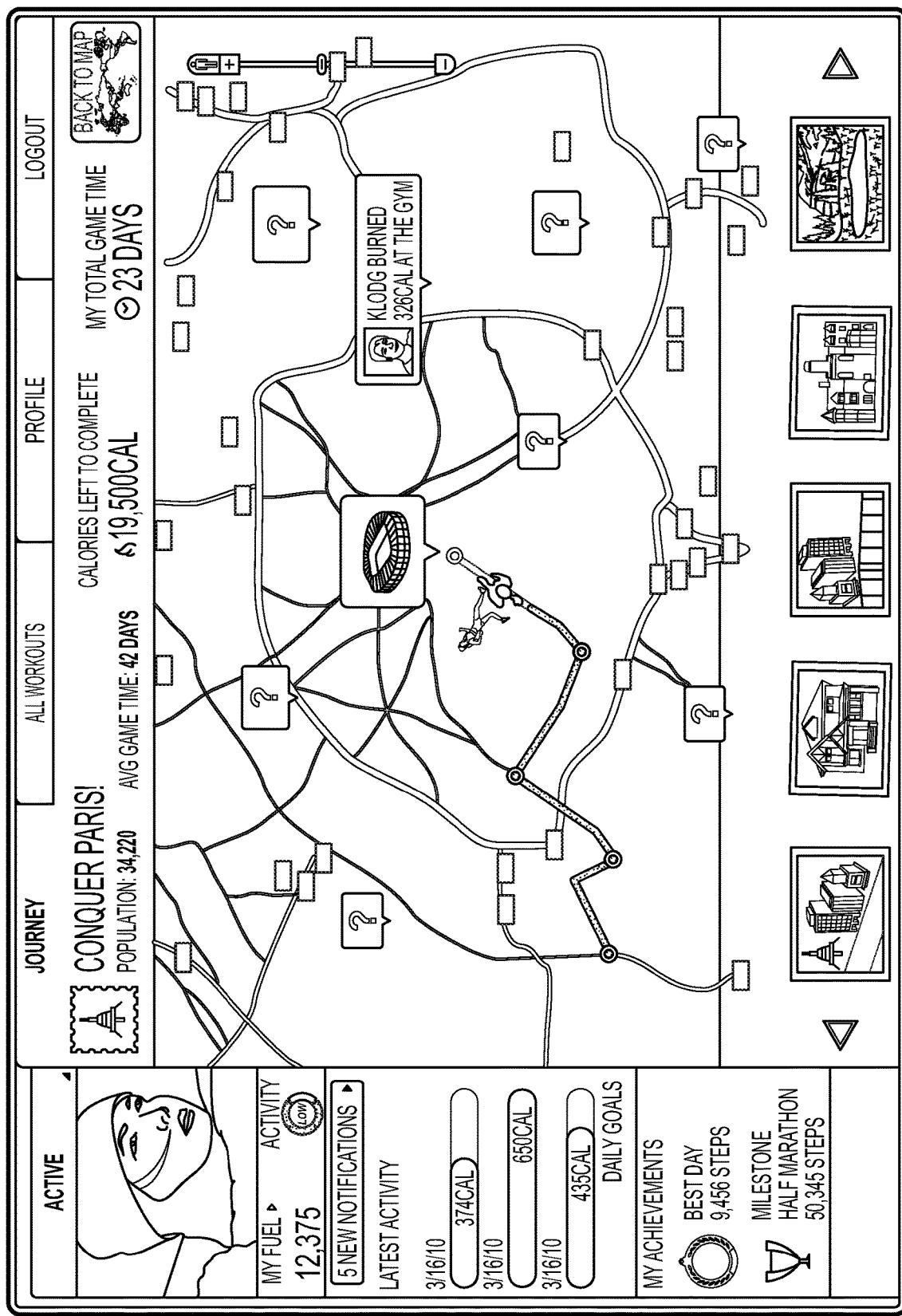

FIG. 85 illustrates another example progress map. In this example map, information about other user's athletic activity is displayed. In particular, the user is informed that a friend or other user has recently burned 326 calories at the gym. A progress map may thus display athletic activity information of users regardless of the type of activity performed. The metrics used to measure various types of athletic activities may, in open or more arrangements, be converted to fuel points. The use of fuel points may allow a tracking system to appropriately track the progress of multiple users performing different activities on a progress map.

Figure 86:
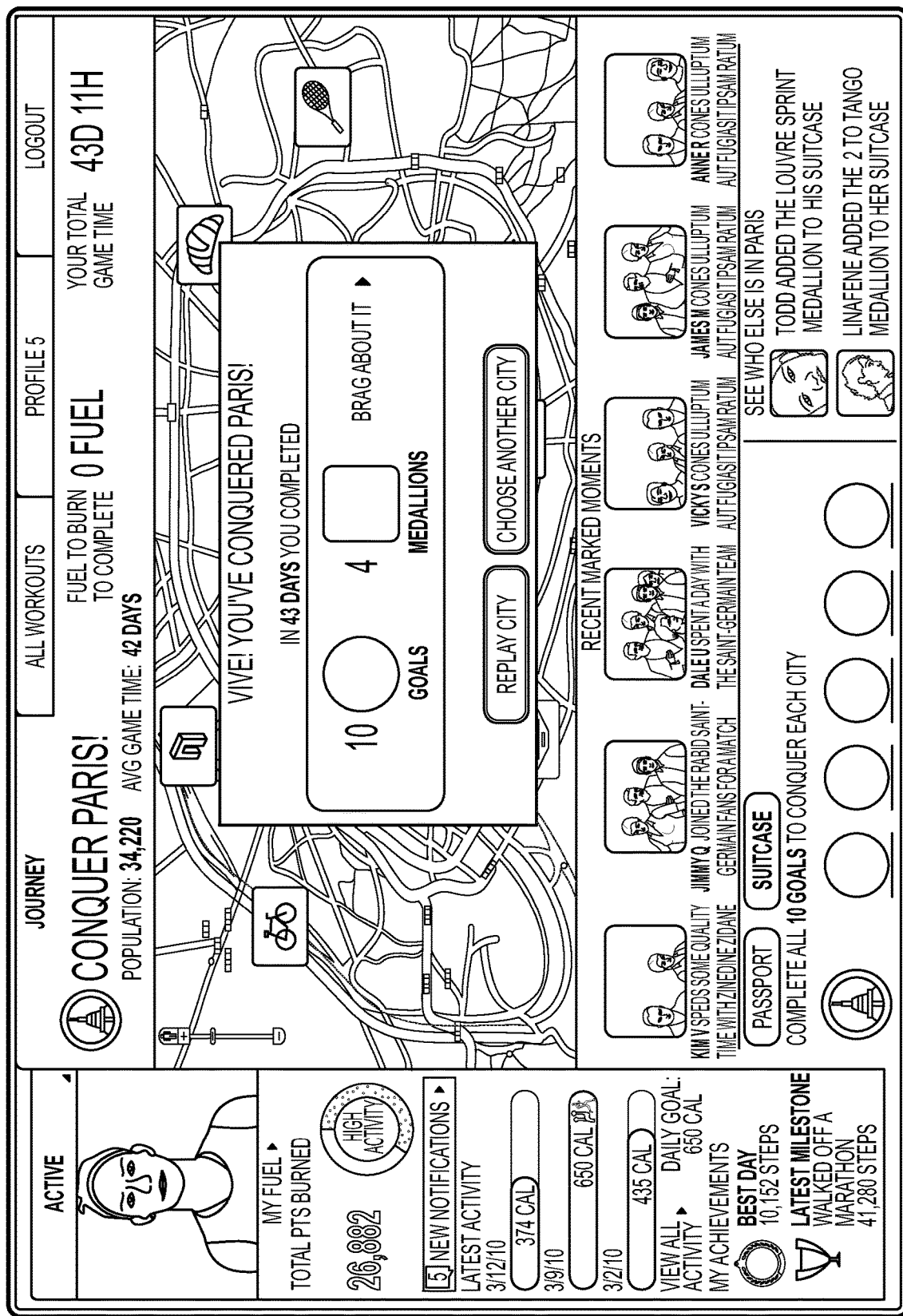

In some arrangements, a summary of a user's athletic activity in a particular city or location may be displayed upon completion of all goals and activity in that location. FIG. 86 illustrates such a summary. The summary may include a number of goals completed and a number of achievements (e.g., medallions) reached. The summary may indicate the amount of time required to complete the goals and activities in the location. The system may further provide the user with options to replay the city or location or to use another location. Replaying the location may reset the data for that location or, alternatively, generate another instance of the location so that data for the current completion is not lost.

Figure 87A:
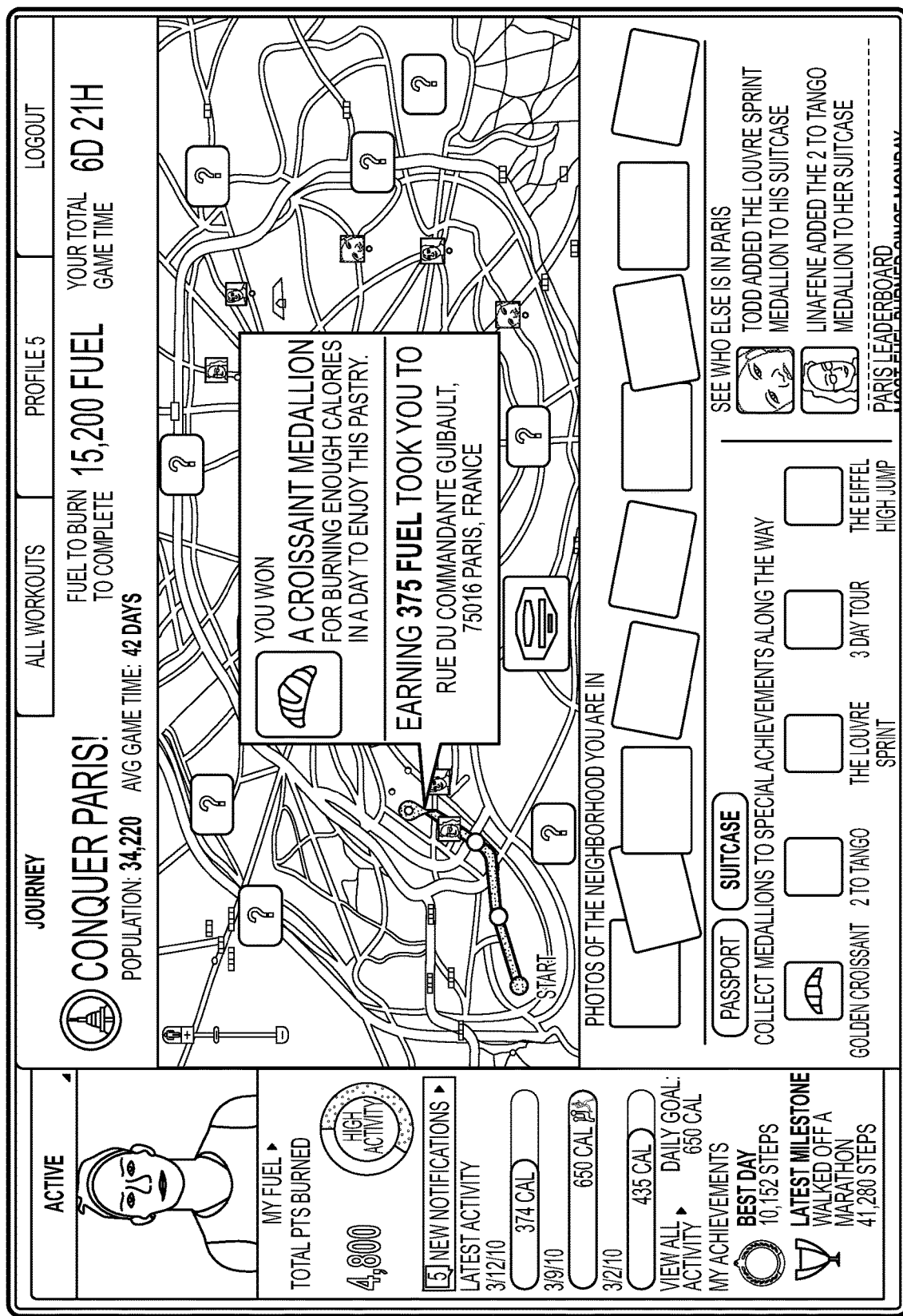
Figure 87B:
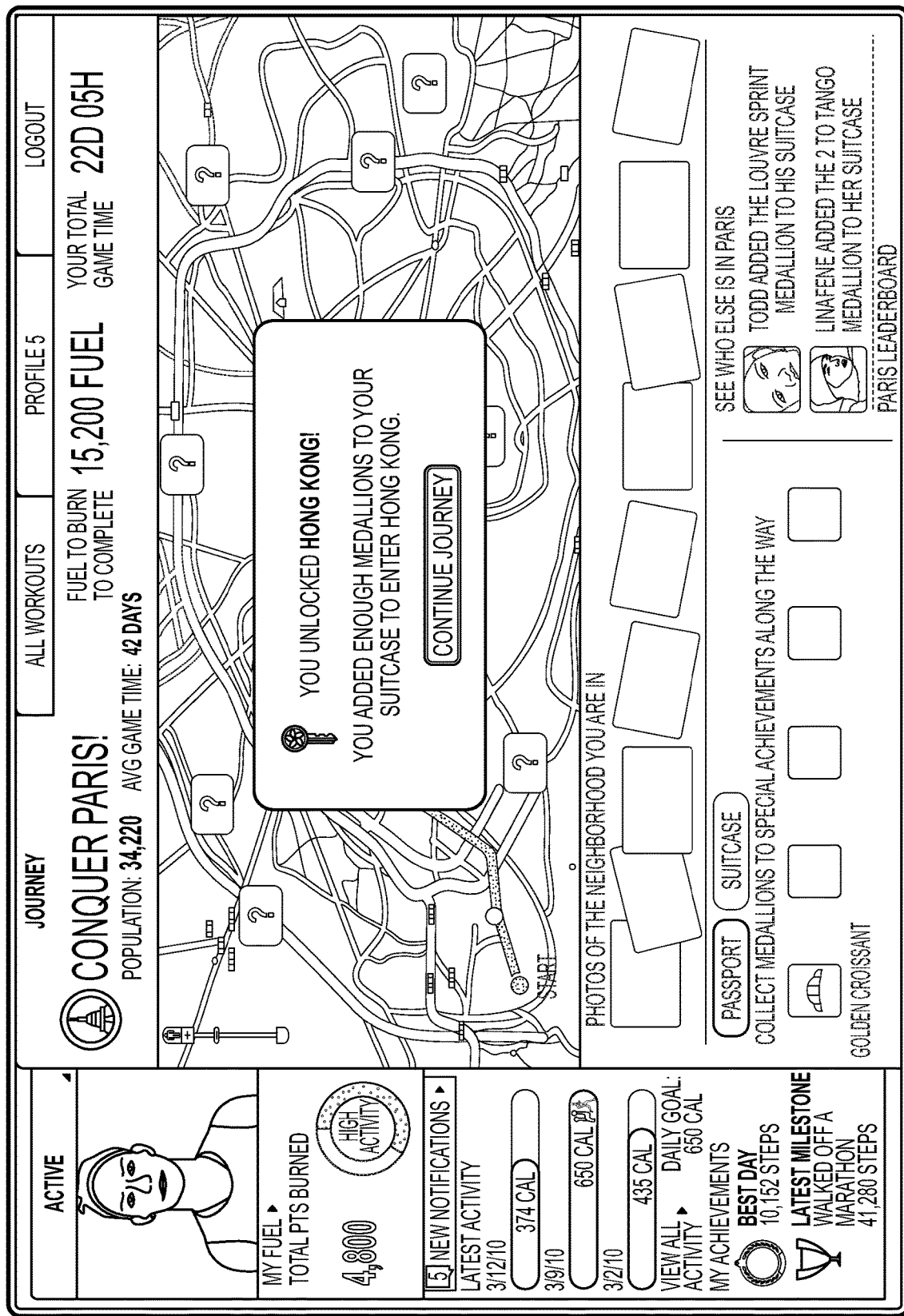
Figure 87C:
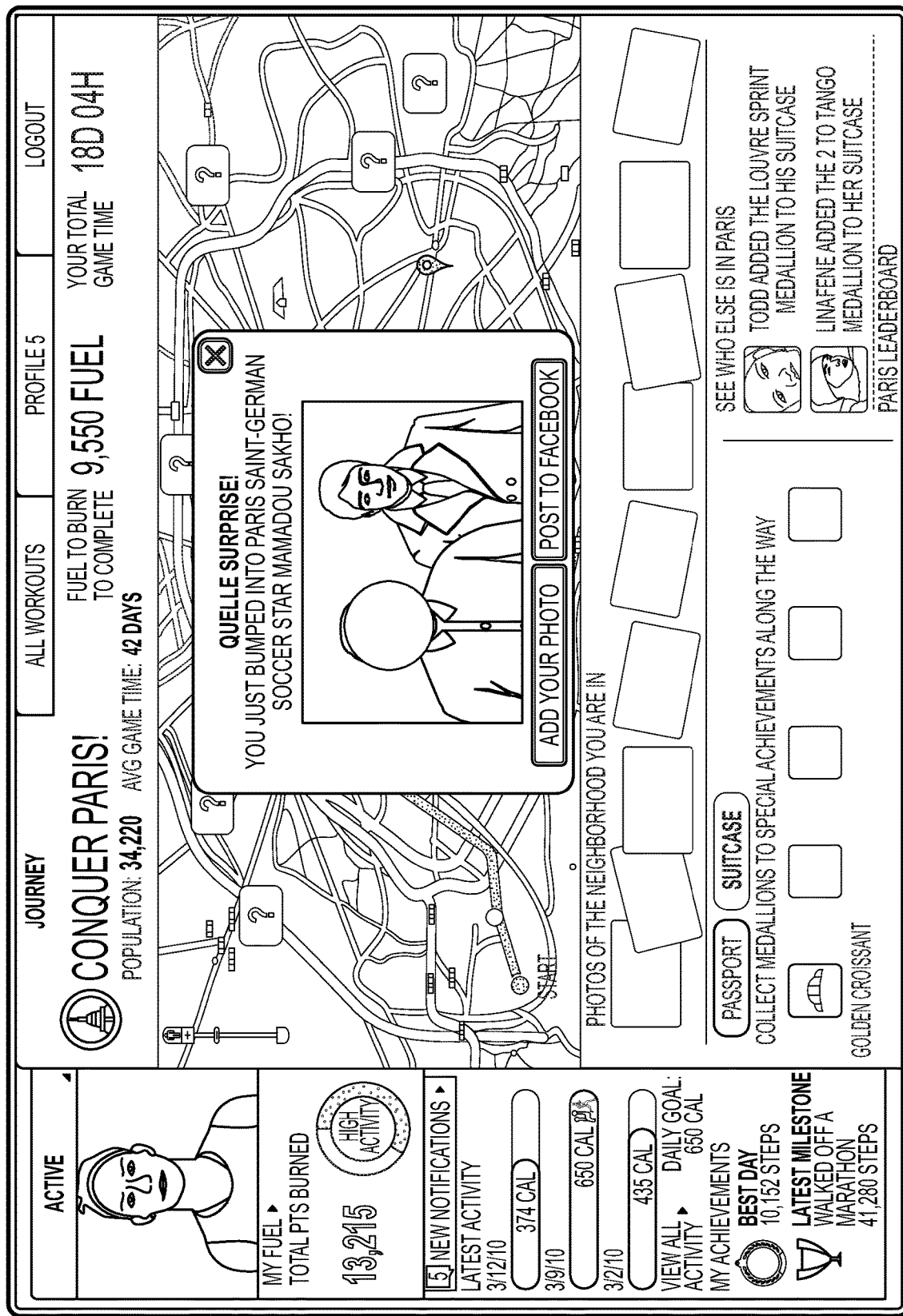

FIGS. 87A-87C illustrate surprise or unexpected achievements or awards that may be earned by progressing through a goal location. Unexpected or surprise achievements may include achievements or goals that are not identified on a progress map or of which a user does not have prior knowledge. In the example of FIG. 87A, a user may be awarded with a medallion representing a food object corresponding to an amount of fuel earned (converted from an amount of calories). For example, a croissant medallion may be awarded using a calorie equivalent of 375 calories for a croissant and upon determining that the user has earned 375 fuel points (based on a conversion rate of 1 calorie=1 fuel point). By earning 375 fuel points in the previous example and achieving the croissant medallion, a user may equate the activity to having burned off a croissant. In another example, FIG. 87B illustrates a user unlocking another city or location. In this example, the unlocking of the location may be conditioned upon the user earning a certain number of medallions or completing a number of goals. Other unlocking conditions may also be used including a number of fuel points earned, a number of locations completed and/or combinations thereof. In yet another example, user may be awarded with surprise postcards for various celebrities, athletes and/or other individuals as illustrated in FIG. 87C. The award of the postcard may be conditioned upon reaching a certain point in a progress path of the goal location, completing a number of goals and the like.

Figure 88:
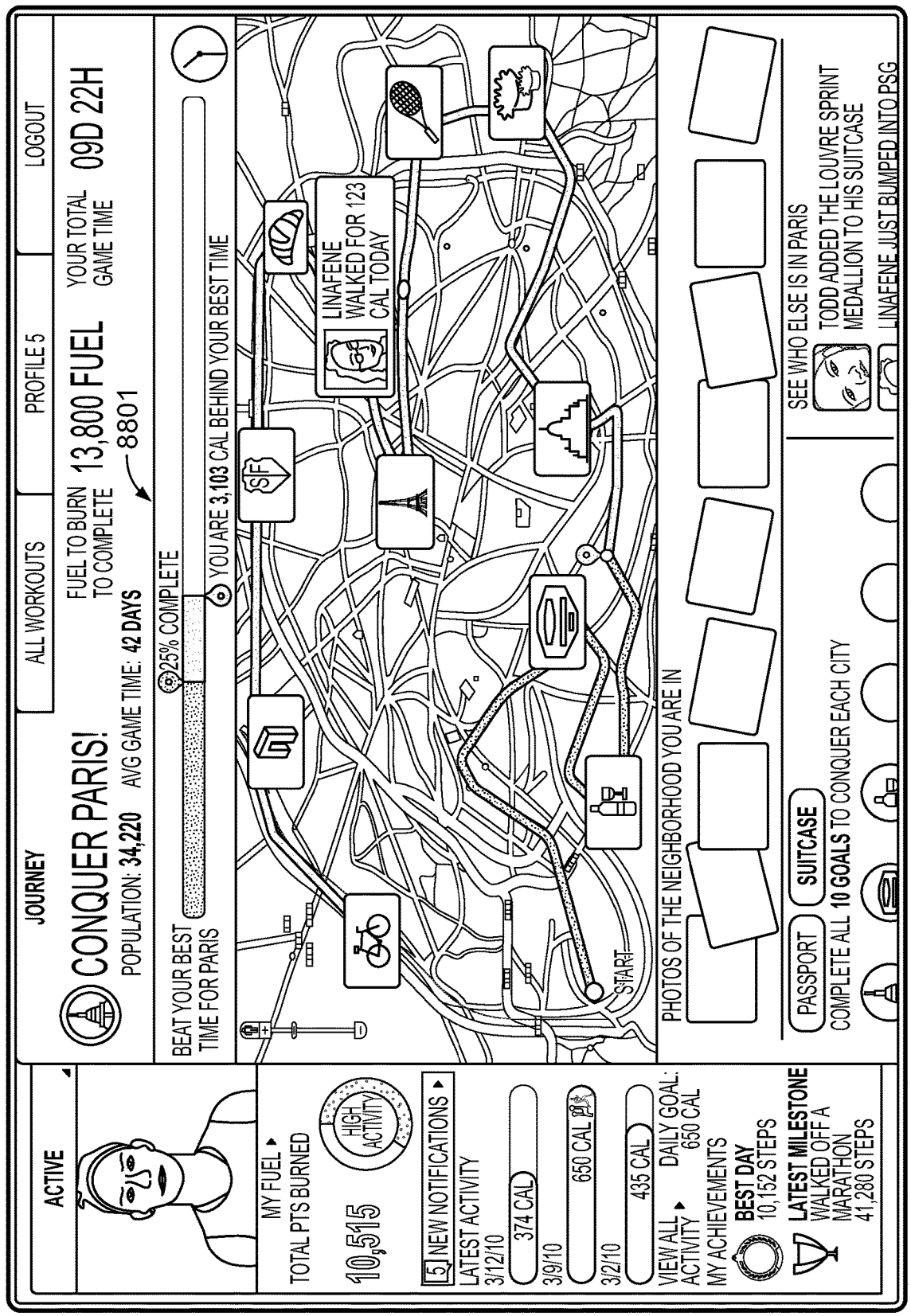

In one or more arrangements, a user may set a goal to compete against himself or herself. For example, the user may wish to beat a previous best time for a particular location. Accordingly, a time bar may be displayed to aid the user in tracking his or her progress versus the previously recorded time. FIG. 88 illustrates an example interface in which a progress bar 8801 is displayed with two bars, one bar 8803*a* indicating a present progress and another 8803*b* indicating a progress made in a previous workout at the same elapsed time. For example, the bars 8803 may represent the number of calories burned and/or fuel earned at a particular point in time since the user started the goal location.

Challenges

Figure 49:
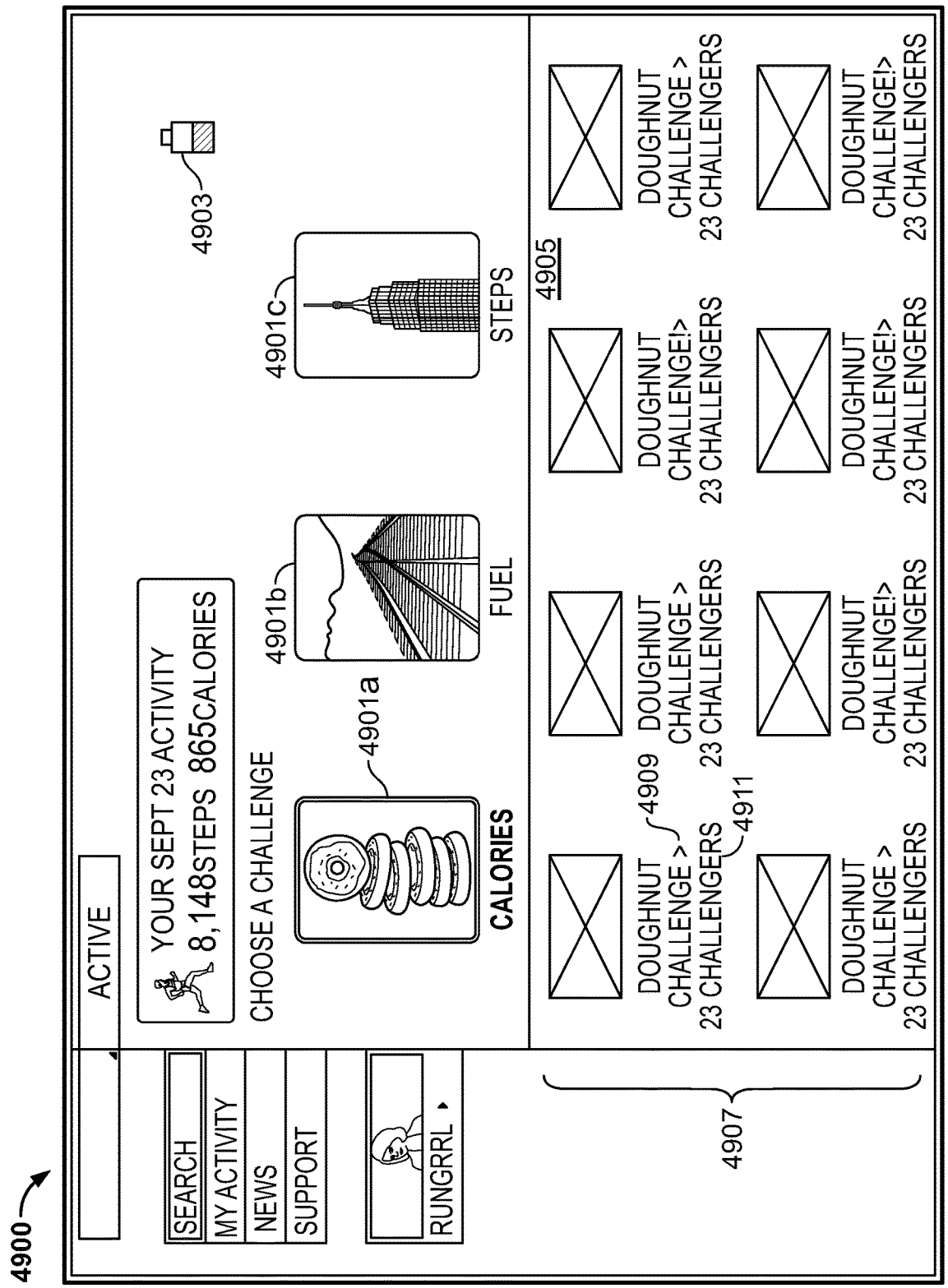
FIGS. 49-52 illustrate interfaces for selecting, engaging in and completing challenges according to one or more aspects described herein.

An athletic activity tracking and monitoring site may further offer the ability for a user to engage in an athletic activity challenge with one or more other registered athletes. FIG. 49 illustrates an example challenge interface 4900 in which a user may select from multiple different types 4901 of challenges. Challenges, as used herein, generally refer to goals that are competitive in nature (between multiple individuals) and have a specified deadline. Challenge types may include calorie challenges, fuel challenges and steps challenges. Calorie challenges may correspond to competitions to burn a certain number of calories while steps challenges may relate to taking a specified number of steps. Fuel challenges, as used herein, may generally refer to a virtual currency challenge. Challenges may be created by a user and published to others. Alternatively or additionally, challenges may be sponsored by an organization as a method of advertisement, fundraising and the like.

The amount of virtual currency achieved or gained may be determined based on a formula that is based on calories, steps or a combination thereof. Other factors may similarly be used in determining an amount of virtual currency to award. Virtual currency may then be spent to purchase actual products or services such as gift cards, gym memberships, digital music players, workout equipment and the like. A currency meter 4903 may be displayed in a portion of interface 4900 to indicate an amount of currency the user has accumulated thus far. The capacity of meter 4903 may be defined based on a user set currency goal or a maximum allowable accumulation of currency as defined by the network sites.

According to one or more arrangements, the virtual currency may be linearly correlated to a metric such as calories since this is a measure of human energy expenditure. From calories, there may be one or more conversion algorithms based on one or more formulas to go between calories and all other metrics. For example, 100 calories may be equated to 1 mile. Another example of an algorithm includes factoring in athlete weight given that there is a correlation between work (energy), force and distance and a correlation between force and weight. In particular, work=force*distance and force=function(weight), hence work=function(weight)*distance. A similar algorithm could go between calories and: steps on a flat surface to calories; steps at a particular incline to calories; bicycle wheel revolutions and wheel diameter on flat surface; steps, revolutions or other measurable metric on a particular brand and model of fitness equipment; and rowing strokes.

Upon selection one of challenge types 4901, bottom section 4905 of interface 4900 may display one or more challenges 4907 of the selected type, which in the illustrated example is calories. Along with the name 4909, each challenge may also indicate a number of challengers 4911 current participating in the challenge. Thus, if a user prefers to take on challenges that are more popular or have more participants, he or she may identify those challenges from section 4905 rather than having to select and view details for each individual challenge.

Figure 50:
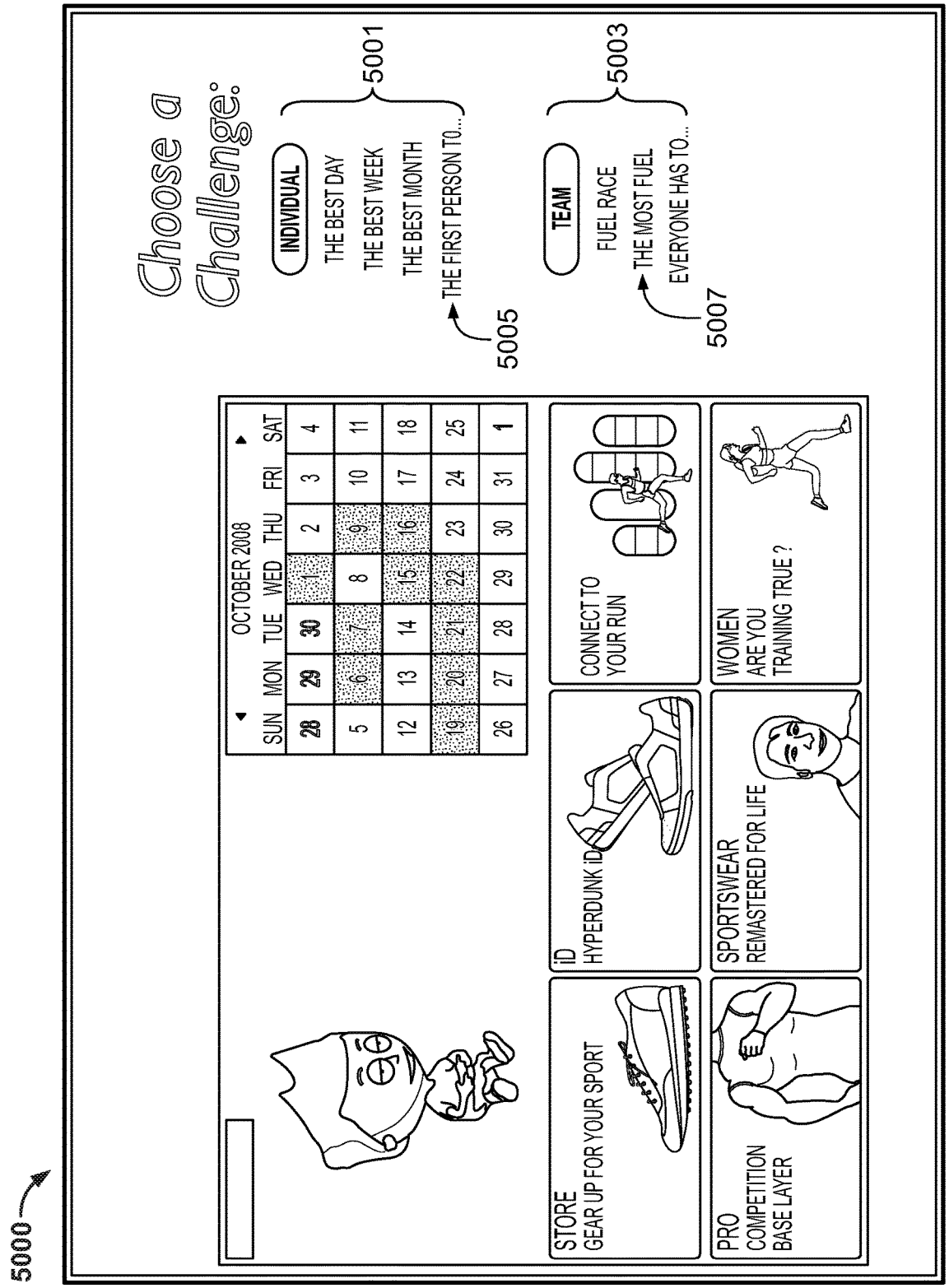

FIG. 50 illustrates an alternative or additional interface 5000 through which a user may select a type of challenge. For example, interface 5000 may include individual challenges category 5001 as well as team challenges category 5003. The user may then select specific challenges 5005 and 5007 from categories 5001 and 5003, respectively. For example, challenges 5005 may include a best day, a best week, a best month or the first person to perform a certain amount of activity. Challenges 5007, on the other hand, may include races for accumulating an amount of virtual currency or a goal that everyone in a team must meet.

Figure 51:
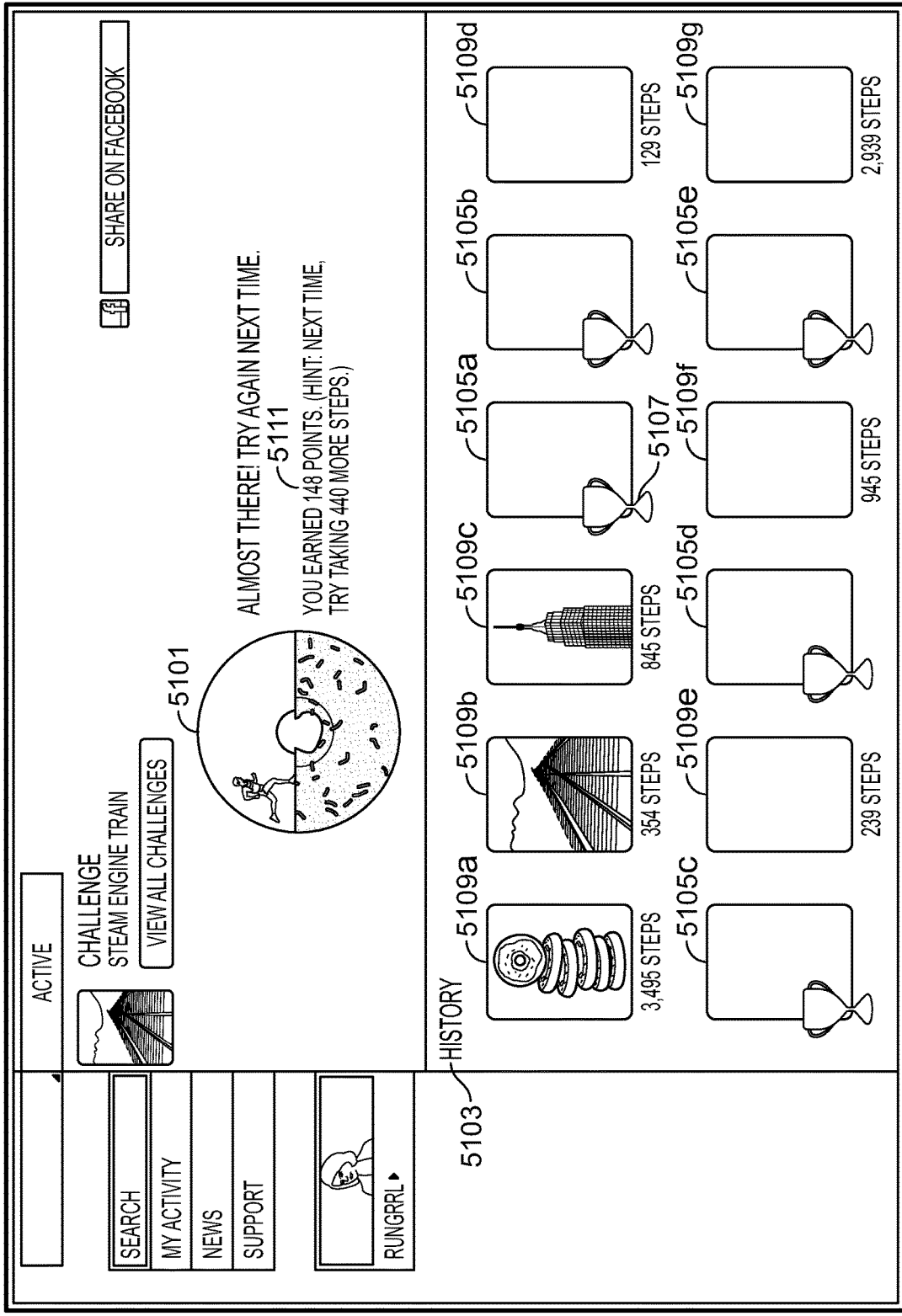

FIG. 51 illustrates an example interface 5100 that indicates a user failed to complete or meet a challenge. As shown, the goal or challenge object 5101 is only partially filled, indicating that the user left the challenge unfinished. The user may have abandoned the challenge or simply failed to achieve the objectives by the challenge deadline. Interface 5100 may further provide a hint or advice for how to complete the challenge in the future (e.g., a number of additional steps that would be required). History section 5103 of interface 5100 provides a list of challenges in which the user has participated. Those challenges 5105 that the user has completed may be marked by a trophy 5107 or some other marker, while challenges 5109 that the user did not complete may indicate the amount completed or a number of points 5111 corresponding thereto at the challenge deadline.

Figure 52:
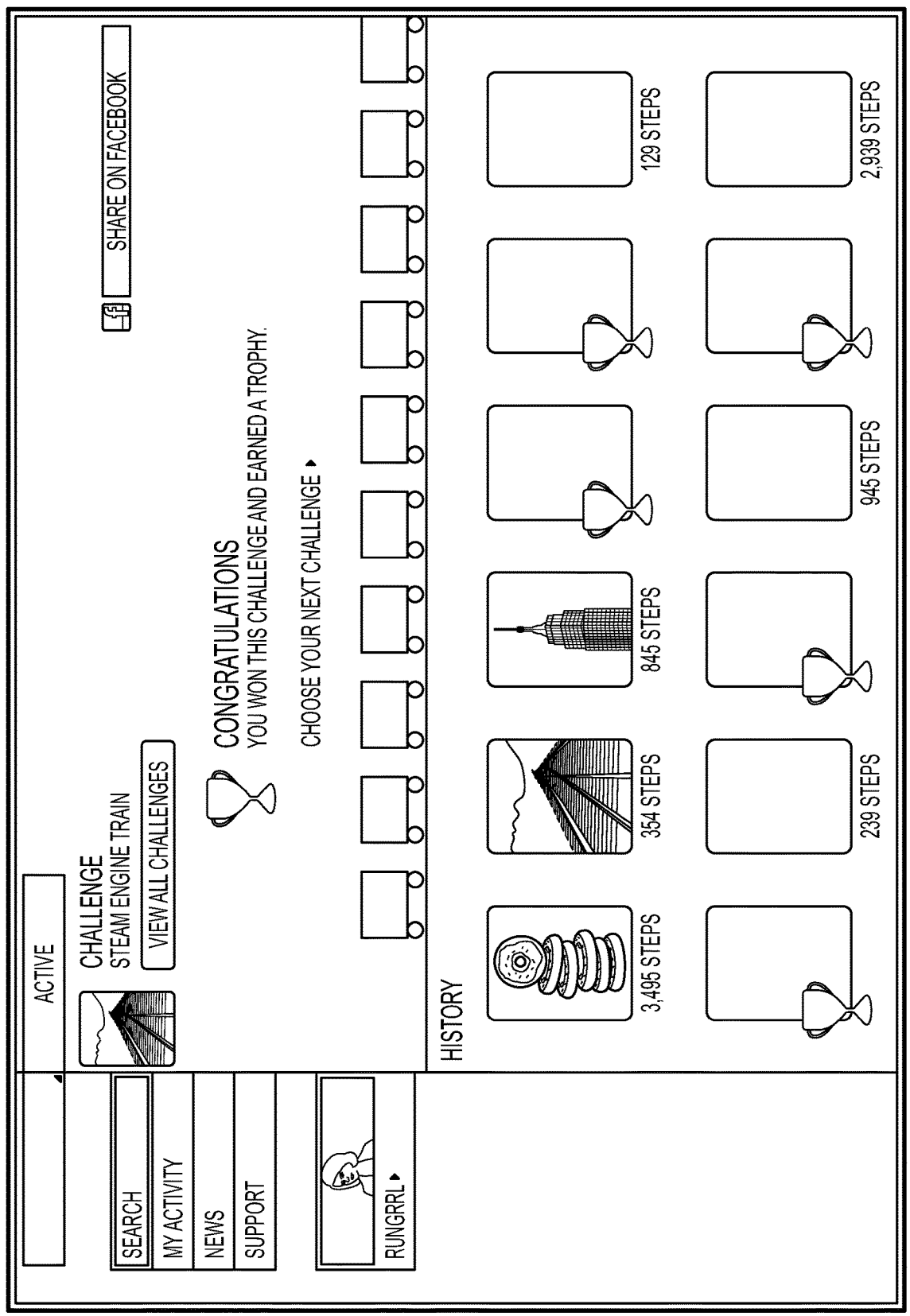

FIG. 52 illustrates an interface indicating that the user was won or completed a challenge.

Figure 89:
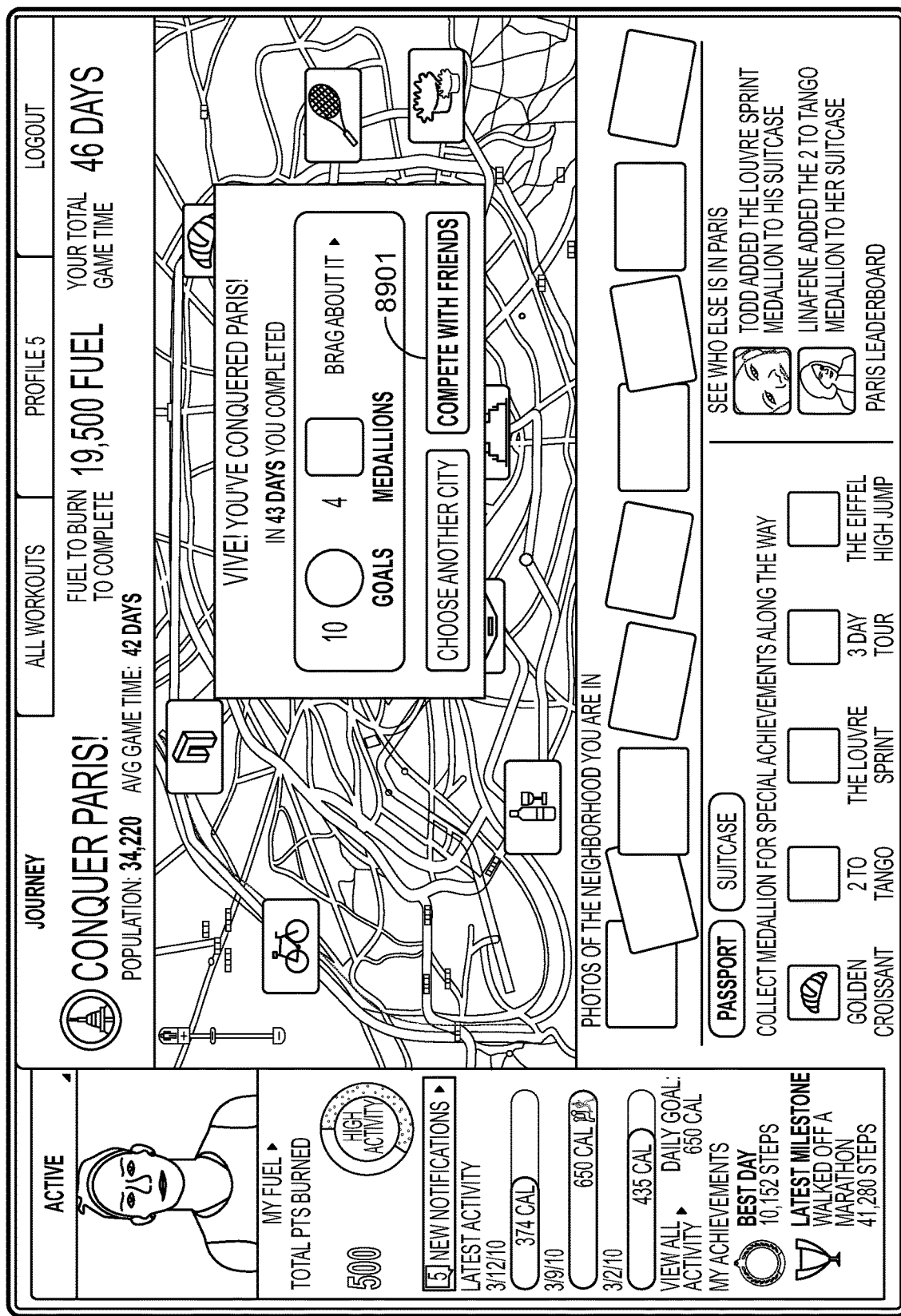

A challenge or competition option might only be available to a user for a particular location upon the user completing all goals for the goal location. Once a user has completed a particular location, the system may offer the user a competition option such as option 8901 of FIG. 89.

Figure 90:
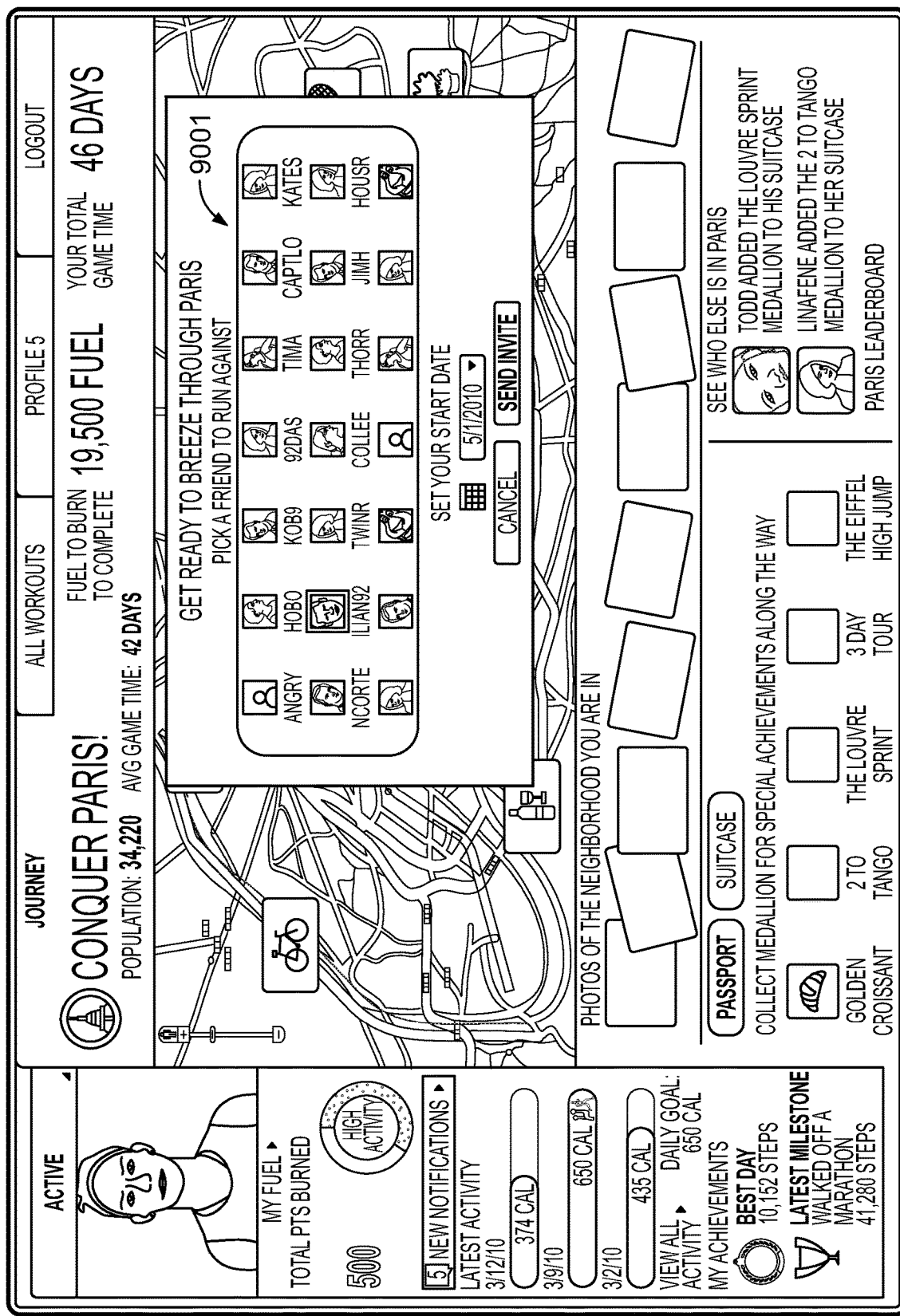
Figure 91:
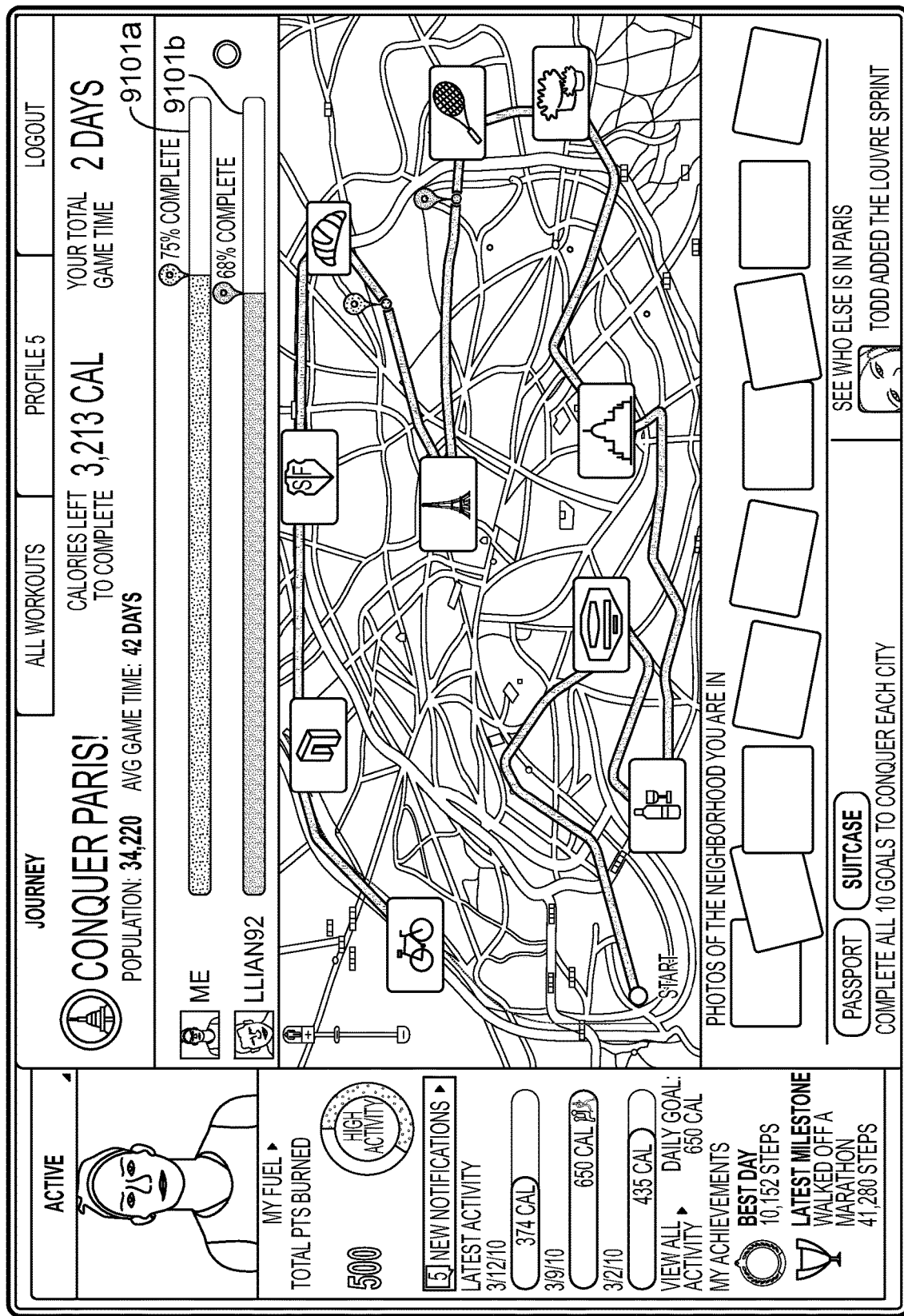

If the user chooses to compete against another individual, the user may be presented with a competitor selection interface. In FIG. 90, for example, the user may select a competitor from list 9001. Additionally, the user may select a start date for the competition. Other parameters may also be defined such as an end date and a personal message to the invitees. A user may also select more than one competitor to invite. Once the parameters of the competition have been defined, the user may transmit an invitation to the selected competitor(s). FIG. 91 illustrates an interface conveying a progress of the competitors through progress bars 9101.

Data Visualization

Figure 53:
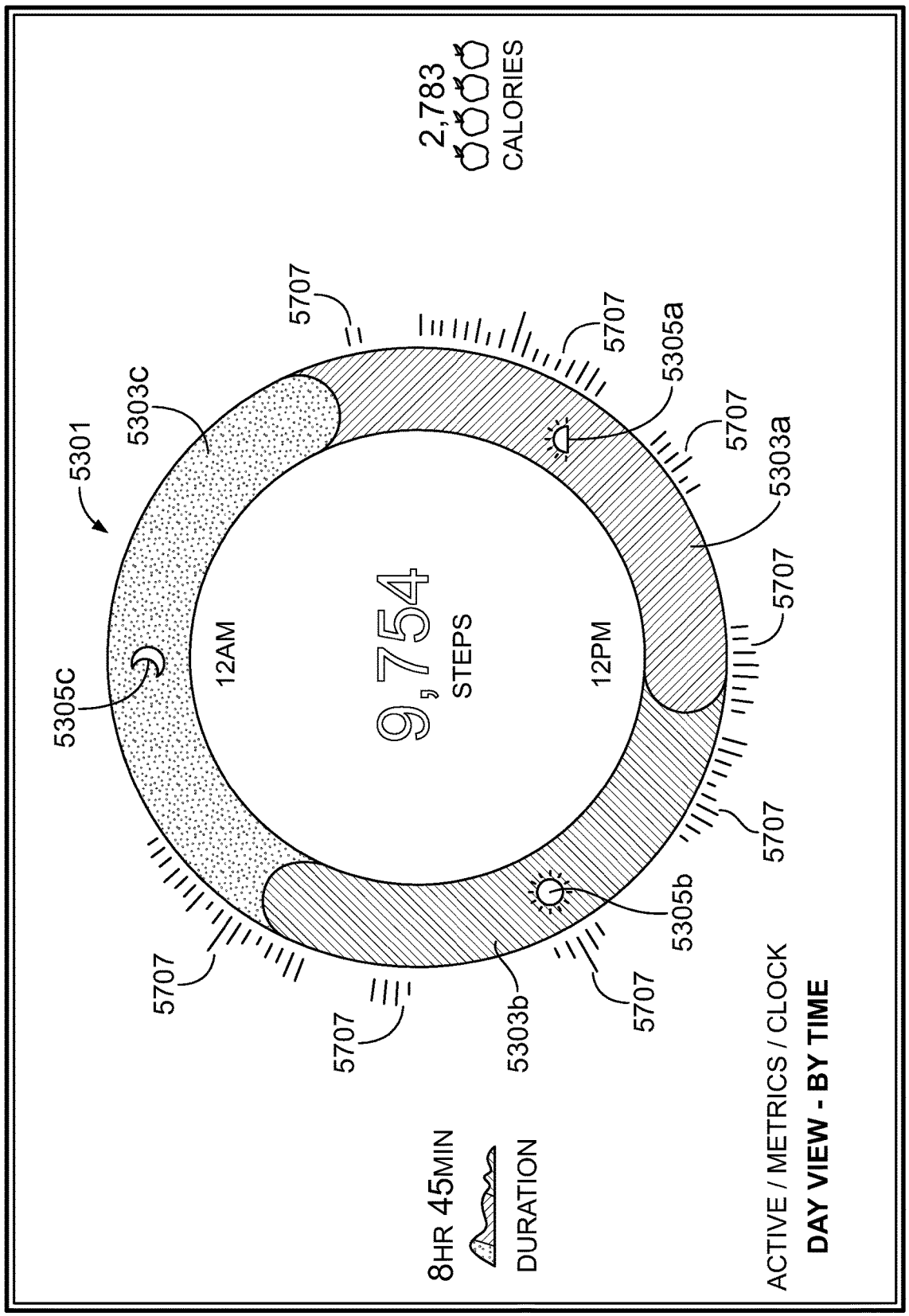
FIGS. 53-73 illustrate various visualizations that may be used for representing workout activity data according to one or more aspects described herein.
Figure 54:
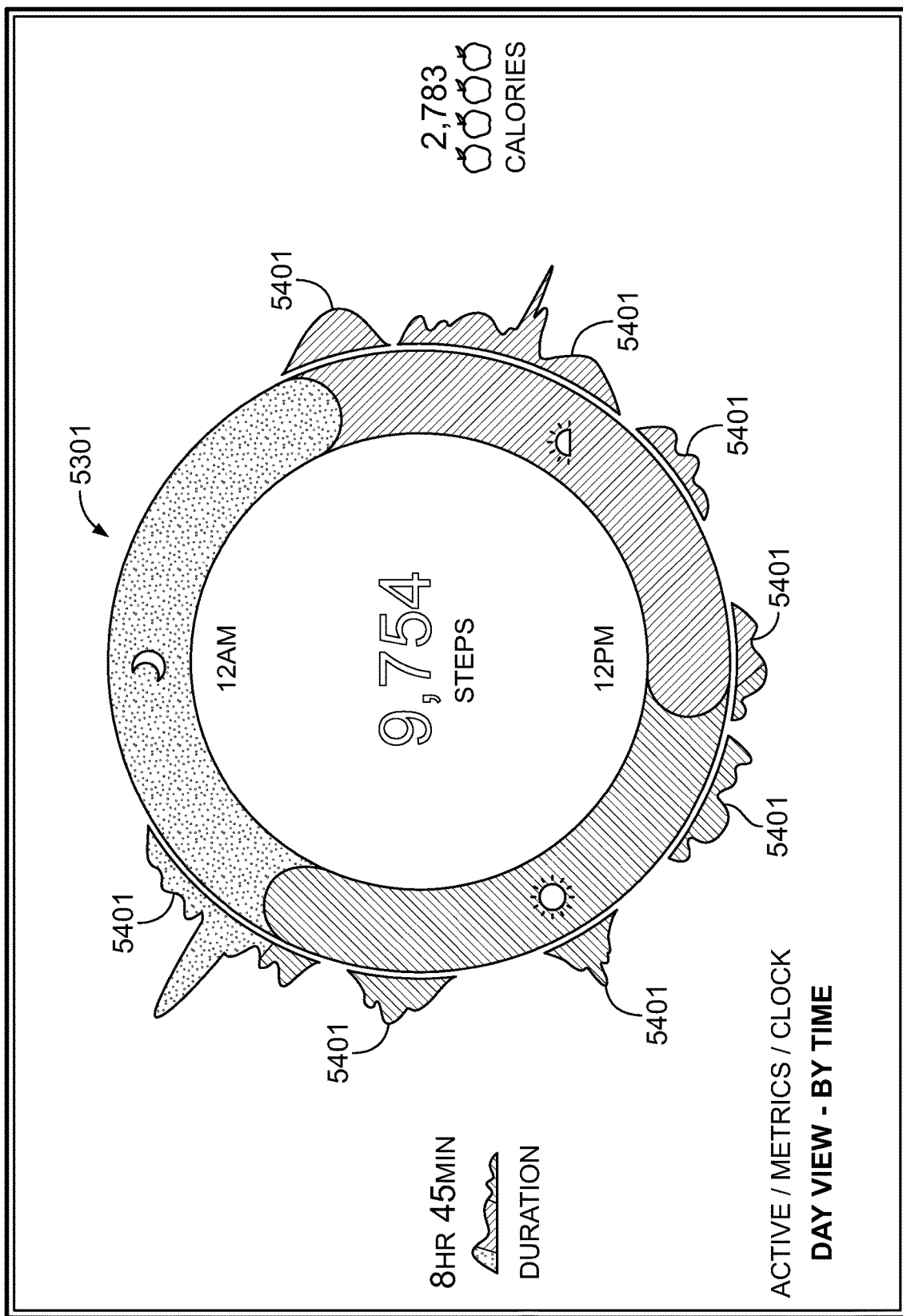
Figure 55:
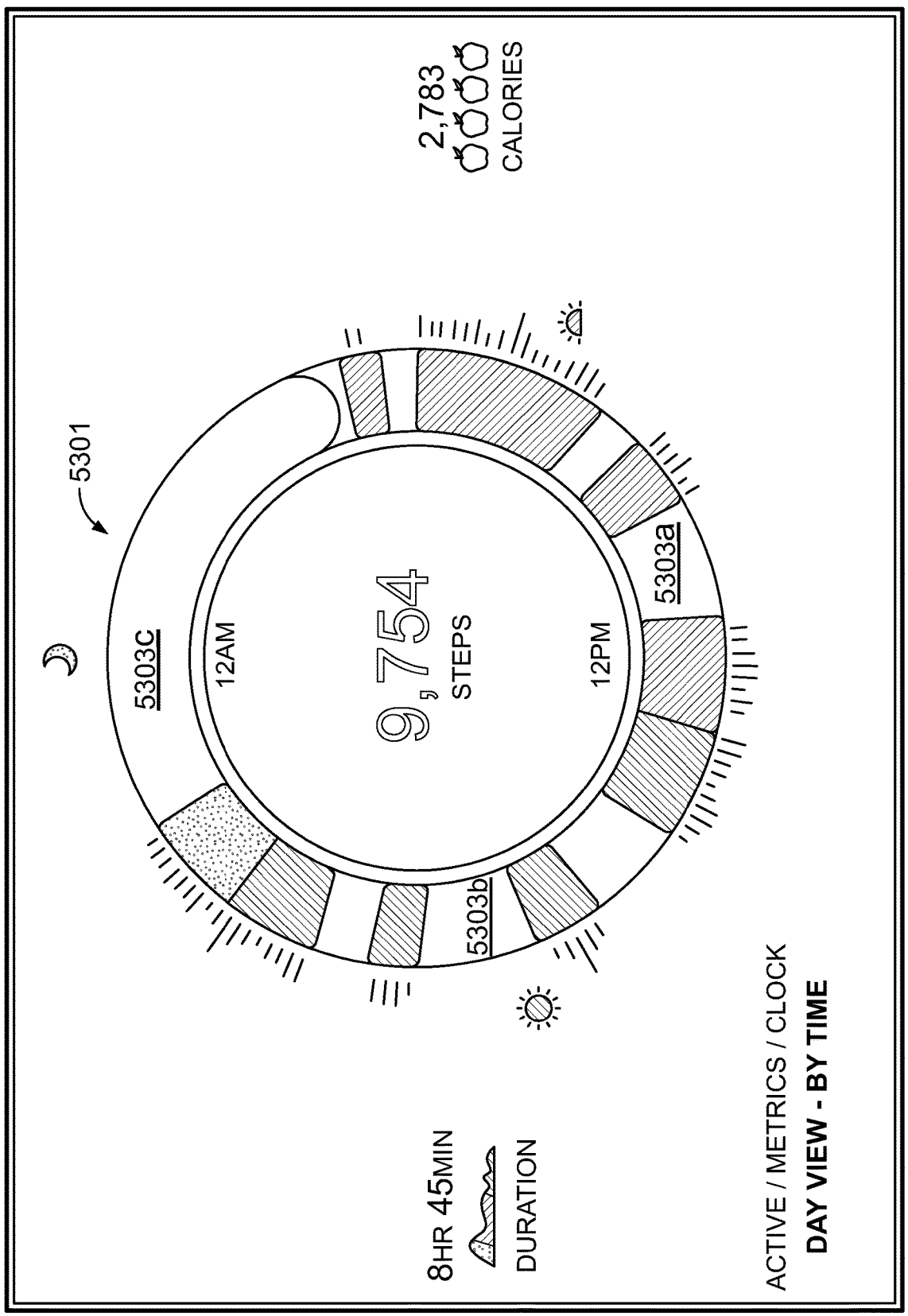

FIGS. 53-73 illustrate a variety of ways in which athletic workout data may be visually represented. For example, FIGS. 53-55 illustrate a clock visualization that provides workout data on a circular object 5301 representing times of the day. Morning, day and night may each be represented by one or more of segments 5303 and icons 5305 on object 5301. The user's athletic activity may be indicated by lines 5307 radiating from object 5301 as in FIG. 53. The length of the lines may represent the amount of athletic activity performed while the location is representative of the time of day at which the activity was performed. In one or more arrangements, the color of the lines may represent a type of activity performed.

Alternatively or additionally, FIG. 54 illustrates that the user's activity may be represented by curvatures 5401 along the object 5301's surface. The height of the curvatures 5401 relative to object 5301's surface may represent the amount of activity performed while the location of the curvatures 5401 is indicative of the time at which the activity was performed.

FIG. 55 illustrates another embodiment of object 5301 that combines color coding and data lines. Color coding refers to the coloring of circular object 5301 in only those segments 5303 or portions thereof corresponding to times at which the user performed or recorded athletic activity. The other portions of segments 5303 may remain uncolored or unshaded if no athletic activity was performed or recorded for those times. The total amount of activity may be indicated in the center of object 5301. Additionally, other detail such as calories burned and amount of time spent working out may be displayed on either side of object 5301.

Figure 56:
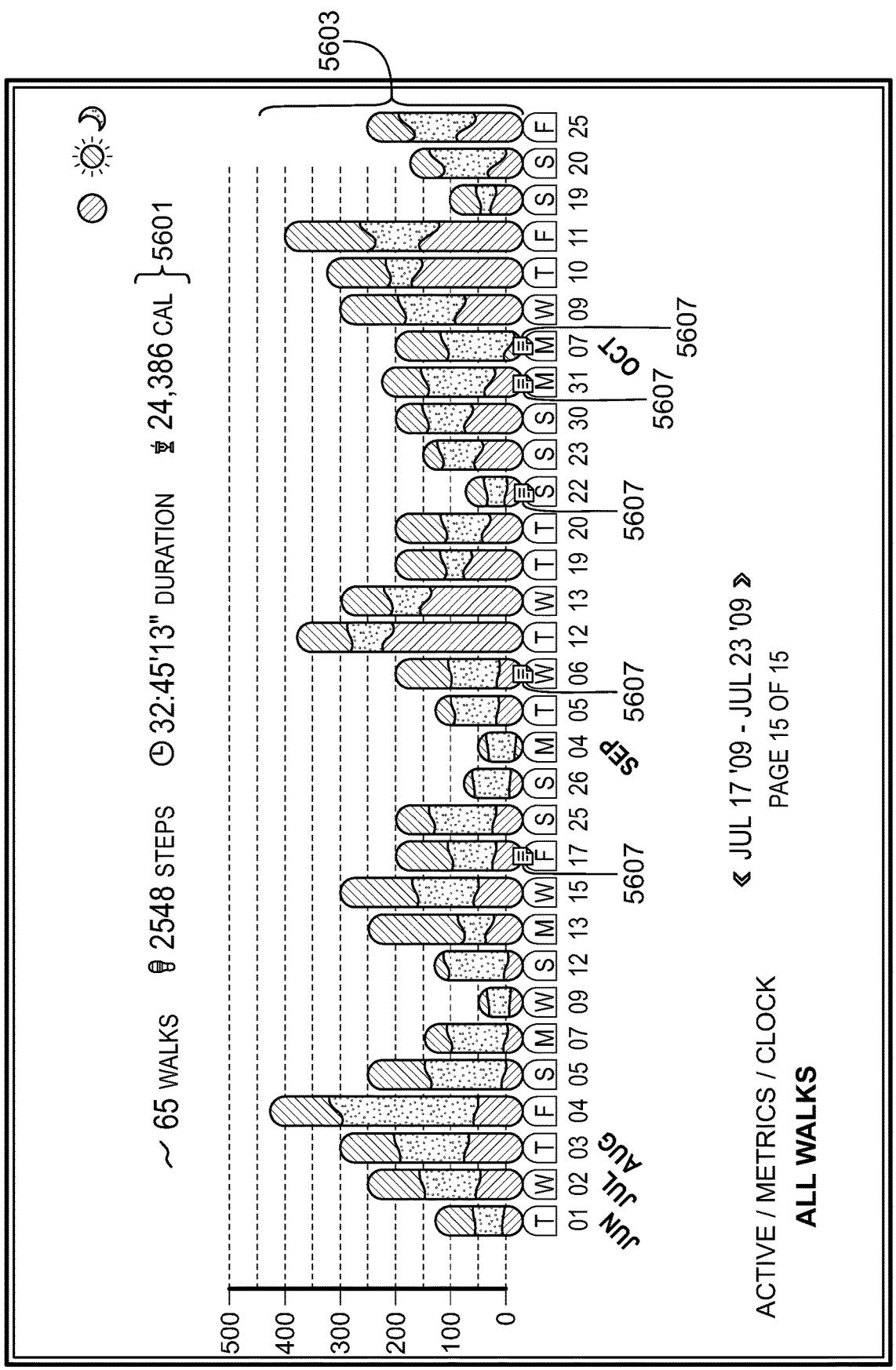

FIGS. 56-59 illustrate various types of bar graphs for representing athletic activity data. In FIG. 56, for example, a number of steps performed is graphed against time (e.g., calendar days). A summary 5601 of athletic activity is provided and includes a number of walks, a number of steps, a duration and a total number of calories burned. Each bar 5603 in graph 5600 may include visual attributes that indicate a time of day at which the user performed a corresponding amount of activity. For example, each of bars 5603 are color coded in three different colors, each color representing a different time of day or period of day. Furthermore, note icons 5607 may be displayed with one or more of bars 5603 if a user has added activity or workout notes thereto. The notes may be viewable by hovering over, clicking or otherwise interacting with bars 5603 or note icons 5607. Accordingly, a user may evaluate his or her performance with a greater level of specificity and detail. A user may further scroll graph 5600 in one or more directions to view additional data not currently displayed using scroll buttons 5605. In one or more configurations, different colors may represent the proportion of time during the day spent in low, medium or high states of activity. It could also break down a day into any variety of different histogram groupings.

Figure 57:
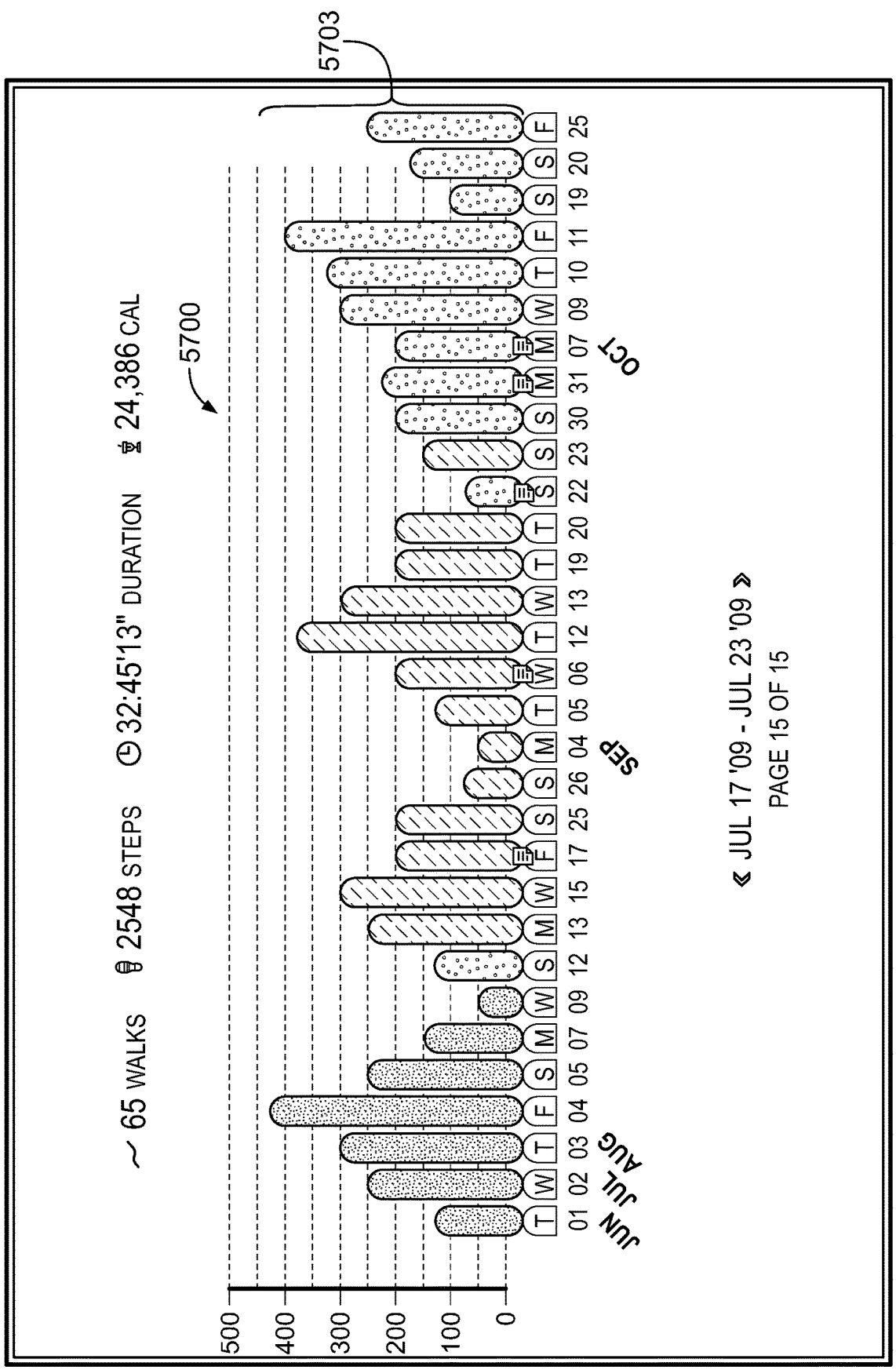
Figure 58:
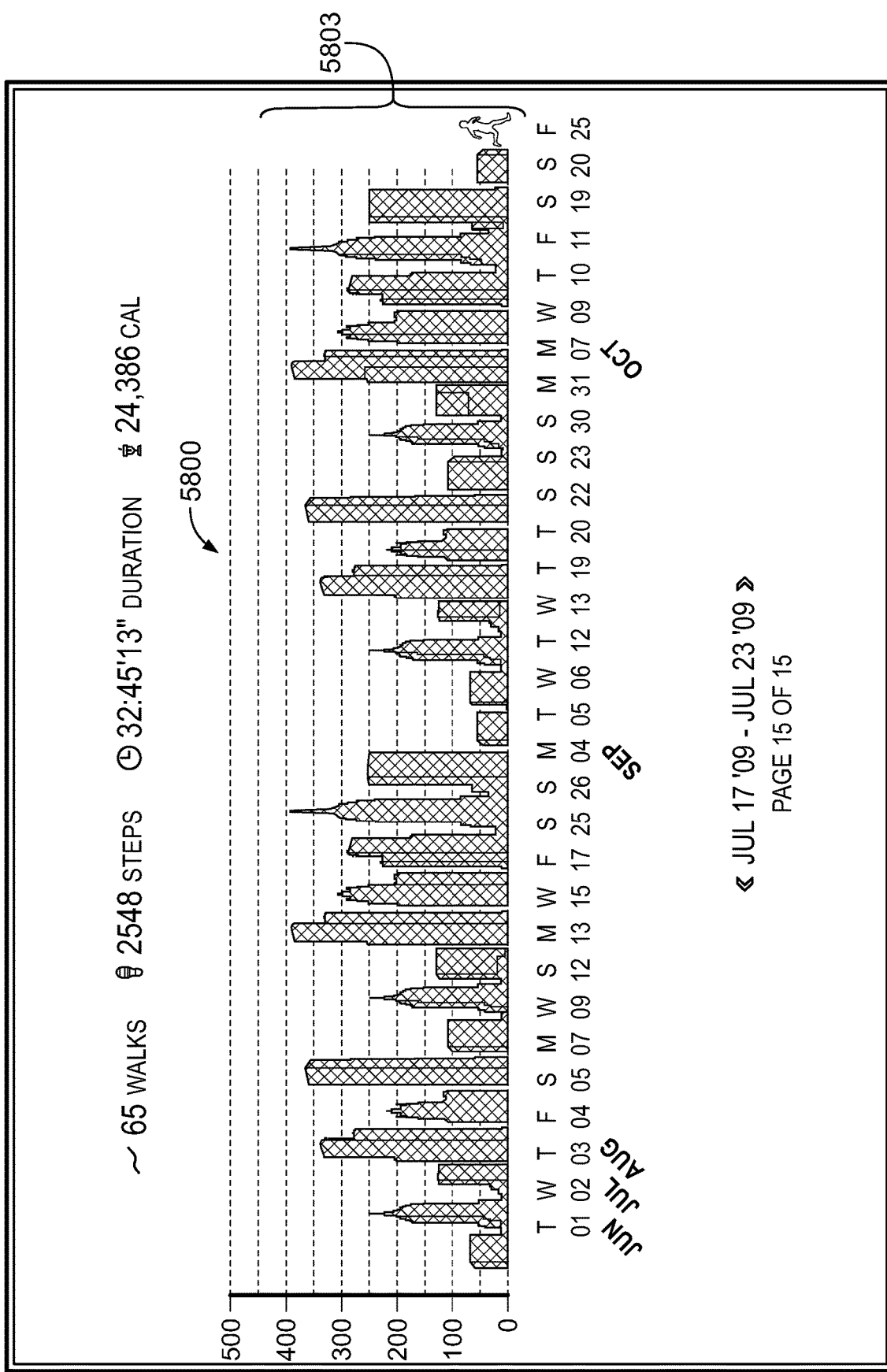
Figure 59:
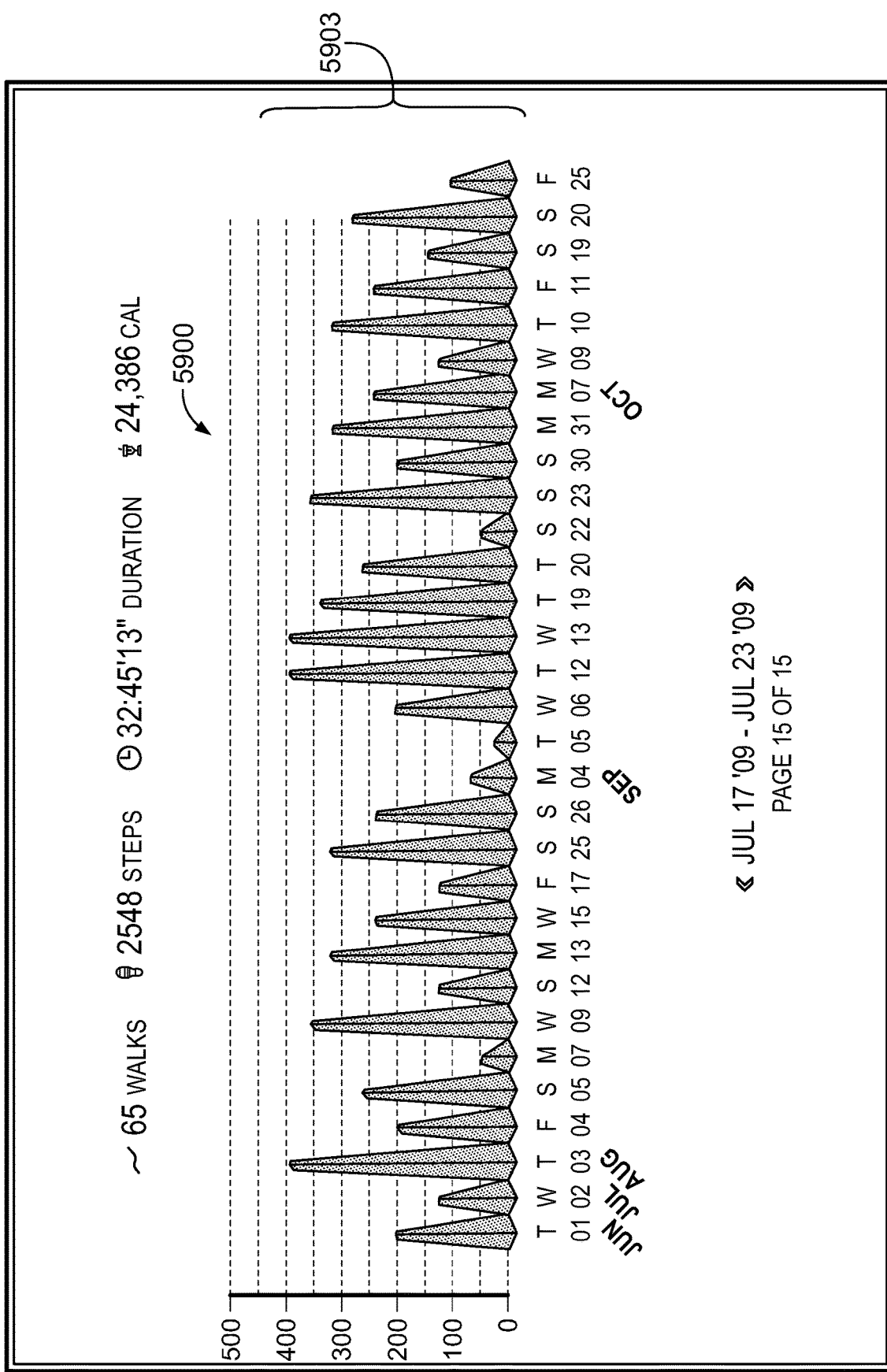

FIGS. 57-59 illustrate bar graphs with different visual characteristics. For example, bars 5703 of graph 5700 have different coloring, patterns and textures while bars 5803 of graph 5800 (FIG. 58) are represented by buildings. In FIG. 59, bars 5903 of graph 5900 have a pyramidal shape. Other shapes, colors, textures, patterns and combinations thereof may further be used to create a bar graph of a user's athletic activity data.

Figure 60:
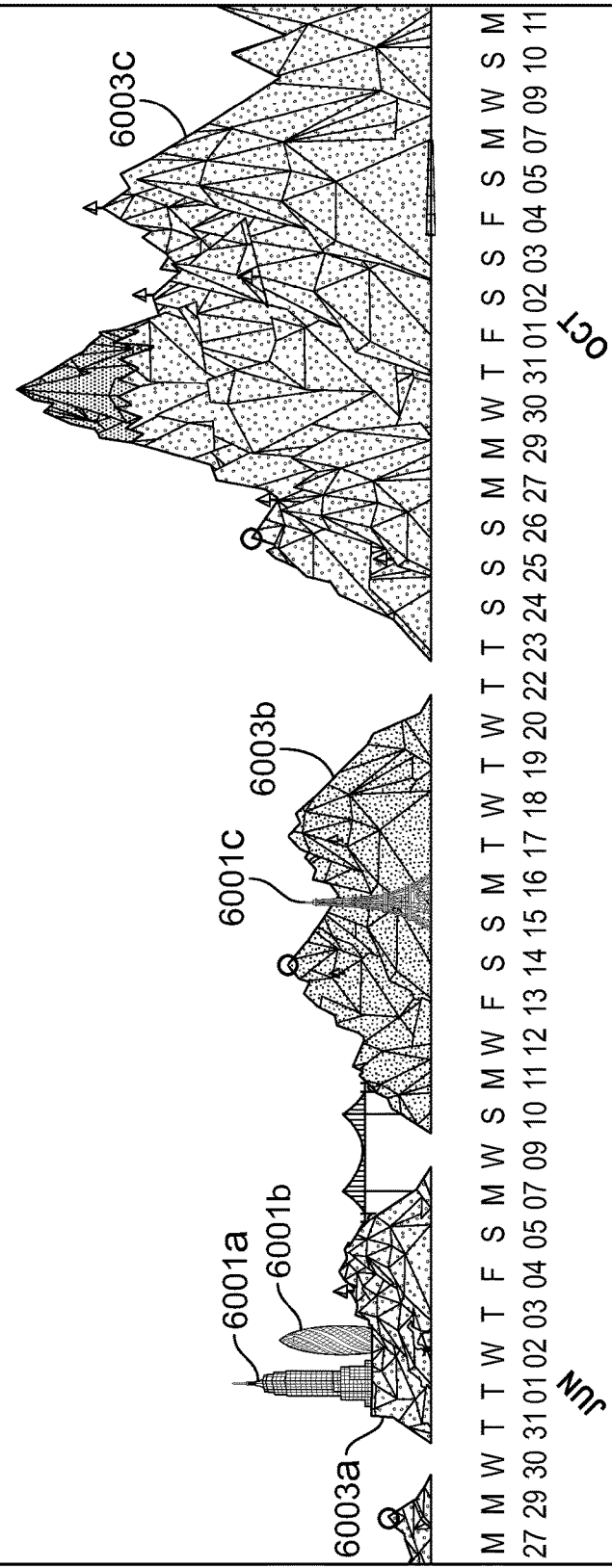
Figure 61:
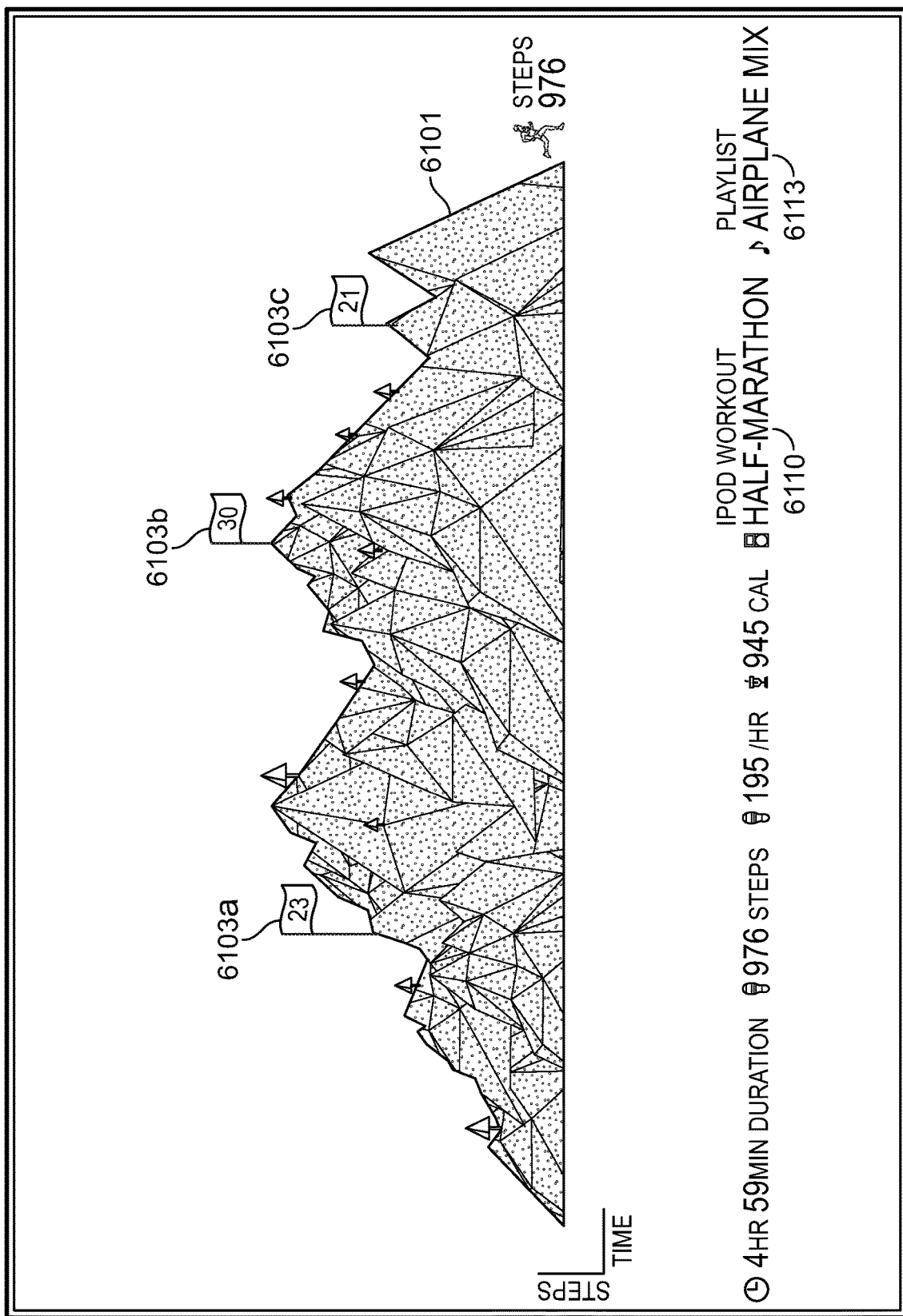
Figure 62:
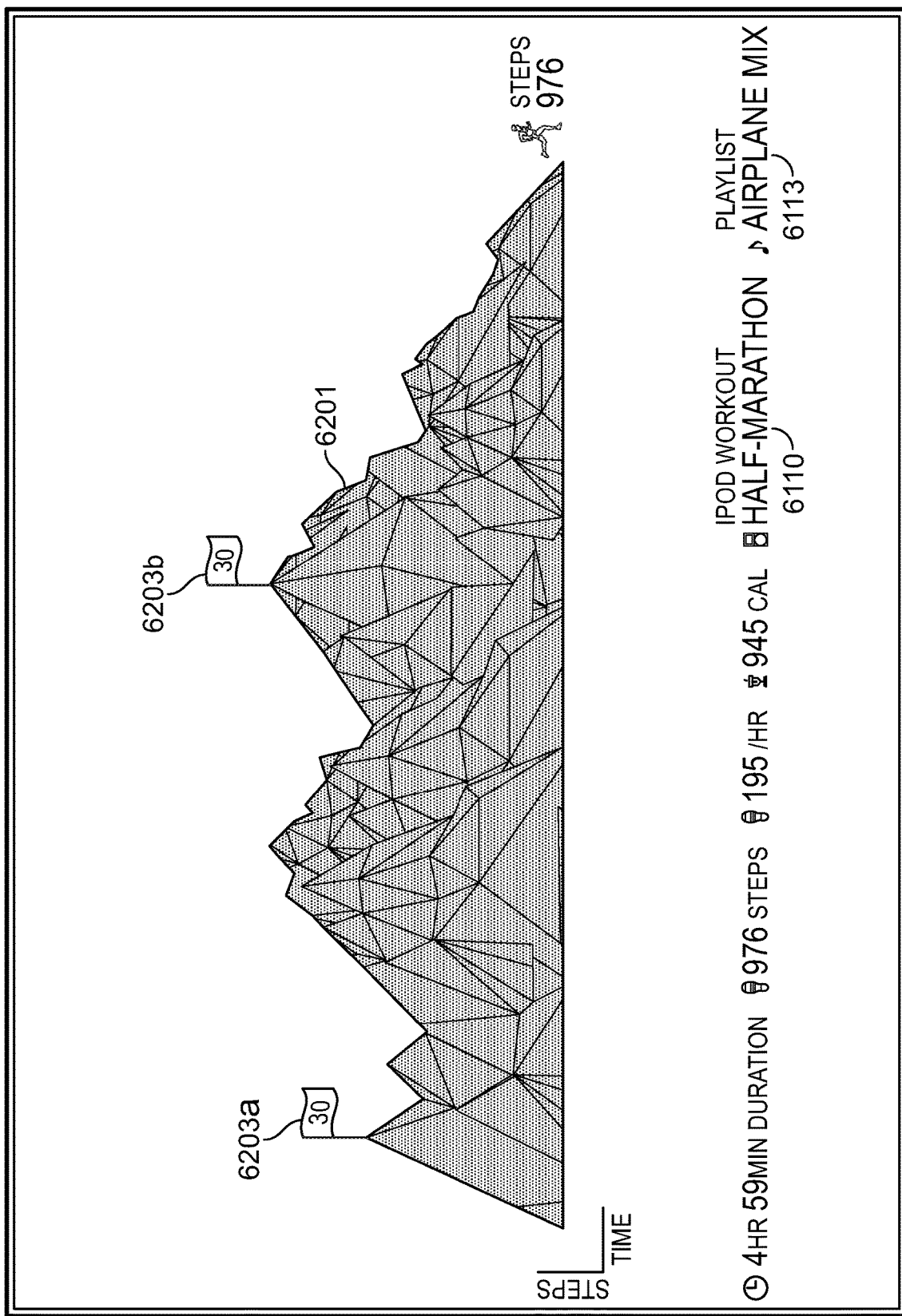

FIGS. 60-62 illustrate bar graphs that use buildings and geographical objects to represent user athletic activity progress. For example, in FIGS. 60 and 61, the peaks, plateaus and slopes of mountains, bridges and other objects may be used to represent numbers of steps taken while in FIG. 62, a glacier is used to illustrate activity data. Additionally, in FIG. 60, buildings 6001 representative of accomplished goals may be displayed in conjunction with geographical objects 6003. Additionally or alternatively, as shown in FIGS. 61 and 62, flags 6103 and 6203, respectively, may be displayed along the geographical objects 6101 and 6201, respectively, indicating a pace of the user at that time. Pace may be defined in steps/minute, steps/hour and the like. The graphs of FIGS. 61 and 62 may further include summary information that includes a workout name 6110 and a music playlist name 6113. For example, the shape of a mountain may be derived or determined from the number of steps taken over a period of time (e.g., more steps=taller peaks, fewer steps=deeper/wider valleys). The style of mountain or glacier could be manually, seasonally, geographically, or otherwise automatically chosen. Additionally or alternatively, flags 6103 and 6203 may represent pace, intermediate goals, steps, calories, or any other periodic data that is relevant for the type of activity being tracked. Furthermore, buildings 6001 and other graphical elements 6003 may represent intermediate goals achieved along a greater journey represented visually by travel from left to right. In the case where a graphical representation of activity is presented over time (as is here), the placement of graphical elements such as buildings can indicate the day upon which that goal was completed.

Figure 63:
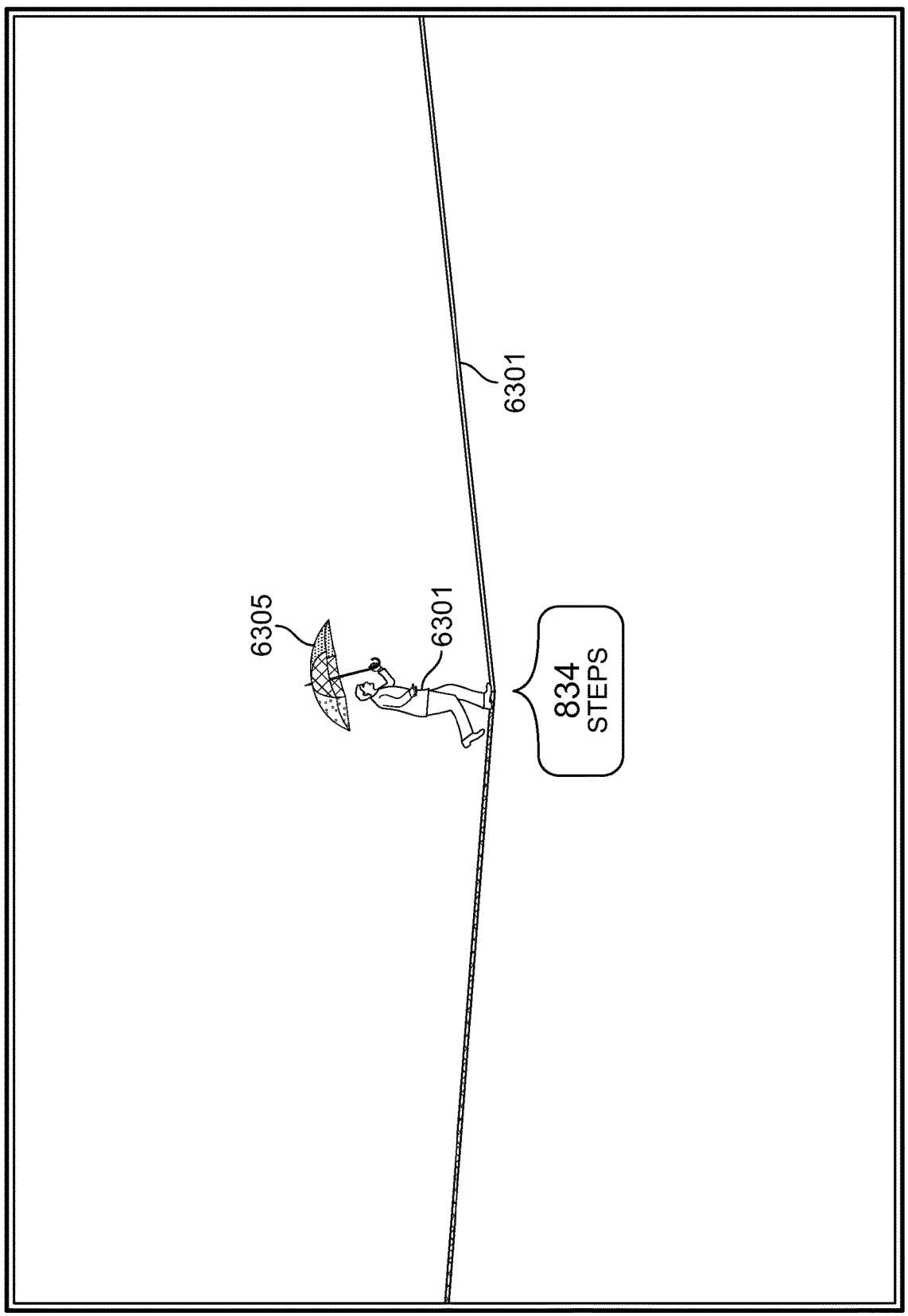
Figure 64:
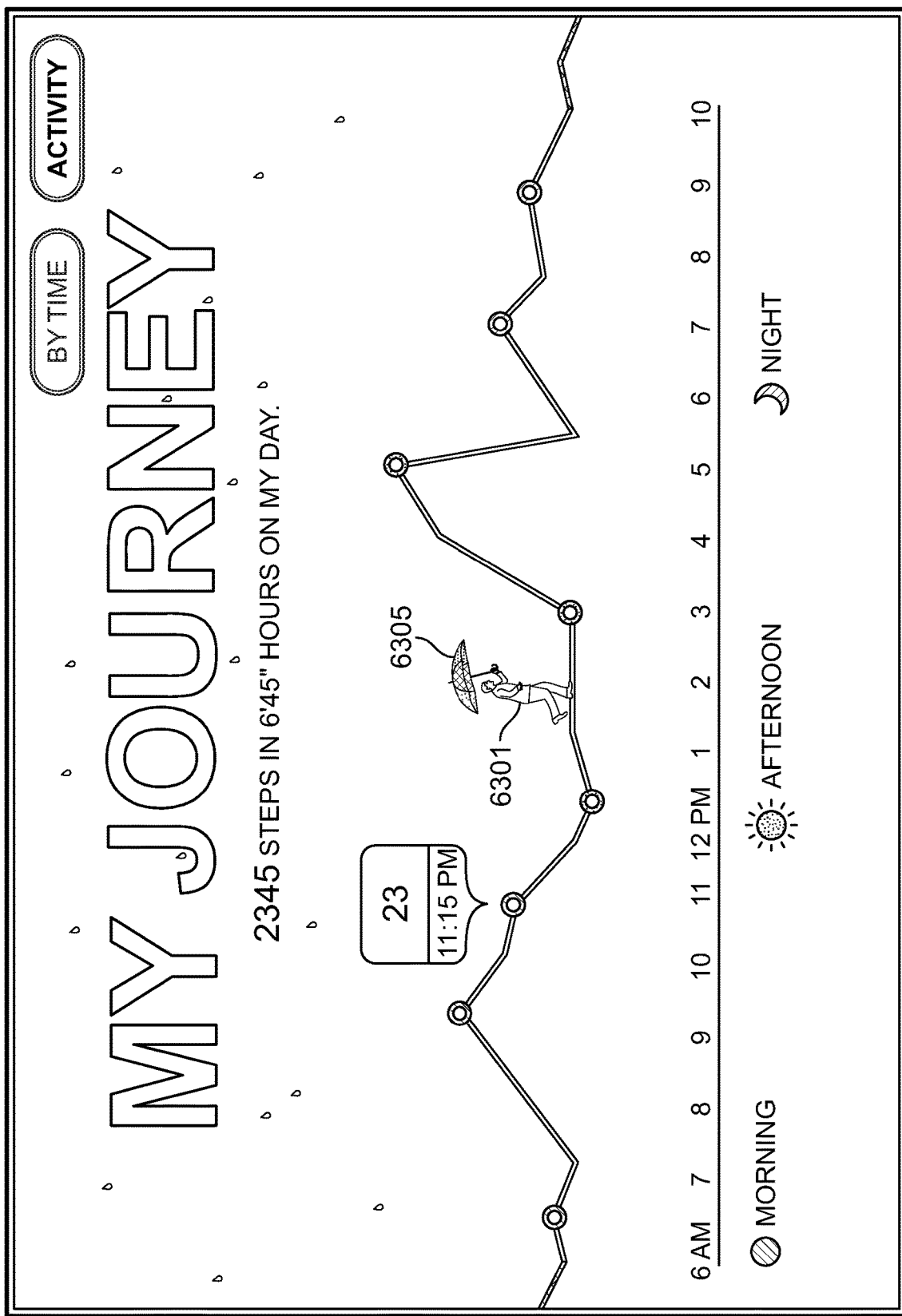
Figure 65:
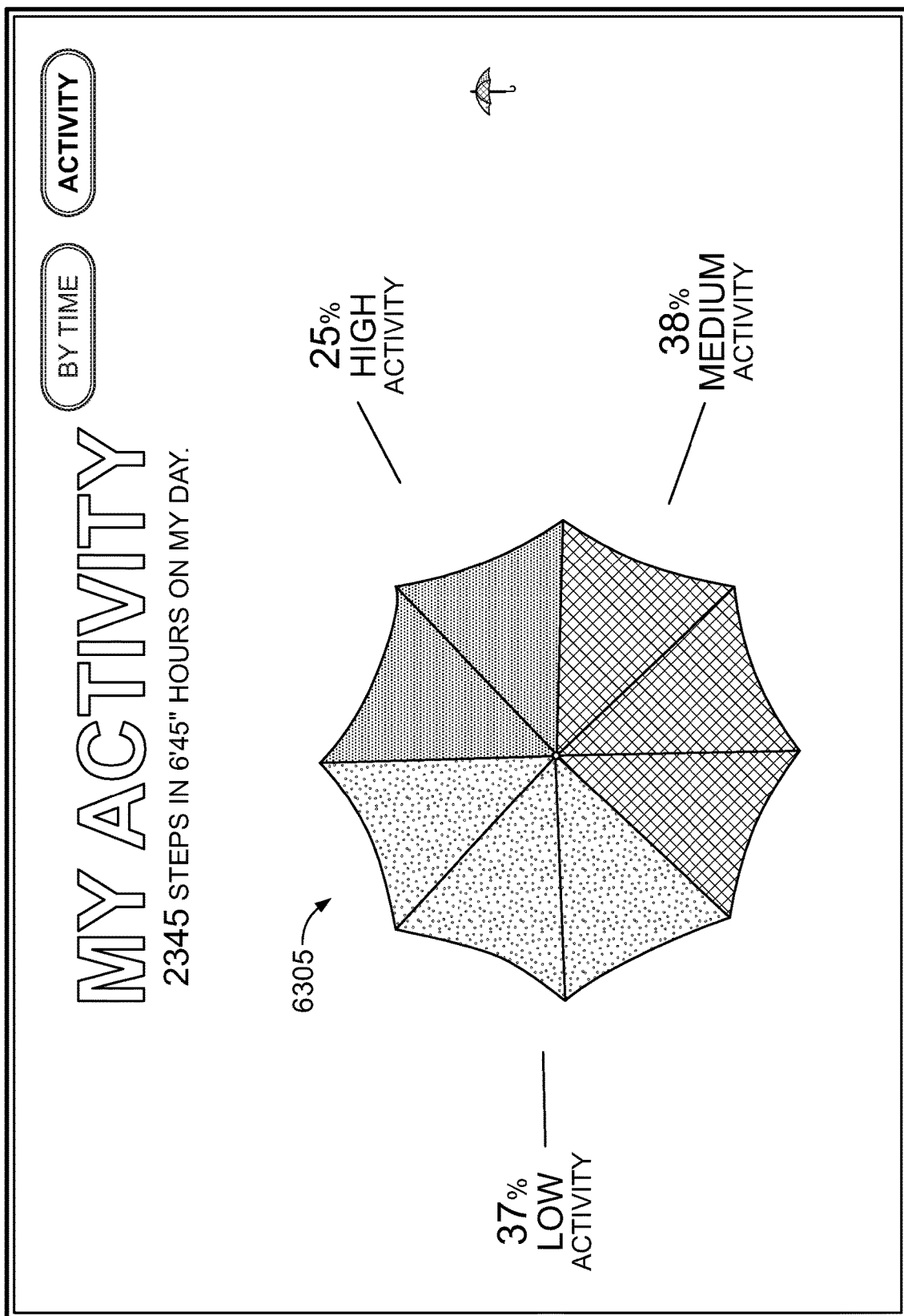

FIGS. 63 and 64 illustrate another visualization of athletic workout data in which an avatar travels along a workout data graph. For example, in FIG. 63, avatar 6301 travels along a tightrope 6303. The position of avatar 6301 along tightrope 6303 indicates a number of steps performed. In FIG. 64, the avatar 6301 is shown travelling along a line graph 6403. Avatar 6301 in each of FIGS. 63 and 64 may carry an object such as an umbrella 6305 which may be representative of the types or levels of activity performed. FIG. 65 illustrates a view of the umbrella object 6305 in which the split between high, medium and low activity is identified.

Figure 66:
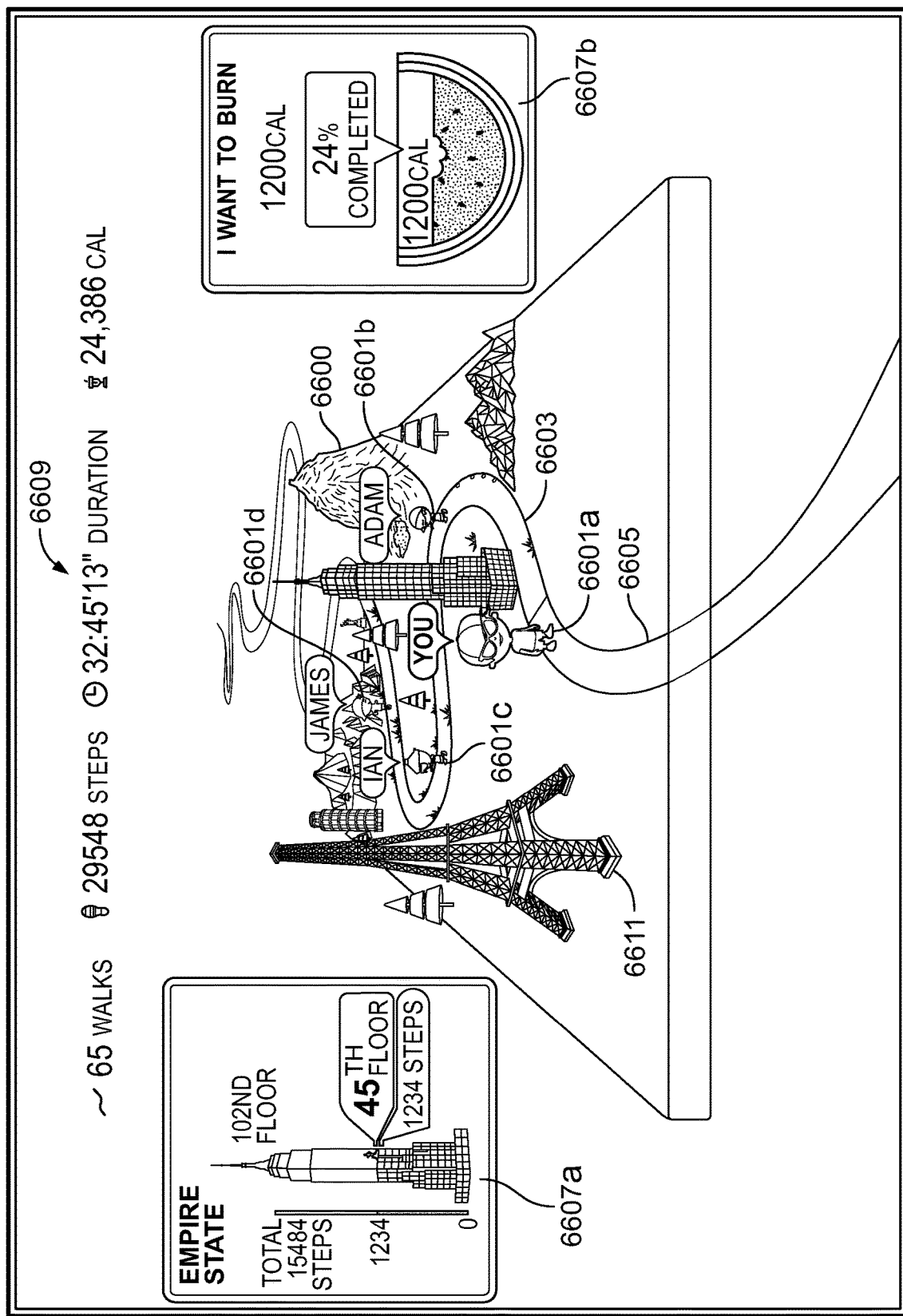

FIG. 66 illustrates a visualization of athletic activity data in a competitive game format and environment 6600. Environment 6600 may be representative of a series of locations or objectives similar to a board game. As a user progresses through the game, the user may be moved ahead in environment 6600 until he or she reaches a specified end point. Multiple players or athletes may populate environment 6600 via avatars 6601 at various points therein. The positions of players' avatars 6601 may represent their relative progress (e.g., relative to other players) or an absolute progress towards an end goal. A virtual path along which avatars 6601 travel may be color coded to represent the different tasks or goals that must be achieved. For example, portion 6603 may correspond to burning 1200 calories while portion 6605 of game environment 6600 may represent taking 1000 steps or a number of steps derived from a certain amount of calories burned or other transformation between different metrics. Goals 6607 corresponding to portions 6603 and 6605 may be displayed on either side of environment 6600 to help the players track their progress toward reaching goals 6607. The user's workout data may be summarized in portion 6609 above game environment 6600. Additionally or alternatively, objects such as Eiffel Tower 6611 may be used to represent objectives or goals to be achieved.

Figure 67:
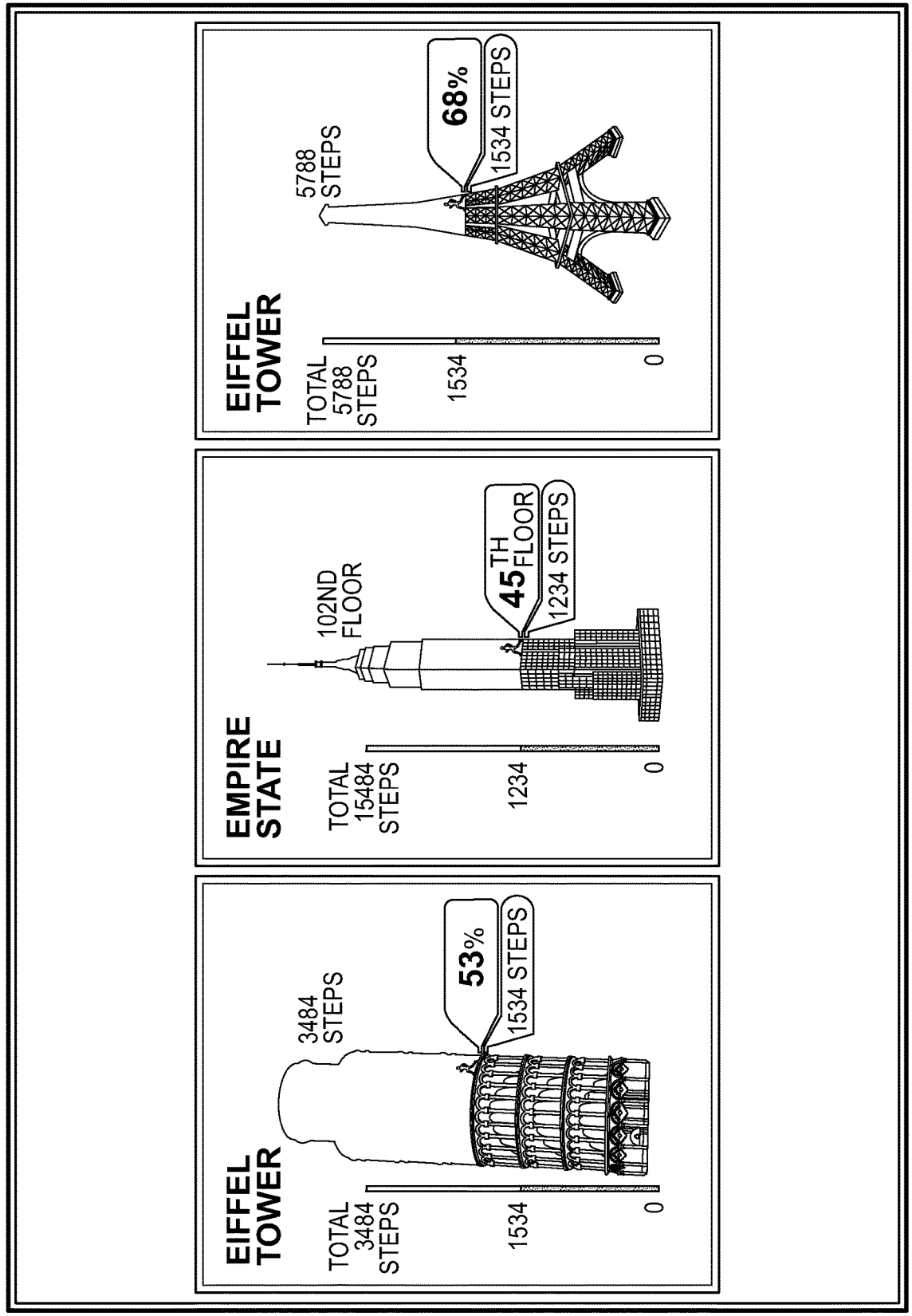
Figure 68:
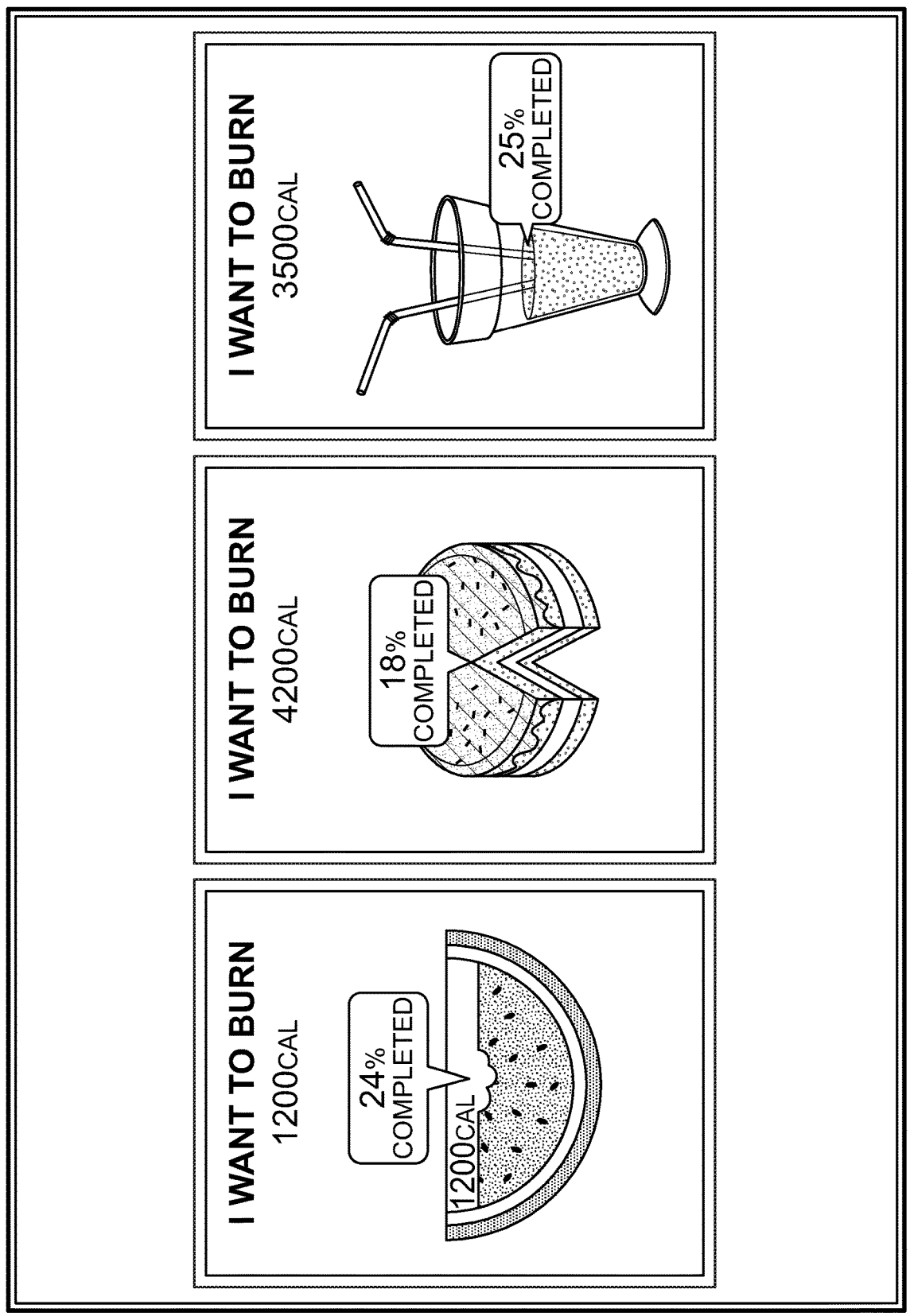

FIGS. 67 and 68 illustrate building and food/beverage items, respectively, that may be used as goal objects as well as their appearance when only a portion of a corresponding goal has been completed.

Figure 69:
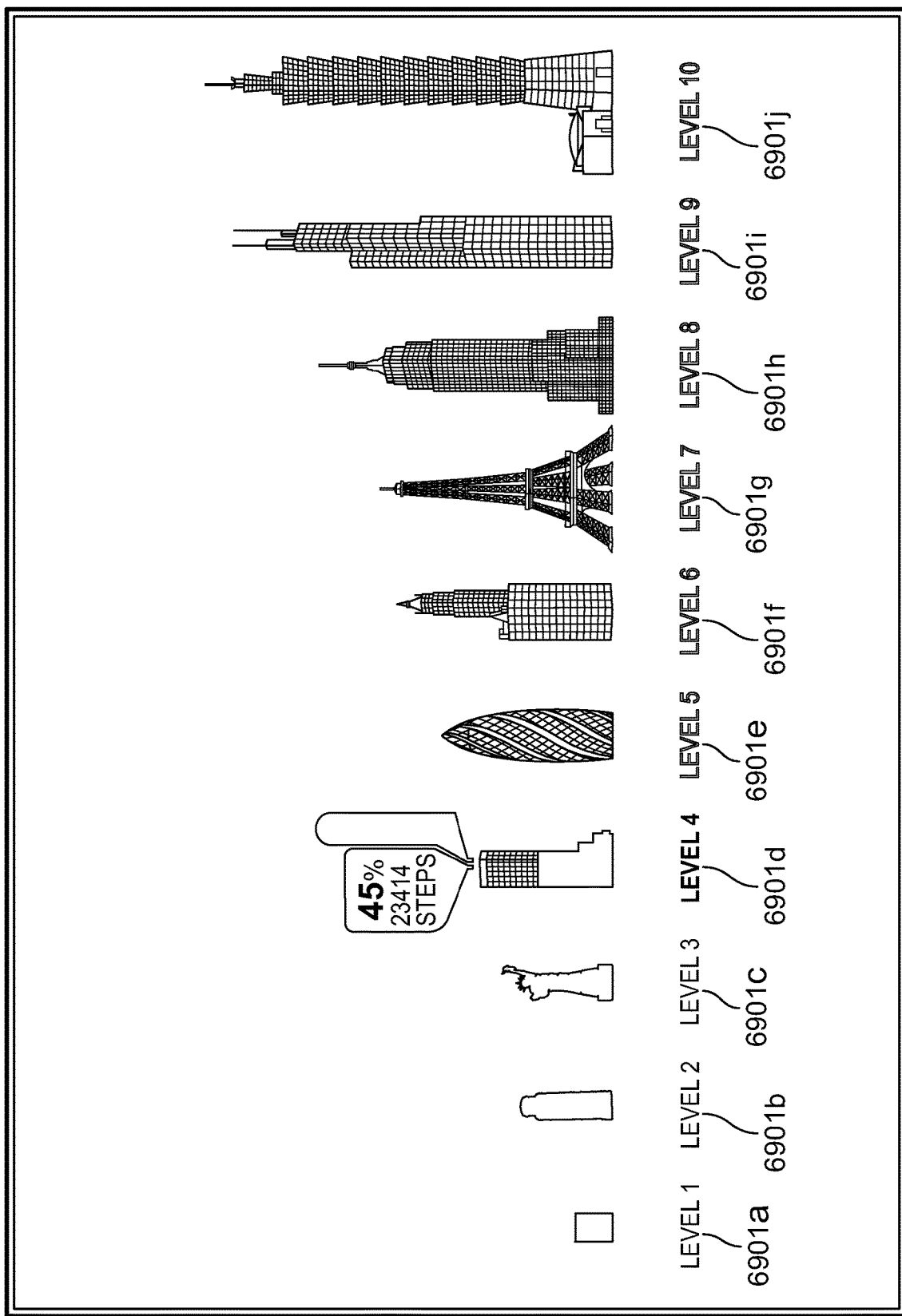

FIG. 69 illustrates a series of goals 6901 that increase in height and difficulty as the user completes each one. For example, the user may start with an office building 6901a and progress to the Tower of Pisa 6901b in level 2. As the user continued to progress, the user may be challenged with goal objects such as the Eiffel Tower 6901g and Taipei 101 6901j that represent more steps or more calories burned. The size of the physical structure corresponding to the goals may increase as a user progresses through a sequence of goals 6901. The size may represent an amount of athletic activity required. For example, the height of building 6901a may represent the number of steps required to complete a corresponding goal. Similarly, the height of structure 6901b may represent the number of steps required to complete that goal. The height of structure 6901b may be larger than the height of building 6901a to provide a more difficult challenge or goal. The size may, alternatively or additionally, correspond to a width, a volume, a surface area, a depth and the like.

Figure 70:
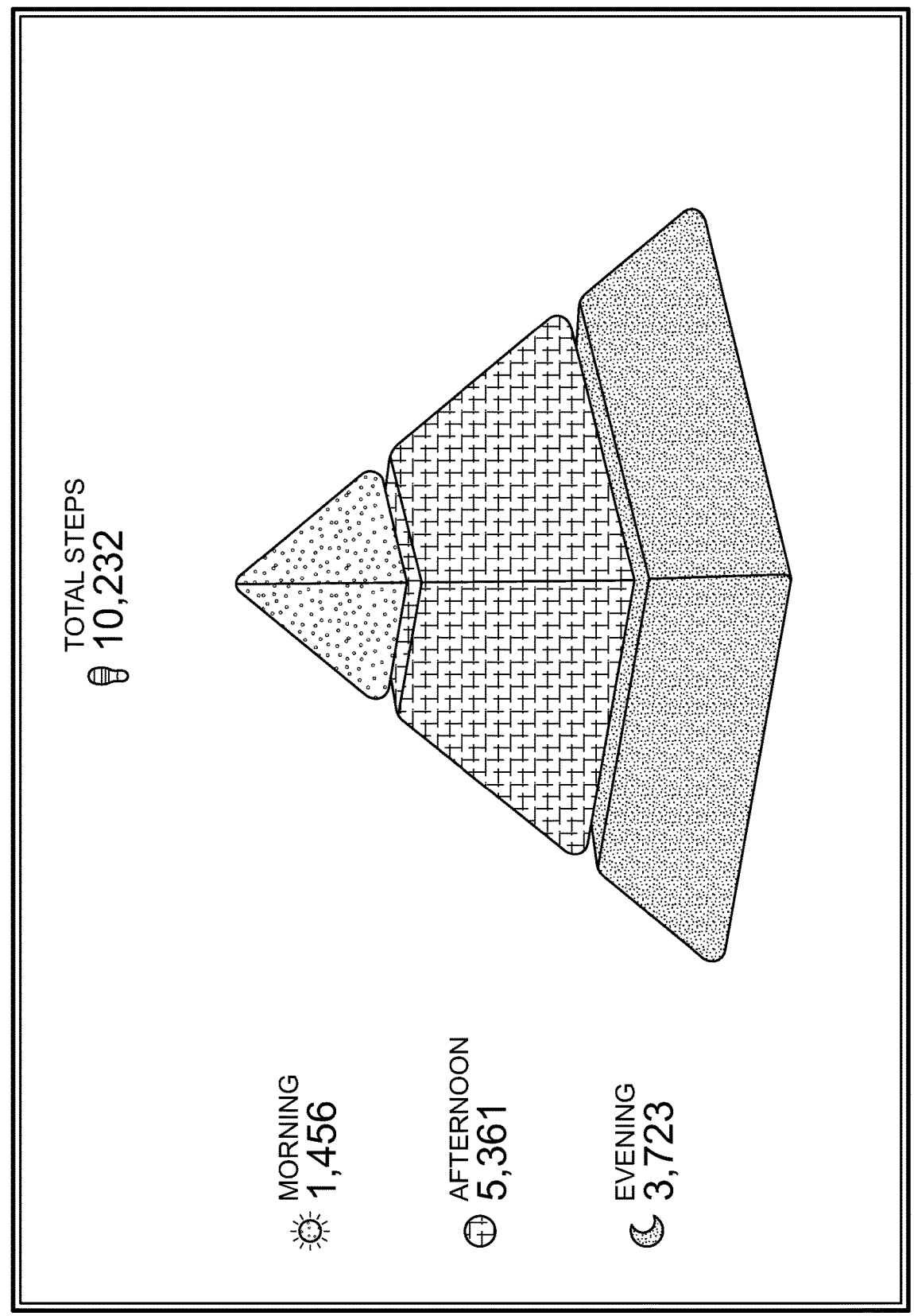
Figure 71:
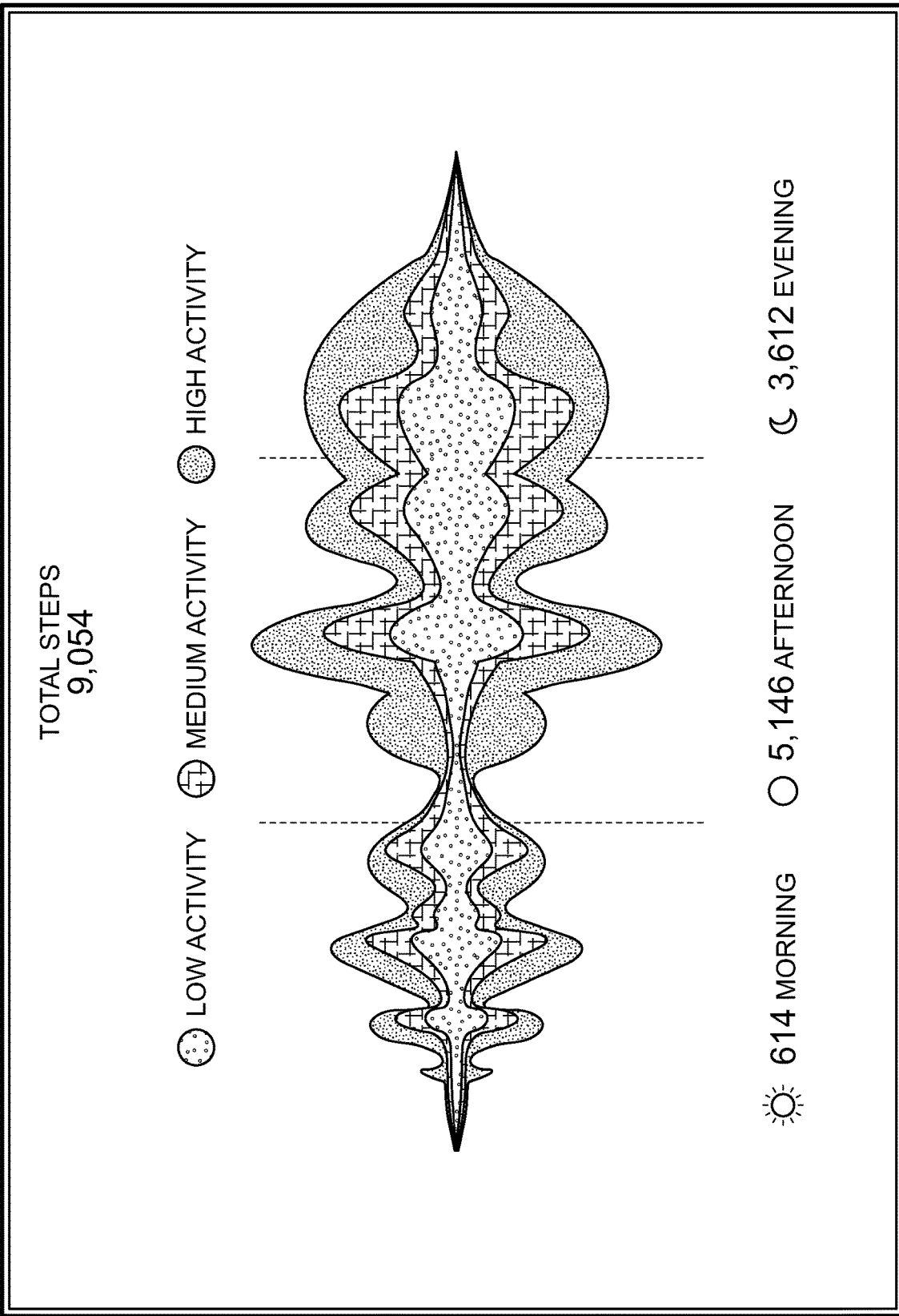
Figure 72:
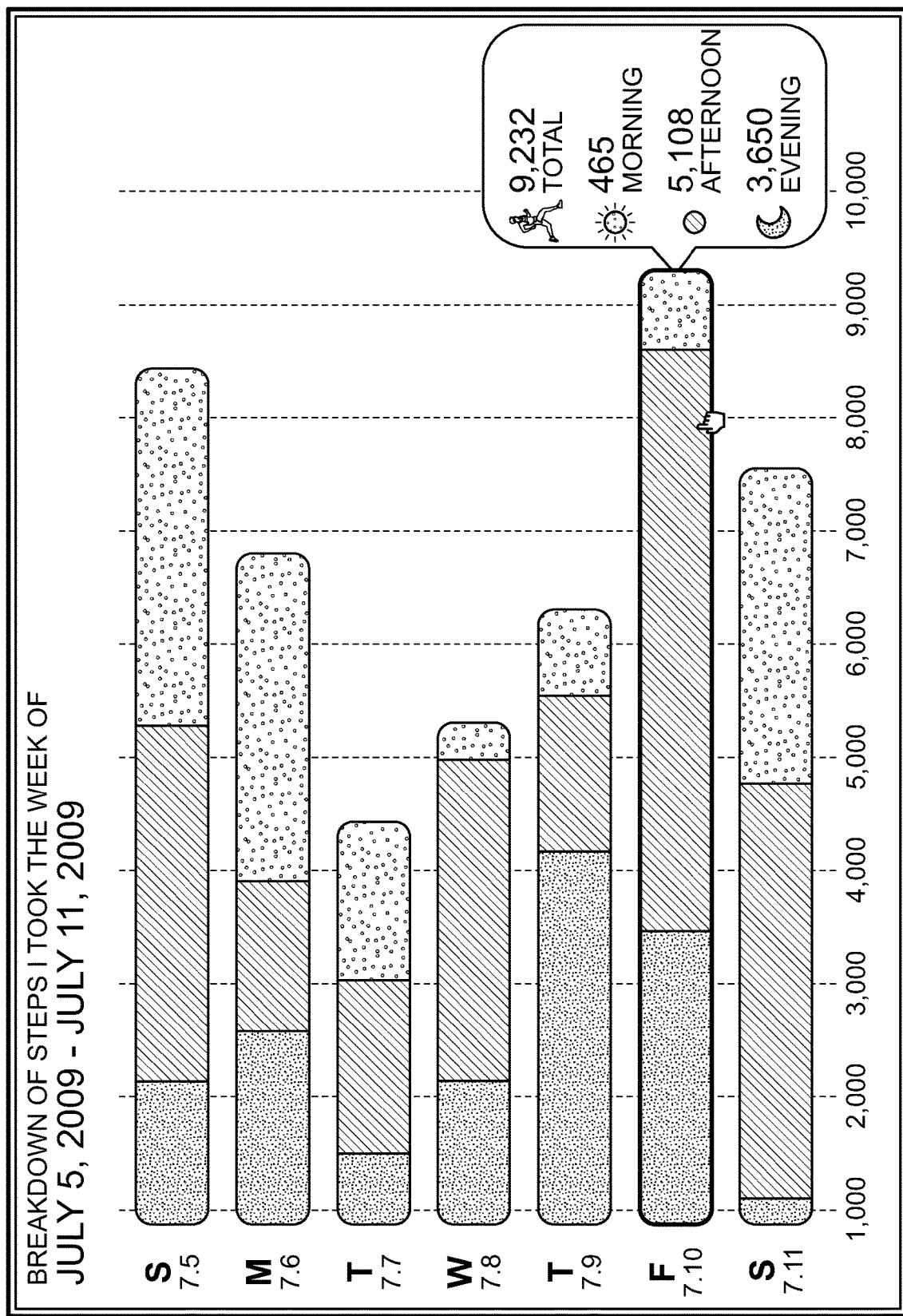
Figure 73:
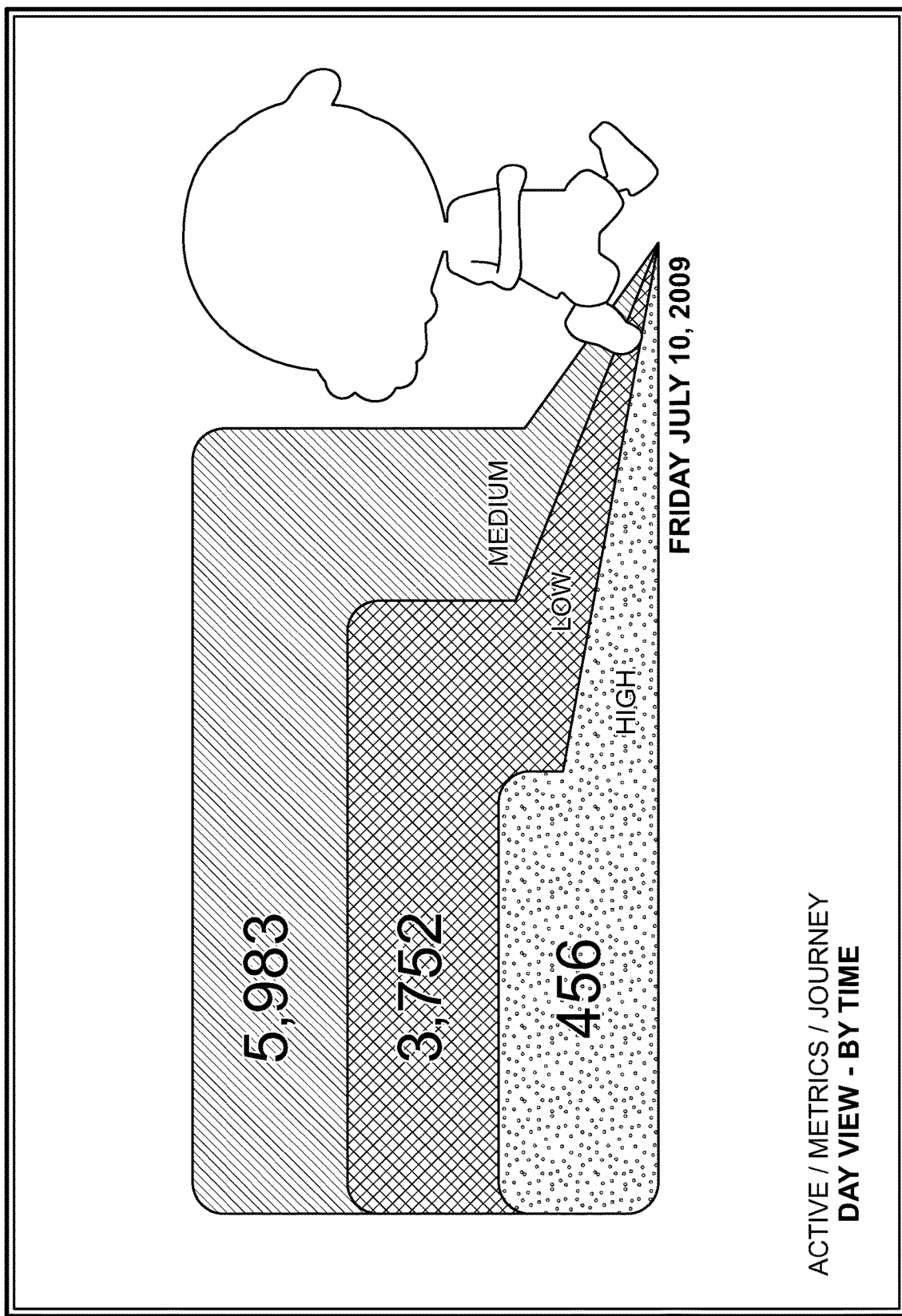

FIGS. 70-73 illustrate additional visualization options and configurations in which workout data may be divided or detailed by time of day (e.g., FIGS. 69 and 71) and/or intensity level (e.g., FIGS. 70 and 72).

Aspects described herein may be equally used with or applied to other types of activities beyond walking and other step-oriented exercises. For example, data for running, skiing, jumping rope, weightlifting and the like may be represented by and processed using the features described herein. In particular, virtual currency may be determined from any type of exercise from which an amount of calories burned may be measured or determined (e.g., according to the formulas and algorithms discussed above).

CONCLUSION

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. An apparatus for athletic activity tracking and monitoring, comprising:
   a display device;
   a processor; and
   memory operatively coupled to the processor and storing computer readable instructions that, when executed, cause the apparatus to:
   receive, from a computing device, data indicating an amount of athletic activity performed by a user;
   determine an activity type corresponding to the received data;
   selectively determine an athletic activity tracking and monitoring network site to transmit the received data based on the determined activity type; and
   display, on the display device and via the athletic activity tracking and monitoring network site, an activity monitoring interface based on the determined activity type, wherein the interface includes a breakdown of the user's activity into low activity, medium activity and high activity metrics, wherein the interface includes a clock visualization on a circular object representing times of a day, wherein the breakdown of the user's activity is represented by a curvature along a surface of the circular object, wherein a height of the curvature relative to the surface represents an amount of activity performed, and wherein the interface includes a message to encourage the user to increase the medium or high activity metrics.

2. The apparatus of claim 1, wherein the message is displayed on a map on the display device.

3. The apparatus of claim 1, wherein the computer readable instructions, when executed, further cause the apparatus to:
   receive a user selection of a first virtual object corresponding to a first athletic activity goal; and
   modify a visual appearance of the first virtual object in accordance with a progress made by the user in completing the first athletic activity goal.

4. The apparatus of claim 3, wherein the first athletic activity goal includes an athletic activity challenge between the user and another user.

5. The apparatus of claim 1, wherein the computer readable instructions, when executed, further cause the apparatus to:
   selectively determine an athletic activity tracking and monitoring site to store the received data based on the determined activity type.

6. The apparatus of claim 1, wherein the computer readable instructions, when executed, further causes the apparatus to:
   receive a first user input selection indicating a theme for an athletic workout plan.

7. The apparatus of claim 6, wherein the computer readable instructions, when executed, further cause the apparatus to:
   receive a second user input selection indicating one or more parameters of the athletic workout plan; and
   in response to receiving the first user input selection, generate one or more athletic activity goals to be completed in the athletic workout plan based on the one or more parameters.

8. The apparatus of claim 7, wherein the computer readable instructions, when executed, further cause the apparatus to:
   assign the one or more goals to one or more goal categories;
   define an order in which the one or more athletic activity goals are to be completed; and
   define an order in which the one or more goal categories are to be completed.

9. The apparatus of claim 8, wherein defining the order in which the one or more goal categories are to be completed comprises specifying that one or more athletic activity goals for a first goal category are required to be completed before permitting a user to engage in one or more athletic activity goals of a second goal category.

10. The apparatus of claim 9, wherein defining the order in which the one or more goal categories are to be completed further comprises locking the second goal category from user selection prior to completion of the first goal category.

11. One or more non-transitory computer readable media storing computer readable instructions that, when executed, cause an apparatus to:
    receive, from a computing device, data indicating an amount of athletic activity performed by a user;
    determine, by a processor, an activity type corresponding to the received data;
    selectively determine an athletic activity tracking and monitoring network site to transmit the received data based on the determined activity type; and
    display, on a display device an activity monitoring interface based on the determined activity type, wherein the interface includes a breakdown of the user's activity into low activity, medium activity and high activity metrics, wherein the interface includes a clock visualization on a circular object representing times of a day, wherein the breakdown of the user's activity is represented by a curvature along a surface of the circular object, wherein a height of the curvature relative to the surface represents an amount of activity performed, and wherein the interface includes a message to encourage the user to increase the medium or high activity metrics.

12. The one or more computer readable media of claim 11, wherein the message is displayed on a map on the display device.

13. The one or more computer readable media of claim 11, wherein the computer readable instructions, when executed, further cause the apparatus to:
    receive a user selection of a first virtual object corresponding to a first athletic activity goal; and
    modify a visual appearance of the first virtual object in accordance with a progress made by the user in completing the first athletic activity goal.

14. The one or more computer readable media of claim 13, wherein the first athletic activity goal includes an athletic activity challenge between the user and another user.

15. The one or more computer readable media of claim 11, wherein the computer readable instructions, when executed, further cause the apparatus to:
selectively determine an athletic activity tracking and monitoring site to store the received data based on the determined activity type.

16. The one or more computer readable media of claim 11, wherein the computer readable instructions, when executed, further causes the apparatus to:
receive a first user input selection indicating a theme for an athletic workout plan.

17. The one or more computer readable media of claim 16, wherein the computer readable instructions, when executed, further cause the apparatus to:
receive a second user input selection indicating one or more parameters of the athletic workout plan; and
in response to receiving the first user input selection, generate one or more athletic activity goals to be completed in the athletic workout plan based on the one or more parameters.

18. The one or more computer readable media of claim 17, wherein the computer readable instructions, when executed, further cause the apparatus to:
assign the one or more goals to one or more goal categories;
define an order in which the one or more athletic activity goals are to be completed; and
define an order in which the one or more goal categories are to be completed.

19. The one or more computer readable media of claim 18, wherein defining the order in which the one or more goal categories are to be completed comprises specifying that one or more athletic activity goals for a first goal category are required to be completed before permitting a user to engage in one or more athletic activity goals of a second goal category.

20. The one or more computer readable media of claim 19, wherein defining the order in which the one or more goal categories are to be completed further comprises locking the second goal category from user selection prior to completion of the first goal category.

\* \* \* \* \*